United States Patent
Shi et al.

(10) Patent No.: US 11,807,626 B2
(45) Date of Patent: Nov. 7, 2023

(54) COMPOUNDS AND METHODS FOR CD73 MODULATION AND INDICATIONS THEREFOR

(71) Applicant: Opna Bio SA, Epalinges (CH)

(72) Inventors: Songyuan Shi, Fremont, CA (US);
John Buell, San Francisco, CA (US);
Zuojun Guo, Pasadena, CA (US);
Cuong Ly, Burlingame, CA (US);
Wayne Spevak, Berkeley, CA (US);
Mark Vander Wal, Berkeley, CA (US);
Jack Walleshauser, Berkeley, CA (US);
Chao Zhang, Moraga, CA (US);
Jiazhong Zhang, Foster City, CA (US)

(73) Assignee: Opna Bio SA, Epalinges (CH)

( * ) Notice: Subject to any disclaimer, the term of this patent is extended or adjusted under 35 U.S.C. 154(b) by 162 days.

(21) Appl. No.: 17/238,121

(22) Filed: Apr. 22, 2021

(65) Prior Publication Data
US 2022/0144805 A1    May 12, 2022

Related U.S. Application Data

(60) Provisional application No. 63/014,523, filed on Apr. 23, 2020.

(51) Int. Cl.
| | |
|---|---|
| *C07D 401/14* | (2006.01) |
| *A61K 31/501* | (2006.01) |
| *A61K 31/506* | (2006.01) |
| *A61K 31/5377* | (2006.01) |
| *A61K 31/55* | (2006.01) |
| *A61K 45/06* | (2006.01) |
| *C07D 405/14* | (2006.01) |
| *C07D 413/14* | (2006.01) |
| *C07D 417/14* | (2006.01) |
| *C07D 487/08* | (2006.01) |
| *C07D 491/107* | (2006.01) |

(52) U.S. Cl.
CPC ......... *C07D 401/14* (2013.01); *A61K 31/501* (2013.01); *A61K 31/506* (2013.01); *A61K 31/5377* (2013.01); *A61K 31/55* (2013.01); *A61K 45/06* (2013.01); *C07D 405/14* (2013.01); *C07D 413/14* (2013.01); *C07D 417/14* (2013.01); *C07D 487/08* (2013.01); *C07D 491/107* (2013.01)

(58) Field of Classification Search
None
See application file for complete search history.

(56) References Cited

U.S. PATENT DOCUMENTS

| | | | |
|---|---|---|---|
| 7,202,266 B2 | 4/2007 | Arnold et al. | |
| 7,348,338 B2 | 3/2008 | Arnold et al. | |
| 7,476,746 B2 | 1/2009 | Artis et al. | |
| 7,491,831 B2 | 2/2009 | Artis et al. | |
| 7,504,509 B2 | 3/2009 | Ibrahim et al. | |
| 7,572,806 B2 | 8/2009 | Arnold et al. | |
| 7,585,859 B2 | 9/2009 | Ibrahim et al. | |
| 7,605,168 B2 | 10/2009 | Ibrahim et al. | |
| 7,723,374 B2 | 5/2010 | Artis et al. | |
| 7,759,475 B2 | 7/2010 | West | |
| 7,846,941 B2 | 12/2010 | Zhang et al. | |
| 7,863,288 B2 | 1/2011 | Ibrahim et al. | |
| 7,893,075 B2 | 2/2011 | Zhang et al. | |
| 8,067,434 B2 | 11/2011 | Ibrahim et al. | |
| 8,110,576 B2 | 2/2012 | Ibrahim et al. | |
| 8,119,637 B2 | 2/2012 | Ibrahim et al. | |
| 8,143,271 B2 | 3/2012 | Ibrahim et al. | |
| 8,153,641 B2 | 4/2012 | Ibrahim et al. | |
| 8,158,636 B2 | 4/2012 | Ibrahim et al. | |
| 8,268,858 B2 | 9/2012 | Wu et al. | |
| 8,367,828 B2 | 2/2013 | Arnold et al. | |
| 8,404,700 B2 | 3/2013 | Ibrahim et al. | |
| 8,415,469 B2 | 4/2013 | Ibrahim et al. | |

(Continued)

FOREIGN PATENT DOCUMENTS

| | | |
|---|---|---|
| WO | WO-2013170113 | 11/2013 |
| WO | WO-2013170115 | 11/2013 |

(Continued)

OTHER PUBLICATIONS

Chemical Abstract Service, Columbus, OH, CAS Registry No. 2223874-15-3, Supplier: Enamine LLC, entered (May 20, 2018).*
Leone et al., Journal for ImmunoTherapy of Cancer, vol. 6, No. 57, pp. 1-9 https://doi.org/10.1186/s40425-018-0360-8 (Year: 2018).*
U.S. Appl. No. 17/220,665, filed Apr. 1, 2021, Albers et al.
U.S. Appl. No. 16/843,700, filed Apr. 8, 2020, Spevak et al.
U.S. Appl. No. 17/161,257, filed Jan. 28, 2021, Zhang et al.
U.S. Appl. No. 17/166,890, filed Feb. 3, 2021, Desai et al.
U.S. Appl. No. 17/180,212, filed Feb. 19, 2021, Ibrahim et al.
U.S. Appl. No. 17/238,076, filed Apr. 22, 2021, Ibrahim et al.
U.S. Appl. No. 17/335,898, filed Jun. 1, 2021, Wu et al.

(Continued)

*Primary Examiner* — Zinna Northington Davis
(74) *Attorney, Agent, or Firm* — Elmore Patent Law Group, P.C.; Joseph C. Zucchero; Carolyn S. Elmore

(57) ABSTRACT

Disclosed are compounds of Formula I:

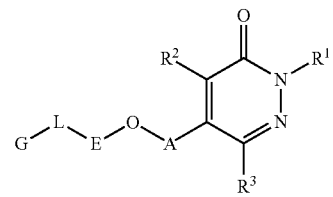

or a pharmaceutically acceptable salt, a solvate, a tautomer, a stereoisomer or a deuterated analog thereof, wherein $R^1$, $R^2$, $R^3$, A, E, L, and G are as described in any of the embodiments described in this disclosure; compositions thereof; and uses thereof.

40 Claims, No Drawings

(56) References Cited

U.S. PATENT DOCUMENTS

| | | |
|---|---|---|
| 8,461,169 B2 | 6/2013 | Zhang et al. |
| 8,470,818 B2 | 6/2013 | Ibrahim et al. |
| 8,470,821 B2 | 6/2013 | Ibrahim et al. |
| 8,642,606 B2 | 2/2014 | Ibrahim et al. |
| 8,673,928 B2 | 3/2014 | Ibrahim et al. |
| 8,722,702 B2 | 5/2014 | Zhang et al. |
| 8,865,735 B2 | 10/2014 | Ibrahim et al. |
| 8,901,118 B2 | 12/2014 | Zhang et al. |
| 8,901,301 B2 | 12/2014 | Ibrahim et al. |
| 8,912,204 B2 | 12/2014 | Ibrahim et al. |
| 9,096,593 B2 | 8/2015 | Zhang et al. |
| 9,150,570 B2 | 10/2015 | Ibrahim |
| 9,169,250 B2 | 10/2015 | Zhang et al. |
| 9,260,437 B2 | 2/2016 | Ibrahim et al. |
| 9,358,235 B2 | 6/2016 | Bollag et al. |
| 9,440,969 B2 | 9/2016 | Ibrahim et al. |
| 9,447,089 B2 | 9/2016 | Desai et al. |
| 9,469,640 B2 | 10/2016 | Wu et al. |
| 9,487,515 B2 | 11/2016 | Zhang et al. |
| 9,550,768 B2 | 1/2017 | Zhang et al. |
| 9,617,267 B2 | 4/2017 | Ibrahim et al. |
| 9,624,213 B2 | 4/2017 | Ibrahim et al. |
| 9,663,517 B2 | 5/2017 | Desai et al. |
| 9,682,981 B2 | 6/2017 | Zhang et al. |
| 9,695,169 B2 | 7/2017 | Ibrahim |
| 9,718,847 B2 | 8/2017 | Zhang et al. |
| 9,730,918 B2 | 8/2017 | Bollag et al. |
| 9,745,298 B2 | 8/2017 | Ibrahim et al. |
| 9,771,363 B2 | 9/2017 | Ibrahim et al. |
| 9,771,369 B2 | 9/2017 | Lin et al. |
| 9,776,998 B2 | 10/2017 | Ibrahim et al. |
| 9,802,932 B2 | 10/2017 | Ibrahim et al. |
| 9,814,714 B2 | 11/2017 | Ibrahim et al. |
| 9,822,109 B2 | 11/2017 | Zhang et al. |
| 9,844,539 B2 | 12/2017 | Wu et al. |
| 9,856,259 B2 | 1/2018 | Shi et al. |
| 9,873,700 B2 | 1/2018 | Zhang et al. |
| 9,938,273 B2 | 4/2018 | Wu et al. |
| 9,975,894 B2 | 5/2018 | Ibrahim et al. |
| 9,994,567 B2 | 6/2018 | Ibrahim et al. |
| 10,040,792 B2 | 8/2018 | Ibrahim et al. |
| 10,123,998 B2 | 11/2018 | Bollag et al. |
| 10,160,747 B2 | 12/2018 | Lin et al. |
| 10,160,755 B2 | 12/2018 | Lin et al. |
| 10,189,833 B2 | 1/2019 | Ibrahim et al. |
| 10,227,357 B2 | 3/2019 | Lin et al. |
| 10,316,032 B2 | 6/2019 | Ibrahim et al. |
| 10,370,374 B2 | 8/2019 | Ibrahim et al. |
| 10,399,975 B2 | 9/2019 | Ibrahim et al. |
| 10,421,761 B2 | 9/2019 | Zhang et al. |
| 10,426,760 B2 | 10/2019 | Wu et al. |
| 10,428,067 B2 | 10/2019 | Zhang et al. |
| 10,435,404 B2 | 10/2019 | Ibrahim et al. |
| 10,501,460 B2 | 12/2019 | Zhang et al. |
| 10,508,085 B2 | 12/2019 | Zhang et al. |
| 10,519,177 B2 | 12/2019 | Zhang et al. |
| 10,577,366 B2 | 3/2020 | Lin et al. |
| 10,584,122 B2 | 3/2020 | Ibrahim et al. |
| 10,647,716 B2 | 5/2020 | Ibrahim et al. |
| 10,703,757 B2 | 7/2020 | Wu et al. |
| 10,717,735 B2 | 7/2020 | Ibrahim et al. |
| 10,730,876 B2 | 8/2020 | Ibrahim et al. |
| 10,829,484 B2 | 11/2020 | Holladay et al. |
| 10,899,761 B2 | 1/2021 | Ibrahim et al. |
| 10,941,142 B2 | 3/2021 | Ibrahim et al. |
| 10,961,240 B2 | 3/2021 | Ibrahim et al. |
| 2017/0157120 A1 | 6/2017 | Ibrahim et al. |
| 2019/0125747 A1 | 5/2019 | Rezaei et al. |
| 2019/0300487 A1 | 10/2019 | Zhang et al. |
| 2020/0299293 A1 | 9/2020 | Ibrahim et al. |
| 2021/0198239 A1 | 7/2021 | Vander Wal et al. |

FOREIGN PATENT DOCUMENTS

| | | |
|---|---|---|
| WO | WO-2014207601 | 12/2014 |
| WO | WO-2017053243 | 3/2017 |
| WO | WO-2019055966 | 3/2019 |
| WO | WO-2019168744 | 9/2019 |
| WO | WO-2020210366 | 10/2020 |
| WO | WO-2021113625 | 6/2021 |

OTHER PUBLICATIONS

U.S. Appl. No. 17/368,582, filed Jul. 6, 2021, Ibrahim et al.
U.S. Appl. No. 17/372,330, filed Jul. 9, 2021, Wu et al.
U.S. Appl. No. 17/372,346, filed Jul. 9, 2021, Wu et al.
U.S. Appl. No. 17/379,837, filed Jul. 19, 2021, Rezaei et al.
U.S. Appl. No. 17/387,775, filed Jul. 28, 2021, Ibrahim et al.
U.S. Appl. No. 17/407,811, filed Aug. 20, 2021, Powell et al.
International Search Report and Written Opinion for International Application No. PCT/US2021/028677 dated Jul. 9, 2021. 14 pages.
Zhao-wei Gao et al., The Roles of CD73 in Cancer, BioMed Research International 2014, vol. 2014, No. 460654, pp. 1-9, XP055361805.

* cited by examiner

COMPOUNDS AND METHODS FOR CD73 MODULATION AND INDICATIONS THEREFOR

CROSS-REFERENCE TO RELATED PATENT APPLICATIONS

This application claims the benefit under 35 U.S.C. § 119(e) of U.S. Provisional Application 63/014,523, filed Apr. 23, 2020, which is hereby incorporated by reference in its entirety.

FIELD

The present invention relates to organic compounds useful for therapy in a mammals, and in particular for modulating CD73 for various diseases associated with the overexpression of CD73.

BACKGROUND

The enzyme CD73, which catalyzes AMP breakdown to adenosine, has been found to be overexpressed in many types of cancer. CD73 is involved in the generation of extracellular adenosine, which modulates T cells' tumor-induced immunosuppressive mechanism whereby tumor-derived CD73 functions as an ecto-enzyme to produce extracellular adenosine that promotes tumor growth by limiting antitumor T cell immunity via adenosine receptor (AR) signaling. More specifically, CD73, a highly conserved ecto-nucleotidase, is a dimeric enzyme that is expressed on the outer leaflet of the plasma membrane. It catalyzes the dephosphorylation of a subset of 5' nucleotides, among which 5'-adenosine monophophates (AMP) is the primary substrate. The adenosine is produced by CD73 catalyzed AMP hydrolysis at high level within tumor microenviroment. It binds to A2a and A2b receptors on immune cells and inhibits immunosurveillance against tumor cells. Blocking CD73 hydrolysis of AMP is a potential therapeutic approach to de-repress anti-tumor immunity. Results with small molecule inhibitors targeting CD73 in murine tumor models suggest that targeted CD73 therapy is an important alternative and realistic approach to effective control of tumor growth. In particular, it helps T cell-based therapy by enhancing the adaptive immune response machinery, which may increase the function of tumor-infiltrating T lymphocytes, and subsequently lead to improved survival in cancer patients.

It has been reported that, based on clinical trial data, CD73 expression is associated with a poor prognosis and reduced anti-tumor immunity in human TNBC and that targeting CD73 could be a promising strategy to reprogram the tumor microenvironment in this BC subtype. (See Bruissert et al., Clinical significance of CD73 in triple-negative breast cancer: multiplex analysis of a phase III clinical trial, *Ann Oncol.* 2018 Apr. 1; 29(4):1056-1062.)

It has also been reported that CD73 is a target for immunotherapy, and clinical studies with CD73 inhibitors may prove beneficial to lung cancer patients. (See Hui et al., Evaluation of CD73 in lung cancer, *Journal of Clinical Oncology* 201735:15.)

It has also been reported that that there is increasing evidence verifying that CD73 is a key regulatory molecule in cancer development, and more specifically, that CD73 is overexpressed in many types of cancer cell lines and patient's biopsies including breast cancer, colorectal cancer, ovarian cancer, gastric cancer, and gallbladder cancer and is also associated with clinical characteristics, or prognosis of cancer patients. Moreover, the positive effect on tumor-bearing mice models demonstrates that anti-CD73 therapy has become a promising approach for the treatment of such cancer patients. (See Zhao-wei Gao et al., The Roles of CD73 in Cancer, *BioMed Research International*, Volume 2014).

It has been further demonstrated that host CD73 plays a prominent role in multiple areas of glioblastoma pathogenesis, including promoting glioblastoma growth, its angiogenesis, and its invasiveness. More specifically, studies have demonstrated a 20-fold increase in A2B adenosine receptor (AR) expression on GB compared with sham, and its inhibition increased glioblastoma chemosensitivity to temozolomide. These findings strongly indicate that blockade or inhibition of CD73 and the A2B AR are prime targets for future glioblastoma therapy. (See Yan. A et al., CD73 Promotes Glioblastoma Pathogenesis and Enhances Its Chemoresistance via A2B Adenosine Receptor Signaling, *J Neurosci.* 2019 May 29; 39(22):4387-4402).

Studies have found that that CD73 activity increases during the proliferative process in glioma cell lines, suggesting an important role of this enzyme during brain tumor development. Taken together, these results suggest an important role of ecto-50-NT/CD73 in glioma cell proliferation. (See Luci Bavaresco et al., The role of ecto-5'-nucleotidase/CD73 in glioma cell line proliferation, *Mol Cell Biochem* (2008) 319:61-68).

It was further found that the overall survival rate was low in the gastric cancer patients with high expression of CD73, and CD73 expression was proven to be an independent predictor for patients with gastric carcinoma. (See Lu X X et al., Expression and clinical significance of CD73 and hypoxia-inducible factor-1α in gastric carcinoma, *World J Gastroenterol.* 2013 Mar. 28; 19(12):1912-8).

Other studies found that there is an increase of CD73 expression certain conditions such as highly invasive phenotype of melanoma cell lines, proliferating chronic lymphocytic leukemia cells, papillary carcinoma (the most common form of thyroid cancer), pancreatic ductal adenocarcinomas, and the stroma of colorectal cancer. It has been found that there is an increase of CD73 mRNA and activity in glioma cell lines, lymph node metastasizing prostate cancer, and human tumor bladder cell lines. (See Luca Antonioli et al., Anti-CD73 in cancer immunotherapy: awakening new opportunities, *Trends Cancer.* 2016 Feb. 1; 2(2): 95-, 109).

It was also reported that inhibiting CD73 to prevent its immunosuppressive effect could be a promising therapeutic target as it might enhance control of leukemia. (See Paolo Bernasconi et al., Targeting Leukemia Stem Cell-Niche Dynamics: A New Challenge in AML Treatment, *Journal of Oncology*, Volume 2019).

Other studies have found a high CD73 expression by pancreatic cancer cells associated with poor patient prognosis independently of clinicopathological factors, and this suggests that CD73 may be a relevant immunotherapeutic target in pancreatic ductal adenocarcinoma and a promising immune prognostic biomarker. (See N. Messaoudi et al., CD73 as a novel immune target and biomarker in pancreatic adenocarcinoma, *HPB* 2018, 20 (S1), S5eS35).

It has also been reported that the expression of CD73 in lymph node metastasizing prostate cancer was higher compared with non-metastasizing ones suggesting that CD73 could be a relevant-specific target for molecular therapy of prostate cancer metastasis. (See Yang Q et al., Overexpression of CD73 in prostate cancer is associated with lymph node metastasis, *Pathol Oncol Res.* 2013 October; 19(4): 811-4).

Other studies have reported that limiting CD73-derived adenosine substantially suppressed microglia-mediated neuroinflammation and improved the viability of dopaminergic neurons and motor behaviours in Parkinson's disease models. The authors concluded that targeting nucleotide metabolic pathways such as CD73 to limit adenosine production and neuroinflammation in Parkinson's disease may be a promising therapeutic strategy. (See Fan Meng et al., CD73-derived adenosine controls inflammation and neurodegeneration by modulating dopamine signaling, *Brain*, Volume 142, Issue 3, March 2019, Pages 700-718).

Hepatic fibrosis is developed as a response to chronic inflammation and ongoing liver injury. This pathological process is driven by activation and accumulation of myofibrablasts. CD73 is upregulated in hepatic stellate cells, portal fibroblasts and in fibrous septa as a result of myofibroblast differentiation. It has been reported that CD73 deficient mice are resistant to development of liver fibrosis suggesting its role and adenosine generation in fibrogenesis. CD73 might be useful in the prevention of liver fibrosis.

Still other studies have reported that CD73 is a novel target for modulation of early Alzheimer's Disease, where synaptic and memory dysfunction in a β-amyloid model of early Alzheimer's disease depends on increased formation of ATP-derived extracellular adenosine which is generated by CD73. (See Gongalves et al., Synaptic and memory dysfunction in a 0-amyloid model of early Alzheimer's disease depends on increased formation of ATP-derived extracellular adenosine, *Neurobiol Dis.* 2019 December; 132:104570).

Compounds that can inhibit CD73, therefore, represent a new class of potential therapeutics capable of modulating the immune response and tumor growth. As there are no CD73 inhibitors that are currently approved for the treatment or prevention of diseases in humans, there is an unmet need for new compounds that are capable of modulating CD73.

SUMMARY

One embodiment of the disclosure relates to novel compounds, as described in any of the embodiments herein, or a pharmaceutically acceptable salt, a solvate, a tautomer, a stereoisomer or a deuterated analog thereof, wherein these novel compounds can modulate CD73.

Another embodiment of this disclosure relates to a compound of Formula I:

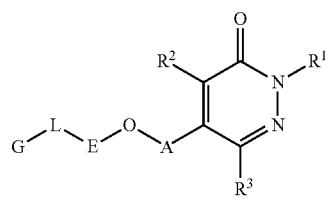

I or a pharmaceutically acceptable salt, a solvate, a tautomer, a stereoisomer, or a deuterated analog thereof, wherein $R^1$, $R^2$, $R^3$, A, E, L, and G are as described in any of the embodiments (including any of the subembodiments thereof) in this disclosure.

Other embodiments and sub-embodiments of Formula I are further described herein in this disclosure.

Another embodiment of the disclosure relates to a pharmaceutical composition comprising a compound according to Formula I or any embodiment and sub-embodiment of Formula I described herein in this disclosure, or a pharmaceutically acceptable salt, a solvate, a tautomer, a stereoisomer or a deuterated analog of any of these compounds, and a pharmaceutically acceptable carrier or excipient.

Another embodiment of the disclosure relates to a pharmaceutical composition comprising a compound according to Formula I, or any embodiment of Formula I described herein in this disclosure, or a pharmaceutically acceptable salt, a solvate, a tautomer, a stereoisomer or a deuterated analog of any of these compounds, and another therapeutic agent.

Another embodiment of this disclosure relates to a method for treating a subject with a disease or condition mediated by CD73, said method comprising administering to the subject an effective amount of a compound according to Formula I, or any embodiment of Formula I described in this disclosure, or a pharmaceutically acceptable salt, a solvate, a tautomer, a stereoisomer or a deuterated analog of any of these compounds, or a pharmaceutical composition of any of the compounds as described in this disclosure, wherein the disease or condition express aberrantly or otherwise CD73, or activating mutations or translocations of any of the foregoing.

Additional embodiments are described are further described in the Detailed Description of this disclosure.

DETAILED DESCRIPTION

I. Definitions

As used herein the following definitions apply unless clearly indicated otherwise:

It is noted here that as used herein and the appended claims, the singular forms "a," "an," and "the" include plural reference unless the context clearly dictates otherwise.

Unless a point of attachment indicates otherwise, the chemical moieties listed in the definitions of the variables of Formula I of this disclosure, and all the embodiments thereof, are to be read from left to right, wherein the right hand side is directly attached to the parent structure as defined. However, if a point of attachment (e.g., a dash "-") is shown on the left hand side of the chemical moiety (e.g., -alkyloxy-$C_1$-$C_6$alkyl), then the left hand side of this chemical moiety is attached directly to the parent moiety as defined.

It is assumed that when considering generic descriptions of compounds described herein for the purpose of constructing a compound, such construction results in the creation of a stable structure. That is, one of ordinary skill in the art would recognize that, theoretically, some constructs would not normally be considered as stable compounds (that is, sterically practical and/or synthetically feasible).

"Alkyl," by itself, or as part of another substituent, means, unless otherwise stated, a straight or branched chain hydrocarbon, having the number of carbon atoms designated (i.e. $C_1$-$C_6$ means one to six carbons). Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms. Examples of alkyl groups include methyl, ethyl, n-propyl, isopropyl, n-butyl, t-butyl, isobutyl, secbutyl, n-pentyl, n-hexyl, n-heptyl, n-octyl, and the like. For each of the definitions herein (e.g., alkyl, alkoxy, arylalkyl, cycloalkylalkyl, heterocycloalkylalkyl, heteroarylalkyl, etc.), when a prefix is not included to indicate the number of carbon atoms in an alkyl portion, the alkyl moiety or portion thereof will have 12 or fewer main chain carbon atoms or 8 or fewer main chain carbon atoms or 6 or fewer main chain carbon atoms. For example, $C_1$-$C_6$alkyl refers to a straight or branched hydrocarbon having 1, 2, 3, 4, 5 or 6 carbon atoms and includes, but is not limited to, —$CH_3$, $C_2$alkyl, $C_3$alkyl, $C_4$alkyl, $C_5$alkyl, $C_6$alkyl, $C_1$-$C_2$alkyl, $C_2$alkyl, $C_3$alkyl, $C_1$-$C_3$alkyl, $C_1$-$C_4$alkyl, $C_1$-$C_5$alkyl, $C_1$-$C_6$alkyl, $C_2$-$C_3$alkyl, $C_2$-$C_4$alkyl, $C_2$-$C_5$alkyl, $C_2$-$C_6$alkyl, $C_3$-$C_4$alkyl, $C_3$-$C_5$alkyl, $C_3$-$C_6$alkyl, $C_4$-$C_5$alkyl, $C_4$-$C_6$alkyl, $C_5$-$C_6$ alkyl and $C_6$alkyl. While it is understood that substitutions are attached at any available atom to produce a stable compound, when optionally substituted alkyl is an R group of a moiety such as —OR (e.g. alkoxy), —SR (e.g. thioalkyl), —NHR (e.g. alkylamino), —C(O)NHR, and the like, substitution of the alkyl R group is such that substitution of the alkyl carbon bound to any O, S, or N of the moiety (except where N is a heteroaryl ring atom) excludes substituents that would result in any O, S, or N of the substituent (except where N is a heteroaryl ring atom) being bound to the alkyl carbon bound to any O, S, or N of the moiety.

"Alkylene" by itself or as part of another substituent means a linear or branched saturated divalent hydrocarbon moiety derived from an alkane having the number of carbon atoms indicated in the prefix. For example, (i.e., $C_1$-$C_6$ means one to six carbons; $C_1$-$C_6$alkylene is meant to include methylene, ethylene, propylene, 2-methylpropylene, pentylene, hexylene and the like). $C_{1-4}$ alkylene includes methylene —$CH_2$—, ethylene —$CH_2CH_2$—, propylene —$CH_2CH_2CH_2$—, and isopropylene —$CH(CH_3)CH_2$—, —$CH_2CH(CH_3)$—, —$CH_2$—$(CH_2)_2CH_2$—, —$CH_2$—$CH(CH_3)CH_2$—, —$CH_2$—$C(CH_3)_2$—$CH_2$—$CH_2CH(CH_3)$—. Typically, an alkyl (or alkylene) group will have from 1 to 24 carbon atoms, with those groups having 10 or fewer, 8 or fewer, or 6 or fewer carbon atoms. When a prefix is not included to indicate the number of carbon atoms in an alkylene portion, the alkylene moiety or portion thereof will have 12 or fewer main chain carbon atoms or 8 or fewer main chain carbon atoms, 6 or fewer main chain carbon atoms, or 4 or fewer main chain carbon atoms, or 3 or fewer main chain carbon atoms, or 2 or fewer main chain carbon atoms, or 1 carbon atom.

"Alkenyl" refers to a linear monovalent hydrocarbon radical or a branched monovalent hydrocarbon radical having the number of carbon atoms indicated in the prefix and containing at least one double bond. For example, $C_2$-$C_6$ alkenyl is meant to include ethenyl, propenyl, and the like. "$C_2$-$C_6$alkenyl$C_1$-$C_6$alkylene" is a group —$C_1$-$C_6$alkylene-$C_2$-$C_6$alkenyl, where alkenyl and alkylene are as defined herein.

The term "alkenylene" refers to a linear divalent hydrocarbon radical or a branched divalent hydrocarbon radical containing at least one double bond and having the number of carbon atoms indicated in the prefix. Examples of such groups include vinyl, 2-propenyl, crotyl, 2-isopentenyl, 2-(butadienyl), 2,4-pentadienyl, 3-(1,4-pentadienyl), and the higher homologs and isomers.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—C≡CH), propargyl (or propynyl, e.g. —C≡CCH3), and the like. When a prefix is not included to indicate the number of carbon atoms in an alkenyl or alkynyl portion, the alkenyl or alkynyl moiety or portion thereof will have 12 or fewer main chain carbon atoms or 8 or fewer main chain carbon atoms, 6 or fewer main chain carbon atoms or 4 or fewer main chain carbon atoms.

The term "alkynylene" refers to a linear divalent hydrocarbon radical or a branched divalent hydrocarbon radical containing at least one triple bond and having the number of carbon atoms indicated in the prefix. Examples of such groups include ethynyl, 1- and 3-propynyl, 3-butynyl, and the higher homologs and isomers.

"Alkoxy" or "alkoxyl" refers to a —O-alkyl group, where alkyl is as defined herein. By way of example, "$C_1$-$C_6$alkoxy" refers to a —O—$C_1$-$C_6$alkyl group, where alkyl is as defined herein. While it is understood that substitutions on alkoxy are attached at any available atom to produce a stable compound, substitution of alkoxy is such that O, S, or N (except where N is a heteroaryl ring atom), are not bound to the alkyl carbon bound to the alkoxy O. Further, where alkoxy is described as a substituent of another moiety, the alkoxy oxygen is not bound to a carbon atom that is bound to an O, S, or N of the other moiety (except where N is a heteroaryl ring atom), or to an alkene or alkyne carbon of the other moiety.

The terms "alkoxyalkyl" and "alkoxyalkylene" refer to an alkyl group substituted with an alkoxy group. By way of example, "$C_1$-$C_6$alkoxy$C_1$-$C_6$alkyl" refers to $C_1$-$C_6$alkyl substituted with a $C_1$-$C_6$alkoxy where alkyl and alkoxy are as defined herein, while "$C_1$-$C_3$alkoxy$C_1$-$C_3$alkylene" refers to $C_1$-$C_3$alkyl substituted with a $C_1$-$C_3$alkoxy where alkylene and alkoxy are as defined herein.

"Amino" or "amine" denotes the group —$NH_2$.

"Aryl" by itself, or as part of another substituent, unless otherwise stated, refers to a monocyclic, bicyclic or polycyclic polyunsaturated aromatic hydrocarbon radical containing 6 to 14 ring carbon atoms, which can be a single ring or multiple rings (up to three rings) which are fused together or linked covalently. Aryl, however, does not encompass or overlap in any way with heteroaryl defined below. If one or more aryl rings are fused with a heteroaryl ring, the resulting ring system is heteroaryl. Non-limiting examples of unsubstituted aryl groups include phenyl, 1-naphthyl and 2-naphthyl. The term "arylene" refers to a divalent aryl, wherein the aryl is as defined herein.

"5-6 membered aromatic ring" refers to a phenyl ring or a 5-6 membered heteroaryl ring as defined herein. For purposes of this disclosure, bridgehead atoms cannot be two adjacent atoms on any particular ring.

A "bridged ring" or a "bridged compound" is a carbocyclic or heterocyclic compound or moiety having two or more rings containing a bridge of one to four carbon atoms that connect two bridgehead atoms. In this disclosure, the phrase "bridged carbocyclic or heterocyclic ring" has the same meaning as the phrase "bridged carbocylic ring or bridged heterocyclic ring." For purposes of this disclosure, two bridgehead atoms in a bridged ring cannot the same atom on any particular ring. A bridged heterocyclic ring refers to a bridged compound having at least one heteroatom. The bridgehead atoms are part of the skeletal framework of the molecule. Bridged rings (or compounds) may be fully carbocyclic (all carbon skeletal atoms). Below is an example of a bridged ring showing each of the bridge and bridgehead atoms.

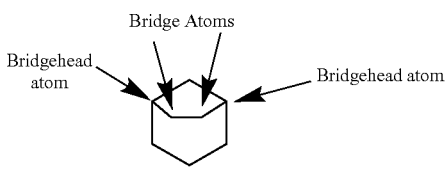

For purposes of this disclosure, a bridged ring is meant to include rings that may optionally have 1-2 $C_1$-$C_3$ alkyl groups which are not attached on either its bridge atoms and bridgehead atoms, and these bridged rings can be substituted as described in this disclosure. Other non-limiting examples of bridged rings include bicyclo[1.1.1]pentane, adamantyl, (1s,5s)-bicyclo[3.3.1]nonane, (1R,5S)-6,6-dimethylbicyclo[3.1.1]heptane, (1R,5S)-6,6-dimethylbicyclo[3.1.1]heptane, (1r,2R,4S,5r,6R,8S)-tetracyclo[3.3.1.0²,⁴.0⁶,⁸]nonane, bicyclo[2.2.1]heptane, bicyclo[2.2.2]octane, and 1-fluorobicyclo[2.2.2]octane.

"Cycloalkyl" or "Carbocycle" or "Carbocyclic" by itself, or as part of another substituent, unless otherwise stated, refers to saturated or partially unsaturated, nonaromatic monocyclic ring, or fused rings, such as bicyclic or tricyclic carbon ring systems, or cubane, having the number of carbon atoms indicated in the prefix or if unspecified having 36, also 46, and also 5-6 ring members per ring, such as cyclopropyl, cyclopentyl, cyclohexyl, where one or two ring carbon atoms may optionally be replaced by a carbonyl. Further, the term cycloalkyl is intended to encompass ring systems fused to an aromatic ring (e.g., of an aryl), regardless of the point of attachment to the remainder of the molecule. Cycloalkyl refers to hydrocarbon rings having the indicated number of ring atoms (e.g., $C_{3-6}$ cycloalkyl and 3-6 membered cycloalkyl both mean three to six ring carbon atoms). The term "cycloalkenyl" refers to a cycloalkyl having at least one unit of unsaturation. A substituent of a cycloalkyl or cycloalkenyl may be at the point of attachment of the cycloalkyl or cycloalkenyl group, forming a quaternary center.

"Cycloalkylalkyl" and "cycloalkylalkylene" refer to an -(alkylene)-cycloalkyl group where alkylene as defined herein has the indicated number of carbon atoms or if unspecified having six or fewer carbon atoms; and cycloalkyl is as defined herein has the indicated number of carbon atoms or if unspecified having 310, also 38, and also 36, ring members per ring. By way of example, 4-6 membered cycloalkyl-$C_1$-$C_6$alkyl refers to a cycloalkyl with 4-6 carbon atoms attached to an alkylene chain with 1-6 carbon atoms, wherein the alkylene chain is attached to the parent moiety. Other exemplary cycloalkylalkyl groups include, e.g., cyclopropylmethylene, cyclobutylethylene, cyclobutylmethylene, and the like. "Cycloalkylalkynylene" refers to a -(alkynylene)-cycloalkyl group, for example, $C_3$-$C_6$cycloalkyl$C_2$-$C_6$alkynylene is a group —($C_2$-$C_6$alkynylene)-$C_3$-$C_6$cycloalkyl. "$C_3$-$C_6$cycloalkylethynylene" is a group —C≡C—$C_3$-$C_6$cycloalkyl.

The term "cyano" refers to the group —CN. The term "$C_1$-$C_6$cyanoalkyl" refers to a $C_1$-$C_6$alkyl, as defined herein, that is substituted with 1, 2 or 3 cyano groups. "$C_1$-$C_6$cyanoalkylethynylene" is a group —C≡C—$C_1$-$C_6$cyanoalkyl.

The term "haloalkyl" refers to an alkyl substituted by one to seven halogen atoms. Haloalkyl includes monohaloalkyl or polyhaloalkyl. For example, the term "$C_1$-$C_6$haloalkyl" is meant to include trifluoromethyl, difluoromethyl, 2,2,2-trifluoroethyl, 4-chlorobutyl, 3-bromopropyl, and the like.

Further, the term "haloalkylene" refers to an alkylene substituted by one to seven halogen atoms.

The term "haloalkoxy" or "haloalkoxyl" refers to a —O-haloalkyl group, where haloalkyl is as defined herein. Haloalkoxyl includes monohaloalkyloxyl or polyhaloalkoxyl. For example, the term "$C_1$-$C_6$haloalkoxyl" is meant to include trifluoromethyloxy, difluoromethyloxy, and the like.

"Halogen" or "halo" refers to all halogens, that is, chloro (Cl), fluoro (F), bromo (Br), or iodo (I).

"Heteroatom" is meant to include oxygen (O), nitrogen (N), and sulfur (S).

"Heteroaryl" refers to a monocyclic or bicyclic aromatic ring radical containing 5-9 ring atoms (also referred to in this disclosure as a 5-9 membered heteroaryl, including monocyclic aromatic ring radicals containing 5 or 6 ring atoms (also referred to in this disclosure as a 5-6 membered heteroaryl), containing one or more, 14, 13, or 12, heteroatoms independently selected from the group consisting of O, S, and N. Any aromatic ring or ring system containing at least one heteroatom is a heteroaryl regardless of the point of attachment (i.e., through any one of the fused rings). Heteroaryl is also intended to include moieties having an oxidized S or N, such as sulfinyl, sulfonyl and Noxide of a tertiary ring nitrogen. A carbon or nitrogen atom is the point of attachment of the heteroaryl ring structure such that a stable compound is produced. Examples of heteroaryl groups include, but are not limited to, pyridyl, pyridazinyl, pyrazinyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, triazinyl, quinoxalinyl, cinnolinyl, phthalazinyl, benzotriazinyl, benzimidazolyl, benzopyrazolyl, benzotriazolyl, benzisoxazolyl, isobenzofuryl, isoindolyl, indolizinyl, thienopyridyl, thienopyrimidinyl, pyrazolopyrimidinyl, imidazopyridines, benzothiaxolyl, benzothienyl, quinolyl, isoquinolyl, indazolyl, pteridinyl and thiadiazolyl. "Nitrogen containing heteroaryl" refers to heteroaryl wherein at least one of the ring heteroatoms is N.

"Heterocycloalkyl" refers to a saturated or partially unsaturated nonaromatic cycloalkyl group that contains from one to five heteroatoms selected from N, O, S (including S(O) and S(O)$_2$), or P (including phosphine oxide) wherein the nitrogen, sulfur, and phosphorous atoms are optionally oxidized, and the nitrogen atom(s) are optionally quarternized, the remaining ring atoms being C, where one or two C atoms may optionally be present as a carbonyl. Further, the term heterocycloalkyl is intended to encompass any ring or ring system containing at least one heteroatom that is not a heteroaryl, regardless of the point of attachment to the remainder of the molecule. Heterocycloalkyl groups include those having a ring with a formally charge-separated aromatic resonance structure, for example, N-methylpyridonyl. The heterocycloalkyl may be substituted with one or two oxo groups, and can include sulfone and sulfoxide derivatives. The heterocycloalkyl may be a monocyclic, a fused bicyclic or a fused polycyclic ring system of 3 to 12, 4 to 10, 5 to 10, or 5 to 6 ring atoms in which one to five ring atoms are heteroatoms selected from —N=, —N—, —O—, —S—, —S(O)—, or —S(O)$_2$— and further wherein one or two ring atoms are optionally replaced by a —C(O)— group. As an example, a 4-6 membered heterocycloalkyl is a heterocycloalkyl with 4-6 ring members having at least one heteroatom. The heterocycloalkyl can also be a heterocyclic alkyl ring fused with a cycloalkyl. Non limiting examples of heterocycloalkyl groups include pyrrolidinyl, piperidinyl, morpholinyl, pyridonyl, and the like. A heterocycloalkyl group can be attached to the remainder of the molecule through a ring carbon or a heteroatom. "Heterocycloalkenyl" refers to a heterocycloalkyl having at least one unit of unsaturation. A substituent of a heterocycloalkyl or heterocycloalkenyl may be at the point of attachment of the heterocycloalkyl or heterocycloalkenyl group, forming a quaternary center.

"Hydroxyl" or "hydroxy" refers to the group OH. The term "hydroxyalkyl" or "hydroxyalkylene" refers to an alkyl group or alkylene group, respectively as defined herein, substituted with 1-5 hydroxy groups.

The term "oxo" refers to C(=O) or (O). In some embodiments, two possible points of attachment on a carbon form an oxo group.

"Optional substituents" or "optionally substituted" as used throughout the disclosure means that the substitution on a compound may or may not occur, and that the description includes instances where the substitution occurs and instances in which the substitution does not. For example, the phrase "optionally substituted with 1-3 $T^1$ groups" means that the $T^1$ group may but need not be present. It is assumed in this disclosure that optional substitution on a compound occurs in a way that would result in a stable compound.

"Spiro carbon atom" is a carbon atom which is common to two rings. A "carbocyclic spiro ring" comprises two cycloalkyl rings joined at one common spiro carbon atom as shown in this example:

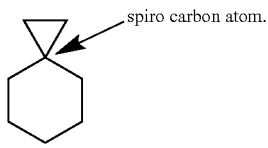

A "heterocyclic spiro ring" comprises a cycloalkyl or heterocycloalkyl ring joined at one common spiro carbon atom to a heterocyclic ring as shown in this example:

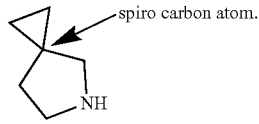

As used herein in connection with compounds of the disclosure, the term "synthesizing" and like terms means chemical synthesis from one or more precursor materials.

As used herein, the term "composition" refers to a formulation suitable for administration to an intended animal subject for therapeutic purposes that contains at least one pharmaceutically active compound and at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

"Pharmaceutically acceptable salt" refers to a salt which is acceptable for administration to a patient, such as a mammal (e.g., salts having acceptable mammalian safety for a given dosage regime). Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. Such salts can be derived from pharmaceutically acceptable inorganic or organic bases and from pharmaceutically-acceptable inorganic or organic acids, depending on the particular substituents found on the compounds described herein.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent.

When compounds of the present disclosure contain relatively acidic functionalities, base addition salts can be obtained by contacting the neutral form of such compounds with a sufficient amount of the desired base (i.e. a primary, secondary, tertiary, quaternary, or cyclic amine; an alkali metal hydroxide; alkaline earth metal hydroxide; or the like), either neat or in a suitable inert solvent. The desired acid can be, for example, a pyranosidyl acid (such as glucuronic acid or galacturonic acid), an alpha-hydroxy acid (such as citric acid or tartaric acid), an amino acid (such as aspartic acid or glutamic acid), an aromatic acid (such as benzoic acid or cinnamic acid), a sulfonic acid (such as p-toluenesulfonic acid or ethanesulfonic acid), or the like. In some embodiments, salts can be derived from pharmaceutically acceptable acids such as acetic, trifluoroacetic, propionic, ascorbic, benzenesulfonic, benzoic, camphorsulfonic, citric, ethanesulfonic, fumaric, glycolic, gluconic, glucoronic, glutamic, hippuric, hydrobromic, hydrochloric, isethionic, lactic, lactobionic, maleic, malic, malonic, mandelic, oxalic, methanesulfonic, mucic, naphthalenesulfonic, nicotinic, nitric, pamoic, pantothenic, phosphoric, succinic, sulfuric, sulfamic, hydroiodic, carbonic, tartaric, p-toluenesulfonic, pyruvic, aspartic, benzoic, cinnamic, anthranilic, mesylic, salicylic, p-hydroxybenzoic, phenylacetic, embonic (pamoic), ethanesulfonic, benzenesulfonic, 2-hydroxyethanesulfonic, sulfanilic, stearic, cyclohexylsulfamic, cyclohexylaminosulfonic, quinic, algenic, hydroxybutyric, galactaric and galacturonic acid and the like.

Also included are salts of amino acids such as arginate and the like, and salts of organic acids like glucuronic or galactunoric acids and the like (see, for example, Berge, S. M. et al., "Pharmaceutical Salts," J. Pharmaceutical Science, 1977, 66:1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

The pharmaceutically acceptable salt of the different compounds may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

The term "deuterated" as used herein alone or as part of a group, means substituted deuterium atoms. The term "deuterated analog" as used herein alone or as part of a group, means a compound containing substituted deuterium atoms in place of hydrogen atoms. The deuterated analog of the disclosure may be a fully or partially deuterium substituted derivative. In some embodiments, the deuterium substituted derivative of the disclosure holds a fully or partially deuterium substituted alkyl, aryl or heteroaryl group.

The disclosure also embraces isotopically-labeled compounds of the present disclosure which are identical to those recited herein, but for the fact that one or more atoms are replaced by an atom having an atomic mass or mass number different from the atomic mass or mass number usually found in nature. All isotopic variations of the compounds of the present disclosure, whether radioactive or not, are intended to be encompassed within the scope of the present disclosure. Examples of isotopes that can be incorporated into compounds of the disclosure include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Unless otherwise stated, when a position is designated specifically as "H" or "hydrogen," the position is understood to have hydrogen at its natural abundance isotopic composition or its isotopes, such as deuterium (D) or tritium ($^3$H). Certain isotopically-labeled compounds of the present disclosure (e.g., those labeled with $^3$H and $^{14}$C) are useful in compound and/or substrate tissue distribution assays. Tritiated (i.e., $^3$H) and carbon-14 (i.e., $^{14}$C) and fluorine-18 ($^{18}$F) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present disclosure can generally be prepared by following procedures analogous to those described in the Schemes and in the Examples herein below, by substituting an isotopically labeled reagent for a non-isotopically labeled reagent.

"Prodrugs" means any compound which releases an active parent drug according to Formula I in vivo when such prodrug is administered to a subject. Prodrugs of a compound of Formula I are prepared by modifying functional groups present in the compound of Formula I in such a way, either in routine manipulation or in vivo, that the modifications may be cleaved in vivo to release the parent compound. Prodrugs may proceed from prodrug form to active form in a single step or may have one or more intermediate forms which may themselves have activity or may be inactive. Some prodrugs are activated enzymatically to yield the active compound, or a compound which, upon further chemical reaction, yields the active compound. Prodrugs include compounds of Formula I wherein a hydroxy, amino, carboxyl or sulfhydryl group in a compound of Formula I is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), amides, guanidines, carbamates (e.g., N,N-dimethylaminocarbonyl) of hydroxy functional groups in compounds of Formula I, and the like. Other examples of prodrugs include, without limitation, carbonates, ureides, solvates, or hydrates of the active compound. Preparation, selection, and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

As described in The Practice of Medicinal Chemistry, Ch. 31-32 (Ed. Wermuth, Academic Press, San Diego, CA, 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the follow types:

(1) Oxidative reactions: Oxidative reactions are exemplified without limitation to reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

(2) Reductive reactions: Reductive reactions are exemplified without limitation to reactions such as reduction of carbonyl functionalities, reduction of alcohol functionalities and carbon-carbon double bonds, reduction of nitrogen-containing functional groups, and other reduction reactions.

(3) Reactions without change in the oxidation state: Reactions without change in the state of oxidation are exemplified without limitation to reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 2004/0077595, incorporated herein by reference.) Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g. stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols.

The term "carrier" is also meant to include microspheres, liposomes, micelles, nanoparticles (naturally-equipped nanocarriers, for example, exosomes), and the like. It is known that exosomes can be highly effective drug carriers, and there are various ways in which drugs can be loaded into exosomes, including those techniques described in J Control Release. 2015 Dec. 10; 219: 396-405, the contents of which are incorporated by reference in its entirety.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic process in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug.

Prodrugs and active metabolites may be identified using routine techniques known in the art. See, e.g., Bertolini et al., 1997, J. Med. Chem., 40:2011-2016; Shan et al., 1997, J Pharm Sci 86(7):756-757; Bagshawe, 1995, Drug Dev. Res., 34:220-230.

"Tautomer" means compounds produced by the phenomenon wherein a proton of one atom of a molecule shifts to another atom. See, Jerry March, Advanced Organic Chemistry: Reactions, Mechanisms and Structures, Fourth Edition, John Wiley & Sons, pages 69-74 (1992). The tautomers also refer to one of two or more structural isomers that exist in equilibrium and are readily converted from one isomeric form to another. Examples of include keto-enol tautomers, such as acetone/propen-2-ol, imine-enamine tautomers and the like, ring-chain tautomers, such as glucose/2,3,4,5,6-pentahydroxy-hexanal and the like, the tautomeric forms of heteroaryl groups containing a —N=C(H)—NH— ring atom arrangement, such as pyrazoles, imidazoles, benzimidazoles, triazoles, and tetrazoles. Where the compound contains, for example, a keto or oxime group or an aromatic moiety, tautomeric isomerism ('tautomerism') can occur. The compounds described herein may have one or more tautomers and therefore include various isomers. A person of ordinary skill in the art would recognize that other tautomeric ring atom arrangements are possible. All such isomeric forms of these compounds are expressly included in the present disclosure.

"Isomers" mean compounds having identical molecular Formulae but which differ in the nature or sequence of bonding of their atoms or in the arrangement of their atoms in space. Isomers that differ in the arrangement of their atoms in space are termed "stereoisomers." "Stereoisomer" and "stereoisomers" refer to compounds that exist in different stereoisomeric forms, for example, if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers." When a compound has an asymmetric center, for example, an atom such as carbon bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture." As another example, stereoisomers include geometric isomers, such as cis- or trans-orientation of substituents on adjacent carbons of a double bond. Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 6th edition J. March, John Wiley and Sons, New York, 2007) differ in the chirality of one or more stereocenters.

"Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

By "assaying" is meant the creation of experimental conditions and the gathering of data regarding a particular result of the exposure to specific experimental conditions. For example, enzymes can be assayed based on their ability to act upon a detectable substrate. A compound can be assayed based on its ability to bind to a particular target molecule or molecules.

As used herein, the terms "ligand" and "modulator" are used equivalently to refer to a compound that changes (i.e., increases or decreases) the activity of a target biomolecule, e.g., an enzyme such as those described herein. Generally a ligand or modulator will be a small molecule, where "small molecule refers to a compound with a molecular weight of 1500 Daltons or less, 1000 Daltons or less, 800 Daltons or less, or 600 Daltons or less. Thus, an "improved ligand" is one that possesses better pharmacological and/or pharmacokinetic properties than a reference compound, where "better" can be defined by one skilled in the relevant art for a particular biological system or therapeutic use.

The term "binds" in connection with the interaction between a target and a potential binding compound indicates that the potential binding compound associates with the target to a statistically significant degree as compared to association with proteins generally (i.e., non-specific binding). Thus, the term "binding compound" refers to a compound that has a statistically significant association with a target molecule. In some embodiments, a binding compound interacts with a specified target with a dissociation constant ($K_D$) of 10 mM or less, 1,000 µM or less, 100 µM or less, 10 µM or less, 1 µM or less, 1,000 nM or less, 100 nM or less, 10 nM or less, or 1 nM or less. In the context of compounds binding to a target, the terms "greater affinity" and "selective" indicates that the compound binds more tightly than a reference compound, or than the same compound in a reference condition, i.e., with a lower dissociation constant. In some embodiments, the greater affinity is at least 2, 3, 4, 5, 8, 10, 50, 100, 200, 400, 500, 1000, or 10,000-fold greater affinity.

The terms "modulate," "modulation," and the like refer to the ability of a compound to increase or decrease the function and/or expression of a target, such as CD73, where such function may include transcription regulatory activity and/or binding. Modulation may occur in vitro or in vivo. Modulation, as described herein, includes the inhibition, antagonism, partial antagonism, activation, agonism or partial agonism of a function or characteristic associated with CD73, either directly or indirectly, and/or the upregulation or downregulation of the expression CD73, either directly or indirectly. In another embodiment, the modulation is direct. Inhibitors or antagonists are compounds that, e.g., bind to, partially or totally block stimulation, decrease, prevent, inhibit, delay activation, inactivate, desensitize, or downregulate signal transduction. Activators or agonists are compounds that, e.g., bind to, stimulate, increase, open, activate, facilitate, enhance activation, activate, sensitize or upregulate signal transduction.

As used herein, the terms "treat," "treating," "therapy," "therapies," and like terms refer to the administration of material, e.g., any one or more compound(s) as described herein in an amount effective to prevent, alleviate, or ameliorate one or more symptoms of a disease or condition, i.e., indication, and/or to prolong the survival of the subject being treated.

The terms "prevent," "preventing," "prevention" and grammatical variations thereof as used herein, refers to a method of partially or completely delaying or precluding the onset or recurrence of a disease, disorder or condition and/or one or more of its attendant symptoms or barring a subject from acquiring or reacquiring a disorder or condition or reducing a subject's risk of acquiring or requiring a disorder or condition or one or more of its attendant symptoms.

As used herein, the term "subject," "animal subject," and the like refers to a living organism including, but not limited to, human and non-human vertebrates, e.g. any mammal, such as a human, other primates, sports animals and animals of commercial interest such as cattle, horses, ovines, or porcines, rodents, or pets such as dogs and cats.

"Unit dosage form" refers to a composition intended for a single administration to treat a subject suffering from a disease or medical condition. Each unit dosage form typically comprises a compound of this disclosure plus one or more pharmaceutically acceptable excipients. Examples of unit dosage forms are individual tablets, individual capsules, bulk powders, liquid solutions, ointments, creams, eye drops, suppositories, emulsions or suspensions. Treatment of the disease or condition may require periodic administration of unit dosage forms, for example: one unit dosage form two or more times a day, one with each meal, one every four hours or other interval, or only one per day. The expression "oral unit dosage form" indicates a unit dosage form designed to be taken orally.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

In the present context, the term "therapeutically effective" or "effective amount" indicates that a compound or material or amount of the compound or material when administered is sufficient or effective to prevent, alleviate, or ameliorate one or more symptoms of a disease, disorder or medical condition being treated, and/or to prolong the survival of the subject being treated. The therapeutically effective amount will vary depending on the compound, the disease, disorder or condition and its severity and the age, weight, etc., of the mammal to be treated. In general, satisfactory results in subjects are indicated to be obtained at a daily dosage of from about 0.1 to about 10 g/kg subject body weight. In some embodiments, a daily dose ranges from about 0.10 to 10.0 mg/kg of body weight, from about 1.0 to 3.0 mg/kg of body weight, from about 3 to 10 mg/kg of body weight, from about 3 to 150 mg/kg of body weight, from about 3 to 100 mg/kg of body weight, from about 10 to 100 mg/kg of body weight, from about 10 to 150 mg/kg of body weight, or from about 150 to 1000 mg/kg of body weight. The dosage can be conveniently administered, e.g., in divided doses up to four times a day or in sustained-release form.

The ability of a compound to inhibit the function of CD73 can be demonstrated in a biochemical assay, e.g., binding assay, or a cellbased assay.

As used herein, the term "CD73 mediated disease or condition" refers to a disease or condition in which the biological function of CD73 affect the development and/or course of the disease or condition, and/or in which modulation of CD73 alters the development, course, and/or symptoms. A CD73 mediated disease or condition includes a disease or condition for which CD73 inhibition provides a therapeutic benefit, e.g. wherein treatment with CD73 inhibitors, including compounds described herein, provides a therapeutic benefit to the subject suffering from or at risk of the disease or condition. A CD73 mediated disease or condition is intended to include a cancer that harbors loss of function mutations in CD73, or a cancer where there is activation of CD73. A CD73 mediated disease or condition is also intended to include various human carcinomas, including those of colon, lung, pancreas, and ovary, as well as diseases or conditions associated with tumor neovascularization, and invasiveness.

Also in the context of compounds binding to a biomolecular target, the term "greater specificity" indicates that a compound binds to a specified target to a greater extent than to another biomolecule or biomolecules that may be present under relevant binding conditions, where binding to such other biomolecules produces a different biological activity than binding to the specified target. Typically, the specificity is with reference to a limited set of other biomolecules, e.g., in the case of CD73. In particular embodiments, the greater specificity is at least 2, 3, 4, 5, 8, 10, 50, 100, 200, 400, 500, or 1000-fold greater specificity.

As used herein in connection with binding compounds or ligands, the term "specific for CD73," and terms of like import mean that a particular compound binds to CD73 to a statistically greater extent than to other targets that may be present in a particular sample. Also, where biological activity other than binding is indicated, the term "specific for CD73" indicates that a particular compound has greater biological effect associated with binding CD73 than to other enzymes, e.g., enzyme activity inhibition.

The term "first line cancer therapy" refers to therapy administered to a subject as an initial regimen to reduce the number of cancer cells. First line therapy is also referred to as induction therapy, primary therapy and primary treatment. First-line therapy can be an administered combination with one or more agents. A summary of currently accepted approaches to first line treatment for certain disease can be found in the NCI guidelines for such diseases.

The term "second line cancer therapy" refers to a cancer treatment that is administered to a subject who does not respond to first line therapy, that is, often first line therapy is administered or who has a recurrence of cancer after being in remission. In certain embodiments, second line therapy that may be administered includes a repeat of the initial successful cancer therapy, which may be any of the treatments described under "first line cancer therapy." A summary of the currently accepted approaches to second line treatment for certain diseases is described in the NCI guidelines for such diseases.

The term "refractory" refers to wherein a subject fails to respond or is otherwise resistant to cancer therapy or treatment. The cancer therapy may be first-line, second-line or any subsequently administered treatment. In certain embodiments, refractory refers to a condition where a subject fails to achieve complete remission after two induction attempts. A subject may be refractory due to a cancer cell's intrinsic resistance to a particular therapy, or the subject may be refractory due to an acquired resistance that develops during the course of a particular therapy.

In addition, abbreviations as used herein have respective meanings as follows:

| | |
|---|---|
| ° C. | Degree Celsius |
| Ac | Acetyl |
| BOC | tert-Butoxycarbonyl |
| DBU | 1,8-Diazabicyclo[5.4.0]undec-7-ene |
| DCM | Dichloromethane |
| DEAE | Diethylaminoethyl |
| DMAP | Dimethylaminopyridine |
| DMEM | Dulbecco's Modified Eagle's Medium |
| DME | Dimethoxyethane |
| DMF | Dimethylformamide |
| DMSO | Dimethylsulfoxide |
| ESI | Electrospray ionization |
| FBS | Fetal bovine serum |
| HPLC | High Performance Liquid Chromatography |
| LCMS | Liquid Chromatography Mass Spectrometry |
| [M + H+]+ or (MH)+ | Mass peak plus hydrogen |
| [M − H−]− or (MH)− | Mass peak minus hydrogen |
| mCPBA | Meta-chloroperoxybenzoic acid |
| Me | Methyl |
| MeOH | Methanol |
| MS | Mass spectrometry |
| PBS | Phosphate buffered saline |
| PTSA | Para-toluenesulfonic acid |
| RT | Room temperature |
| S-Phos | 2-Dicyclohexylphosphino-2',6'-dimethoxybiphenyl |
| TBAF | Tetrabutylammonium fluoride |
| TLC | Thin-layer chromatography |
| THF | Tetrahydrofuran |
| n-Bu | n-Butyl |
| N | Normal |
| IC$_{50}$ | Half maximal (50%) inhibitory concentration |
| RP | Reverse phase |
| X-Phos | 2-Dicyclohexylphosphino-2',4',6'-triisopropylbiphenyl |

II. Compounds

Compounds contemplated herein are described with reference to both generic formulae and specific compounds. In addition, the compounds described herein may exist in a number of different forms or derivatives, all within the scope of the present disclosure. These include, for example, tautomers, stereoisomers, racemic mixtures, regioisomers, salts, prodrugs (e.g. carboxylic acid esters), solvated forms, and active metabolites.

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present disclosure may exist as stereoisomers as defined herein. All such single stereoisomers, racemates and mixtures thereof are intended to be within the scope of the present disclosure. Unless specified to the contrary, all such stereoisomeric forms are included within the formulae provided herein.

In some embodiments, a chiral compound of the present disclosure is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form.

For compounds in which synthesis involves addition of a single group at a double bond, particularly a carbon-carbon double bond, the addition may occur at either of the double bond-linked atoms. For such compounds, the present disclosure includes both such regioisomers.

In addition to the present formulae and compounds described herein, the disclosure also includes prodrugs (generally pharmaceutically acceptable prodrugs), active metabolic derivatives (active metabolites), and their pharmaceutically acceptable salts.

Unless specified to the contrary, specification of a compound herein includes a pharmaceutically acceptable salt, a solvate, a tautomer, a stereoisomer, or a deuterated analog of such compound.

In some embodiments, compounds of the disclosure are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In some instances, the amorphous form of the complex is facilitated by additional processing, such as by spray-drying, mechanochemical methods such as roller compaction, or microwave irradiation of the parent compound mixed with the acid or base. Such methods may also include addition of ionic and/or non-ionic polymer systems, including, but not limited to, hydroxypropyl methyl cellulose acetate succinate (HPMCAS) and methacrylic acid copolymer (e.g. Eudragit® L100-55), that further stabilize the amorphous nature of the complex. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

Compound Embodiments

Embodiment 1 of this disclosure relates to a compound having Formula I:

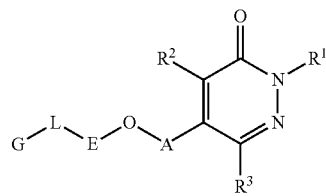

or a pharmaceutically acceptable salt, a solvate, a tautomer, a stereoisomer, or a deuterated analog thereof, wherein:

A is a 5-6 membered aromatic ring or a 4-7 membered nitrogen containing heterocycloalkyl, wherein A is substituted with 0-3 $R^4$, provided that when ring A is a 4-7 membered nitrogen containing heterocycloalkyl, then the pyridazinone moiety of Formula I is attached to a nitrogen atom of A;

E is phenyl or a 5 or 6 membered heteroaryl, wherein E is substituted with 0-3 Q and 0-1 $R^{11}$, provided that when E is a 5 or 6 membered heteroaryl, 0 is not attached to a heteroatom of E;

L is absent, —C(O)N(H)—, $C_0$-$C_3$alkylene, —N(H)—, or —O—; G is one of the following groups:

(a) cycloalkyl substituted with 0-4 $T^1$ and 0-1 $T^2$;
(b) cycloalkenyl substituted with 0-4 $T^1$ and 0-1 $T^2$;
(c) a bridged carbocylic ring substituted with 0-4 $T^1$ and 0-1 $T^2$;
(d) a carbocyclic spiro ring containing two cycloalkyl groups joined by one common spiro carbon atom, wherein the carbocyclic spiro ring is substituted with 0-4 $T^1$ and 0-1 $T^2$;
(e) a heterocyclic spiro ring containing two cyclic groups with at least one heteroatom, wherein the two cyclic groups are joined by one common spiro carbon atom, wherein the heterocyclic spiro ring is substituted with 0-3 $T^5$, 0-1 $T^6$;

(f) phenyl substituted with 0-4 $T^1$ and 0-1 $T^4$;
(g) heterocycloalkyl substituted with 0-4 $T^5$ and 0-1 $T^6$;
(h) heterocycloalkenyl substituted with 0-4 $T^5$ and 0-1 $T^6$
(i) a bridged heterocylic ring substituted with 0-4 $T^5$ and 0-1 $T^6$; or
(j) heteroaryl substituted with 0-3 $T^5$ and 0-1 $T^3$;

each Q is independently halogen, CN, or alkyl optionally substituted with 1-3 halogens;

each $T^1$ is independently halogen, hydroxyl, alkyl optionally substituted with 1-3 $R^b$, alkenyl optionally substituted with 1-3 $R^b$, alkynyl optionally substituted with 1-3 $R^b$, CN, cyanoalkyl, alkoxyl optionally substituted with 1-3 $R^b$, or alkoxyalkyl optionally substituted with 1-3 $R^b$;

$T^2$ is —$(CH_2)_{0-3}$—$N(R^9)SO_2$—$R^7$, —$(CH_2)_{0-3}$—$SO_2$—$R^7$, —$(CH_2)_{0-3}$—$SO_2N(R^8)R^9$, —$(CH_2)_{0-3}$—$N(R^9)SO_2N(R^8)R^9$, —$(CH_2)_{0-3}$—$N(R^9)C(O)N(R^8)R^9$, —$(CH_2)_{0-3}$—$N(R^9)C(O)R^8$, —$(CH_2)_{0-3}$—$N(R^9)C(O)OR^9$, —$(CH_2)_{0-3}$—$N(R^8)R^9$, —$(CH_2)_{0-3}$—$C(O)N(R^8)R^9$, —$(CH_2)_{0-3}$—$C(O)OR^9$, —$(CH_2)_{0-3}$—$C(O)R^{10}$, —$(CH_2)_{0-3}$—$C(O)H$, —$(CH_2)_{0-3}$—$N(R^9)C(O)R^{10}$, —$(CH_2)_{0-3}$cycloalkyl optionally substituted with 1-4 $Z^3$, —$(CH_2)_{0-3}$-phenyl optionally substituted with 1-3 $Z^5$, or —$(CH_2)_{0-3}$heteroaryl optionally substituted with 1-3 $Z^5$;

$T^3$ is —$(CH_2)_{0-3}$—$C(O)N(R^8)R^9$, —$(CH_2)_{0-3}$—$N(R^8)R^9$, —$(CH_2)_{0-3}$—$C(O)OR^9$, —$(CH_2)_{0-3}$-cycloalkyl, —$(CH_2)_{0-3}$-cycloalkenyl, —$(CH_2)_{0-3}$-heterocycloalkyl, —$(CH_2)_{0-3}$-heterocycloalkenyl, —O— heterocycloalkyl optionally substituted with 4-chloropyridazin-3-one-5-yl, or —$(CH_2)_{0-3}$-bridged carbocyclic ring, wherein the —$(CH_2)_{0-3}$-cycloalkyl, —$(CH_2)_{0-3}$-cycloalkenyl, —$(CH_2)_{0-3}$-heterocycloalkyl, —$(CH_2)_{0-3}$-heterocycloalkenyl, or —$(CH_2)_{0-3}$-bridged carbocyclic are each optionally substituted with 1-3 $Z^5$ and 0-1 $Z^1$, provided that when $T^3$ is attached to a heteroatom of G, G cannot be attached to an oxygen or nitrogen atom of $T^3$;

$T^4$ is —$(CH_2)_{0-3}C(O)OR^9$, —$(CH_2)_{0-3}$—$N(R^9)C(O)R^8$, —$(CH_2)_{0-3}$—$N(R^9)SO_2$—$R^7$, —$(CH_2)_{0-3}$—$SO_2$—$R^7$, —$(CH_2)_{0-3}$—$SO_2N(R^8)R^9$, —$(CH_2)_{0-3}$—$N(R^9)C(O)N(R^8)R^9$, or $N(R^a)_2$;

each $T^5$ is independently halogen, hydroxyl, alkyl optionally substituted with 1-3 $R^b$, alkenyl optionally substituted with 1-3 $R^b$, alkynyl optionally substituted with 1-3 $R^b$, CN, cyanoalkyl, alkoxyl optionally substituted with 1-3 $R^b$, or alkoxyalkyl optionally substituted with 1-3 $R^b$, provided that when $T^5$ is attached to a heteroatom of G, $T^5$ cannot be halogen, hydroxyl, CN, or alkoxyl optionally substituted with 1-3 $R^b$;

$T^6$ is —$(CH_2)_{0-3}$—$N(R^9)SO_2$—$R^7$, —$(CH_2)_{0-3}$—$SO_2$—$R^7$, —$(CH_2)_{0-3}$—$SO_2N(R^8)R^9$, —$(CH_2)_{0-3}$—$N(R^9)SO_2N(R^8)R^9$, —$(CH_2)_{0-3}$—$N(R^9)C(O)N(R^8)R^9$, —$(CH_2)_{0-3}$—$N(R^9)C(O)R^8$, —$(CH_2)_{0-3}$—$N(R^9)C(O)OR^9$, —$(CH_2)_{0-3}$—$N(R^8)R^9$, —$(CH_2)_{0-3}$—$C(O)$—$N(R^8)R^9$, —$(CH_2)_{0-3}$—$C(O)OR^9$, —$(CH_2)_{0-3}$—$C(O)R^{10}$, —$(CH_2)_{0-3}$—$N(R^9)C(O)R^{10}$, —N(H)C(H)C=O, —$(CH_2)_{0-3}$cycloalkyl optionally substituted with 1-4 $Z^3$, —$(CH_2)_{0-2}$heterocycloalkyl optionally substituted with 1-4 $Z^3$, —$(CH_2)_{0-3}$heteroaryl optionally substituted with 1-3 $Z^5$, or 4-chloropyridazin-3-one-5-yl, provided that when $T^6$ is attached to a heteroatom of G, G cannot be attached to a nitrogen or oxygen atom of $T^6$.

$R^a$ is H or alkyl;

$R^b$ is halogen, CN, $CF_3$, or hydroxyl, provided that not more than 1 $R^b$ can be $CF_3$;

$R^1$ is H, alkoxyalkyl, alkenyl substituted with 0-4 $Z^2$, or $C_2$-$C_6$alkyl substituted with 0-4 $Z^2$.

$R^2$ is H, halogen, alkyl, alkenyl, alkoxyl, haloalkyl, $CF_3$, or CN;

$R^3$ is H, halogen, alkyl, CN, or haloalkyl;

each $R^4$ is independently halogen, CN, or alkyl optionally substituted with 1-3 halogens;

$R^7$ is alkyl optionally substituted with 1-4 $Z^4$, —$C_0$-$C_3$alkyl-cycloalkyl optionally substituted with 1-4 $Z^3$, —$C_0$-$C_3$alkyl-phenyl optionally substituted with 1-4 $Z^3$, —$C_0$-$C_3$alkyl-heteroaryl optionally substituted with 1-3 $Z^5$, or —$C_0$-$C_3$alkyl-heterocycloalkyl optionally substituted with 1-3 $Z^5$;

$R^8$ is H, alkyl optionally substituted with 1-4 $Z^4$, alkenyl optionally substituted with 1-4 $Z^4$, —$C_0$-$C_3$alkyl-cycloalkyl optionally substituted with 1-4 $Z^3$, —$C_0$-$C_3$alkyl-phenyl optionally substituted with 1-4 $Z^3$, —$C_0$-$C_3$alkyl-heteroaryl optionally substituted with 1-3 $Z^5$, —$C_0$-$C_3$alkyl-heterocycloalkyl optionally substituted with 1-3 $Z^5$, or a bridged carbocylic ring substituted with 0-5 $T^1$;

each $R^9$ is independently H or alkyl optionally substituted with 1-4 $Z^4$;

$R^{10}$ is alkyl substituted with 0-4 $Z^4$, —$C_0$-$C_3$alkyl-cycloalkyl optionally substituted with 1-4 $Z^3$, —$C_0$-$C_3$alkyl-phenyl optionally substituted with 1-4 $Z^3$, —$C_0$-$C_3$alkyl-heteroaryl optionally substituted with 1-3 $Z^5$, or —$C_0$-$C_3$alkyl-heterocycloalkyl optionally substituted with 1-3 $Z^5$;

$R^{11}$ is $NH_2$;

$Z^1$ is cyanoalkyl, —$(CH_2)_{0-2}$—C(O)O$R^9$, —$(CH_2)_{0-2}$—C(O)—N($R^8$)$R^9$, provided that when $Z^1$ is attached to a heteroatom, then $Z^1$ is not C(O)O$R^9$;

each $Z^2$ is independently hydroxyl, halogen, $NH_2$, or CN, provided that not more than 1 $Z^2$ can be $NH_2$;

each $Z^3$ is independently alkyl, halogen, haloalkyl, hydroxyl, hydroxyalkyl, alkoxyl, alkoxyalkyl, or CN;

each $Z^4$ is independently hydroxyl, halogen, alkoxyl, or CN; and each $Z^5$ is independently alkyl, haloalkyl, hydroxyl, hydroxyalkyl, halogen, alkoxyl, alkoxyalkyl, CN, or cyanoalkyl, provided that when $Z^5$ is attached to a heteroatom, then $Z^5$ is not halogen, hydroxyl, alkoxyl, or CN.

Subembodiments of Embodiment 1

Embodiment 1(a) relates to Embodiment 1 wherein A is a 5-6 membered aromatic ring wherein A is substituted with 0-3 $R^4$.

Embodiment 1(b) relates to Embodiment 1 wherein A is a 4-7 membered nitrogen containing heterocycloalkyl, provided that the pyridazinone moiety of Formula I is attached to a nitrogen atom of A.

Embodiment 1(c) relates to any one of Embodiments 1, 1(a) or 1(b), wherein E is phenyl substituted with 0-3 Q and 0-1 $R^{11}$.

Embodiment 1(d) relates to any one of Embodiments 1, 1(a) or 1(b), wherein E is or a 5 or 6 membered heteroaryl, wherein E is substituted with 0-3 Q and 0-1 $R^{11}$, provided that O is not attached to a heteroatom of E.

Embodiment 1(e) relates to any one of Embodiments 1, 1(a), 1(b), 1(c) or 1(d), wherein L is absent, Embodiment 1(f) relates to any one of Embodiments 1, 1(a), 1(b), 1(c) or 1(d), wherein L is —C(O)N(H)—.

Embodiment 1(g) relates to any one of Embodiments 1, 1(a), 1(b), 1(c) or 1(d), wherein L is $C_0$-$C_3$alkylene.

Embodiment 1(h) relates to any one of Embodiments 1, 1(a), 1(b), 1(c) or 1(d), wherein L is —N(H)—.

Embodiment 1(i) relates to any one of Embodiments 1, 1(a), 1(b), 1(c) or 1(d), wherein L is —O—.

Embodiment 1(j) relates to any one of Embodiments 1, 1(a), 1(b), 1(c), 1(d), 1(e), 1(f), 1(g), 1(h) or 1(i), wherein G is cycloalkyl substituted with 0-4 $T^1$ and 0-1 $T^2$.

Embodiment 1(k) relates to any one of Embodiments 1, 1(a), 1(b), 1(c), 1(d), 1(e), 1(f), 1(g), 1(h) or 1(i), wherein G is cycloalkenyl substituted with 0-4 $T^1$ and 0-1 $T^2$.

Embodiment 1(l) relates to any one of Embodiments 1, 1(a), 1(b), 1(c), 1(d), 1(e), 1(f), 1(g), 1(h) or 1(i), wherein G is a bridged carbocylic ring substituted with 0-4 $T^1$ and 0-1 $T^2$.

Embodiment 1(m) relates to any one of Embodiments 1, 1(a), 1(b), 1(c), 1(d), 1(e), 1(f), 1(g), 1(h) or 1(i), wherein G is a carbocyclic spiro ring containing two cycloalkyl groups joined by one common spiro carbon atom, wherein the carbocyclic spiro ring is substituted with 0-4 $T^1$ and 0-1 $T^2$.

Embodiment 1(n) relates to any one of Embodiments 1, 1(a), 1(b), 1(c), 1(d), 1(e), 1(f), 1(g), 1(h) or 1(i), wherein G is a heterocyclic spiro ring containing two cyclic groups with at least one heteroatom, wherein the two cyclic groups are joined by one common spiro carbon atom, wherein the heterocyclic spiro ring is substituted with 0-3 $T^5$, 0-1 $T^6$.

Embodiment 1(o) relates to any one of Embodiments 1, 1(a), 1(b), 1(c), 1(d), 1(e), 1(f), 1(g), 1(h) or 1(i), wherein G is phenyl substituted with 0-4 $T^1$ and 0-1 $T^4$.

Embodiment 1(p) relates to any one of Embodiments 1, 1(a), 1(b), 1(c), 1(d), 1(e), 1(f), 1(g), 1(h) or 1(i), wherein G is heterocycloalkyl substituted with 0-4 $T^5$ and 0-1 $T^6$.

Embodiment 1(q) relates to any one of Embodiments 1, 1(a), 1(b), 1(c), 1(d), 1(e), 1(f), 1(g), 1(h) or 1(i), wherein G is heterocycloalkenyl substituted with 0-4 $T^5$ and 0-1 $T^6$.

Embodiment 1(r) relates to any one of Embodiments 1, 1(a), 1(b), 1(c), 1(d), 1(e), 1(f), 1(g), 1(h) or 1(i), wherein G is a bridged heterocylic ring substituted with 0-4 $T^5$ and 0-1 $T^6$.

Embodiment 1(s) relates to any one of Embodiments 1, 1(a), 1(b), 1(c), 1(d), 1(e), 1(f), 1(g), 1(h) or 1(i), wherein G is heteroaryl substituted with 0-3 $T^5$ and 0-1 $T^3$.

Embodiment 1(t) relates to any one of Embodiments 1, 1(a), 1(b), 1(c), 1(d), 1(e), 1(f), 1(g), 1(h), 1(i), 1(j), 1(k), 1(l) or 1(m), wherein $T^2$ is —$(CH_2)_{0-3}$—N($R^9$)$SO_2$—$R^7$.

Embodiment 1(u) relates to any one of Embodiments 1, 1(a), 1(b), 1(c), 1(d), 1(e), 1(f), 1(g), 1(h), 1(i), 1(j), 1(k), 1(l) or 1(m), wherein $T^2$ is —$(CH_2)_{0-3}$—$SO_2$—$R^7$.

Embodiment 1(v) relates to any one of Embodiments 1, 1(a), 1(b), 1(c), 1(d), 1(e), 1(f), 1(g), 1(h), 1(i), 1(j), 1(k), 1(l) or 1(m), wherein $T^2$ is —$(CH_2)_{0-3}$—N($R^9$)$SO_2$N($R^8$)$R^9$.

Embodiment 1(w) relates to any one of Embodiments 1, 1(a), 1(b), 1(c), 1(d), 1(e), 1(f), 1(g), 1(h), 1(i), 1(j), 1(k), 1(l) or 1(m), wherein $T^2$ is —$(CH_2)_{0-3}$—N($R^9$)C(O)N($R^8$)$R^9$.

Embodiment 1(x) relates to any one of Embodiments 1, 1(a), 1(b), 1(c), 1(d), 1(e), 1(f), 1(g), 1(h), 1(i), 1(j), 1(k), 1(l) or 1(m), wherein $T^2$ is —$(CH_2)_{0-3}$—N($R^9$)C(O)$R^8$.

Embodiment 1(y) relates to any one of Embodiments 1, 1(a), 1(b), 1(c), 1(d), 1(e), 1(f), 1(g), 1(h), 1(i), 1(j), 1(k), 1(l) or 1(m), wherein $T^2$ is —$(CH_2)_{0-3}$—N($R^9$)C(O)O$R^9$.

Embodiment 1(z) relates to any one of Embodiments 1, 1(a), 1(b), 1(c), 1(d), 1(e), 1(f), 1(g), 1(h), 1(i), 1(j), 1(k), 1(l) or 1(m), wherein $T^2$ is —$(CH_2)_{0-3}$—N($R^8$)$R^9$.

Embodiment 1(aa) relates to any one of Embodiments 1, 1(a), 1(b), 1(c), 1(d), 1(e), 1(f), 1(g), 1(h), 1(i), 1(j), 1(k), 1(l) or 1(m), wherein $T^2$ is —$(CH_2)_{0-3}$—C(O)N($R^8$)$R^9$.

Embodiment 1(ab) relates to any one of Embodiments 1, 1(a), 1(b), 1(c), 1(d), 1(e), 1(f), 1(g), 1(h), 1(i), 1(j), 1(k), 1(l) or 1(m), wherein $T^2$ is —$(CH_2)_{0-3}$—C(O)O$R^9$.

Embodiment 1(ac) relates to any one of Embodiments 1, 1(a), 1(b), 1(c), 1(d), 1(e), 1(f), 1(g), 1(h), 1(i), 1(j), 1(k), 1(l) or 1(m), wherein $T^2$ is —$(CH_2)_{0-3}$—C(O)$R^{11}$.

Embodiment 1(ad) relates to any one of Embodiments 1, 1(a), 1(b), 1(c), 1(d), 1(e), 1(f), 1(g), 1(h), 1(i), 1(j), 1(k), 1(l) or 1(m), wherein $T^2$ is —$(CH_2)_{0-3}$—C(O)H.

Embodiment 1(ae) relates to any one of Embodiments 1, 1(a), 1(b), 1(c), 1(d), 1(e), 1(f), 1(g), 1(h), 1(i), 1(j), 1(k), 1(l) or 1(m), wherein $T^2$ is —$(CH_2)_{0-3}$—$N(R^9)C(O)R^{10}$.

Embodiment 1(af) relates to any one of Embodiments 1, 1(a), 1(b), 1(c), 1(d), 1(e), 1(f), 1(g), 1(h), 1(i), 1(j), 1(k), 1(l) or 1(m), wherein $T^2$ is —$(CH_2)_{0-3}$cycloalkyl optionally substituted with 1-4 $Z^3$.

Embodiment 1(ag) relates to any one of Embodiments 1, 1(a), 1(b), 1(c), 1(d), 1(e), 1(f), 1(g), 1(h), 1(i), 1(j), 1(k), 1(l) or 1(m), wherein $T^2$ is —$(CH_2)_{0-3}$-phenyl optionally substituted with 1-3 $Z^5$.

Embodiment 1(ah) relates to any one of Embodiments 1, 1(a), 1(b), 1(c), 1(d), 1(e), 1(f), 1(g), 1(h), 1(i), 1(j), 1(k), 1(l) or 1(m), wherein $T^2$ is —$(CH_2)_{0-3}$-phenyl optionally substituted with 1-3 $Z^5$.

Embodiment 1(ai) relates to any one of Embodiments 1, 1(a), 1(b), 1(c), 1(d), 1(e), 1(f), 1(g), 1(h), 1(i), 1(j), 1(k), 1(l) or 1(m), wherein $T^2$ is —$(CH_2)_{0-3}$heteroaryl optionally substituted with 1-3 $Z^5$.

Embodiment 1(aj) relates to any one of Embodiments 1, 1(a), 1(b), 1(c), 1(d), 1(e), 1(f), 1(g), 1(h), 1(i), or 1(s), wherein $T^3$ is —$(CH_2)_{0-3}$—$C(O)N(R^8)R^9$.

Embodiment 1(ak) relates to any one of Embodiments 1, 1(a), 1(b), 1(c), 1(d), 1(e), 1(f), 1(g), 1(h), 1(i), or 1(s), wherein $T^3$ is —$(CH_2)_{0-3}$—$N(R^8)R^9$, provided that when $T^3$ is attached to a heteroatom of G, $T^3$ cannot be —$N(R^8)R^9$.

Embodiment 1(al) relates to any one of Embodiments 1, 1(a), 1(b), 1(c), 1(d), 1(e), 1(f), 1(g), 1(h), 1(i), or 1(s), wherein $T^3$ is —$(CH_2)_{0-3}$—$C(O)OR^9$.

Embodiment 1(am) relates to any one of Embodiments 1, 1(a), 1(b), 1(c), 1(d), 1(e), 1(f), 1(g), 1(h), 1(i), or 1(s), wherein $T^3$ is —$(CH_2)_{0-3}$-cycloalkyl optionally substituted with 1-3 $Z^5$ and 0-1 $Z^1$.

Embodiment 1(an) relates to any one of Embodiments 1, 1(a), 1(b), 1(c), 1(d), 1(e), 1(f), 1(g), 1(h), 1(i), or 1(s), wherein $T^3$ is —$(CH_2)_{0-3}$-heterocycloalkyl optionally substituted with 1-3 $Z^5$ and 0-1 $Z^1$, provided that when $T^3$ is attached to a heteroatom of G, G cannot be attached to a nitrogen or oxygen atom of $T^3$.

Embodiment 1(ao) relates to any one of Embodiments 1, 1(a), 1(b), 1(c), 1(d), 1(e), 1(f), 1(g), 1(h), 1(i), or 1(s), wherein $T^3$ is —O-heterocycloalkyl optionally substituted with 4-chloropyridazin-3-one-5-yl, provided that —O-heterocycloalkyl is not attached to a heteroatom of G.

Embodiment 1(ap) relates to any one of Embodiments 1, 1(a), 1(b), 1(c), 1(d), 1(e), 1(f), 1(g), 1(h), 1(i), or 1(s), wherein $T^3$ is —$(CH_2)_{0-3}$-bridged carbocyclic ring optionally substituted with 1-3 $Z^5$ and 0-1 $Z^1$.

Embodiment 1(aq) relates to any one of Embodiments 1, 1(a), 1(b), 1(c), 1(d), 1(e), 1(f), 1(g), 1(h) or 1(i), wherein $T^4$ is —$(CH_2)_{0-3}C(O)OR^9$.

Embodiment 1(ar) relates to any one of Embodiments 1, 1(a), 1(b), 1(c), 1(d), 1(e), 1(f), 1(g), 1(h), 1(i) or 1(o), wherein $T^4$ is —$(CH_2)_{0-3}$—$N(R^9)SO_2$—$R^7$.

Embodiment 1(as) relates to any one of Embodiments 1, 1(a), 1(b), 1(c), 1(d), 1(e), 1(f), 1(g), 1(h), 1(i) or 1(o), wherein $T^4$ is —$(CH_2)_{0-3}$—$SO_2$—$R^7$.

Embodiment 1(at) relates to any one of Embodiments 1, 1(a), 1(b), 1(c), 1(d), 1(e), 1(f), 1(g), 1(h), 1(i) or 1(o), wherein $T^4$ is —$(CH_2)_{0-3}$—$SO_2N(R^8)R^9$.

Embodiment 1(au) relates to any one of Embodiments 1, 1(a), 1(b), 1(c), 1(d), 1(e), 1(f), 1(g), 1(h), 1(i) or 1(o), wherein $T^4$ is —$(CH_2)_{0-3}$—$N(R^9)C(O)N(R^8)R^9$.

Embodiment 1(av) relates to any one of Embodiments 1, 1(a), 1(b), 1(c), 1(d), 1(e), 1(f), 1(g), 1(h), 1(i) or 1(o), wherein $T^4$ is $N(R^a)_2$.

Embodiment 1(aw) relates to any one of Embodiments 1, 1(a), 1(b), 1(c), 1(d), 1(e), 1(f), 1(g), 1(h), 1(i), 1(n), 1(p), 1(q) or 1(r), wherein $T^6$ is —$(CH_2)_{0-3}$—$N(R^9)SO_2$—$R^7$, provided that when $T^6$ is attached to a heteroatom of G, then $T^6$ cannot be —$N(R^9)SO_2$—$R^7$.

Embodiment 1(ax) relates to any one of Embodiments 1, 1(a), 1(b), 1(c), 1(d), 1(e), 1(f), 1(g), 1(h), 1(i), 1(n), 1(p), 1(q) or 1(r), wherein $T^6$ is —$(CH_2)_{0-3}$—$SO_2$—$R^7$.

Embodiment 1(ay) relates to any one of Embodiments 1, 1(a), 1(b), 1(c), 1(d), 1(e), 1(f), 1(g), 1(h), 1(i), 1(n), 1(p), 1(q) or 1(r), wherein $T^6$ is —$(CH_2)_{0-3}$—$SO_2N(R^8)R^9$.

Embodiment 1(az) relates to any one of Embodiments 1, 1(a), 1(b), 1(c), 1(d), 1(e), 1(f), 1(g), 1(h), 1(i), 1(n), 1(p), 1(q) or 1(r), wherein $T^6$ is —$(CH_2)_{0-3}$—$N(R^9)SO_2N(R^8)R^9$ provided that when $T^6$ is attached to a heteroatom of G, then $T^6$ cannot be —$N(R^9)SO_2N(R^8)R^9$.

Embodiment 1(ba) relates to any one of Embodiments 1, 1(a), 1(b), 1(c), 1(d), 1(e), 1(f), 1(g), 1(h), 1(i), 1(n), 1(p), 1(q) or 1(r), wherein $T^6$ is —$(CH_2)_{0-3}$—$N(R^9)C(O)N(R^8)R^9$, provided that when $T^6$ is attached to a heteroatom of G, then $T^6$ cannot be —$N(R^9)C(O)N(R^8)R^9$.

Embodiment 1(bb) relates to any one of Embodiments 1, 1(a), 1(b), 1(c), 1(d), 1(e), 1(f), 1(g), 1(h), 1(i), 1(n), 1(p), 1(q) or 1(r), wherein $T^6$ is —$(CH_2)_{0-3}$—$N(R^9)C(O)R^8$, provided that when $T^6$ is attached to a heteroatom of G, then $T^6$ cannot be $N(R^9)C(O)R^8$.

Embodiment 1(bc) relates to any one of Embodiments 1, 1(a), 1(b), 1(c), 1(d), 1(e), 1(f), 1(g), 1(h), 1(i), 1(n), 1(p), 1(q) or 1(r), wherein $T^6$ is —$(CH_2)_{0-3}$—$N(R^9)C(O)OR^9$, provided that when $T^6$ is attached to a heteroatom of G, then $T^6$ cannot be —$N(R^9)C(O)OR^9$.

Embodiment 1(bd) relates to any one of Embodiments 1, 1(a), 1(b), 1(c), 1(d), 1(e), 1(f), 1(g), 1(h), 1(i), 1(n), 1(p), 1(q) or 1(r), wherein $T^6$ is —$(CH_2)_{0-3}$—$N(R^8)R^9$, provided that when $T^6$ is attached to a heteroatom of G, then $T^6$ cannot be —$N(R^8)R^9$.

Embodiment 1(be) relates to any one of Embodiments 1, 1(a), 1(b), 1(c), 1(d), 1(e), 1(f), 1(g), 1(h), 1(i), 1(n), 1(p), 1(q) or 1(r), wherein $T^6$ is —$(CH_2)_{0-3}$—$C(O)$—$N(R^8)R^9$.

Embodiment 1(bf) relates to any one of Embodiments 1, 1(a), 1(b), 1(c), 1(d), 1(e), 1(f), 1(g), 1(h), 1(i), 1(n), 1(p), 1(q) or 1(r), wherein $T^6$ is —$(CH_2)_{0-3}$—$C(O)OR^9$.

Embodiment 1(bg) relates to any one of Embodiments 1, 1(a), 1(b), 1(c), 1(d), 1(e), 1(f), 1(g), 1(h), 1(i), 1(n), 1(p), 1(q) or 1(r), wherein $T^6$ is —$(CH_2)_{0-3}$—$C(O)R^{11}$.

Embodiment 1(bh) relates to any one of Embodiments 1, 1(a), 1(b), 1(c), 1(d), 1(e), 1(f), 1(g), 1(h), 1(i), 1(n), 1(p), 1(q) or 1(r), wherein $T^6$ is —$(CH_2)_{0-3}$—$N(R^9)C(O)R^{10}$, provided that when $T^6$ is attached to a heteroatom of G, then $T^6$ cannot be —$N(R^9)C(O)R^{10}$.

Embodiment 1(bi) relates to any one of Embodiments 1, 1(a), 1(b), 1(c), 1(d), 1(e), 1(f), 1(g), 1(h), 1(i), 1(n), 1(p), 1(q) or 1(r), wherein $T^6$ is —N(H)C(H)C=O, provided that $T^6$ is not attached to a heteroatom of G.

Embodiment 1(bj) relates to any one of Embodiments 1, 1(a), 1(b), 1(c), 1(d), 1(e), 1(f), 1(g), 1(h), 1(i), 1(n), 1(p), 1(q) or 1(r), wherein $T^6$ is —$(CH_2)_{0-3}$cycloalkyl optionally substituted with 1-4 $Z^3$.

Embodiment 1(bk) relates to any one of Embodiments 1, 1(a), 1(b), 1(c), 1(d), 1(e), 1(f), 1(g), 1(h), 1(i), 1(n), 1(p), 1(q) or 1(r), wherein $T^6$ is —$(CH_2)_{0-2}$heterocycloalkyl optionally substituted with 1-4 $Z^3$, provided that when $T^6$ is attached to a heteroatom of G, G cannot be attached to a nitrogen or oxygen atom of $T^6$.

Embodiment 1(bl) relates to any one of Embodiments 1, 1(a), 1(b), 1(c), 1(d), 1(e), 1(f), 1(g), 1(h), 1(i), 1(n), 1(p), 1(q) or 1(r), wherein $T^6$ is —$(CH_2)_{0-3}$heteroaryl optionally substituted with 1-3 $Z^5$, provided that when $T^6$ is attached to a heteroatom of G, G cannot be attached to a nitrogen or oxygen atom of $T^6$.

Embodiment 1(bm) relates to any one of Embodiments 1, 1(a), 1(b), 1(c), 1(d), 1(e), 1(f), 1(g), 1(h), 1(i), 1(j), 1(k), 1(l), 1(m), 1(n), 1(o), 1(p), 1(q), 1(r), 1(s), 1(t), 1(u), 1(v), 1(w), 1(x), 1(y), 1(z), 1(aa), 1(ab), 1(ac), 1(ad), 1(ae), 1(af), 1(ag), 1(ah), 1(ai), 1(aj), 1(ak), 1(al), 1(am), 1(an), 1(ao), 1(ap), 1(aq), 1(ar), 1(as), 1(at), 1(au), 1(av), 1(aw), 1(ax), 1(ay), 1(az), 1(ba), 1(bb), 1(bc), 1(bd), 1(be), 1(bf), 1(bg), 1(bh), 1(bi), 1(bj), (bk) or 1(bl), wherein $R^1$ is hydrogen.

Embodiment 1(bn) relates to any one of Embodiments 1, 1(a), 1(b), 1(c), 1(d), 1(e), 1(f), 1(g), 1(h), 1(i), 1(j), 1(k), 1(l), 1(m), 1(n), 1(o), 1(p), 1(q), 1(r), 1(s), 1(t), 1(u), 1(v), 1(w), 1(x), 1(y), 1(z), 1(aa), 1(ab), 1(ac), 1(ad), 1(ae), 1(af), 1(ag), 1(ah), 1(ai), 1(aj), 1(ak), 1(al), 1(am), 1(an), 1(ao), 1(ap), 1(aq), 1(ar), 1(as), 1(at), 1(au), 1(av), 1(aw), 1(ax), 1(ay), 1(az), 1(ba), 1(bb), 1(bc), 1(bd), 1(be), 1(bf), 1(bg), 1(bh), 1(bi), 1(bj), (bk) or 1(bl), wherein $R^1$ is $C_2$-$C_6$alkyl substituted with 0-4 hydroxyl.

Embodiment 1(bo) relates to any one of Embodiments 1, 1(a), 1(b), 1(c), 1(d), 1(e), 1(f), 1(g), 1(h), 1(i), 1(j), 1(k), 1(l), 1(m), 1(n), 1(o), 1(p), 1(q), 1(r), 1(s), 1(t), 1(u), 1(v), 1(w), 1(x), 1(y), 1(z), 1(aa), 1(ab), 1(ac), 1(ad), 1(ae), 1(af), 1(ag), 1(ah), 1(ai), 1(aj), 1(ak), 1(al), 1(am), 1(an), 1(ao), 1(ap), 1(aq), 1(ar), 1(as), 1(at), 1(au), 1(av), 1(aw), 1(ax), 1(ay), 1(az), 1(ba), 1(bb), 1(bc), 1(bd), 1(be), 1(bf), 1(bg), 1(bh), 1(bi), 1(bj), (bk), 1(bl), 1(bm) or 1(bn), wherein $R^2$ is halogen.

Embodiment 1(bp) relates to any one of Embodiments 1, 1(a), 1(b), 1(c), 1(d), 1(e), 1(f), 1(g), 1(h), 1(i), 1(j), 1(k), 1(l), 1(m), 1(n), 1(o), 1(p), 1(q), 1(r), 1(s), 1(t), 1(u), 1(v), 1(w), 1(x), 1(y), 1(z), 1(aa), 1(ab), 1(ac), 1(ad), 1(ae), 1(af), 1(ag), 1(ah), 1(ai), 1(aj), 1(ak), 1(al), 1(am), 1(an), 1(ao), 1(ap), 1(aq), 1(ar), 1(as), 1(at), 1(au), 1(av), 1(aw), 1(ax), 1(ay), 1(az), 1(ba), 1(bb), 1(bc), 1(bd), 1(be), 1(bf), 1(bg), 1(bh), 1(bi), 1(bj), (bk), 1(bl), 1(bm) or 1(bn), wherein $R^2$ is CN.

Embodiment 1(bq) relates to any one of Embodiments 1, 1(a), 1(b), 1(c), 1(d), 1(e), 1(f), 1(g), 1(h), 1(i), 1(j), 1(k), 1(l), 1(m), 1(n), 1(o), 1(p), 1(q), 1(r), 1(s), 1(t), 1(u), 1(v), 1(w), 1(x), 1(y), 1(z), 1(aa), 1(ab), 1(ac), 1(ad), 1(ae), 1(af), 1(ag), 1(ah), 1(ai), 1(aj), 1(ak), 1(al), 1(am), 1(an), 1(ao), 1(ap), 1(aq), 1(ar), 1(as), 1(at), 1(au), 1(av), 1(aw), 1(ax), 1(ay), 1(az), 1(ba), 1(bb), 1(bc), 1(bd), 1(be), 1(bf), 1(bg), 1(bh), 1(bi), 1(bj), (bk), 1(bl), 1(bm), 1(bn), 1(bo) or 1(bp), wherein $R^3$ is H.

Embodiment 2 of this disclosure relates to the compound according to Embodiment 1, 1, wherein ring A is azetidine, pyrrolidine, piperidine, imidazole, thiazole, or pyrazolyl.

Subembodiments of Embodiment 2

Embodiment 2(a) of this disclosure relates to the compound according to Embodiment 2, wherein ring A is azetidine.

Embodiment 2(b) of this disclosure relates to the compound according to Embodiment 2, wherein ring A is pyrrolidine.

Embodiment 2(c) of this disclosure relates to the compound according to Embodiment 2, wherein ring A is piperidine.

Embodiment 2(d) of this disclosure relates to the compound according to Embodiment 2, wherein ring A is imidazole.

Embodiment 2(e) of this disclosure relates to the compound according to Embodiment 2, wherein ring A is thiazole.

Embodiment 2(f) of this disclosure relates to the compound according to Embodiment 2, wherein ring A is azetidine.

Embodiment 2(g) of this disclosure relates to the compound according to Embodiment 2, wherein ring A is pyrazolyl.

Embodiment 3 of this disclosure relates to the compound according to Embodiment 1 having Formula II:

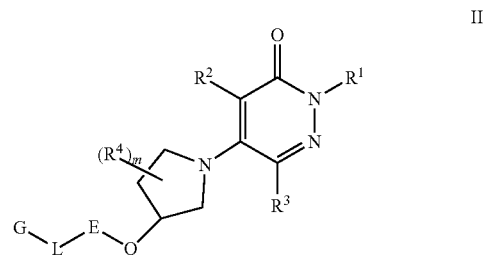

II or a pharmaceutically acceptable salt, a solvate, a tautomer, a stereoisomer, or a deuterated analog thereof, wherein L is absent, —N(H)—, or —O—; and m is 0-2.

Embodiment 4 of this disclosure relates to the compound according to Embodiment 1 having Formula IIIa or IIIb:

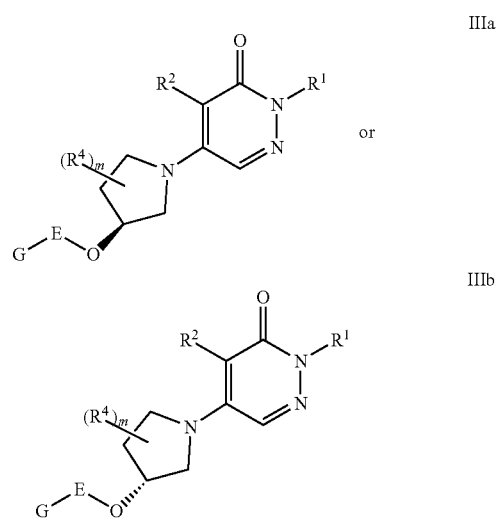

or a pharmaceutically acceptable salt, a solvate, a tautomer, a stereoisomer, or a deuterated analog thereof, wherein:

E is phenyl or a 6 membered heteroaryl, wherein E is substituted with 0-2 Q, provided that when E is a 6 membered heteroaryl, 0 is not attached to a heteroatom of E;

G is one of the following groups:
(a) $C_3$-$C_6$cycloalkyl substituted with 0-3 $T^1$ and 0-1 $T^2$;
(b) $C_3$-$C_6$cycloalkenyl substituted with 0-3 $T^1$ and 0-1 $T^2$;
(c) a 5-9 membered bridged carbocyclic ring substituted with 0-3 $T^1$ and 0-1 $T^2$;
(d) a 5-9 membered carbocyclic spiro ring containing two cycloalkyl groups joined by one common spiro carbon atom, wherein the carbocyclic spiro ring is substituted with 0-3 Ti and 0-1 $T^2$;

(e) a 6-9 membered heterocyclic spiro ring containing two cyclic groups with at least one heteroatom, wherein the two cyclic groups are joined by one common spiro carbon atom, wherein the heterocyclic spiro ring is substituted with 0-3 $T^5$, 0-1 $T^6$; (f) phenyl substituted with 0-3 $T^1$ and 0-1 $T^4$;

(g) a 4-6 membered heterocycloalkyl substituted with 0-3 $T^5$ and 0-1 $T^6$;

(h) a 4-6 membered heterocycloalkenyl substituted with 0-3 $T^5$ and 0-1 $T^6$;

(i) a 5-9 membered bridged heterocyclic ring substituted with 0-3 $T^5$ and 0-1 $T^6$; or (j) a 5-6 membered heteroaryl substituted with 0-3 $T^5$ and 0-1 $T^3$;

each Q is independently halogen, CN, or $C_1$-$C_3$alkyl optionally substituted with 1-3 halogens;

each $T^1$ is independently halogen, hydroxyl, $C_1$-$C_6$alkyl optionally substituted with 1-3 $R^b$, $C_2$-$C_5$alkenyl optionally substituted with 1-3 $R^b$, $C_2$-$C_5$alkynyl optionally substituted with 1-3 $R^b$, CN, $C_1$-$C_6$cyanoalkyl, $C_1$-$C_6$alkoxyl optionally substituted with 1-3 $R^b$, or $C_1$-$C_6$alkoxy$C_1$-$C_6$alkyl optionally substituted with 1-3 $R^b$;

$T^2$ is —$(CH_2)_{0-2}$—$N(R^9)SO_2$—$R^7$, —$(CH_2)_{0-2}$—$SO_2$—$R^7$, —$(CH_2)_{0-2}$—$SO_2N(R^8)R^9$, —$(CH_2)_{0-2}$—$N(R^9)SO_2N(R^8)R^9$, —$(CH_2)_{0-2}$—$N(R^9)C(O)N(R^8)R^9$, —$(CH_2)_{0-2}$—$N(R^9)C(O)R^8$, —$(CH_2)_{0-2}$—$N(R^9)C(O)OR^9$, —$(CH_2)_{0-2}$—$N(R^8)R^9$, —$(CH_2)_{0-2}$—$C(O)N(R^8)R^9$, —$(CH_2)_{0-2}$—$C(O)OR^9$, —$(CH_2)_{0-2}$—$C(O)R^{10}$, —$(CH_2)_{0-2}$—$C(O)H$, —$(CH_2)_{0-2}$—$N(R^9)C(O)R^{10}$, —$(CH_2)_{0-2}C_3$-$C_6$cycloalkyl optionally substituted with 1-4 $Z^3$, —$(CH_2)_{0-2}$-phenyl optionally substituted with 1-3 $Z^5$, or —$(CH_2)_{0-2}$-5-6 membered heteroaryl optionally substituted with 1-3 $Z^5$;

$T^3$ is —$(CH_2)_{0-2}$—$C(O)N(R^8)R^9$, —$(CH_2)_{0-2}$—$N(R^8)R^9$, —$(CH_2)_{0-2}$—$C(O)OR^9$, —$(CH_2)_{0-2}$—$C_3$-$C_6$cycloalkyl, —$(CH_2)_{0-2}$-5-6 membered heterocycloalkyl, —O—5-6 membered heterocycloalkyl optionally substituted with 4-chloropyridazin-3-one-5-yl, or —$(CH_2)_{0-2}$-5-9 membered bridged carbocylic ring, wherein the —$(CH_2)_{0-2}$—$C_3$-$C_6$cycloalkyl, —$(CH_2)_{0-2}$-5-6 membered heterocycloalkyl or —$(CH_2)_{0-2}$-5-9 membered bridged carbocyclic are each optionally substituted with 1-3 $Z^5$ and 0-1 $Z^1$, provided that when $T^3$ is attached to a heteroatom of G, G is not attached to an oxygen or nitrogen atom of $T^3$;

$T^4$ is —$(CH_2)_{0-2}C(O)OR^9$, —$(CH_2)_{0-2}$—$N(R^9)C(O)R^8$, —$(CH_2)_{0-2}$—$N(R^9)SO_2$—$R^7$, —$(CH_2)_{0-2}$—$SO_2$—$R^7$, —$(CH_2)_{0-2}$—$SO_2N(R^8)R^9$, —$(CH_2)_{0-2}$—$N(R^9)C(O)N(R^8)R^9$, or $N(R^a)_2$;

each $T^5$ is independently halogen, hydroxyl, $C_1$-$C_6$alkyl optionally substituted with 1-3 $R^b$, $C_2$-$C_6$alkenyl optionally substituted with 1-3 $R^b$, $C_2$-$C_6$alkynyl optionally substituted with 1-3 $R^b$, CN, $C_1$-$C_6$cyanoalkyl, $C_1$-$C_6$alkoxyl optionally substituted with 1-3 $R^b$, or $C_1$-$C_6$alkoxy$C_1$-$C_6$alkyl optionally substituted with 1-3 $R^b$, provided that when $T^5$ is attached to a heteroatom of G, $T^5$ cannot be halogen, hydroxyl, CN, or $C_1$-$C_6$alkoxyl optionally substituted with 1-3 $R^b$;

$T^6$ is —$(CH_2)_{0-2}$—$N(R^9)SO_2$—$R^7$, —$(CH_2)_{0-2}$—$SO_2$—$R^7$, —$(CH_2)_{0-2}$—$SO_2N(R^8)R^9$, —$(CH_2)_{0-2}$—$N(R^9)SO_2N(R^8)R^9$, —$(CH_2)_{0-2}$—$N(R^9)C(O)N(R^8)R^9$, —$(CH_2)_{0-2}$—$N(R^9)C(O)R^8$, —$(CH_2)_{0-2}$—$N(R^9)C(O)OR^9$, —$(CH_2)_{0-2}$—$N(R^8)R^9$, —$(CH_2)_{0-2}$—$C(O)$—$N(R^8)R^9$, —$(CH_2)_{0-2}$—$C(O)OR^9$, —$(CH_2)_{0-2}$—$C(O)R^{10}$, —$(CH_2)_{0-2}$—$N(R^9)C(O)R^{10}$, —$N(H)C(H)=O$, —$(CH_2)_{0-2}$—$C_3$-$C_6$cycloalkyl optionally substituted with 1-4 $Z^3$, —$(CH_2)_{0-2}$-5-6 membered heterocycloalkyl optionally substituted with 1-4 $Z^3$, —$(CH_2)_{0-3}$-5-6 membered heteroaryl optionally substituted with 1-3 $Z^5$, or 4-chloropyridazin-3-one-5-yl, provided that when $T^6$ is attached to a heteroatom of G, G is not attached to an oxygen or nitrogen atom of $T^6$;

$R^a$ is H or $C_1$-$C_6$alkyl;

$R^b$ is halogen, CN, $CF_3$, or hydroxyl, provided that not more than 1 $R^b$ can be $CF_3$;

each $R^1$ is hydrogen, $C_1$-$C_6$alkoxy$C_1$-$C_6$alkyl, $C_2$-$C_6$alkenyl substituted with 1-4 $Z^2$, or $C_2$-$C_6$alkyl substituted with 1-4 $Z^2$;

$R^2$ is H, halogen, $C_1$-$C_6$alkyl, $C_2$-$C_6$alkenyl, $C_1$-$C_6$alkoxyl, $C_1$-$C_6$haloalkyl, $CF_3$, or CN;

$R^3$ is H, halogen, $C_1$-$C_6$alkyl, CN, or $C_1$-$C_6$haloalkyl;

each $R^4$ is independently halogen, CN, or $C_1$-$C_3$alkyl optionally substituted with 1-3 halogens;

$R^7$ is $C_1$-$C_6$alkyl optionally substituted with 1-4 $Z^4$, —$C_0$-$C_2$alkyl-$C_3$-$C_6$cycloalkyl optionally substituted with 1-4 $Z^3$, —$C_0$-$C_2$alkyl-phenyl optionally substituted with 1-4 $Z^3$, —$C_0$-$C_2$alkyl-5-6 membered heteroaryl optionally substituted with 1-3 $Z^5$, or —$C_0$-$C_2$alkyl-5-6 membered heterocycloalkyl optionally substituted with 1-3 $Z^5$;

$R^8$ is H, $C_1$-$C_6$alkyl optionally substituted with 1-4 $Z^4$, $C_2$-$C_6$alkenyl optionally substituted with 1-4 $Z^4$, —$C_0$-$C_2$alkyl-$C_3$-$C_6$cycloalkyl optionally substituted with 1-4 $Z^3$, —$C_0$-$C_2$alkyl-phenyl optionally substituted with 1-4 $Z^3$, —$C_0$-$C_2$alkyl-5-6 membered heteroaryl optionally substituted with 1-3 $Z^5$, —$C_0$-$C_2$alkyl-5-6 membered heterocycloalkyl optionally substituted with 1-3 $Z^5$, or a 5-9 membered bridged carbocylic ring substituted with 0-4 Ti;

each $R^9$ is independently H or $C_1$-$C_6$alkyl optionally substituted with 1-4 $Z^4$;

$R^{10}$ is $C_1$-$C_6$alkyl substituted with 0-4 $Z^4$, —$C_0$-$C_2$alkyl-$C_3$-$C_6$cycloalkyl optionally substituted with 1-4 $Z^3$, —$C_0$-$C_2$alkyl-phenyl optionally substituted with 1-4 $Z^3$, —$C_0$-$C_2$alkyl-5-6 membered heteroaryl optionally substituted with 1-3 $Z^5$, or —$C_0$-$C_2$alkyl-5-6 membered heterocycloalkyl optionally substituted with 1-3 $Z^5$;

$R^{11}$ is $NH_2$;

$Z^1$ is $C_1$-$C_6$cyanoalkyl, —$(CH_2)_{0-2}$—$C(O)OR^9$, —$(CH_2)_{0-2}$—$C(O)$—$N(R^8)R^9$, provided that when $Z^1$ is attached to a heteroatom, then $Z^1$ is not —$C(O)OR$;

each $Z^2$ is independently hydroxyl, halogen, CN;

each $Z^3$ is independently $C_1$-$C_6$alkyl, halogen, $C_1$-$C_6$haloalkyl, hydroxyl, $C_1$-$C_6$hydroxyalkyl, $C_1$-$C_6$alkoxyl, or CN;

each $Z^4$ is independently, hydroxyl, halogen, $C_1$-$C_6$alkoxyl, or CN; and each $Z^5$ is independently $C_1$-$C_6$alkyl, $C_1$-$C_6$haloalkyl, hydroxyl, $C_1$-$C_6$hydroxyalkyl, halogen, $C_1$-$C_6$alkoxyl, CN, or $C_1$-$C_6$cyanoalkyl, provided that when $Z^5$ is attached to a heteroatom, then $Z^5$ is not halogen, hydroxyl, $C_1$-$C_6$alkoxyl, or CN.

Subembodiments of Embodiment 4

Embodiment 4(a) of this disclosure relates to the compound according to Embodiment 4 having Formula IIIa, or a pharmaceutically acceptable salt, a solvate, a tautomer, a stereoisomer, or a deuterated analog thereof.

Embodiment 4(b) of this disclosure relates to the compound according to Embodiment 4 having Formula IIIb, or a pharmaceutically acceptable salt, a solvate, a tautomer, a stereoisomer, or a deuterated analog thereof.

Embodiment 4(c) of this disclosure relates to the compound according to Embodiment 4, 4(a) or 4(b), wherein G is $C_3$-$C_6$cycloalkyl substituted with 0-3 $T^1$ and 0-1 $T^2$.

Embodiment 4(d) of this disclosure relates to the compound according to Embodiment 4, 4(a) or 4(b), wherein G is $C_3$-$C_6$cycloalkenyl substituted with 0-3 $T^1$ and 0-1 $T^2$.

Embodiment 4(e) of this disclosure relates to the compound according to Embodiment 4, 4(a) or 4(b), wherein G is a 5-9 membered bridged carbocylic ring substituted with 0-3 $T^1$ and 0-1 $T^2$.

Embodiment 4(f) of this disclosure relates to the compound according to Embodiment 4, 4(a) or 4(b), wherein G is a 5-9 membered carbocyclic spiro ring containing two cycloalkyl groups joined by one common spiro carbon atom, wherein the carbocyclic spiro ring is substituted with 0-3 $T^1$ and 0-1 $T^2$.

Embodiment 4(g) of this disclosure relates to the compound according to Embodiment 4, 4(a) or 4(b), wherein G is a 6-9 membered heterocyclic spiro ring containing two cyclic groups with at least one heteroatom, wherein the two cyclic groups are joined by one common spiro carbon atom, wherein the heterocyclic spiro ring is substituted with 0-3 $T^5$, 0-1 $T^6$.

Embodiment 4(h) of this disclosure relates to the compound according to Embodiment 4, 4(a) or 4(b), wherein G is phenyl substituted with 0-3 $T^1$ and 0-1 $T^4$.

Embodiment 4(i) of this disclosure relates to the compound according to Embodiment 4, 4(a) or 4(b), wherein G is a 4-6 membered heterocycloalkyl substituted with 0-3 $T^5$ and 0-1 $T^6$.

Embodiment 4(j) of this disclosure relates to the compound according to Embodiment 4, 4(a) or 4(b), wherein G is a 4-6 membered heterocycloalkenyl substituted with 0-3 $T^5$ and 0-1 $T^6$.

Embodiment 4(k) of this disclosure relates to the compound according to Embodiment 4, 4(a) or 4(b), wherein G is a 5-9 membered bridged heterocylic ring substituted with 0-3 $T^5$ and 0-1 $T^6$.

Embodiment 4(l) of this disclosure relates to the compound according to Embodiment 4, 4(a) or 4(b), wherein G is a 5-6 membered heteroaryl substituted with 0-3 $T^5$ and 0-1 $T^3$.

Embodiment 4(m) of this disclosure relates to the compound according to Embodiment 4, 4(a), 4(b), 4(c), 4(d), 4(e) or 4(f), wherein $T^2$ is —$(CH_2)_{0-2}$—$N(R^9)SO_2$—$R^7$.

Embodiment 4(n) of this disclosure relates to the compound according to Embodiment 4, 4(a), 4(b), 4(c), 4(d), 4(e) or 4(f), wherein $T^2$ is —$(CH_2)_{0-2}$—$SO_2$—$R^7$.

Embodiment 4(o) of this disclosure relates to the compound according to Embodiment 4, 4(a), 4(b), 4(c), 4(d), 4(e) or 4(f), wherein $T^2$ is —$(CH_2)_{0-2}$—$SO_2N(R^8)R^9$.

Embodiment 4(p) of this disclosure relates to the compound according to Embodiment 4, 4(a), 4(b), 4(c), 4(d), 4(e) or 4(f), wherein $T^2$ is —$(CH_2)_{0-2}$—$N(R^9)SO_2N(R^8)R^9$.

Embodiment 4(q) of this disclosure relates to the compound according to Embodiment 4, 4(a), 4(b), 4(c), 4(d), 4(e) or 4(f), wherein $T^2$ is —$(CH_2)_{0-2}$—$N(R^9)C(O)N(R^8)R^9$.

Embodiment 4(r) of this disclosure relates to the compound according to Embodiment 4, 4(a), 4(b), 4(c), 4(d), 4(e) or 4(f), wherein $T^2$ is —$(CH_2)_{0-2}$—$N(R^9)C(O)R^8$.

Embodiment 4(s) of this disclosure relates to the compound according to Embodiment 4, 4(a), 4(b), 4(c), 4(d), 4(e) or 4(f), wherein $T^2$ is —$(CH_2)_{0-2}$—$N(R^9)C(O)OR^9$.

Embodiment 4(t) of this disclosure relates to the compound according to Embodiment 4, 4(a), 4(b), 4(c), 4(d), 4(e) or 4(f), wherein $T^2$ is —$(CH_2)_{0-2}$—$N(R^8)R^9$.

Embodiment 4(u) of this disclosure relates to the compound according to Embodiment 4, 4(a), 4(b), 4(c), 4(d), 4(e) or 4(f), wherein $T^2$ is —$(CH_2)_{0-2}$—$C(O)N(R^8)R^9$.

Embodiment 4(v) of this disclosure relates to the compound according to Embodiment 4, 4(a), 4(b), 4(c), 4(d), 4(e) or 4(f), wherein $T^2$ is —$(CH_2)_{0-2}$—$C(O)OR^9$.

Embodiment 4(w) of this disclosure relates to the compound according to Embodiment 4, 4(a), 4(b), 4(c), 4(d), 4(e) or 4(f), wherein $T^2$ is —$(CH_2)_{0-2}$—$C(O)R^{10}$.

Embodiment 4(x) of this disclosure relates to the compound according to Embodiment 4, 4(a), 4(b), 4(c), 4(d), 4(e) or 4(f), wherein $T^2$ is —$(CH_2)_{0-2}$—$C(O)H$.

Embodiment 4(y) of this disclosure relates to the compound according to Embodiment 4, 4(a), 4(b), 4(c), 4(d), 4(e) or 4(f), wherein $T^2$ is —$(CH_2)_{0-2}$—$N(R^9)C(O)R^{10}$.

Embodiment 4(z) of this disclosure relates to the compound according to Embodiment 4, 4(a), 4(b), 4(c), 4(d), 4(e) or 4(f), wherein $T^2$ is —$(CH_2)_{0-2}$-$C_3$-$C_6$cycloalkyl optionally substituted with 1-4 $Z^3$.

Embodiment 4(aa) of this disclosure relates to the compound according to Embodiment 4, 4(a), 4(b), 4(c), 4(d), 4(e) or 4(f), wherein $T^2$ is —$(CH_2)_{0-2}$-phenyl optionally substituted with 1-3 $Z^5$.

Embodiment 4(ab) of this disclosure relates to the compound according to Embodiment 4, 4(a), 4(b), 4(c), 4(d), 4(e) or 4(f), wherein $T^2$ is —$(CH_2)_{0-2}$-5-6 membered heteroaryl optionally substituted with 1-3 $Z^5$.

Embodiment 4(ac) of this disclosure relates to the compound according to Embodiment 4, 4(a), 4(b) or 4(l), wherein $T^3$ is —$(CH_2)_{0-2}$—$C(O)N(R^8)R^9$.

Embodiment 4(ad) of this disclosure relates to the compound according to Embodiment 4, 4(a), 4(b) or 4(l), wherein $T^3$ is —$(CH_2)_{0-2}$—$N(R^8)R^9$, provided that $T^3$ is attached to a heteroatom of G, G is not attached to $N(R^8)R^9$.

Embodiment 4(ae) of this disclosure relates to the compound according to Embodiment 4, 4(a), 4(b) or 4(l), wherein $T^3$ is —$(CH_2)_{0-2}$—$C(O)OR^9$.

Embodiment 4(af) of this disclosure relates to the compound according to Embodiment 4, 4(a), 4(b) or 4(l), wherein $T^3$ is —$(CH_2)_{0-2}$—$C_3$-$C_6$cycloalkyl optionally substituted with 1-3 $Z^5$ and 0-1 $Z^1$.

Embodiment 4(ag) of this disclosure relates to the compound according to Embodiment 4, 4(a), 4(b) or 4(l), wherein $T^3$ is —$(CH_2)_{0-2}$-5-6 membered heterocycloalkyl optionally substituted with 1-3 $Z^5$ and 0-1 $Z^1$, provided that when $T^3$ is not attached to a heteroatom of G.

Embodiment 4(ah) of this disclosure relates to the compound according to Embodiment 4, 4(a), 4(b) or 4(l), wherein $T^3$ is —O—5-6 membered heterocycloalkyl optionally substituted with 4-chloropyridazin-3-one-5-yl.

Embodiment 4(ai) of this disclosure relates to the compound according to Embodiment 4, 4(a), 4(b) or 4(l), wherein $T^3$ is —$(CH_2)_{0-2}$-5-9 membered bridged carbocyclic ring optionally substituted with 1-3 $Z^5$ and 0-1 $Z^1$.

Embodiment 4(aj) of this disclosure relates to the compound according to Embodiment 4, 4(a), 4(b) or 4(h), wherein $T^4$ is —$(CH_2)_{0-2}C(O)OR^9$.

Embodiment 4(ak) of this disclosure relates to the compound according to Embodiment 4, 4(a), 4(b) or 4(h), wherein $T^4$ is —$(CH_2)_{0-2}$—$N(R^9)C(O)R^8$.

Embodiment 4(al) of this disclosure relates to the compound according to Embodiment 4, 4(a), 4(b) or 4(h), wherein $T^4$ is —$(CH_2)_{0-2}$—$N(R^9)SO_2$—$R^7$.

Embodiment 4(am) of this disclosure relates to the compound according to Embodiment 4, 4(a), 4(b) or 4(h), wherein $T^4$ is —$(CH_2)_{0-2}$—$SO_2$—$R^7$.

Embodiment 4(an) of this disclosure relates to the compound according to Embodiment 4, 4(a), 4(b) or 4(h), wherein $T^4$ is —$(CH_2)_{0-2}$—$SO_2N(R^8)R^9$.

Embodiment 4(ao) of this disclosure relates to the compound according to Embodiment 4, 4(a), 4(b) or 4(h), wherein $T^4$ is —$(CH_2)_{0-2}$—$N(R^9)C(O)N(R^8)R^9$.

Embodiment 4(ap) of this disclosure relates to the compound according to Embodiment 4, 4(a), 4(b) or 4(h), wherein $T^4$ is $N(R^a)_2$.

Embodiment 4(aq) of this disclosure relates to the compound according to Embodiment 4, 4(a), 4(b), 4(g), 4(i), 4(j) or 4(k), wherein $T^6$ is $-(CH_2)_{0-2}-N(R^9)SO_2-R^7$, provided that when $T^6$ is attached to a heteroatom of G, G is not attached to $-N(R^9)SO_2-R^7$.

Embodiment 4(ar) of this disclosure relates to the compound according to Embodiment 4, 4(a), 4(b), 4(g), 4(i), 4(j) or 4(k), wherein $T^6$ is $-(CH_2)_{0-2}-SO_2-R^7$.

Embodiment 4(as) of this disclosure relates to the compound according to Embodiment 4, 4(a), 4(b), 4(g), 4(i), 4(j) or 4(k), wherein $T^6$ is $-(CH_2)_{0-2}-SO_2N(R')R$.

Embodiment 4(at) of this disclosure relates to the compound according to Embodiment 4, 4(a), 4(b), 4(g), 4(i), 4(j) or 4(k), wherein $T^6$ is $-(CH_2)_{0-2}-N(R^9)SO_2N(R^8)R^9$, provided that when $T^6$ is attached to a heteroatom of G, G is not attached to $-N(R^9)SO_2N(R^8)R^9$.

Embodiment 4(au) of this disclosure relates to the compound according to Embodiment 4, 4(a), 4(b), 4(g), 4(i), 4(j) or 4(k), wherein $T^6$ is $-(CH_2)_{0-2}-N(R^9)C(O)N(R^8)R^9$, provided that when $T^6$ is attached to a heteroatom of G, G is not attached to $-N(R^9)C(O)N(R^8)R^9$.

Embodiment 4(av) of this disclosure relates to the compound according to Embodiment 4, 4(a), 4(b), 4(g), 4(i), 4(j) or 4(k), wherein $T^6$ is $-(CH_2)_{0-2}-N(R^9)C(O)R^8$, provided that when $T^6$ is attached to a heteroatom of G, G is not attached to $-N(R^9)C(O)R^8$.

Embodiment 4(aw) of this disclosure relates to the compound according to Embodiment 4, 4(a), 4(b), 4(g), 4(i), 4(j) or 4(k), wherein $T^6$ is $-(CH_2)_{0-2}-N(R^9)C(O)OR^9$, provided that when $T^6$ is attached to a heteroatom of G, G is not attached to $-N(R^9)C(O)OR^9$.

Embodiment 4(ax) of this disclosure relates to the compound according to Embodiment 4, 4(a), 4(b), 4(g), 4(i), 4(j) or 4(k), wherein $T^6$ is $-(CH_2)_{0-2}-N(R^8)R^9$, provided that when $T^6$ is attached to a heteroatom of G, G is not attached to $-N(R^8)R^9$.

Embodiment 4(ay) of this disclosure relates to the compound according to Embodiment 4, 4(a), 4(b), 4(g), 4(i), 4(j) or 4(k), wherein $T^6$ is $-(CH_2)_{0-2}-C(O)-N(R^8)R^9$.

Embodiment 4(az) of this disclosure relates to the compound according to Embodiment 4, 4(a), 4(b), 4(g), 4(i), 4(j) or 4(k), wherein $T^6$ is $-(CH_2)_{0-2}-C(O)OR^9$.

Embodiment 4(ba) of this disclosure relates to the compound according to Embodiment 4, 4(a), 4(b), 4(g), 4(i), 4(j) or 4(k), wherein $T^6$ is $-(CH_2)_{0-2}-C(O)R^{10}$.

Embodiment 4(bb) of this disclosure relates to the compound according to Embodiment 4, 4(a), 4(b), 4(g), 4(i), 4(j) or 4(k), wherein $T^6$ is $-(CH_2)_{0-2}-N(R^9)C(O)R^{10}$, provided that when $T^6$ is attached to a heteroatom of G, G is not attached to $-N(R^9)C(O)R^{10}$.

Embodiment 4(bc) of this disclosure relates to the compound according to Embodiment 4, 4(a), 4(b), 4(g), 4(i), 4(j) or 4(k), wherein $T^6$ is $-N(H)C(H)C=O$, provided that $T^6$ is not attached to a heteroatom of G.

Embodiment 4(bd) of this disclosure relates to the compound according to Embodiment 4, 4(a), 4(b), 4(g), 4(i), 4(j) or 4(k), wherein $T^6$ is $-(CH_2)_{0-2}-C_3-C_6$ cycloalkyl optionally substituted with 1-4 $Z^3$.

Embodiment 4(be) of this disclosure relates to the compound according to Embodiment 4, 4(a), 4(b), 4(g), 4(i), 4(j) or 4(k), wherein $T^6$ is $-(CH_2)_{0-2}$-5-6 membered heterocycloalkyl optionally substituted with 1-4 $Z^3$, provided that when $T^6$ is attached to a heteroatom of G, G is not attached to an oxygen or nitrogen atom of 5-6 membered heterocycloalkyl.

Embodiment 4(bf) of this disclosure relates to the compound according to Embodiment 4, 4(a), 4(b), 4(g), 4(i), 4(j) or 4(k), wherein $T^6$ is $-(CH_2)_{0-3}$-5-6 membered heteroaryl optionally substituted with 1-3 $Z^5$, provided that when $T^6$ is attached to a heteroatom of G, G is not attached to an oxygen or nitrogen atom of 5-6 membered heteroaryl.

Embodiment 4(bg) of this disclosure relates to the compound according to Embodiment 4, 4(a), 4(b), 4(g), 4(i), 4(j) or 4(k), wherein $T^6$ is or 4-chloropyridazin-3-one-5-yl.

Embodiment 4(bh) relates to any one of Embodiments 4, 4(a), 4(b), 4(c), 4(d), 4(e), 4(f), 4(g), 4(h), 4(i), 4(j), 4(k), 4(l), 4(m), 4(n), 4(o), 4(p), 4(q), 4(r), 4(s), 4(t), 4(u), 4(v), 4(w), 4(x), 4(y), 4(z), 4(aa), 4(ab), 4(ac), 4(ad), 4(ae), 4(af), 4(ag), 4(ah), 4(ai), 4(aj), 4(ak), 4(al), 4(am), 4(an), 4(ao), 4(ap), 4(aq), 4(ar), 4(as), 4(at), 4(au), 4(av), 4(aw), 4(ax), 4(ay), 4(az), 4(ba), 4(bb), 4(bc), 4(bd), (be), 4(bf), or 4(bg), wherein $R^1$ is hydrogen.

Embodiment 4(bi) relates to any one of Embodiments 4, 4(a), 4(b), 4(c), 4(d), 4(e), 4(f), 4(g), 4(h), 4(i), 4(j), 4(k), 4(l), 4(m), 4(n), 4(o), 4(p), 4(q), 4(r), 4(s), 4(t), 4(u), 4(v), 4(w), 4(x), 4(y), 4(z), 4(aa), 4(ab), 4(ac), 4(ad), 4(ae), 4(af), 4(ag), 4(ah), 4(ai), 4(aj), 4(ak), 4(al), 4(am), 4(an), 4(ao), 4(ap), 4(aq), 4(ar), 4(as), 4(at), 4(au), 4(av), 4(aw), 4(ax), 4(ay), 4(az), 4(ba), 4(bb), 4(bc), 4(bd), (be), 4(bf), or 4(bg), wherein $R^1$ is $C_2$-$C_6$ alkyl substituted with 0-4 hydroxyl.

Embodiment 4(bj) relates to any one of Embodiments 4, 4(a), 4(b), 4(c), 4(d), 4(e), 4(f), 4(g), 4(h), 4(i), 4(j), 4(k), 4(l), 4(m), 4(n), 4(o), 4(p), 4(q), 4(r), 4(s), 4(t), 4(u), 4(v), 4(w), 4(x), 4(y), 4(z), 4(aa), 4(ab), 4(ac), 4(ad), 4(ae), 4(af), 4(ag), 4(ah), 4(ai), 4(aj), 4(ak), 4(al), 4(am), 4(an), 4(ao), 4(ap), 4(aq), 4(ar), 4(as), 4(at), 4(au), 4(av), 4(aw), 4(ax), 4(ay), 4(az), 4(ba), 4(bb), 4(bc), 4(bd), (be), 4(bf), or 4(bg), wherein $R^2$ is halogen.

Embodiment 4(bk) relates to any one of Embodiments 4, 4(a), 4(b), 4(c), 4(d), 4(e), 4(f), 4(g), 4(h), 4(i), 4(j), 4(k), 4(l), 4(m), 4(n), 4(o), 4(p), 4(q), 4(r), 4(s), 4(t), 4(u), 4(v), 4(w), 4(x), 4(y), 4(z), 4(aa), 4(ab), 4(ac), 4(ad), 4(ae), 4(af), 4(ag), 4(ah), 4(ai), 4(aj), 4(ak), 4(al), 4(am), 4(an), 4(ao), 4(ap), 4(aq), 4(ar), 4(as), 4(at), 4(au), 4(av), 4(aw), 4(ax), 4(ay), 4(az), 4(ba), 4(bb), 4(bc), 4(bd), (be), 4(bf), or 4(bg), wherein $R^2$ is CN.

Embodiment 4(bl) relates to any one of Embodiments 14, 4(a), 4(b), 4(c), 4(d), 4(e), 4(f), 4(g), 4(h), 4(i), 4(j), 4(k), 4(l), 4(m), 4(n), 4(o), 4(p), 4(q), 4(r), 4(s), 4(t), 4(u), 4(v), 4(w), 4(x), 4(y), 4(z), 4(aa), 4(ab), 4(ac), 4(ad), 4(ae), 4(af), 4(ag), 4(ah), 4(ai), 4(aj), 4(ak), 4(al), 4(am), 4(an), 4(ao), 4(ap), 4(aq), 4(ar), 4(as), 4(at), 4(au), 4(av), 4(aw), 4(ax), 4(ay), 4(az), 4(ba), 4(bb), 4(bc), 4(bd), (be), 4(bf), or 4(bg), wherein $R^3$ is H.

Embodiment 5 of this disclosure relate to the compound according to any of the preceding embodiments, wherein:

E is phenyl or a 6 membered heteroaryl, wherein E is substituted with 0-1 Q, provided that when E is a 6 membered heteroaryl, O is not attached to a heteroatom of E;

G is one of the following groups:
(a) $C_3$-$C_6$ cycloalkyl substituted with 0-2 $T^1$ and 0-1 $T^2$;
(b) $C_3$-$C_6$ cycloalkenyl substituted with 0-2 $T^1$ and 0-1 $T^2$;
(c) a 5-9 membered bridged carbocyclic ring substituted with 0-2 $T^1$ and 0-1 $T^2$;
(d) a 5-9 membered carbocyclic spiro ring containing two cycloalkyl groups joined by one common spiro carbon atom, wherein the carbocyclic spiro ring is substituted with 0-2 Ti and 0-1 $T^2$;

(e) a 6-9 membered heterocyclic spiro ring containing two cyclic groups with at least one heteroatom, wherein the two cyclic groups are joined by one common spiro carbon atom, wherein the heterocyclic spiro ring is substituted with 0-2 $T^5$, 0-1 $T^6$;

(f) phenyl substituted with 0-2 $T^1$ and 0-1 $T^4$;

(g) a 4-6 membered heterocycloalkyl substituted with 0-2 $T^5$ and 0-1 $T^6$;

(h) a 4-6 membered heterocycloalkenyl substituted with 0-2 $T^5$ and 0-1 $T^6$;

(i) a 5-9 membered bridged heterocyclic ring substituted with 0-2 $T^5$ and 0-1 $T^6$; or (j) a 5-6 membered heteroaryl substituted with 0-2 $T^5$ and 0-1 $T^3$;

each Q is independently halogen, CN, or $C_1$-$C_4$alkyl optionally substituted with 1-3 halogens;

each $T^1$ is independently halogen, hydroxyl, $C_1$-$C_4$alkyl optionally substituted with 1-3 $R^b$, $C_2$-$C_4$alkenyl optionally substituted with 1-3 $R^b$, $C_2$-$C_4$alkynyl optionally substituted with 1-3 $R^b$, CN, $C_1$-$C_4$cyanoalkyl, $C_1$-$C_4$alkoxyl optionally substituted with 1-3 $R^b$, or $C_1$-$C_4$alkoxyC$_1$-$C_4$alkyl optionally substituted with 1-3 $R^b$;

$T^2$ is —(CH$_2$)$_{0-1}$—N(R$^9$)SO$_2$—R$^7$, —(CH$_2$)$_{0-1}$—SO$_2$—R$^7$, —(CH$_2$)$_{0-1}$—SO$_2$N(R$^8$)R$^9$, —(CH$_2$)$_{0-1}$—N(R$^9$)SO$_2$N(R$^8$)R$^9$, —(CH$_2$)$_{0-1}$—N(R$^9$)C(O)N(R$^8$)R$^9$, —(CH$_2$)$_{0-1}$—N(R$^9$)C(O)R$^8$, —(CH$_2$)$_{0-1}$—N(R$^9$)C(O)OR$^9$, —(CH$_2$)$_{0-1}$—N(R$^8$)R$^9$, —(CH$_2$)$_{0-1}$—C(O)N(R$^8$)R$^9$, —(CH$_2$)$_{0-1}$—C(O)OR$^9$, —(CH$_2$)$_{0-1}$—C(O)R$^{10}$, —(CH$_2$)$_{0-1}$—C(O)H, —(CH$_2$)$_{0-1}$—N(R$^9$)C(O)R$^{10}$, —(CH$_2$)$_{0-2}$C$_3$-C$_6$cycloalkyl optionally substituted with 1-3 $Z^3$, —(CH$_2$)$_{0-1}$-phenyl optionally substituted with 1-3 $Z^5$, or —(CH$_2$)$_{0-1}$-5-6 membered heteroaryl optionally substituted with 1-3 $Z^5$;

$T^3$ is —(CH$_2$)$_{0-2}$—C(O)N(R$^8$)R$^9$, —(CH$_2$)$_{0-2}$—N(R$^8$)R$^9$, —(CH$_2$)$_{0-2}$—C(O)OR$^9$, —(CH$_2$)$_{0-2}$—C$_3$-C$_6$cycloalkyl, —(CH$_2$)$_{0-2}$-5-6 membered heterocycloalkyl, —O—5-6 membered heterocycloalkyl optionally substituted with 4-chloropyridazin-3-one-5-yl, or —(CH$_2$)$_{0-2}$-5-9 membered bridged carbocylic ring, wherein the —(CH$_2$)$_{0-2}$—C$_3$-C$_6$cycloalkyl, —(CH$_2$)$_{0-1}$-5-6 membered heterocycloalkyl, or —(CH$_2$)$_{0-2}$-5-9 membered bridged carbocyclic are each optionally substituted with 1-3 $Z^5$ and 0-1 $Z^1$, provided that when $T^3$ is attached to a heteroatom of G, G is not attached to an oxygen or nitrogen atom of $T^3$;

$T^4$ is —(CH$_2$)$_{0-1}$C(O)OR$^9$, —(CH$_2$)$_{0-1}$—N(R$^9$)C(O)R$^8$, —(CH$_2$)$_{0-1}$—N(R$^9$)SO$_2$—R$^7$, —(CH$_2$)$_{0-1}$—SO$_2$—R$^7$, —(CH$_2$)$_{0-1}$—SO$_2$N(R$^8$)R$^9$, —(CH$_2$)$_{0-1}$—N(R$^9$)C(O)N(R$^8$)R$^9$, or N(R$^a$)$_2$;

each $T^5$ is independently halogen, hydroxyl, $C_1$-$C_4$alkyl optionally substituted with 1-3 $R^b$, $C_2$-$C_4$alkenyl optionally substituted with 1-3 $R^b$, $C_2$-$C_4$alkynyl optionally substituted with 1-3 $R^b$, CN, $C_1$-$C_4$cyanoalkyl, $C_1$-$C_4$alkoxyl optionally substituted with 1-3 $R^b$, or $C_1$-$C_4$alkoxyC$_1$-$C_4$alkyl optionally substituted with 1-3 $R^b$, provided that when $T^5$ is attached to a heteroatom of G, $T^5$ cannot be halogen, hydroxyl, CN, or $C_1$-$C_4$alkoxyl optionally substituted with 1-3 $R^b$;

$T^6$ is —(CH$_2$)$_{0-1}$—N(R$^9$)SO$_2$—R$^7$, —(CH$_2$)$_{0-1}$—SO$_2$—R$^7$, —(CH$_2$)$_{0-1}$—SO$_2$N(R$^8$)R$^9$, —(CH$_2$)$_{0-1}$—N(R$^9$)SO$_2$N(R$^8$)R$^9$, —(CH$_2$)$_{0-1}$—N(R$^9$)C(O)N(R$^8$)R$^9$, —(CH$_2$)$_{0-1}$—N(R$^9$)C(O)R$^8$, —(CH$_2$)$_{0-1}$—N(R$^9$)C(O)OR$^9$, —(CH$_2$)$_{0-1}$—N(R$^8$)R$^9$, —(CH$_2$)$_{0-1}$—C(O)—N(R$^8$)R$^9$, —(CH$_2$)$_{0-1}$—C(O)OR$^9$, —(CH$_2$)$_{0-1}$—C(O)R$^{10}$, —(CH$_2$)$_{0-1}$—N(R$^9$)C(O)R$^{10}$, —N(H)C(H)C=O, —(CH$_2$)$_{0-1}$—C$_3$-C$_6$cycloalkyl optionally substituted with 1-4 $Z^3$, —(CH$_2$)$_{0-1}$-5-6 membered heterocycloalkyl optionally substituted with 1-4 $Z^3$, —(CH$_2$)$_{0-1}$-5-6 membered heteroaryl optionally substituted with 1-3 $Z^5$, or 4-chloropyridazin-3-one-5-yl, provided that when $T^6$ is attached to a heteroatom of G, G is not attached to an oxygen or nitrogen atom of $T^6$;

$R^a$ is H or $C_1$-$C_4$alkyl;

$R^b$ is F, Cl, CN, CF$_3$, or hydroxyl, provided that not more than 1 $R^b$ can be CF$_3$;

$R^1$ is H, $C_1$-$C_4$alkoxyC$_1$-$C_4$alkyl, $C_2$-$C_4$alkenyl substituted with 1-3 $Z^2$, or $C_2$-$C_4$alkyl substituted with 1-3 $Z^2$;

$R^2$ is H, halogen, $C_1$-$C_4$alkyl, $C_2$-$C_4$alkenyl, $C_1$-$C_4$alkoxyl, $C_1$-$C_4$haloalkyl, CF$_3$, or CN;

$R^3$ is H, halogen, $C_1$-$C_4$alkyl, CN, or $C_1$-$C_4$haloalkyl;

each $R^4$ is independently halogen, CN, or $C_1$-$C_4$alkyl optionally substituted with 1-3 halogens;

$R^7$ is $C_1$-$C_4$alkyl optionally substituted with 1-3 $Z^4$, —C$_0$-C$_3$alkyl-C$_3$-C$_6$cycloalkyl optionally substituted with 1-3 $Z^3$, —C$_0$-C$_3$alkyl-phenyl optionally substituted with 1-3 $Z^3$, —C$_0$-C$_1$alkyl-5-6 membered heteroaryl optionally substituted with 1-3 $Z^5$, or —C$_0$-C$_1$alkyl-5-6 membered heterocycloalkyl optionally substituted with 1-3 $Z^5$;

$R^8$ is H, $C_1$-$C_4$alkyl optionally substituted with 1-3 $Z^4$, $C_2$-$C_4$alkenyl optionally substituted with 1-3 $Z^4$, —C$_0$-C$_1$alkyl-C$_3$-C$_6$cycloalkyl optionally substituted with 1-3 $Z^3$, —C$_0$-C$_1$alkyl-phenyl optionally substituted with 1-3 $Z^3$, —C$_0$-C$_1$alkyl-5-6 membered heteroaryl optionally substituted with 1-3 $Z^5$, —C$_0$-C$_1$alkyl-5-6 membered heterocycloalkyl optionally substituted with 1-3 $Z^5$, or a 5-9 membered bridged carbocylic ring substituted with 0-3 Ti;

each $R^9$ is independently H or $C_1$-$C_4$alkyl optionally substituted with 1-3 $Z^4$;

$R^{10}$ is $C_1$-$C_4$alkyl substituted with 0-3 $Z^4$, —C$_0$-C$_1$alkyl-C$_3$-C$_6$cycloalkyl optionally substituted with 1-3 $Z^3$, —C$_0$-C$_1$alkyl-phenyl optionally substituted with 1-3 $Z^3$, —C$_0$-C$_1$alkyl-5-6 membered heteroaryl optionally substituted with 1-3 $Z^5$, or —C$_0$-C$_1$alkyl-5-6 membered heterocycloalkyl optionally substituted with 1-3 $Z^5$;

$Z^1$ is $C_1$-$C_4$cyanoalkyl, —(CH$_2$)$_{0-1}$—C(O)OR$^9$, —(CH$_2$)$_{0-1}$—C(O)—N(R$^8$)R$^9$, provided that when $Z^1$ is attached to a heteroatom, then $Z^1$ is not —C(O)OR$^9$;

each $Z^2$ is independently hydroxyl, halogen, CN;

each $Z^3$ is independently $C_1$-$C_4$alkyl, halogen, $C_1$-$C_4$haloalkyl, hydroxyl, $C_1$-$C_4$hydroxyalkyl, $C_1$-$C_4$alkoxyl, or CN;

each $Z^4$ is independently, hydroxyl, halogen, $C_1$-$C_4$alkoxyl, or CN; and each $Z^5$ is independently $C_1$-$C_4$alkyl, $C_1$-$C_6$haloalkyl, hydroxyl, $C_1$-$C_4$hydroxyalkyl, halogen, $C_1$-$C_4$alkoxyl, CN, or $C_1$-$C_4$cyanoalkyl, provided that when $Z^5$ is attached to a heteroatom, then $Z^5$ is not halogen, hydroxyl, $C_1$-$C_4$alkoxyl, or CN.

Subembodiments of Embodiment 5

Embodiment 5(a) of this disclosure relates to Embodiment 5, wherein E is phenyl substituted with 0-1 Q.

Embodiment 5(b) of this disclosure relates to Embodiment 5, wherein E is a 6 membered heteroaryl substituted with 0-1 Q, provided that O is not attached to a heteroatom of E.

Embodiment 5(c) of this disclosure relates to Embodiment 5, 5(a) or 5(b), wherein G is $C_3$-$C_6$cycloalkyl substituted with 0-2 $T^1$ and 0-1 $T^2$.

Embodiment 5(d) of this disclosure relates to Embodiment 5, 5(a) or 5(b), wherein G is $C_3$-$C_6$cycloalkenyl substituted with 0-2 $T^1$ and 0-1 $T^2$.

Embodiment 5(e) of this disclosure relates to Embodiment 5, 5(a) or 5(b), wherein G is a 5-9 membered bridged carbocylic ring substituted with 0-2 $T^1$ and 0-1 $T^2$.

Embodiment 5(f) of this disclosure relates to Embodiment 5, 5(a) or 5(b), wherein G is a 5-9 membered carbocyclic spiro ring containing two cycloalkyl groups joined by one common spiro carbon atom, wherein the carbocyclic spiro ring is substituted with 0-2 $T^1$ and 0-1 $T^2$.

Embodiment 5(g) of this disclosure relates to Embodiment 5, 5(a) or 5(b), wherein G is a 6-9 membered heterocyclic spiro ring containing two cyclic groups with at least one heteroatom, wherein the two cyclic groups are joined by one common spiro carbon atom, wherein the heterocyclic spiro ring is substituted with 0-2 $T^5$, 0-1 $T^6$.

Embodiment 5(h) of this disclosure relates to Embodiment 5, 5(a) or 5(b), wherein G is phenyl substituted with 0-2 $T^1$ and 0-1 $T^4$.

Embodiment 5(i) of this disclosure relates to Embodiment 5, 5(a) or 5(b), wherein G is a 4-6 membered heterocycloalkyl substituted with 0-2 $T^5$ and 0-1 $T^6$.

Embodiment 5(j) of this disclosure relates to Embodiment 5, 5(a) or 5(b), wherein G is a 4-6 membered heterocycloalkenyl substituted with 0-2 $T^5$ and 0-1 $T^6$.

Embodiment 5(k) of this disclosure relates to Embodiment 5, 5(a) or 5(b), wherein G is a 5-9 membered bridged heterocylic ring substituted with 0-2 $T^5$ and 0-1 $T^6$.

Embodiment 5(l) of this disclosure relates to Embodiment 5, 5(a) or 5(b), wherein G is a 5-6 membered heteroaryl substituted with 0-2 $T^5$ and 0-1 $T^3$.

Embodiment 5(m) of this disclosure relates to the compound according to Embodiment 5, 5(a), 5(b), 5(c), 5(d), 5(e) or 5(f), wherein $T^2$ is —$(CH_2)_{0-1}$—$N(R^9)SO_2$—$R^7$.

Embodiment 5(n) of this disclosure relates to the compound according to Embodiment 5, 5(a), 5(b), 5(c), 5(d), 5(e) or 5(f), wherein $T^2$ is —$(CH_2)_{0-1}$—$SO_2$—$R^7$.

Embodiment 5(o) of this disclosure relates to the compound according to Embodiment 5, 5(a), 5(b), 5(c), 5(d), 5(e) or 5(f), wherein $T^2$ is —$(CH_2)_{0-1}$—$SO_2N(R^8)R^9$.

Embodiment 5(p) of this disclosure relates to the compound according to Embodiment 5, 5(a), 5(b), 5(c), 5(d), 5(e) or 5(f), wherein $T^2$ is —$(CH_2)_{0-1}$—$N(R^9)SO_2N(R^8)R^9$.

Embodiment 5(q) of this disclosure relates to the compound according to Embodiment 5, 5(a), 5(b), 5(c), 5(d), 5(e) or 5(f), wherein $T^2$ is —$(CH_2)_{0-1}$—$N(R^9)C(O)N(R^8)R^9$.

Embodiment 5(r) of this disclosure relates to the compound according to Embodiment 5, 5(a), 5(b), 5(c), 5(d), 5(e) or 5(f), wherein $T^2$ is —$(CH_2)_{0-1}$—$N(R^9)C(O)R^8$.

Embodiment 5(s) of this disclosure relates to the compound according to Embodiment 5, 5(a), 5(b), 5(c), 5(d), 5(e) or 5(f), wherein $T^2$ is —$(CH_2)_{0-1}$—$N(R^9)C(O)OR^9$.

Embodiment 5(t) of this disclosure relates to the compound according to Embodiment 5, 5(a), 5(b), 5(c), 5(d), 5(e) or 5(f), wherein $T^2$ is —$(CH_2)_{0-1}$—$N(R^8)R^9$.

Embodiment 5(u) of this disclosure relates to the compound according to Embodiment 5, 5(a), 5(b), 5(c), 5(d), 5(e) or 5(f), wherein $T^2$ is —$(CH_2)_{0-1}$—$C(O)N(R^8)R^9$.

Embodiment 5(v) of this disclosure relates to the compound according to Embodiment 5, 5(a), 5(b), 5(c), 5(d), 5(e) or 5(f), wherein $T^2$ is —$(CH_2)_{0-1}$—$C(O)OR^9$.

Embodiment 5(w) of this disclosure relates to the compound according to Embodiment 5, 5(a), 5(b), 5(c), 5(d), 5(e) or 5(f), wherein $T^2$ is —$(CH_2)_{0-1}$—$C(O)R^{10}$.

Embodiment 5(x) of this disclosure relates to the compound according to Embodiment 5, 5(a), 5(b), 5(c), 5(d), 5(e) or 5(f), wherein $T^2$ is —$(CH_2)_{0-1}$—$C(O)H$.

Embodiment 5(y) of this disclosure relates to the compound according to Embodiment 5, 5(a), 5(b), 5(c), 5(d), 5(e) or 5(f), wherein $T^2$ is —$(CH_2)_{0-1}$—$N(R^9)C(O)R^{10}$.

Embodiment 5(z) of this disclosure relates to the compound according to Embodiment 5, 5(a), 5(b), 5(c), 5(d), 5(e) or 5(f), wherein $T^2$ is —$(CH_2)_{0-2}C_3$-$C_6$cycloalkyl optionally substituted with 1-3 $Z^3$.

Embodiment 5(aa) of this disclosure relates to the compound according to Embodiment 5, 5(a), 5(b), 5(c), 5(d), 5(e) or 5(f), wherein $T^2$ is —$(CH_2)_{0-1}$-phenyl optionally substituted with 1-3 $Z^5$.

Embodiment 5(ab) of this disclosure relates to the compound according to Embodiment 5, 5(a), 5(b), 5(c), 5(d), 5(e) or 5(f), wherein $T^2$ is —$(CH_2)_{0-1}$-5-6 membered heteroaryl optionally substituted with 1-3 $Z^5$.

Embodiment 5(ac) of this disclosure relates to the compound according to Embodiment 5, 5(a), 5(b), or 5(l), wherein $T^3$ is —$(CH_2)_{0-2}$—$C(O)N(R^8)R^9$.

Embodiment 5(ad) of this disclosure relates to the compound according to Embodiment 5, 5(a), 5(b), or 5(l), wherein $T^3$ is —$(CH_2)_{0-2}$—$N(R^8)R^9$, provided that when $T^3$ is attached to a heteroatom of G, G is not attached to —$N(R^8)R^9$.

Embodiment 5(ae) of this disclosure relates to the compound according to Embodiment 5, 5(a), 5(b), or 5(l), wherein $T^3$ is —$(CH_2)_{0-2}$—$C(O)OR^9$.

Embodiment 5(af) of this disclosure relates to the compound according to Embodiment 5, 5(a), 5(b), or 5(l), wherein $T^3$ is —$(CH_2)_{0-2}$—$C_3$-$C_6$cycloalkyl optionally substituted with 1-3 $Z^5$ and 0-2 $Z^1$.

Embodiment 5(ag) of this disclosure relates to the compound according to Embodiment 5, 5(a), 5(b), or 5(l), wherein $T^3$ is —$(CH_2)_{0-2}$-5-6 membered heterocycloalkyl optionally substituted with 1-3 $Z^5$ and 0-1 $Z^1$, provided that when $T^3$ is attached to a heteroatom of G, G is not attached to an oxygen or nitrogen atom of the 5-6 membered heterocycloalkyl.

Embodiment 5(ah) of this disclosure relates to the compound according to Embodiment 5, 5(a), 5(b), or 5(l), wherein $T^3$ is —O—5-6 membered heterocycloalkyl optionally substituted with 4-chloropyridazin-3-one-5-yl.

Embodiment 5(ai) of this disclosure relates to the compound according to Embodiment 5, 5(a), 5(b), or 5(l), wherein $T^3$ is —$(CH_2)_{0-2}$-5-9 membered bridged carbocyclic ring optionally substituted with 1-3 $Z^5$ and 0-1 $Z^1$.

Embodiment 5(aj) of this disclosure relates to the compound according to Embodiment 5, 5(a), 5(b), or 5(h), wherein $T^4$ is —$(CH_2)_{0-1}C(O)OR^9$.

Embodiment 5(ak) of this disclosure relates to the compound according to Embodiment 5, 5(a), 5(b), or 5(h), wherein $T^4$ is —$(CH_2)_{0-1}$—$N(R^9)C(O)R^8$.

Embodiment 5(al) of this disclosure relates to the compound according to Embodiment 5, 5(a), 5(b), or 5(h), wherein $T^4$ is —$(CH_2)_{0-1}$—$N(R^9)SO_2$—R, Embodiment 5(am) of this disclosure relates to the compound according to Embodiment 5, 5(a), 5(b), or 5(h), wherein $T^4$ is —$(CH_2)_{0-1}$—$SO_2$—$R^7$.

Embodiment 5(an) of this disclosure relates to the compound according to Embodiment 5, 5(a), 5(b), or 5(h), wherein $T^4$ is —$(CH_2)_{0-1}$—$SO_2N(R^8)R^9$.

Embodiment 5(ao) of this disclosure relates to the compound according to Embodiment 5, 5(a), 5(b), or 5(h), wherein $T^4$ is —$(CH_2)_{0-1}$—$N(R^9)C(O)N(R^8)R^9$.

Embodiment 5(ap) of this disclosure relates to the compound according to Embodiment 5, 5(a), 5(b), or 5(h), wherein $T^4$ is $N(R^a)_2$.

Embodiment 5(aq) of this disclosure relates to the compound according to Embodiment 5, 5(a), 5(b), 5(g), 5(i), 5(j) or 5(k), wherein $T^6$ is —$(CH_2)_{0-1}$—$N(R^9)SO_2$—$R^7$, provided that when $T^6$ is attached to a heteroatom of G, G is not attached to —$N(R^9)SO_2$—$R^7$.

Embodiment 5(ar) of this disclosure relates to the compound according to Embodiment 5, 5(a), 5(b), 5(g), 5(i), 5(j) or 5(k), wherein $T^6$ is —$(CH_2)_{0-1}$—$SO_2$—$R^7$.

Embodiment 5(as) of this disclosure relates to the compound according to Embodiment 5, 5(a), 5(b), 5(g), 5(i), 5(j) or 5(k), wherein $T^6$ is —$(CH_2)_{0-1}$—$SO_2N(R^8)R^9$.

Embodiment 5(at) of this disclosure relates to the compound according to Embodiment 5, 5(a), 5(b), 5(g), 5(i), 5(j) or 5(k), wherein $T^6$ is —$(CH_2)_{0-1}$—$N(R^9)SO_2N(R^8)R^9$, provided that when $T^6$ is attached to a heteroatom of G, G is not attached to —$N(R^9)SO_2N(R^8)R^9$.

Embodiment 5(au) of this disclosure relates to the compound according to Embodiment 5, 5(a), 5(b), 5(g), 5(i), 5(j) or 5(k), wherein $T^6$ is —$(CH_2)_{0-1}$—$N(R^9)C(O)N(R^8)R^9$, provided that when $T^6$ is attached to a heteroatom of G, G is not attached to —$N(R^9)C(O)N(R^8)R^9$.

Embodiment 5(av) of this disclosure relates to the compound according to Embodiment 5, 5(a), 5(b), 5(g), 5(i), 5(j) or 5(k), wherein $T^6$ is —$(CH_2)_{0-1}$—$N(R^9)C(O)R^8$, provided that when $T^6$ is attached to a heteroatom of G, G is not attached to —$N(R^9)C(O)R^8$.

Embodiment 5(aw) of this disclosure relates to the compound according to Embodiment 5, 5(a), 5(b), 5(g), 5(i), 5(j) or 5(k), wherein $T^6$ is —$(CH_2)_{0-1}$—$N(R^9)C(O)OR^9$, provided that when $T^6$ is attached to a heteroatom of G, G is not attached to —$N(R^9)C(O)OR^9$.

Embodiment 5(ax) of this disclosure relates to the compound according to Embodiment 5, 5(a), 5(b), 5(g), 5(i), 5(j) or 5(k), wherein $T^6$ is —$(CH_2)_{0-1}$—$N(R^8)R^9$, provided that when $T^6$ is attached to a heteroatom of G, G is not attached to —$N(R^8)R^9$.

Embodiment 5(ay) of this disclosure relates to the compound according to Embodiment 5, 5(a), 5(b), 5(g), 5(i), 5(j) or 5(k), wherein $T^6$ is —$(CH_2)_{0-1}$—$C(O)$—$N(R^8)R^9$.

Embodiment 5(az) of this disclosure relates to the compound according to Embodiment 5, 5(a), 5(b), 5(g), 5(i), 5(j) or 5(k), wherein $T^6$ is —$(CH_2)_{0-1}$—$C(O)OR^9$.

Embodiment 5(ba) of this disclosure relates to the compound according to Embodiment 5, 5(a), 5(b), 5(g), 5(i), 5(j) or 5(k), wherein $T^6$ is —$(CH_2)_{0-1}$—$C(O)R^{10}$.

Embodiment 5(bb) of this disclosure relates to the compound according to Embodiment 5, 5(a), 5(b), 5(g), 5(i), 5(j) or 5(k), wherein $T^6$ is —$(CH_2)_{0-1}$—$N(R^9)C(O)R^{10}$, provided that when $T^6$ is attached to a heteroatom of G, G is not attached to —$N(R^9)C(O)R^{10}$.

Embodiment 5(bc) of this disclosure relates to the compound according to Embodiment 5, 5(a), 5(b), 5(g), 5(i), 5(j) or 5(k), wherein $T^6$ is —N(H)C(H)C=O, provided that $T^6$ is not attached to a heteroatom of G.

Embodiment 5(bd) of this disclosure relates to the compound according to Embodiment 5, 5(a), 5(b), 5(g), 5(i), 5(j) or 5(k), wherein $T^6$ is —$(CH_2)_{0-1}$—$C_3$-$C_6$cycloalkyl optionally substituted with 1-4 $Z^3$.

Embodiment 5(be) of this disclosure relates to the compound according to Embodiment 5, 5(a), 5(b), 5(g), 5(i), 5(j) or 5(k), wherein $T^6$ is —$(CH_2)_{0-1}$-5-6 membered heterocycloalkyl optionally substituted with 1-4 $Z^3$, provided that when $T^6$ is attached to a heteroatom of G, G is not attached to a heteroatom of 5-6 membered heteroaryl.

Embodiment 5(bf) of this disclosure relates to the compound according to Embodiment 5, 5(a), 5(b), 5(g), 5(i), 5(j) or 5(k), wherein $T^6$ is —$(CH_2)_{0-1}$-5-6 membered heteroaryl optionally substituted with 1-3 $Z^5$, provided that when $T^6$ is attached to a heteroatom of G, G is not attached to a heteroatom of 5-6 membered heteroaryl.

Embodiment 5(bg) relates to any one of Embodiments 5, 5(a), 5(b), 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(y), 5(z), 5(aa), 5(ab), 5(ac), 5(ad), 5(ae), 5(af), 5(ag), 5(ah), 5(ai), 5(aj), 5(ak), 5(al), 5(am), 5(an), 5(ao), 5(ap), 5(aq), 5(ar), 5(as), 5(at), 5(au), 5(av), 5(aw), 5(ax), 5(ay), 5(az), 5(ba), 5(bb), 5(bc), 5(bd), 5(be) or 5(bf), wherein $R^1$ is hydrogen.

Embodiment 5(bh) relates to any one of Embodiments 5, 5(a), 5(b), 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(y), 5(z), 5(aa), 5(ab), 5(ac), 5(ad), 5(ae), 5(af), 5(ag), 5(ah), 5(ai), 5(aj), 5(ak), 5(al), 5(am), 5(an), 5(ao), 5(ap), 5(aq), 5(ar), 5(as), 5(at), 5(au), 5(av), 5(aw), 5(ax), 5(ay), 5(az), 5(ba), 5(bb), 5(bc), 5(bd), 5(be) or 5(bf), wherein $R^1$ is $C_2$-$C_4$alkyl substituted with 0-4 hydroxyl.

Embodiment 5(bi) relates to any one of Embodiments 5, 5(a), 5(b), 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(y), 5(z), 5(aa), 5(ab), 5(ac), 5(ad), 5(ae), 5(af), 5(ag), 5(ah), 5(ai), 5(aj), 5(ak), 5(al), 5(am), 5(an), 5(ao), 5(ap), 5(aq), 5(ar), 5(as), 5(at), 5(au), 5(av), 5(aw), 5(ax), 5(ay), 5(az), 5(ba), 5(bb), 5(bc), 5(bd), 5(be) or 5(bf), wherein $R^2$ is halogen.

Embodiment 5(bj) relates to any one of Embodiments 5, 5(a), 5(b), 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(y), 5(z), 5(aa), 5(ab), 5(ac), 5(ad), 5(ae), 5(af), 5(ag), 5(ah), 5(ai), 5(aj), 5(ak), 5(al), 5(am), 5(an), 5(ao), 5(ap), 5(aq), 5(ar), 5(as), 5(at), 5(au), 5(av), 5(aw), 5(ax), 5(ay), 5(az), 5(ba), 5(bb), 5(bc), 5(bd), 5(be) or 5(bf), wherein $R^2$ is CN.

Embodiment 5(bk) relates to any one of Embodiments 5, 5(a), 5(b), 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(y), 5(z), 5(aa), 5(ab), 5(ac), 5(ad), 5(ae), 5(af), 5(ag), 5(ah), 5(ai), 5(aj), 5(ak), 5(al), 5(am), 5(an), 5(ao), 5(ap), 5(aq), 5(ar), 5(as), 5(at), 5(au), 5(av), 5(aw), 5(ax), 5(ay), 5(az), 5(ba), 5(bb), 5(bc), 5(bd), 5(be) or 5(bf), wherein $R^3$ is H.

Embodiment 6 of this embodiment relates to the compound according to any of the preceding Embodiments 1, 2, 3, 4 or 5, wherein $R^1$ is hydrogen.

Embodiment 7 of this embodiment relates to the compound according to any of Embodiments 1, 2, 3, 4, or 5, wherein $R^1$ is $C_1$-$C_4$alkoxy$C_1$-$C_4$alkyl, $C_2$-$C_4$alkenyl substituted with 1-3 $Z^2$, or $C_2$-$C_4$alkyl substituted with 1-3 $Z^2$;

Embodiment 8 of this disclosure relates to the compound according to any of Embodiments 1, 2, 3, 4, or 5, wherein
$R^1$ is —$CH_2CH_2OH$, —$CH_2CH_2CH_2OH$, —$CH_2CH(OH)CH_2OH$, or —$CH_2CH(CH_3)OH$;
$R^2$ is Cl, Br, $CF_3$, or CN; and
E is pyridyl, phenyl, pyrimidinyl, or pyridazinyl.

Subembodiments of Embodiment 8

Embodiment 8(a) of this disclosure relates to Embodiment 8 wherein $R^1$ is —$CH_2CH_2OH$; $R^2$ is Cl; and E is pyridyl.

Embodiment 8(b) of this disclosure relates to Embodiment 8 wherein $R^1$ is —$CH_2CH_2CH_2OH$; $R^2$ is Cl; and E is pyridyl.

Embodiment 8(c) of this disclosure relates to Embodiment 8 wherein $R^1$ is —$CH_2CH(OH)CH_2OH$; $R^2$ is Cl; and E is pyridyl.

Embodiment 8(d) of this disclosure relates to Embodiment 8 wherein $R^1$ is —$CH_2CH(CH_3)OH$; $R^2$ is Cl; and E is pyridyl.

Embodiment 9 of this disclosure relates to the compound according to Embodiment 8, wherein $R^2$ is Cl.

Embodiment 10 of this disclosure relates to the compound according to any one of Embodiments 1, 2, 3, 4, or 5, wherein
- $R^1$ is H;
- $R^2$ is Cl, Br, $CF_3$, or CN;
- $R^4$ is halogen; and
- E is pyridyl, phenyl, pyrimidinyl, or pyridazinyl.

Subembodiment of Embodiment 10

Embodiment 10(a) of this disclosure relates to Embodiment 10 wherein E is pyridyl.

Embodiment 11 of this disclosure relates to the compound according to Embodiment 10, wherein $R^2$ is Cl.

Embodiment 12 of this disclosure relates to a compound according to any of Embodiments 1-5 having any one of the following formulae:

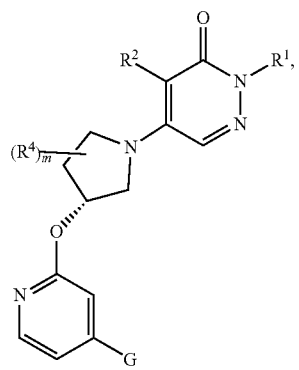

IV(a)

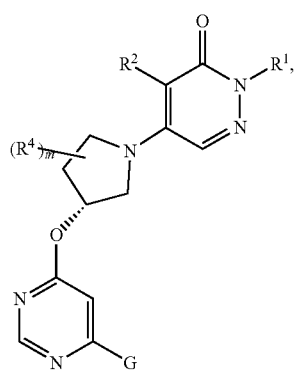

IV(b)

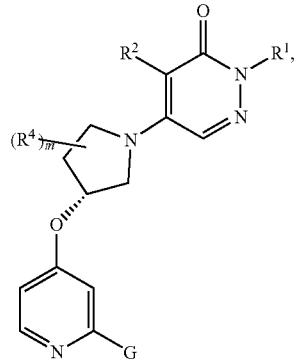

IV(c)

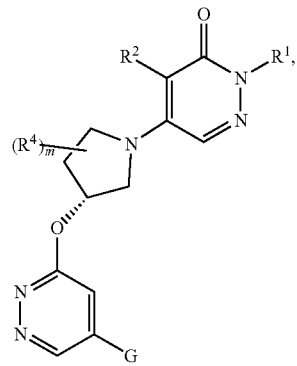

IV(d)

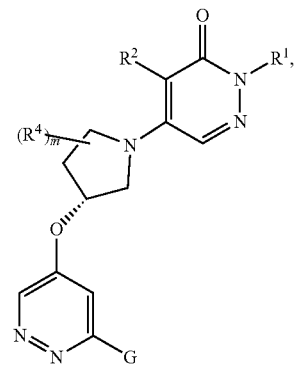

IV(e)

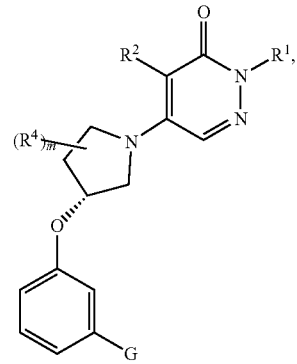

IV(f)

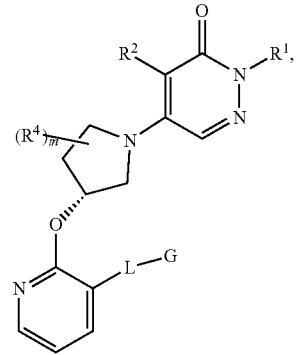

IV(g)

-continued

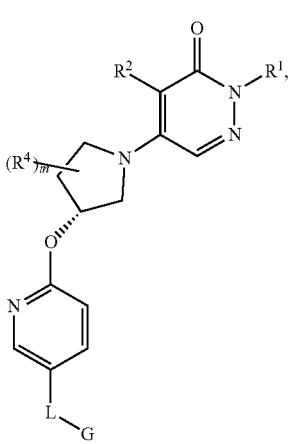

(IVh)

Subembodiments of Embodiment 12

Embodiment 12(a) of this disclosure relates to Embodiment 12, wherein G is $C_3$-$C_6$cycloalkyl substituted with 0-2 $T^1$ and 0-1 $T^2$.

Embodiment 12(b) of this disclosure relates to Embodiment 12, wherein G is $C_3$-$C_6$cycloalkenyl substituted with 0-2 $T^1$ and 0-1 $T^2$.

Embodiment 12(c) of this disclosure relates to Embodiment 12, wherein G is a 5-9 membered bridged carbocylic ring substituted with 0-2 $T^1$ and 0-1 $T^2$.

Embodiment 12(d) of this disclosure relates to Embodiment 12, wherein G is a 5-9 membered carbocyclic spiro ring containing two cycloalkyl groups joined by one common spiro carbon atom, wherein the carbocyclic spiro ring is substituted with 0-2 $T^1$ and 0-1 $T^2$.

Embodiment 12(e) of this disclosure relates to Embodiment 12, wherein G is a 6-9 membered heterocyclic spiro ring containing two cyclic groups with at least one heteroatom, wherein the two cyclic groups are joined by one common spiro carbon atom, wherein the heterocyclic spiro ring is substituted with 0-2 $T^5$, 0-1 $T^6$.

Embodiment 12(f) of this disclosure relates to Embodiment 12, wherein G is phenyl substituted with 0-2 $T^1$ and 0-1 $T^4$.

Embodiment 12(g) of this disclosure relates to Embodiment 12, wherein G is a 4-6 membered heterocycloalkyl substituted with 0-2 $T^5$ and 0-1 $T^6$.

Embodiment 12(h) of this disclosure relates to Embodiment 12, wherein G is a 4-6 membered heterocycloalkenyl substituted with 0-2 $T^5$ and 0-1 $T^6$.

Embodiment 12(i) of this disclosure relates to Embodiment 12, wherein G is a 5-9 membered bridged heterocylic ring substituted with 0-2 $T^5$ and 0-1 $T^6$.

Embodiment 12(j) of this disclosure relates to Embodiment 12, wherein G is a 5-6 membered heteroaryl substituted with 0-2 $T^5$ and 0-1 $T^3$.

Embodiment 12(k) of this disclosure relates to the compound according to Embodiment 12, 12(a), 12(b), 12(c) or 12(d), wherein $T^2$ is —$(CH_2)_{0-1}$—N($R^9$)$SO_2$—$R^7$.

Embodiment 12(l) of this disclosure relates to the compound according to Embodiment 12, 12(a), 12(b), 12(c) or 12(d), wherein $T^2$ is —$(CH_2)_{0-1}$—$SO_2$—$R^7$.

Embodiment 12(m) of this disclosure relates to the compound according to Embodiment 12, 12(a), 12(b), 12(c) or 12(d), wherein $T^2$ is —$(CH_2)_{0-1}$—$SO_2$N($R^8$)$R^9$.

Embodiment 12(n) of this disclosure relates to the compound according to Embodiment 12, 12(a), 12(b), 12(c) or 12(d), wherein $T^2$ is —$(CH_2)_{0-1}$—N($R^9$)$SO_2$N($R^8$)$R^9$.

Embodiment 12(o) of this disclosure relates to the compound according to Embodiment 12, 12(a), 12(b), 12(c) or 12(d), wherein $T^2$ is —$(CH_2)_{0-1}$—N($R^9$)C(O)N($R^8$)$R^9$.

Embodiment 12(p) of this disclosure relates to the compound according to Embodiment 12, 12(a), 12(b), 12(c) or 12(d), wherein $T^2$ is —$(CH_2)_{0-1}$—N($R^9$)C(O)$R^8$.

Embodiment 12(q) of this disclosure relates to the compound according to Embodiment 12, 12(a), 12(b), 12(c) or 12(d), wherein $T^2$ is —$(CH_2)_{0-1}$—N($R^9$)C(O)O$R^9$.

Embodiment 12(r) of this disclosure relates to the compound according to Embodiment 12, 12(a), 12(b), 12(c) or 12(d), wherein $T^2$ is —$(CH_2)_{0-1}$—N($R^8$)$R^9$.

Embodiment 12(s) of this disclosure relates to the compound according to Embodiment 12, 12(a), 12(b), 12(c) or 12(d), wherein $T^2$ is —$(CH_2)_{0-1}$—C(O)N($R^8$)$R^9$.

Embodiment 12(t) of this disclosure relates to the compound according to Embodiment 12, 12(a), 12(b), 12(c) or 12(d), wherein $T^2$ is —$(CH_2)_{0-1}$—C(O)O$R^9$.

Embodiment 12(u) of this disclosure relates to the compound according to Embodiment 12, 12(a), 12(b), 12(c) or 12(d), wherein $T^2$ is —$(CH_2)_{0-1}$—C(O)$R^{10}$.

Embodiment 12(v) of this disclosure relates to the compound according to Embodiment 12, 12(a), 12(b), 12(c) or 12(d), wherein $T^2$ is —$(CH_2)_{0-1}$—C(O)H.

Embodiment 12(w) of this disclosure relates to the compound according to Embodiment 12, 12(a), 12(b), 12(c) or 12(d), wherein $T^2$ is —$(CH_2)_{0-1}$—N($R^9$)C(O)$R^{10}$.

Embodiment 12(x) of this disclosure relates to the compound according to Embodiment 5, 12, 12(a), 12(b), 12(c) or 12(d), wherein $T^2$ is —$(CH_2)_{0-2}$$C_3$-$C_6$cycloalkyl optionally substituted with 1-3 $Z^3$.

Embodiment 12(y) of this disclosure relates to the compound according to 12, 12(a), 12(b), 12(c) or 12(d), wherein $T^2$ is —$(CH_2)_{0-1}$-phenyl optionally substituted with 1-3 $Z^5$.

Embodiment 12(z) of this disclosure relates to the compound according to 12, 12(a), 12(b), 12(c) or 12(d), wherein $T^2$ is —$(CH_2)_{0-1}$-5-6 membered heteroaryl optionally substituted with 1-3 $Z^5$.

Embodiment 12(aa) of this disclosure relates to the compound according to Embodiment 12 or 12(j), wherein $T^3$ is —$(CH_2)_{0-2}$—C(O)N($R^8$)$R^9$.

Embodiment 12(ab) of this disclosure relates to the compound according to Embodiment 12 or 12(j), wherein $T^3$ is —$(CH_2)_{0-2}$—N($R^8$)$R^9$, provided that when $T^3$ is attached to a heteroatom of G, G is not attached to —N($R^8$)$R^9$.

Embodiment 12(ac) of this disclosure relates to the compound according to Embodiment 12 or 12(j), wherein $T^3$ is —$(CH_2)_{0-2}$—C(O)O$R^9$.

Embodiment 12(ad) of this disclosure relates to the compound according to Embodiment 12 or 12(j), wherein $T^3$ is —$(CH_2)_{0-2}$—$C_3$-$C_6$cycloalkyl optionally substituted with 1-3 $Z^5$ and 0-1 $Z^1$.

Embodiment 12(ae) of this disclosure relates to the compound according to Embodiment 12 or 12(j), wherein $T^3$ is —$(CH_2)_{0-2}$-5-6 membered heterocycloalkyl optionally substituted with 1-3 $Z^5$ and 0-1 $Z^1$, provided that when $T^3$ is attached to a heteroatom of G, G is not attached to an oxygen or nitrogen atom of the 5-6 membered heterocycloalkyl.

Embodiment 12(af) of this disclosure relates to the compound according to Embodiment 12 or 12(j), wherein $T^3$ is —O—5-6 membered heterocycloalkyl optionally substituted with 4-chloropyridazin-3-one-5-yl.

Embodiment 12(ag) of this disclosure relates to the compound according to Embodiment 12 or 12(j), wherein $T^3$ is —(CH$_2$)$_{0-2}$-5-9 membered bridged carbocyclic ring optionally substituted with 1-3 Z$^5$ and 0-1 Z$^1$.

Embodiment 12(ah) of this disclosure relates to the compound according to Embodiment 12 or 12(j), wherein T$^4$ is —(CH$_2$)$_{0-1}$C(O)OR$^9$.

Embodiment 12(ai) of this disclosure relates to the compound according to Embodiment 12 or 12(j), wherein T$^4$ is —(CH$_2$)$_{0-1}$—N(R$^9$)C(O)R$^8$.

Embodiment 12(aj) of this disclosure relates to the compound according to Embodiment 12 or 12(j), wherein T$^4$ is —(CH$_2$)$_{0-1}$—N(R$^9$)SO$_2$—R, Embodiment 12(ak) of this disclosure relates to the compound according to Embodiment 12 or 12(j), wherein T$^4$ is —(CH$_2$)$_{0-1}$—SO$_2$—R$^7$.

Embodiment 12(al) of this disclosure relates to the compound according to Embodiment 12 or 12(j), wherein T$^4$ is —(CH$_2$)$_{0-1}$—SO$_2$N(R$^8$)R$^9$.

Embodiment 12(am) of this disclosure relates to the compound according to Embodiment 12 or 12(j), wherein T$^4$ is —(CH$_2$)$_{0-1}$—N(R$^9$)C(O)N(R$^8$)R$^9$.

Embodiment 12(an) of this disclosure relates to the compound according to Embodiment 12 or 12(j), wherein T$^4$ is N(R$^a$)$_2$.

Embodiment 12(ao) of this disclosure relates to the compound according to Embodiment 12, 12(e), 12(g), 12(h) or 12(i), wherein T$^6$ is —(CH$_2$)$_{0-1}$—N(R$^9$)SO$_2$—R$^7$, provided that when T$^6$ is attached to a heteroatom of G, G is not attached to —N(R$^9$)SO$_2$—R$^7$.

Embodiment 12(ap) of this disclosure relates to the compound according to Embodiment 12, 12(e), 12(g), 12(h) or 12(i), wherein T$^6$ is —(CH$_2$)$_{0-1}$—SO$_2$—R$^7$.

Embodiment 12(aq) of this disclosure relates to the compound according to Embodiment 12, 12(e), 12(g), 12(h) or 12(i), wherein T$^6$ is —(CH$_2$)$_{0-1}$—SO$_2$N(R$^8$)R$^9$.

Embodiment 12(ar) of this disclosure relates to the compound according to Embodiment 12, 12(e), 12(g), 12(h) or 12(i), wherein T$^6$ is —(CH$_2$)$_{0-1}$—N(R$^9$)SO$_2$N(R$^8$)R$^9$, provided that when T$^6$ is attached to a heteroatom of G, G is not attached to —N(R$^9$)SO$_2$N(R$^8$)R$^9$.

Embodiment 12(as) of this disclosure relates to the compound according to Embodiment 12, 12(e), 12(g), 12(h) or 12(i), wherein T$^6$ is —(CH$_2$)$_{0-1}$—N(R$^9$)C(O)N(R$^8$)R$^9$, provided that when T$^6$ is attached to a heteroatom of G, G is not attached to —N(R$^9$)C(O)N(R$^8$)R$^9$.

Embodiment 12(at) of this disclosure relates to the compound according to Embodiment 12, 12(e), 12(g), 12(h) or 12(i), wherein T$^6$ is —(CH$_2$)$_{0-1}$—N(R$^9$)C(O)R$^8$, provided that when T$^6$ is attached to a heteroatom of G, G is not attached to —N(R$^9$)C(O)R$^8$.

Embodiment 12(au) of this disclosure relates to the compound according to Embodiment 12, 12(e), 12(g), 12(h) or 12(i), wherein T$^6$ is —(CH$_2$)$_{0-1}$—N(R$^9$)C(O)OR$^9$, provided that when T$^6$ is attached to a heteroatom of G, G is not attached to —N(R$^9$)C(O)OR$^9$.

Embodiment 12(av) of this disclosure relates to the compound according to Embodiment 12, 12(e), 12(g), 12(h) or 12(i), wherein T$^6$ is —(CH$_2$)$_{0-1}$—N(R$^8$)R$^9$, provided that when T$^6$ is attached to a heteroatom of G, G is not attached to —N(R$^8$)R$^9$.

Embodiment 12(aw) of this disclosure relates to the compound according to Embodiment 12, 12(e), 12(g), 12(h) or 12(i), wherein T$^6$ is —(CH$_2$)$_{0-1}$—C(O)—N(R$^8$)R$^9$.

Embodiment 12(ax) of this disclosure relates to the compound according to Embodiment 12, 12(e), 12(g), 12(h) or 12(i), wherein T$^6$ is —(CH$_2$)$_{0-1}$—C(O)OR$^9$.

Embodiment 12(ay) of this disclosure relates to the compound according to Embodiment 12, 12(e), 12(g), 12(h) or 12(i), wherein T$^6$ is —(CH$_2$)$_{0-1}$—C(O)R$^{10}$.

Embodiment 12(az) of this disclosure relates to the compound according to Embodiment 12, 12(e), 12(g), 12(h) or 12(i), wherein T$^6$ is —(CH$_2$)$_{0-1}$—N(R$^9$)C(O)R$^{10}$, provided that when T$^6$ is attached to a heteroatom of G, G is not attached to —N(R$^9$)C(O)R$^{10}$.

Embodiment 12(ba) of this disclosure relates to the compound according to Embodiment 12, 12(e), 12(g), 12(h) or 12(i), wherein T$^6$ is —N(H)C(H)C=O, provided that T$^6$ is not attached to a heteroatom of G.

Embodiment 12(bb) of this disclosure relates to the compound according to Embodiment 12, 12(e), 12(g), 12(h) or 12(i), wherein T$^6$ is —(CH$_2$)$_{0-1}$—C$_3$-C$_6$cycloalkyl optionally substituted with 1-4 Z$^3$.

Embodiment 12(bc) of this disclosure relates to the compound according to Embodiment 12, 12(e), 12(g), 12(h) or 12(i), wherein T$^6$ is —(CH$_2$)$_{0-1}$-5-6 membered heterocycloalkyl optionally substituted with 1-4 Z$^3$, provided that when T$^6$ is attached to a heteroatom of G, G is not attached to a heteroatom of 5-6 membered heteroaryl.

Embodiment 12(bd) of this disclosure relates to the compound according to Embodiment 12, 12(e), 12(g), 12(h) or 12(i), wherein T$^6$ is —(CH$_2$)$_{0-1}$-5-6 membered heteroaryl optionally substituted with 1-3 Z$^5$, provided that when T$^6$ is attached to a heteroatom of G, G is not attached to a heteroatom of 5-6 membered heteroaryl.

Embodiment 12(be) relates to any one of Embodiments 12, 12(a), 12(b), 12(c), 12(d), 12(e), 12(f), 12(g), 12(h), 12(i), 12(j), 12(k), 12(l), 12(m), 12(n), 12(o), 12(p), 12(q), 12(r), 12(s), 12(t), 12(u), 12(v), 12(w), 12(x), 12(y), 12(z), 12(aa), 12(ab), 12(ac), 12(ad), 12(ae), 12(af), 12(ag), 12(ah), 12(ai), 12(aj), 12(ak), 12(al), 12(am), 12(an), 12(ao), 12(ap), 12(aq), 12(ar), 12(as), 12(at), 12(au), 12(av), 12(aw), 12(ax), 12(ay), 12(az), 12(ba), 12(bb), 12(bc) or 12(bd), wherein R$^1$ is hydrogen.

Embodiment 12(bf) relates to any one of Embodiments 12, 12(a), 12(b), 12(c), 12(d), 12(e), 12(f), 12(g), 12(h), 12(i), 12(j), 12(k), 12(l), 12(m), 12(n), 12(o), 12(p), 12(q), 12(r), 12(s), 12(t), 12(u), 12(v), 12(w), 12(x), 12(y), 12(z), 12(aa), 12(ab), 12(ac), 12(ad), 12(ae), 12(af), 12(ag), 12(ah), 12(ai), 12(aj), 12(ak), 12(al), 12(am), 12(an), 12(ao), 12(ap), 12(aq), 12(ar), 12(as), 12(at), 12(au), 12(av), 12(aw), 12(ax), 12(ay), 12(az), 12(ba), 12(bb), 12(bc) or 12(bd), wherein R$^1$ is C$_2$-C$_4$alkyl substituted with 0-4 hydroxyl.

Embodiment 12(bg) relates to any one of Embodiments 12, 12(a), 12(b), 12(c), 12(d), 12(e), 12(f), 12(g), 12(h), 12(i), 12(j), 12(k), 12(l), 12(m), 12(n), 12(o), 12(p), 12(q), 12(r), 12(s), 12(t), 12(u), 12(v), 12(w), 12(x), 12(y), 12(z), 12(aa), 12(ab), 12(ac), 12(ad), 12(ae), 12(af), 12(ag), 12(ah), 12(ai), 12(aj), 12(ak), 12(al), 12(am), 12(an), 12(ao), 12(ap), 12(aq), 12(ar), 12(as), 12(at), 12(au), 12(av), 12(aw), 12(ax), 12(ay), 12(az), 12(ba), 12(bb), 12(bc) or 12(bd), wherein R$^2$ is Cl.

Embodiment 12(bh) relates to any one of Embodiments 12, 12(a), 12(b), 12(c), 12(d), 12(e), 12(f), 12(g), 12(h), 12(i), 12(j), 12(k), 12(l), 12(m), 12(n), 12(o), 12(p), 12(q), 12(r), 12(s), 12(t), 12(u), 12(v), 12(w), 12(x), 12(y), 12(z), 12(aa), 12(ab), 12(ac), 12(ad), 12(ae), 12(af), 12(ag), 12(ah), 12(ai), 12(aj), 12(ak), 12(al), 12(am), 12(an), 12(ao), 12(ap), 12(aq), 12(ar), 12(as), 12(at), 12(au), 12(av), 12(aw), 12(ax), 12(ay), 12(az), 12(ba), 12(bb), 12(bc) or 12(bd), wherein R$^2$ is CN.

Embodiment 13 relates to a compound according to any of Embodiments 1-5 having any one of the following formulae:

V(a)
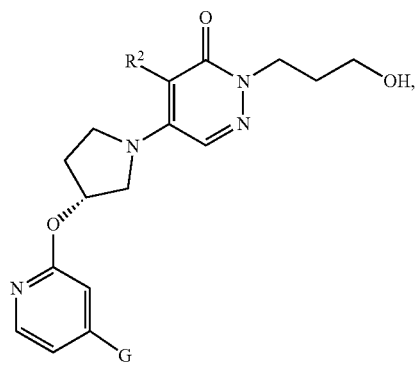
V(b)
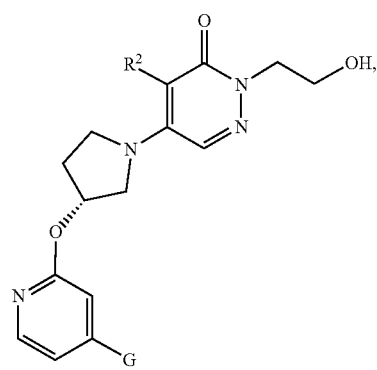
V(c)
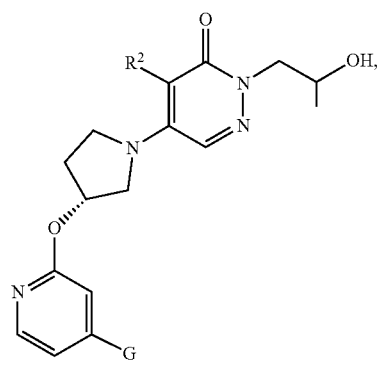
V(d)
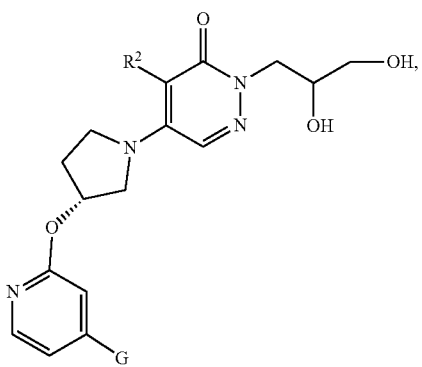
-continued
V(e)
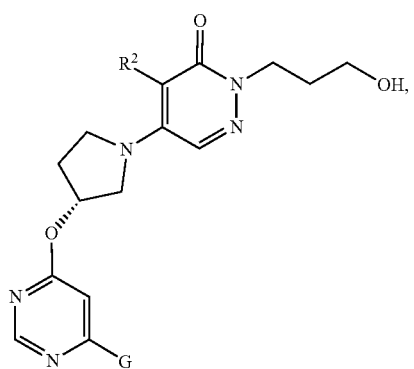
V(f)
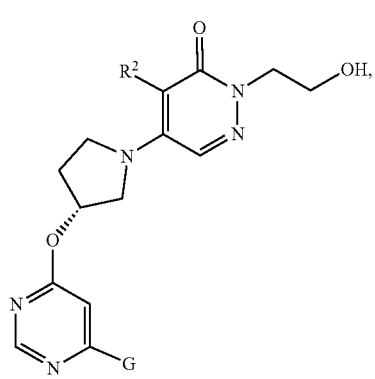
V(g)
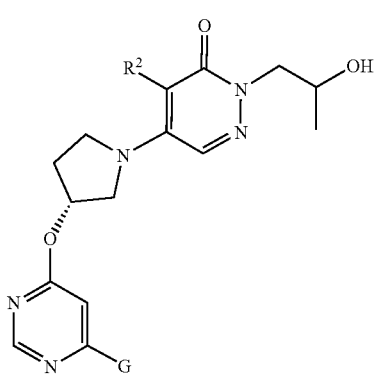
V(h)
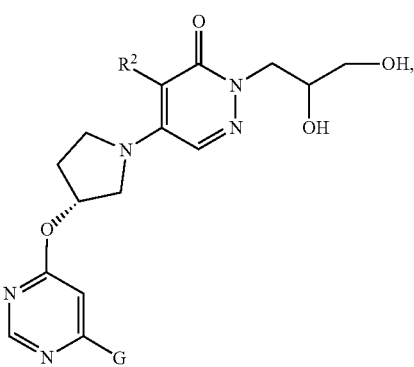

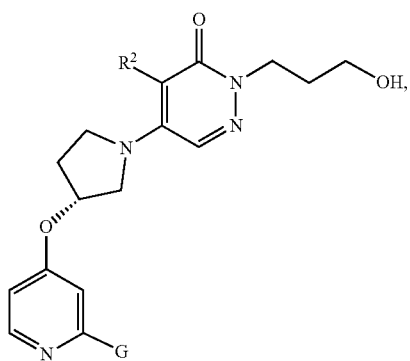
V(i)
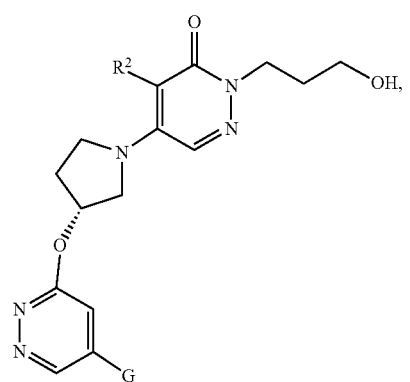
V(m)
V(j)
V(n)
V(k)
V(o)
V(l)
V(p)

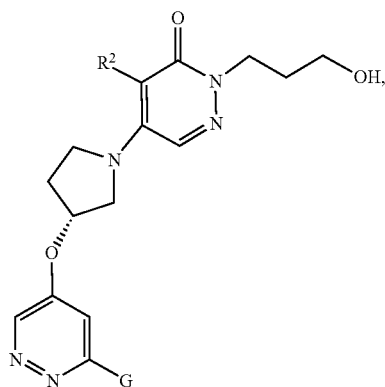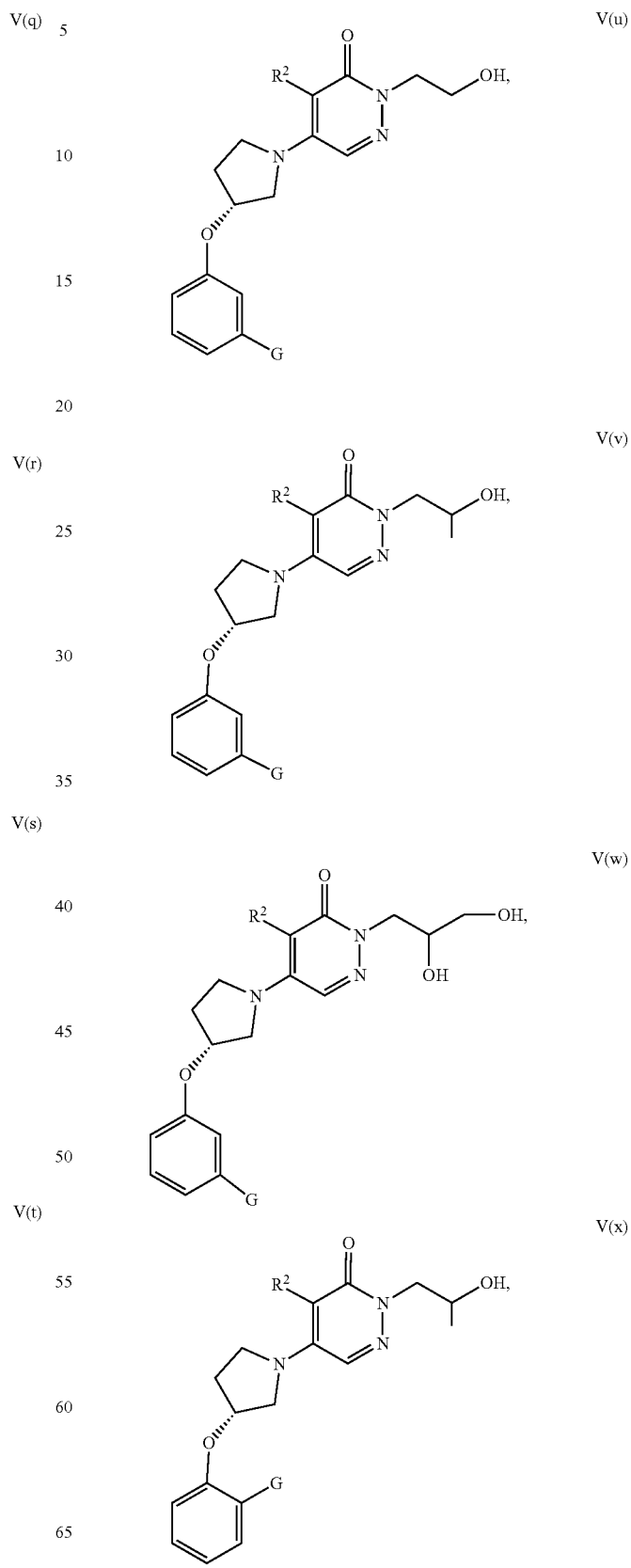

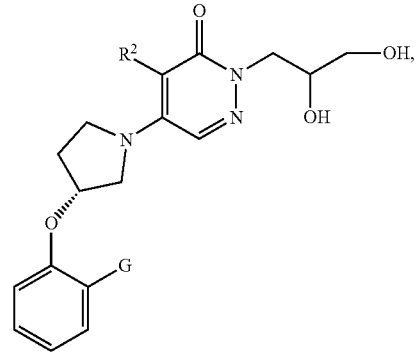
V(y)
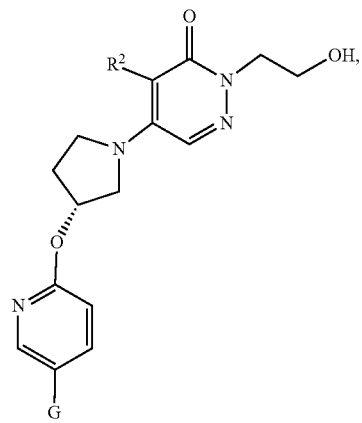
V(ac)
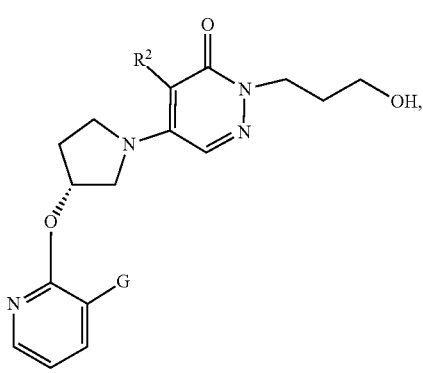
V(z)
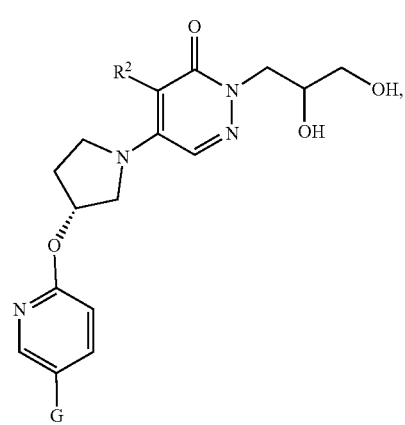
V(ad)
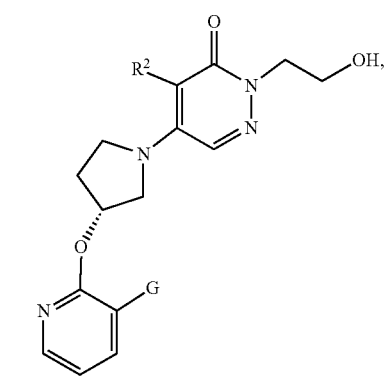
V(aa)
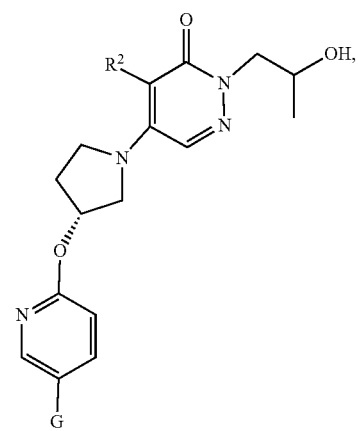
V(ae)
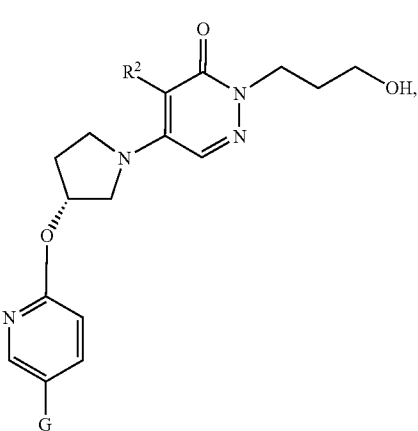
V(ab)
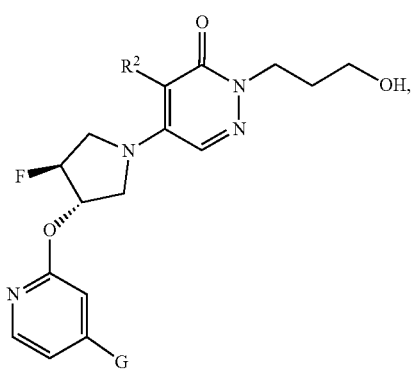
V(af)

V(ag)
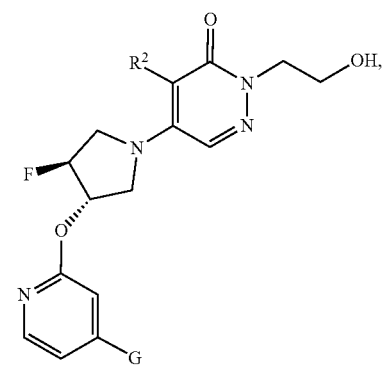
V(ah)
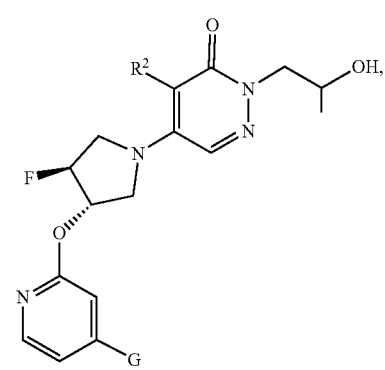
V(ai)
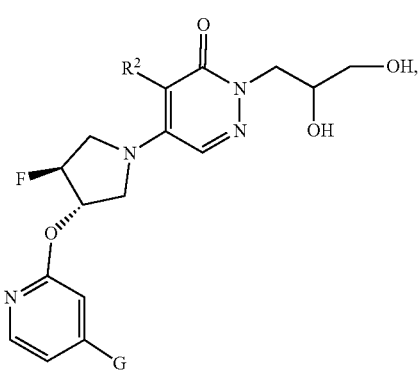
V(aj)
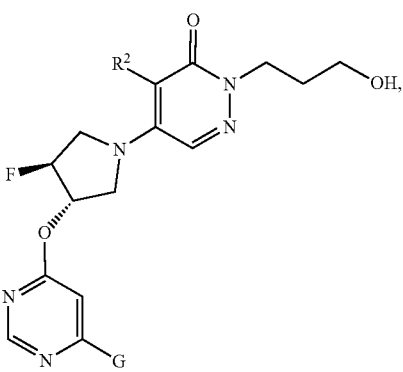
V(ak)
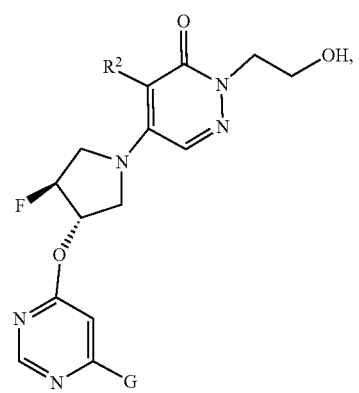
V(al)
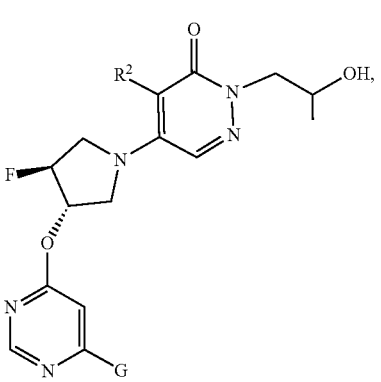
V(am)
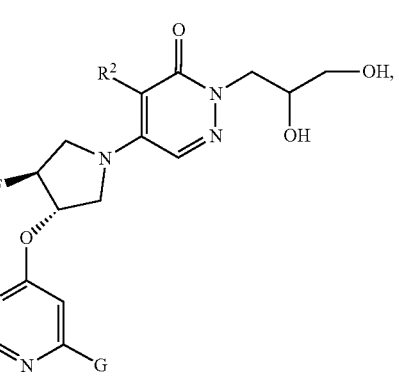
V(an)
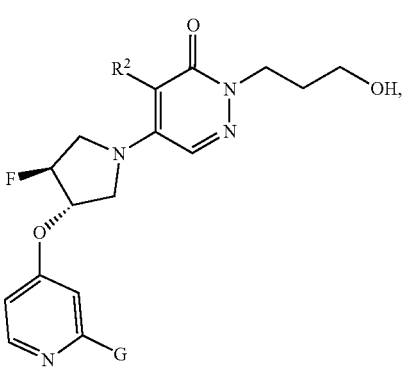

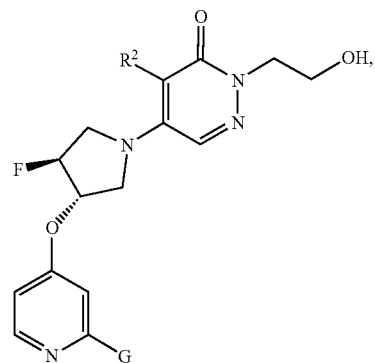
V(ao)
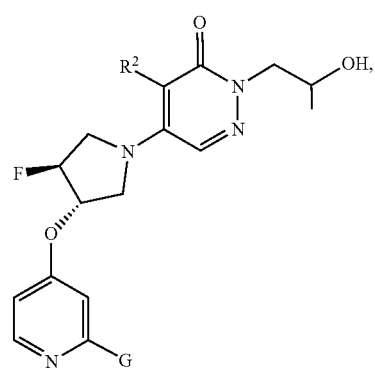
V(ap)
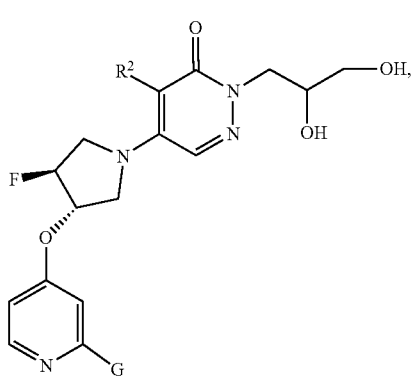
V(aq)
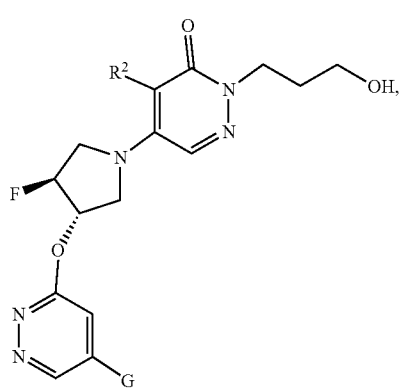
V(ar)
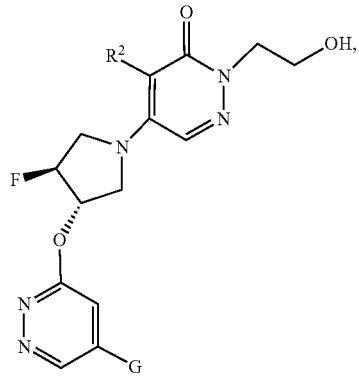
V(as)
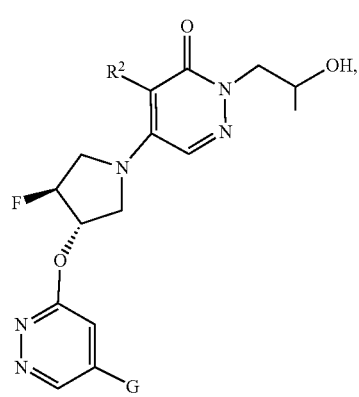
V(at)
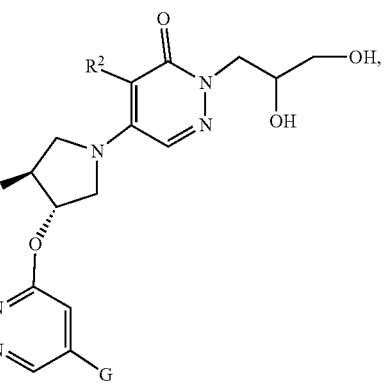
V(au)
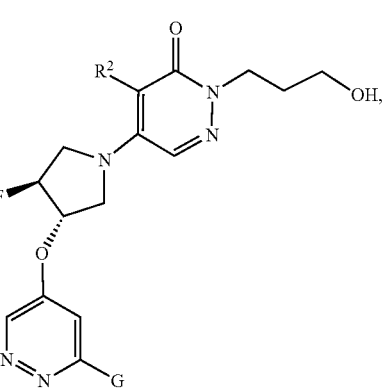
V(av)

V(aw) 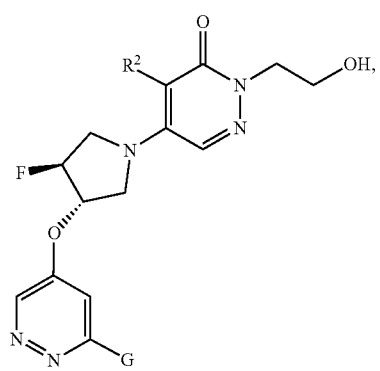
V(ax) 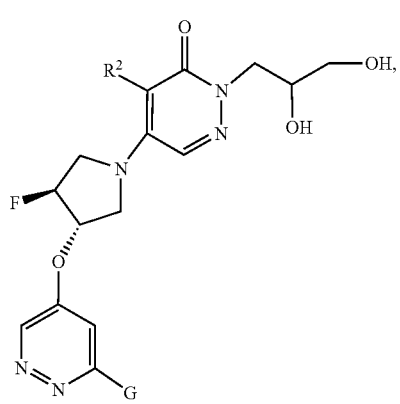
V(ay) 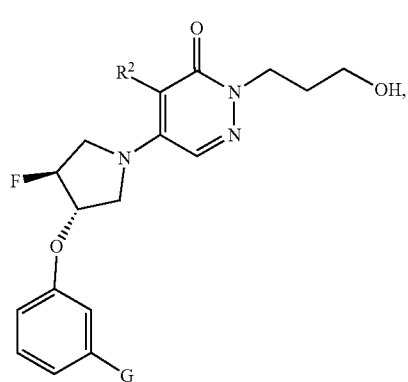
V(az) 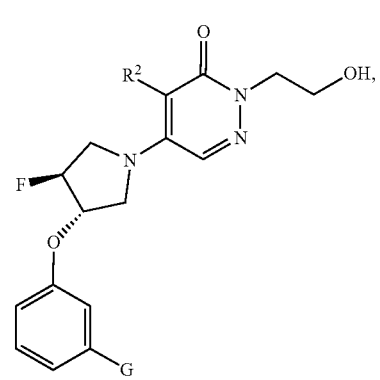
V(ba) 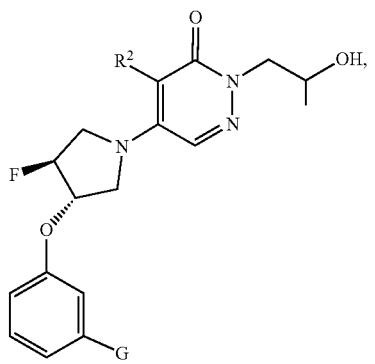
V(bb) 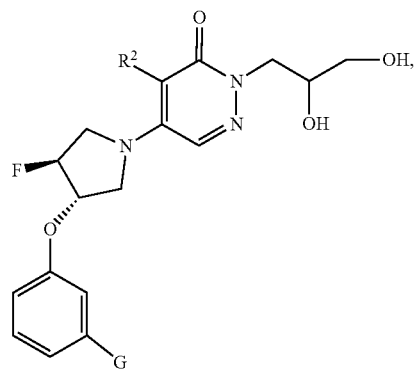
V(bc) 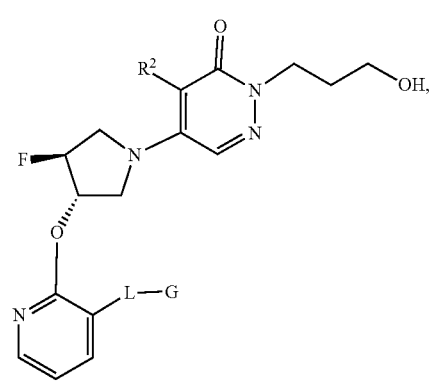
V(bd) 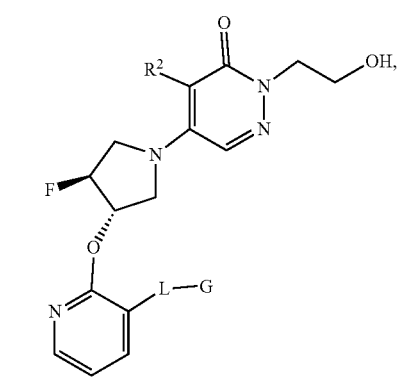

V(be)
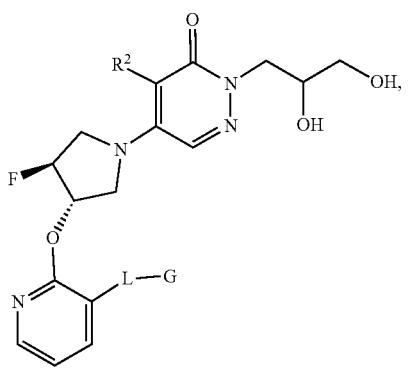

V(bf)
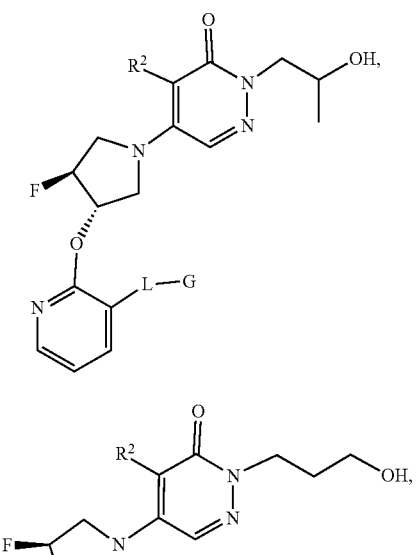

V(bg)
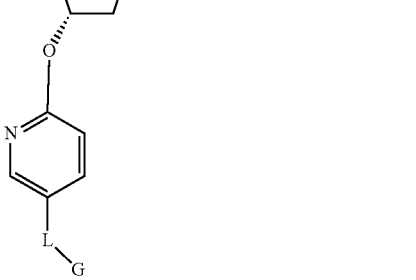

V(bh)
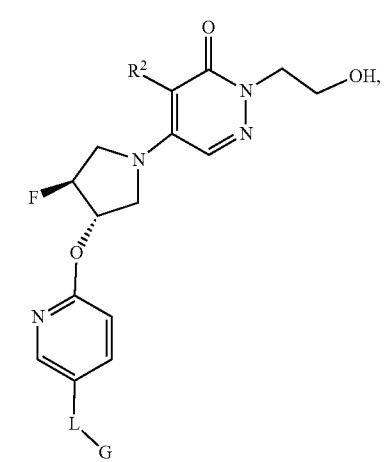

V(bi)
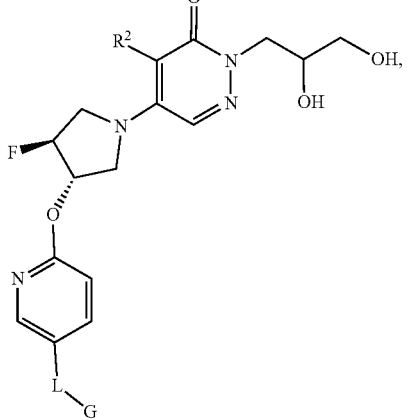

V(bj)
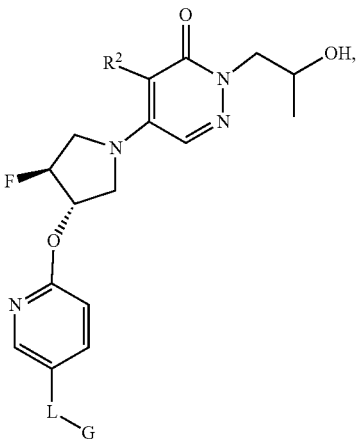

or a pharmaceutically acceptable salt thereof, wherein $R^2$ is Cl, Br, $CF_3$, or CN.

Subembodiments of Embodiment 13

Embodiment 13(a) of this disclosure relates to Embodiment 13, wherein G is $C_3$-$C_6$cycloalkyl substituted with 0-2 $T^1$ and 0-1 $T^2$.

Embodiment 13(b) of this disclosure relates to Embodiment 13, wherein G is $C_3$-$C_6$cycloalkenyl substituted with 0-2 $T^1$ and 0-1 $T^2$.

Embodiment 13(c) of this disclosure relates to Embodiment 13, wherein G is a 5-9 membered bridged carbocylic ring substituted with 0-2 $T^1$ and 0-1 $T^2$.

Embodiment 13(d) of this disclosure relates to Embodiment 13, wherein G is a 5-9 membered carbocyclic spiro ring containing two cycloalkyl groups joined by one common spiro carbon atom, wherein the carbocyclic spiro ring is substituted with 0-2 $T^1$ and 0-1 $T^2$.

Embodiment 13(e) of this disclosure relates to Embodiment 13, wherein G is a 6-9 membered heterocyclic spiro ring containing two cyclic groups with at least one heteroatom, wherein the two cyclic groups are joined by one common spiro carbon atom, wherein the heterocyclic spiro ring is substituted with 0-2 $T^5$, 0-1 $T^6$.

Embodiment 13(f) of this disclosure relates to Embodiment 13, wherein G is phenyl substituted with 0-2 $T^1$ and 0-1 $T^4$.

Embodiment 13(g) of this disclosure relates to Embodiment 13, wherein G is a 4-6 membered heterocycloalkyl substituted with 0-2 $T^5$ and 0-1 $T^6$.

Embodiment 13(h) of this disclosure relates to Embodiment 13, wherein G is a 4-6 membered heterocycloalkenyl substituted with 0-2 $T^5$ and 0-1 $T^6$.

Embodiment 13(i) of this disclosure relates to Embodiment 13, wherein G is a 5-9 membered bridged heterocylic ring substituted with 0-2 $T^5$ and 0-1 $T^6$.

Embodiment 13(j) of this disclosure relates to Embodiment 13, wherein G is a 5-6 membered heteroaryl substituted with 0-2 $T^5$ and 0-1 $T^3$.

Embodiment 13(k) of this disclosure relates to the compound according to Embodiment 13, 13(a), 13(b), 13(c) or 13(d), wherein $T^2$ is —$(CH_2)_{0-1}$—$N(R^9)SO_2$—$R^7$.

Embodiment 13(l) of this disclosure relates to the compound according to Embodiment 13, 13(a), 13(b), 13(c) or 13(d), wherein $T^2$ is —$(CH_2)_{0-1}$—$SO_2$—$R^7$.

Embodiment 13(m) of this disclosure relates to the compound according to Embodiment 13, 13(a), 13(b), 13(c) or 13(d), wherein $T^2$ is —$(CH_2)_{0-1}$—$SO_2N(R^8)R^9$.

Embodiment 13(n) of this disclosure relates to the compound according to Embodiment 13, 13(a), 13(b), 13(c) or 13(d), wherein $T^2$ is —$(CH_2)_{0-1}$—$N(R^9)SO_2N(R^8)R^9$.

Embodiment 13(o) of this disclosure relates to the compound according to Embodiment 13, 13(a), 13(b), 13(c) or 13(d), wherein $T^2$ is —$(CH_2)_{0-1}$—$N(R^9)C(O)N(R^8)R^9$.

Embodiment 13(p) of this disclosure relates to the compound according to Embodiment 13, 13(a), 13(b), 13(c) or 13(d), wherein $T^2$ is —$(CH_2)_{0-1}$—$N(R^9)C(O)R^8$.

Embodiment 13(q) of this disclosure relates to the compound according to Embodiment 13, 13(a), 13(b), 13(c) or 13(d), wherein $T^2$ is —$(CH_2)_{0-1}$—$N(R^9)C(O)OR^9$.

Embodiment 13(r) of this disclosure relates to the compound according to Embodiment 13, 13(a), 13(b), 13(c) or 13(d), wherein $T^2$ is —$(CH_2)_{0-1}$—$N(R^8)R^9$.

Embodiment 13(s) of this disclosure relates to the compound according to Embodiment 13, 13(a), 13(b), 13(c) or 13(d), wherein $T^2$ is —$(CH_2)_{0-1}$—$C(O)N(R^8)R^9$.

Embodiment 13(t) of this disclosure relates to the compound according to Embodiment 13, 13(a), 13(b), 13(c) or 13(d), wherein $T^2$ is —$(CH_2)_{0-1}$—$C(O)OR^9$.

Embodiment 13(u) of this disclosure relates to the compound according to Embodiment 13, 13(a), 13(b), 13(c) or 13(d), wherein $T^2$ is —$(CH_2)_{0-1}$—$C(O)R^{10}$.

Embodiment 13(v) of this disclosure relates to the compound according to Embodiment 13, 13(a), 13(b), 13(c) or 13(d), wherein $T^2$ is —$(CH_2)_{0-1}$—$C(O)H$.

Embodiment 13(w) of this disclosure relates to the compound according to Embodiment 13, 13(a), 13(b), 13(c) or 13(d), wherein $T^2$ is —$(CH_2)_{0-1}$—$N(R^9)C(O)R^{10}$.

Embodiment 13(x) of this disclosure relates to the compound according to Embodiment 5, 13, 13(a), 13(b), 13(c) or 13(d), wherein $T^2$ is —$(CH_2)_{0-2}C_3$-$C_6$cycloalkyl optionally substituted with 1-3 $Z^3$.

Embodiment 13(y) of this disclosure relates to the compound according to 13, 13(a), 13(b), 13(c) or 13(d), wherein $T^2$ is —$(CH_2)_{0-1}$-phenyl optionally substituted with 1-3 $Z^5$.

Embodiment 13(z) of this disclosure relates to the compound according to 13, 13(a), 13(b), 13(c) or 13(d), wherein $T^2$ is —$(CH_2)_{0-1}$-5-6 membered heteroaryl optionally substituted with 1-3 $Z^5$.

Embodiment 13(aa) of this disclosure relates to the compound according to Embodiment 13 or 13(j), wherein $T^3$ is —$(CH_2)_{0-2}$—$C(O)N(R^8)R^9$.

Embodiment 13(ab) of this disclosure relates to the compound according to Embodiment 13 or 13(j), wherein $T^3$ is —$(CH_2)_{0-2}$—$N(R^8)R^9$, provided that when $T^3$ is attached to a heteroatom of G, G is not attached to —$N(R^8)R^9$.

Embodiment 13(ac) of this disclosure relates to the compound according to Embodiment 13 or 13(j), wherein $T^3$ is —$(CH_2)_{0-2}$—$C(O)OR^9$.

Embodiment 13(ad) of this disclosure relates to the compound according to Embodiment 13 or 13(j), wherein $T^3$ is —$(CH_2)_{0-2}$—$C_3$-$C_6$cycloalkyl optionally substituted with 1-3 $Z^5$ and 0-1 $Z^1$.

Embodiment 13(ae) of this disclosure relates to the compound according to Embodiment 13 or 13(j), wherein $T^3$ is —$(CH_2)_{0-2}$-5-6 membered heterocycloalkyl optionally substituted with 1-3 $Z^5$ and 0-1 $Z^1$, provided that when $T^3$ is attached to a heteroatom of G, G is not attached to an oxygen or nitrogen atom of the 5-6 membered heterocycloalkyl.

Embodiment 13(af) of this disclosure relates to the compound according to Embodiment 13 or 13(j), wherein $T^3$ is is —O—5-6 membered heterocycloalkyl optionally substituted with 4-chloropyridazin-3-one-5-yl.

Embodiment 13(ag) of this disclosure relates to the compound according to Embodiment 13 or 13(j), wherein $T^3$ is —$(CH_2)_{0-2}$-5-9 membered bridged carbocyclic ring optionally substituted with 1-3 $Z^5$ and 0-1 $Z^1$.

Embodiment 13(ah) of this disclosure relates to the compound according to Embodiment 13 or 13(j), wherein $T^4$ is —$(CH_2)_{0-1}C(O)OR^9$.

Embodiment 13(ai) of this disclosure relates to the compound according to Embodiment 13 or 13(j), wherein $T^4$ is —$(CH_2)_{0-1}$—$N(R^9)C(O)R^8$.

Embodiment 13(aj) of this disclosure relates to the compound according to Embodiment 13 or 13(j), wherein $T^4$ is —$(CH_2)_{0-1}$—$N(R^9)SO_2$—R.

Embodiment 13(ak) of this disclosure relates to the compound according to Embodiment 13 or 13(j), wherein $T^4$ is —$(CH_2)_{0-1}$—$SO_2$—$R^7$.

Embodiment 13(al) of this disclosure relates to the compound according to Embodiment 13 or 13(j), wherein $T^4$ is —$(CH_2)_{0-1}$—$SO_2N(R^8)R^9$.

Embodiment 13(am) of this disclosure relates to the compound according to Embodiment 13 or 13(j), wherein $T^4$ is —$(CH_2)_{0-1}$—$N(R^9)C(O)N(R^8)R^9$.

Embodiment 13(an) of this disclosure relates to the compound according to Embodiment 13 or 13(j), wherein $T^4$ is $N(R^a)_2$.

Embodiment 13(ao) of this disclosure relates to the compound according to Embodiment 13, 13(e), 13(g), 13(h) or 13(i), wherein $T^6$ is —$(CH_2)_{0-1}$—$N(R^9)SO_2$—$R^7$, provided that when $T^6$ is attached to a heteroatom of G, G is not attached to —$N(R^9)SO_2$—$R^7$.

Embodiment 13(ap) of this disclosure relates to the compound according to Embodiment 13, 13(e), 13(g), 13(h) or 13(i), wherein $T^6$ is —$(CH_2)_{0-1}$—$SO_2$—$R^7$.

Embodiment 13(aq) of this disclosure relates to the compound according to Embodiment 13, 13(e), 13(g), 13(h) or 13(i), wherein $T^6$ is —$(CH_2)_{0-1}$—$SO_2N(R^8)R^9$.

Embodiment 13(ar) of this disclosure relates to the compound according to Embodiment 13, 13(e), 13(g), 13(h) or 13(i), wherein $T^6$ is —$(CH_2)_{0-1}$—$N(R^9)SO_2N(R^8)R^9$, provided that when $T^6$ is attached to a heteroatom of G, G is not attached to —$N(R^9)SO_2N(R^8)R^9$.

Embodiment 13(as) of this disclosure relates to the compound according to Embodiment 13, 13(e), 13(g), 13(h) or 13(i), wherein $T^6$ is —$(CH_2)_{0-1}$—$N(R^9)C(O)N(R^8)R^9$, provided that when $T^6$ is attached to a heteroatom of G, G is not attached to —$N(R^9)C(O)N(R^8)R^9$.

Embodiment 13(at) of this disclosure relates to the compound according to Embodiment 13, 13(e), 13(g), 13(h) or 13(i), wherein T⁶ is —(CH$_2$)$_{0-1}$—N(R⁹)C(O)R⁸, provided that when T⁶ is attached to a heteroatom of G, G is not attached to —N(R⁹)C(O)R⁸.

Embodiment 13(au) of this disclosure relates to the compound according to Embodiment 13, 13(e), 13(g), 13(h) or 13(i), wherein T⁶ is —(CH$_2$)$_{0-1}$—N(R⁹)C(O)OR⁹, provided that when T⁶ is attached to a heteroatom of G, G is not attached to —N(R⁹)C(O)OR⁹.

Embodiment 13(av) of this disclosure relates to the compound according to Embodiment 13, 13(e), 13(g), 13(h) or 13(i), wherein T⁶ is —(CH$_2$)$_{0-1}$—N(R⁸)R⁹, provided that when T⁶ is attached to a heteroatom of G, G is not attached to —N(R⁸)R⁹.

Embodiment 13(aw) of this disclosure relates to the compound according to Embodiment 13, 13(e), 13(g), 13(h) or 13(i), wherein T⁶ is —(CH$_2$)$_{0-1}$—C(O)—N(R⁸)R⁹.

Embodiment 13(ax) of this disclosure relates to the compound according to Embodiment 13, 13(e), 13(g), 13(h) or 13(i), wherein T⁶ is —(CH$_2$)$_{0-1}$—C(O)OR⁹.

Embodiment 13(ay) of this disclosure relates to the compound according to Embodiment 13, 13(e), 13(g), 13(h) or 13(i), wherein T⁶ is —(CH$_2$)$_{0-1}$—C(O)R¹⁰.

Embodiment 13(az) of this disclosure relates to the compound according to Embodiment 13, 13(e), 13(g), 13(h) or 13(i), wherein T⁶ is —(CH$_2$)$_{0-1}$—N(R⁹)C(O)R¹⁰, provided that when T⁶ is attached to a heteroatom of G, G is not attached to —N(R⁹)C(O)R¹⁰.

Embodiment 13(ba) of this disclosure relates to the compound according to Embodiment 13, 13(e), 13(g), 13(h) or 13(i), wherein T⁶ is —N(H)C(H)C=O, provided that T⁶ is not attached to a heteroatom of G.

Embodiment 13(bb) of this disclosure relates to the compound according to Embodiment 13, 13(e), 13(g), 13(h) or 13(i), wherein T⁶ is —(CH$_2$)$_{0-1}$—C$_3$-C$_6$cycloalkyl optionally substituted with 1-4 Z³.

Embodiment 13(bc) of this disclosure relates to the compound according to Embodiment 13, 13(e), 13(g), 13(h) or 13(i), wherein T⁶ is —(CH$_2$)$_{0-1}$-5-6 membered heterocycloalkyl optionally substituted with 1-4 Z³, provided that when T⁶ is attached to a heteroatom of G, G is not attached to a heteroatom of 5-6 membered heteroaryl.

Embodiment 13(bd) of this disclosure relates to the compound according to Embodiment 13, 13(e), 13(g), 13(h) or 13(i), wherein T⁶ is —(CH$_2$)$_{0-1}$-5-6 membered heteroaryl optionally substituted with 1-3 Z⁵, provided that when T⁶ is attached to a heteroatom of G, G is not attached to a heteroatom of 5-6 membered heteroaryl.

Embodiment 13(be) relates to any one of Embodiments 13, 13(a), 13(b), 13(c), 13(d), 13(e), 13(f), 13(g), 13(h), 13(i), 13(j), 13(k), 13(l), 13(m), 13(n), 13(o), 13(p), 13(q), 13(r), 13(s), 13(t), 13(u), 13(v), 13(w), 13(x), 13(y), 13(z), 13(aa), 13(ab), 13(ac), 13(ad), 13(ae), 13(af), 13(ag), 13(ah), 13(ai), 13(aj), 13(ak), 13(al), 13(am), 13(an), 13(ao), 13(ap), 13(aq), 13(ar), 13(as), 13(at), 13(au), 13(av), 13(aw), 13(ax), 13(ay), 13(az), 13(ba), 13(bb), 13(bc) or 13(bd), wherein R² is Cl.

Embodiment 13(bf) relates to any one of Embodiments 13, 13(a), 13(b), 13(c), 13(d), 13(e), 13(f), 13(g), 13(h), 13(i), 13(j), 13(k), 13(l), 13(m), 13(n), 13(o), 13(p), 13(q), 13(r), 13(s), 13(t), 13(u), 13(v), 13(w), 13(x), 13(y), 13(z), 13(aa), 13(ab), 13(ac), 13(ad), 13(ae), 13(af), 13(ag), 13(ah), 13(ai), 13(aj), 13(ak), 13(al), 13(am), 13(an), 13(ao), 13(ap), 13(aq), 13(ar), 13(as), 13(at), 13(au), 13(av), 13(aw), 13(ax), 13(ay), 13(az), 13(ba), 13(bb), 13(bc) or 13(bd), wherein R² is CN.

Embodiment 14 relates to a compound according to any of Embodiments 1-5 having any one of the following formulae:

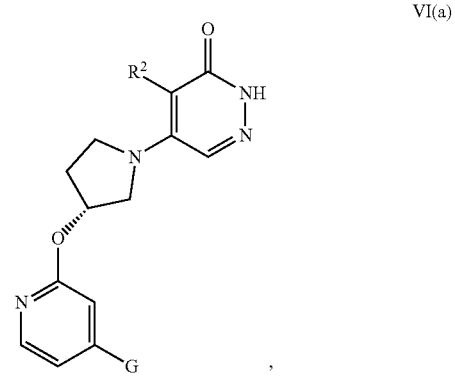

VI(a)

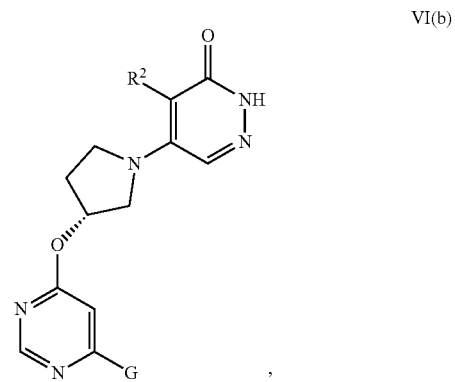

VI(b)

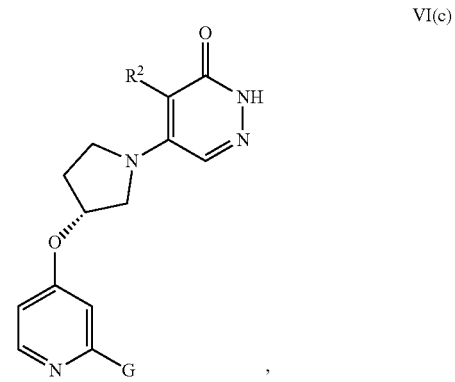

VI(c)

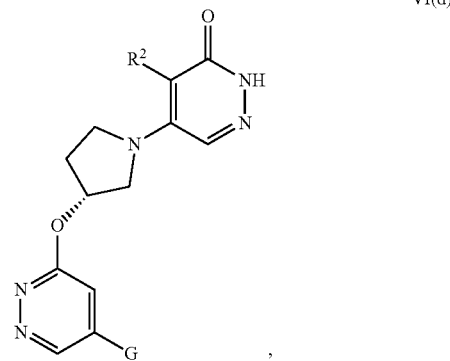

VI(d)

VI(e)
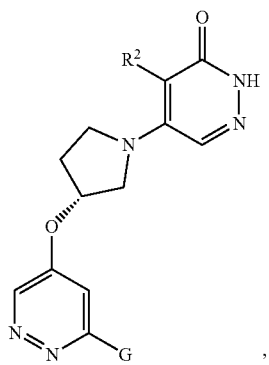
VI(f)
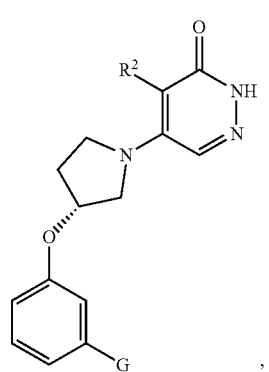
VI(g)
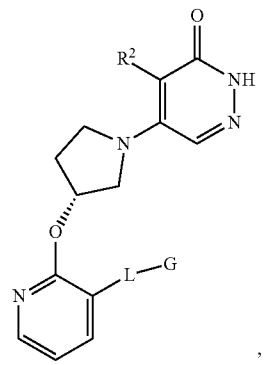
VI(h)
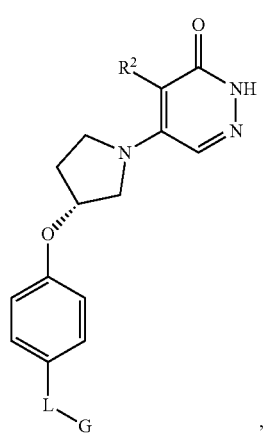
VI(i)
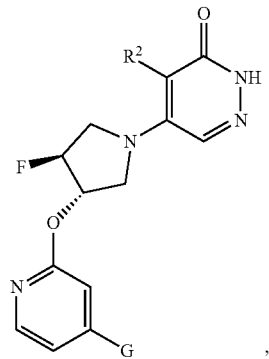
VI(j)
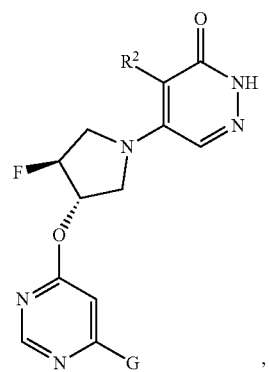
VI(k)
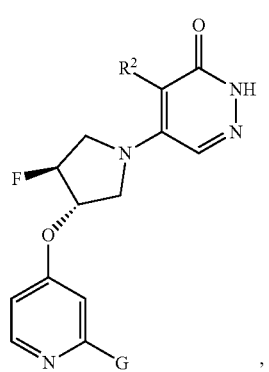
VI(l)
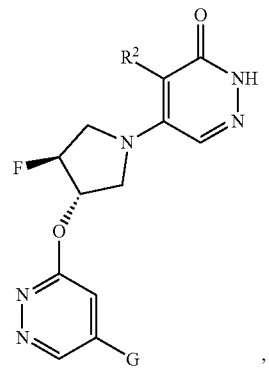

-continued

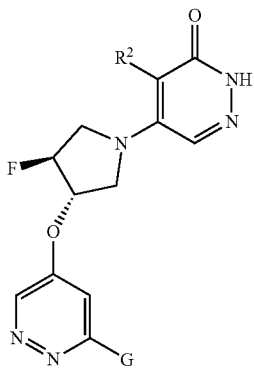
VI(m)

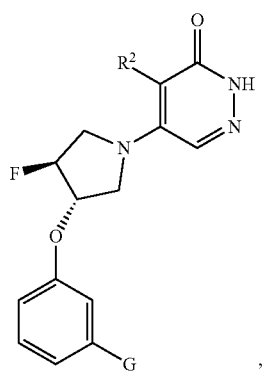
VI(o)

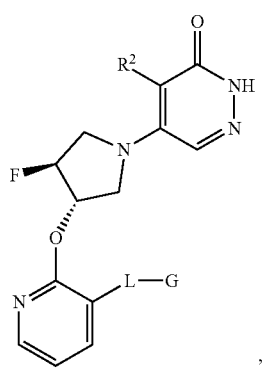
VI(p)

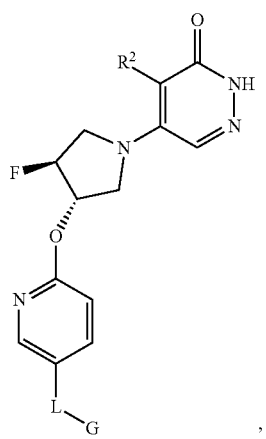
VI(q)

or a pharmaceutically acceptable salt thereof, wherein $R^2$ is Cl, Br, $CF_3$, or CN.

Subembodiments of Embodiment 14

Embodiment 14(a) of this disclosure relates to Embodiment 14, wherein G is $C_3$-$C_6$cycloalkyl substituted with 0-2 $T^1$ and 0-1 $T^2$.

Embodiment 14(b) of this disclosure relates to Embodiment 14, wherein G is $C_3$-$C_6$cycloalkenyl substituted with 0-2 $T^1$ and 0-1 $T^2$.

Embodiment 14(c) of this disclosure relates to Embodiment 14, wherein G is a 5-9 membered bridged carbocylic ring substituted with 0-2 $T^1$ and 0-1 $T^2$.

Embodiment 14(d) of this disclosure relates to Embodiment 14, wherein G is a 5-9 membered carbocyclic spiro ring containing two cycloalkyl groups joined by one common spiro carbon atom, wherein the carbocyclic spiro ring is substituted with 0-2 $T^1$ and 0-1 $T^2$.

Embodiment 14(e) of this disclosure relates to Embodiment 14, wherein G is a 6-9 membered heterocyclic spiro ring containing two cyclic groups with at least one heteroatom, wherein the two cyclic groups are joined by one common spiro carbon atom, wherein the heterocyclic spiro ring is substituted with 0-2 $T^5$, 0-1 $T^6$.

Embodiment 14(f) of this disclosure relates to Embodiment 14, wherein G is phenyl substituted with 0-2 $T^1$ and 0-1 $T^4$.

Embodiment 14(g) of this disclosure relates to Embodiment 14, wherein G is a 4-6 membered heterocycloalkyl substituted with 0-2 $T^5$ and 0-1 $T^6$.

Embodiment 14(h) of this disclosure relates to Embodiment 14, wherein G is a 4-6 membered heterocycloalkenyl substituted with 0-2 $T^5$ and 0-1 $T^6$.

Embodiment 14(i) of this disclosure relates to Embodiment 14, wherein G is a 5-9 membered bridged heterocylic ring substituted with 0-2 $T^5$ and 0-1 $T^6$.

Embodiment 14(j) of this disclosure relates to Embodiment 14, wherein G is a 5-6 membered heteroaryl substituted with 0-2 $T^5$ and 0-1 $T^3$.

Embodiment 14(k) of this disclosure relates to the compound according to Embodiment 14, 14(a), 14(b), 14(c) or 14(d), wherein $T^2$ is —$(CH_2)_{0-1}$—N($R^9$)$SO_2$—$R^7$.

Embodiment 14(l) of this disclosure relates to the compound according to Embodiment 14, 14(a), 14(b), 14(c) or 14(d), wherein $T^2$ is —$(CH_2)_{0-1}$—$SO_2$—$R^7$.

Embodiment 14(m) of this disclosure relates to the compound according to Embodiment 14, 14(a), 14(b), 14(c) or 14(d), wherein $T^2$ is —$(CH_2)_{0-1}$—$SO_2$N($R^8$)$R^9$.

Embodiment 14(n) of this disclosure relates to the compound according to Embodiment 14, 14(a), 14(b), 14(c) or 14(d), wherein $T^2$ is —$(CH_2)_{0-1}$—N($R^9$)$SO_2$N($R^8$)$R^9$.

Embodiment 14(o) of this disclosure relates to the compound according to Embodiment 14, 14(a), 14(b), 14(c) or 14(d), wherein $T^2$ is —$(CH_2)_{0-1}$—N($R^9$)C(O)N($R^8$)$R^9$.

Embodiment 14(p) of this disclosure relates to the compound according to Embodiment 14, 14(a), 14(b), 14(c) or 14(d), wherein $T^2$ is —$(CH_2)_{0-1}$—N($R^9$)C(O)$R^8$.

Embodiment 14(q) of this disclosure relates to the compound according to Embodiment 14, 14(a), 14(b), 14(c) or 14(d), wherein $T^2$ is —$(CH_2)_{0-1}$—N($R^9$)C(O)O$R^9$.

Embodiment 14(r) of this disclosure relates to the compound according to Embodiment 14, 14(a), 14(b), 14(c) or 14(d), wherein $T^2$ is —$(CH_2)_{0-1}$—N($R^8$)$R^9$.

Embodiment 14(s) of this disclosure relates to the compound according to Embodiment 14, 14(a), 14(b), 14(c) or 14(d), wherein $T^2$ is —$(CH_2)_{0-1}$—C(O)N($R^8$)$R^9$.

Embodiment 14(t) of this disclosure relates to the compound according to Embodiment 14, 14(a), 14(b), 14(c) or 14(d), wherein $T^2$ is —$(CH_2)_{0-1}$—C(O)O$R^9$.

Embodiment 14(u) of this disclosure relates to the compound according to Embodiment 14, 14(a), 14(b), 14(c) or 14(d), wherein $T^2$ is $-(CH_2)_{0-1}-C(O)R^{10}$.

Embodiment 14(v) of this disclosure relates to the compound according to Embodiment 14, 14(a), 14(b), 14(c) or 14(d), wherein $T^2$ is $-(CH_2)_{0-1}-C(O)H$.

Embodiment 14(w) of this disclosure relates to the compound according to Embodiment 14, 14(a), 14(b), 14(c) or 14(d), wherein $T^2$ is $-(CH_2)_{0-1}-N(R^9)C(O)R^{10}$.

Embodiment 14(x) of this disclosure relates to the compound according to Embodiment 5, 14, 14(a), 14(b), 14(c) or 14(d), wherein $T^2$ is $-(CH_2)_{0-2}C_3$-$C_6$cycloalkyl optionally substituted with 1-3 $Z^3$.

Embodiment 14(y) of this disclosure relates to the compound according to 14, 14(a), 14(b), 14(c) or 14(d), wherein $T^2$ is $-(CH_2)_{0-1}$-phenyl optionally substituted with 1-3 $Z^5$.

Embodiment 14(z) of this disclosure relates to the compound according to 14, 14(a), 14(b), 14(c) or 14(d), wherein $T^2$ is $-(CH_2)_{0-1}$-5-6 membered heteroaryl optionally substituted with 1-3 $Z^5$.

Embodiment 14(aa) of this disclosure relates to the compound according to Embodiment 14 or 14(j), wherein $T^3$ is $-(CH_2)_{0-2}-C(O)N(R^8)R^9$.

Embodiment 14(ab) of this disclosure relates to the compound according to Embodiment 14 or 14(j), wherein $T^3$ is $-(CH_2)_{0-2}-N(R^8)R^9$, provided that when $T^3$ is attached to a heteroatom of G, G is not attached to $-N(R^8)R^9$.

Embodiment 14(ac) of this disclosure relates to the compound according to Embodiment 14 or 14(j), wherein $T^3$ is $-(CH_2)_{0-2}-C(O)OR^9$.

Embodiment 14(ad) of this disclosure relates to the compound according to Embodiment 14 or 14(j), wherein $T^3$ is $-(CH_2)_{0-2}-C_3$-$C_6$cycloalkyl optionally substituted with 1-3 $Z^5$ and 0-1 $Z^1$.

Embodiment 14(ae) of this disclosure relates to the compound according to Embodiment 14 or 14(j), wherein $T^3$ is $-(CH_2)_{0-2}$-5-6 membered heterocycloalkyl optionally substituted with 1-3 $Z^5$ and 0-1 $Z^1$, provided that when $T^3$ is attached to a heteroatom of G, G is not attached to an oxygen or nitrogen atom of the 5-6 membered heterocycloalkyl.

Embodiment 14(af) of this disclosure relates to the compound according to Embodiment 14 or 14(j), wherein $T^3$ is $-O-$5-6 membered heterocycloalkyl optionally substituted with 4-chloropyridazin-3-one-5-yl.

Embodiment 14(ag) of this disclosure relates to the compound according to Embodiment 14 or 14(j), wherein $T^3$ is $-(CH_2)_{0-2}$-5-9 membered bridged carbocyclic ring optionally substituted with 1-3 $Z^5$ and 0-1 $Z^1$.

Embodiment 14(ah) of this disclosure relates to the compound according to Embodiment 14 or 14(j), wherein $T^4$ is $-(CH_2)_{0-1}C(O)OR^9$.

Embodiment 14(ai) of this disclosure relates to the compound according to Embodiment 14 or 14(j), wherein $T^4$ is $-(CH_2)_{0-1}-N(R^9)C(O)R^8$.

Embodiment 14(aj) of this disclosure relates to the compound according to Embodiment 14 or 14(j), wherein $T^4$ is $-(CH_2)_{0-1}-N(R^9)SO_2-R$.

Embodiment 14(ak) of this disclosure relates to the compound according to Embodiment 14 or 14(j), wherein $T^4$ is $-(CH_2)_{0-1}-SO_2-R^7$.

Embodiment 14(al) of this disclosure relates to the compound according to Embodiment 14 or 14(j), wherein $T^4$ is $-(CH_2)_{0-1}-SO_2N(R^8)R^9$.

Embodiment 14(am) of this disclosure relates to the compound according to Embodiment 14 or 14(j), wherein $T^4$ is $-(CH_2)_{0-1}-N(R^9)C(O)N(R^8)R^9$.

Embodiment 14(an) of this disclosure relates to the compound according to Embodiment 14 or 14(j), wherein $T^4$ is $N(R^a)_2$.

Embodiment 14(ao) of this disclosure relates to the compound according to Embodiment 14, 14(e), 14(g), 14(h) or 14(i), wherein $T^6$ is $-(CH_2)_{0-1}-N(R^9)SO_2-R^7$, provided that when $T^6$ is attached to a heteroatom of G, G is not attached to $-N(R^9)SO_2-R^7$.

Embodiment 14(ap) of this disclosure relates to the compound according to Embodiment 14, 14(e), 14(g), 14(h) or 14(i), wherein $T^6$ is $-(CH_2)_{0-1}-SO_2-R^7$.

Embodiment 14(aq) of this disclosure relates to the compound according to Embodiment 14, 14(e), 14(g), 14(h) or 14(i), wherein $T^6$ is $-(CH_2)_{0-1}-SO_2N(R^8)R^9$.

Embodiment 14(ar) of this disclosure relates to the compound according to Embodiment 14, 14(e), 14(g), 14(h) or 14(i), wherein $T^6$ is $-(CH_2)_{0-1}-N(R^9)SO_2N(R^8)R^9$, provided that when $T^6$ is attached to a heteroatom of G, G is not attached to $-N(R^9)SO_2N(R^8)R^9$.

Embodiment 14(as) of this disclosure relates to the compound according to Embodiment 14, 14(e), 14(g), 14(h) or 14(i), wherein $T^6$ is $-(CH_2)_{0-1}-N(R^9)C(O)N(R^8)R^9$, provided that when $T^6$ is attached to a heteroatom of G, G is not attached to $-N(R^9)C(O)N(R^8)R^9$.

Embodiment 14(at) of this disclosure relates to the compound according to Embodiment 14, 14(e), 14(g), 14(h) or 14(i), wherein $T^6$ is $-(CH_2)_{0-1}-N(R^9)C(O)R^8$, provided that when $T^6$ is attached to a heteroatom of G, G is not attached to $-N(R^9)C(O)R^8$.

Embodiment 14(au) of this disclosure relates to the compound according to Embodiment 14, 14(e), 14(g), 14(h) or 14(i), wherein $T^6$ is $-(CH_2)_{0-1}-N(R^9)C(O)OR^9$, provided that when $T^6$ is attached to a heteroatom of G, G is not attached to $-N(R^9)C(O)OR^9$.

Embodiment 14(av) of this disclosure relates to the compound according to Embodiment 14, 14(e), 14(g), 14(h) or 14(i), wherein $T^6$ is $-(CH_2)_{0-1}-N(R^8)R^9$, provided that when $T^6$ is attached to a heteroatom of G, G is not attached to $-N(R^8)R^9$.

Embodiment 14(aw) of this disclosure relates to the compound according to Embodiment 14, 14(e), 14(g), 14(h) or 14(i), wherein $T^6$ is $-(CH_2)_{0-1}-C(O)-N(R^8)R^9$.

Embodiment 14(ax) of this disclosure relates to the compound according to Embodiment 14, 14(e), 14(g), 14(h) or 14(i), wherein $T^6$ is $-(CH_2)_{0-1}-C(O)OR^9$.

Embodiment 14(ay) of this disclosure relates to the compound according to Embodiment 14, 14(e), 14(g), 14(h) or 14(i), wherein $T^6$ is $-(CH_2)_{0-1}-C(O)R^{10}$.

Embodiment 14(az) of this disclosure relates to the compound according to Embodiment 14, 14(e), 14(g), 14(h) or 14(i), wherein $T^6$ is $-(CH_2)_{0-1}-N(R^9)C(O)R^{10}$, provided that when $T^6$ is attached to a heteroatom of G, G is not attached to $-N(R^9)C(O)R^{10}$.

Embodiment 14(ba) of this disclosure relates to the compound according to Embodiment 14, 14(e), 14(g), 14(h) or 14(i), wherein $T^6$ is $-N(H)C(H)C=O$, provided that $T^6$ is not attached to a heteroatom of G.

Embodiment 14(bb) of this disclosure relates to the compound according to Embodiment 14, 14(e), 14(g), 14(h) or 14(i), wherein $T^6$ is $-(CH_2)_{0-1}-C_3$-$C_6$cycloalkyl optionally substituted with 1-4 $Z^3$.

Embodiment 14(bc) of this disclosure relates to the compound according to Embodiment 14, 14(e), 14(g), 14(h) or 14(i), wherein $T^6$ is $-(CH_2)_{0-1}$-5-6 membered heterocycloalkyl optionally substituted with 1-4 $Z^3$, provided that when $T^6$ is attached to a heteroatom of G, G is not attached to a heteroatom of 5-6 membered heteroaryl.

Embodiment 14(bd) of this disclosure relates to the compound according to Embodiment 14, 14(e), 14(g), 14(h) or 14(i), wherein $T^6$ is —$(CH_2)_{0-1}$-5-6 membered heteroaryl optionally substituted with 1-3 $Z^5$, provided that when $T^6$ is attached to a heteroatom of G, G is not attached to a heteroatom of 5-6 membered heteroaryl.

Embodiment 14(be) relates to any one of Embodiments 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(y), 14(z), 14(aa), 14(ab), 14(ac), 14(ad), 14(ae), 14(af), 14(ag), 14(ah), 14(ai), 14(aj), 14(ak), 14(al), 14(am), 14(an), 14(ao), 14(ap), 14(aq), 14(ar), 14(as), 14(at), 14(au), 14(av), 14(aw), 14(ax), 14(ay), 14(az), 14(ba), 14(bb), 14(bc) or 14(bd), wherein $R^2$ is Cl.

Embodiment 14(bf) relates to any one of Embodiments 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(y), 14(z), 14(aa), 14(ab), 14(ac), 14(ad), 14(ae), 14(af), 14(ag), 14(ah), 14(ai), 14(aj), 14(ak), 14(al), 14(am), 14(an), 14(ao), 14(ap), 14(aq), 14(ar), 14(as), 14(at), 14(au), 14(av), 14(aw), 14(ax), 14(ay), 14(az), 14(ba), 14(bb), 14(bc) or 14(bd), wherein $R^2$ is CN.

Embodiment 15 relates to a compound according to Embodiment 12 having one of Formulae IV(a), IV(b), IV(c), IV(d), IV(e), IV(f), or pharmaceutically acceptable salt thereof, or any subembodiment of Formulae IV(a), IV(b), IV(c), IV(d), IV(e), IV(f), or a pharmaceutically acceptable salt thereof.

Embodiment 16 relates to a compound according to Embodiment 13 having one of Formulae V(a), V(b), V(c), V(d), V(e), V(f), V(g), V(h), V(i), V(j), V(k), V(l), V(m), V(n), V(o), V(p), V(q), V(r), V(s), V(t), V(u), V(v), V(w), V(af), V(ag), V(ah), V(ai), V(aj), V(ak), V(al), V(am), V(an), V(ao), V(ap), V(aq), V(ar), V(as), V(at), V(au), V(av), V(aw), V(ay), V(az), V(ba), V(bb), or a pharmaceutically acceptable salt thereof, or any subembodiment of Formulae V(a), V(b), V(c), V(d), V(e), V(f), V(g), V(h), V(i), V(j), V(k), V(l), V(m), V(n), V(o), V(p), V(q), V(r), V(s), V(t), V(u), V(v), V(w), V(af), V(ag), V(ah), V(ai), V(aj), V(ak), V(al), V(am), V(an), V(ao), V(ap), V(aq), V(ar), V(as), V(at), V(au), V(av), V(aw), V(ay), V(az), V(ba), V(bb), or a pharmaceutically acceptable salt thereof.

Embodiment 17 relates to a compound according to Embodiment 14 having one of Formulae VI(a), VI(b), VI(c), VI(d), VI(e), VI(f), VI(g), VI(h), VI(i), VI(j), VI(k), VI(l), VI(m), VO(n), VI(o), or a pharmaceutically acceptable salt thereof, or any subembodiment of Formulae VI(a), VI(b), VI(c), VI(d), VI(e), VI(f), VI(g), VI(h), VI(i), VI(j), VI(k), VI(l), VI(m), VO(n), VI(o), or a pharmaceutically acceptable salt thereof.

Embodiment 18 relates to a compound according to any one of the preceding embodiments, wherein G is one of the following groups:
  (a) $C_3$-$C_6$cycloalkyl substituted with 0-2 $T^1$ and 0-1 $T^2$;
  (b) $C_3$-$C_6$cycloalkenyl substituted with 0-2 $T^1$ and 0-1 $T^2$;
  (c) a 6-9 membered heterocyclic spiro ring containing two cyclic groups with at least one heteroatom, wherein the two cyclic groups are joined by one common spiro carbon atom, wherein the heterocyclic spiro ring is substituted with 0-2 $T^5$, 0-1 $T^6$;
  (d) phenyl substituted with 0-2 $T^1$ and 0-1 $T^4$;
  (e) a 5-6 membered heterocycloalkyl substituted with 0-2 $T^5$ and 0-1 $T^6$;
  (f) a 5-6 membered heterocycloalkenyl substituted with 0-2 $T^5$ and 0-1 $T^6$;
  (g) a 5-9 membered bridged heterocylic ring substituted with 0-2 $T^5$ and 0-1 $T^6$; or
  (h) a 5-6 membered heteroaryl substituted with 0-2 $T^5$ and 0-1 $T^3$.

Embodiment 19 relates to a compound according to Embodiment 16, wherein G is pyrazolyl, isoxazolyl, indolyl, 1,2,3-triazolyl, imidazolyl, thiazolyl, or pyrrolyl each of which is substituted with 0-2 $T^5$ and 0-1 $T^3$.

Subembodiments of Embodiment 19

Embodiment 19(a) relates to a compound according to Embodiment 19, wherein G is pyrazolyl substituted with 0-2 $T^5$ and 0-1 $T^3$.

Embodiment 19(b) relates to a compound according to Embodiment 19, wherein G is isoxazolyl substituted with 0-2 $T^5$ and 0-1 $T^3$.

Embodiment 19(c) relates to a compound according to Embodiment 19, wherein G is indolyl substituted with 0-2 $T^5$ and 0-1 $T^3$.

Embodiment 19(d) relates to a compound according to Embodiment 19, wherein G is 1,2,3-triazolyl substituted with 0-2 $T^5$ and 0-1 $T^3$.

Embodiment 19(e) relates to a compound according to Embodiment 19, wherein G is imidazolyl substituted with 0-2 $T^5$ and 0-1 $T^3$.

Embodiment 19(f) relates to a compound according to Embodiment 19, wherein G is thiazolyl substituted with 0-2 $T^5$ and 0-1 $T^3$.

Embodiment 19(g) relates to a compound according to Embodiment 19, wherein G is pyrrolyl substituted with 0-2 $T^5$ and 0-1 $T^3$.

Embodiment 20 relates to a compound according to Embodiment 16, wherein G is 2,5-dihydropyrrolyl, or 3,6-dihydropyranyl, each of which is substituted with 0-2 $T^5$ and 0-1 $T^6$.

Subembodiments of Embodiment 20

Embodiment 20(a) relates to a compound according to Embodiment 20, wherein G is piperazinyl substituted with 0-2 $T^5$ and 0-1 $T^6$.

Embodiment 20(b) relates to a compound according to Embodiment 20, wherein G is piperidine substituted with 0-2 $T^5$ and 0-1 $T^6$.

Embodiment 20(c) relates to a compound according to Embodiment 20, wherein G is pyrrolidine substituted with 0-2 $T^5$ and 0-1 $T^6$.

Embodiment 20(d) relates to a compound according to Embodiment 20, wherein G is tetrahydropyran substituted with 0-2 $T^5$ and 0-1 $T^6$.

Embodiment 20(e) relates to a compound according to Embodiment 20, wherein G is morpholinyl substituted with 0-2 $T^5$ and 0-1 $T^6$.

Embodiment 20(f) relates to a compound according to Embodiment 20, wherein G is 1,2,3,6-tetrahydropyridinyl substituted with 0-2 $T^5$ and 0-1 $T^6$.

Embodiment 20(g) relates to a compound according to Embodiment 20, wherein G is 2,5-dihydropyrrolyl substituted with 0-2 $T^5$ and 0-1 $T^6$.

Embodiment 20(h) relates to a compound according to Embodiment 20, wherein G is 3,6-dihydropyranyl substituted with 0-2 $T^5$ and 0-1 $T^6$.

Embodiment 21 relates to a compound according to Embodiment 16, wherein G is (1R,5S)-3,8-diazabicyclo

[3.2.1]octanyl, (1R,5S)-3-azabicyclo[3.2.1]octanyl, or (1R,5S)-8-azabicyclo[3.2.1]octanyl, each of which is substituted with 0-2 $T^5$ and 0-1 $T^6$.

Subembodiments of Embodiment 21

Embodiment 21(a) relates to a compound according to Embodiment 21, wherein G is (1R,5S)-3,8-diazabicyclo[3.2.1]octanyl substituted with 0-2 $T^5$ and 0-1 $T^6$.

Embodiment 21(b) relates to a compound according to Embodiment 21, wherein G is (1R,5S)-3-azabicyclo[3.2.1]octanyl substituted with 0-2 $T^5$ and 0-1 $T^6$.

Embodiment 21(c) relates to a compound according to Embodiment 21, wherein G is (1R,5S)-8-azabicyclo[3.2.1]octanyl substituted with 0-2 $T^5$ and 0-1 $T^6$.

Embodiment 22 relates to a compound according to Embodiment 16, wherein G is cyclohexyl, cyclopentyl, cyclohexenyl, cyclopentenyl, each of which is substituted with 0-2 Ti and 0-1 $T^2$.

Subembodiments of Embodiment 22

Embodiment 22(a) relates to a compound according to Embodiment 22, wherein G is cyclohexyl substituted with 0-2 $T^1$ and 0-1 $T^2$.

Embodiment 22(b) relates to a compound according to Embodiment 22, wherein G is cyclopentyl substituted with 0-2 $T^1$ and 0-1 $T^2$.

Embodiment 22(c) relates to a compound according to Embodiment 22, wherein G is cyclohexenyl substituted with 0-2 $T^1$ and 0-1 $T^2$.

Embodiment 22(d) relates to a compound according to Embodiment 22, wherein G is cyclopentenyl substituted with 0-2 $T^1$ and 0-1 $T^2$.

Embodiment 23 relates to a compound according to any one of Embodiments 1-17, wherein $T^3$ is —CH$_2$C(O)N(H)cyclopropyl, —CH$_2$C(O)N(H)CH$_3$, —CH$_2$—COOH, oxetanyl, —(CH$_2$)$_{0-2}$cyclopropyl, —(CH$_2$)$_{0-2}$cyclobutyl, —(CH$_2$)$_{0-2}$-tetrahydropyran, —(CH$_2$)$_{0-2}$-tetrahydrofuran, —(CH$_2$)$_{0-2}$azetidinyl, —(CH$_2$)$_{0-2}$pyrolidinyl, or —(CH$_2$)$_{0-2}$morpholinyl.

Embodiment 24 relates to a compound according to any one of Embodiments 1-17, wherein G is one of the following formulae:

(a)
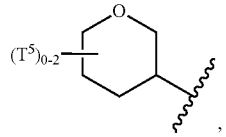

(b)
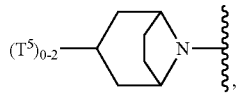

(c)
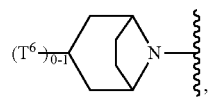

(d)
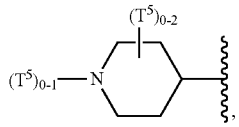

(e)
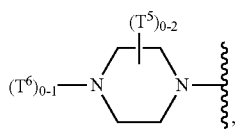

(f)
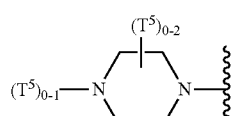

(g)
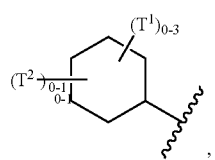

(h)
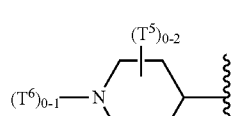

(i)
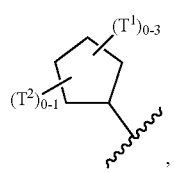

(j)
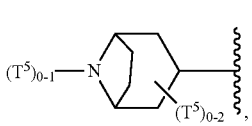

(k)
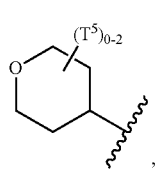

(l)
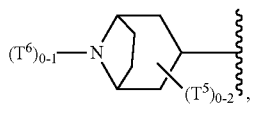

(m)
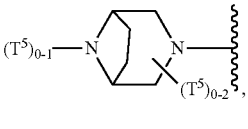

(n)
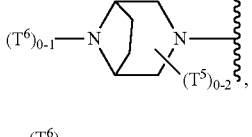

(o)
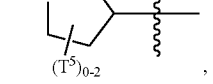

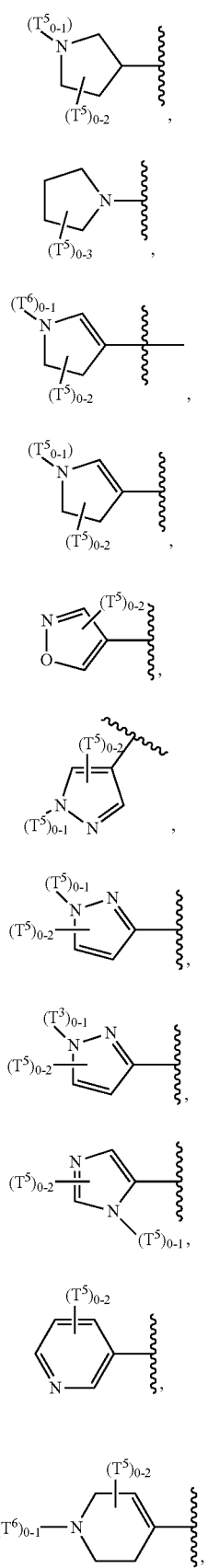
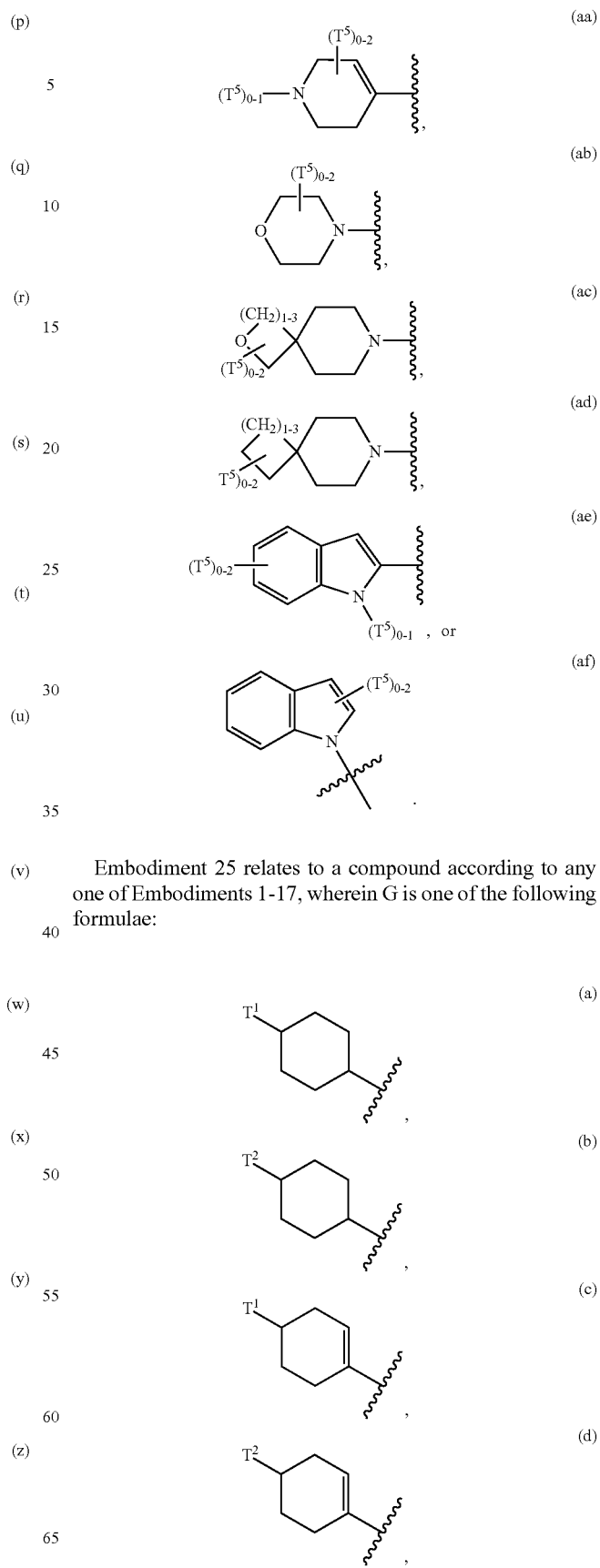
Embodiment 25 relates to a compound according to any one of Embodiments 1-17, wherein G is one of the following formulae:

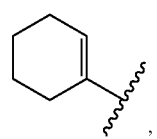 (e)
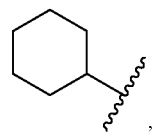 (f)
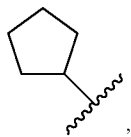 (g)
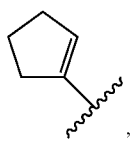 (h)
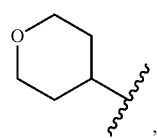 (i)
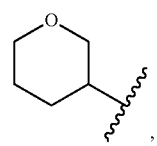 (j)
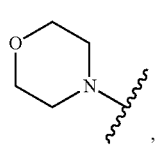 (k)
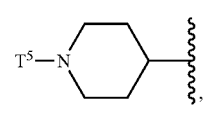 (l)
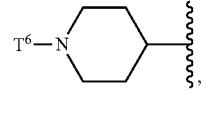 (m)
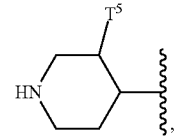 (n)
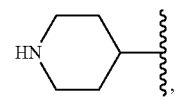 (o)
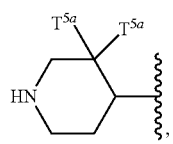 (p)
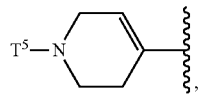 (q)
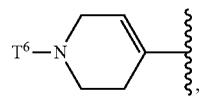 (r)
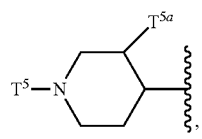 (s)
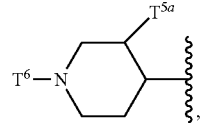 (t)
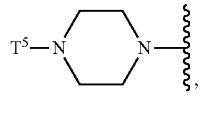 (u)
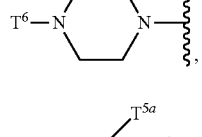 (v)
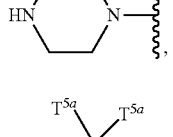 (w)
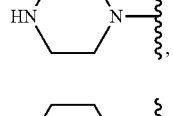 (x)
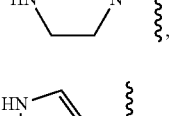 (y)
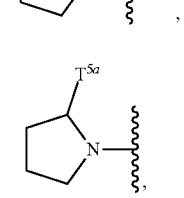 (z)
(aa)

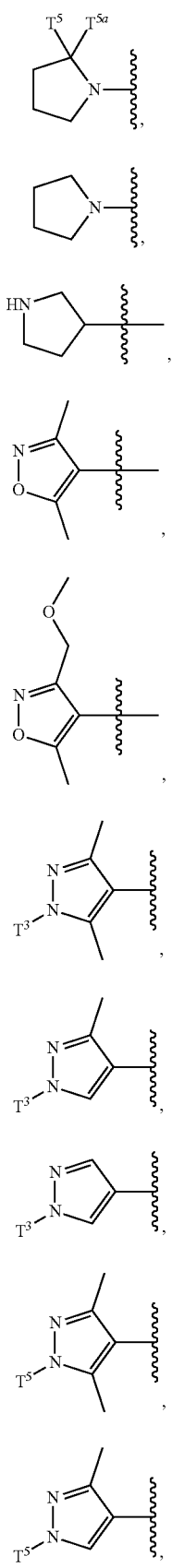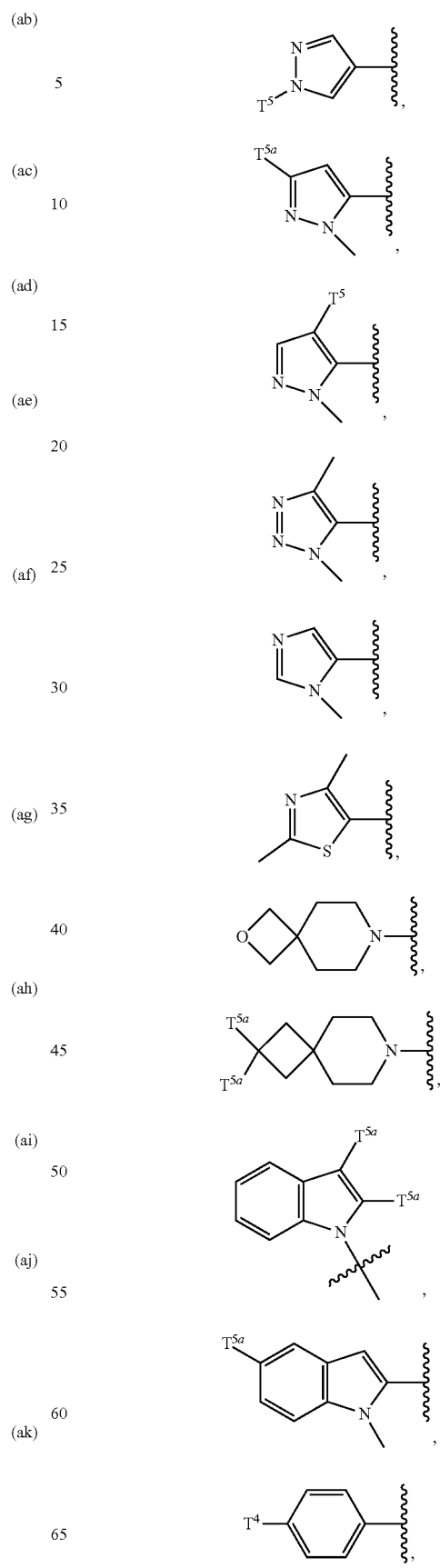

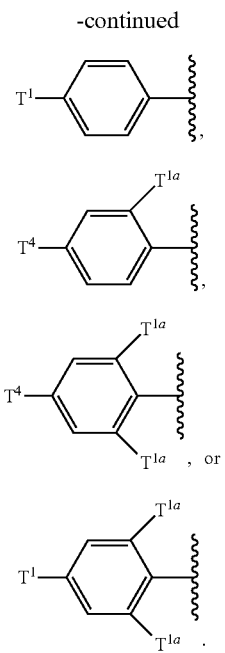

each $T^{1a}$ is independently F, Cl, or $CH_3$; and
each $T^{5a}$ is independently F, Cl, or $CH_3$.

Embodiment 26 relates to a compound according to Embodiment 25, wherein G is one of formulae (a), (b), (c), (d), (e), (f), (g), or (h), Embodiment 27 relates to a compound according to Embodiment 25, wherein G is one of formulae (i), (j), (k), (l), (m), (n), (o), (p), (q), (r), (s), (t), (u), (v), (w), (x), (y), (z), (aa), (ab), (ac), or (ad).

Embodiment 28 relates to a compound according to Embodiment 25, wherein G is one of formulae (ae), (af), (ag), (ah), (ai), (aj), (ak), (al), (am), (an), (ao), (ap), or (aq).

Embodiment 29 relates to a compound according to Embodiment 25, wherein G is one of formulae (ar) or (as).

Embodiment 30 relates to a compound according to Embodiment 25, wherein G is one of formulae (at) or (au).

Embodiment 31 relates to a compound according to Embodiment 25, wherein G is one of formulae (av), (aw), (ax), (ay), or (az).

Embodiment 32 relates to a compound according to any one of Embodiments 1-25 or 27, wherein $T^6$ oxetanylmethylene, —C(O)CH$_2$OH, —C(O)OH, —SO$_2$CH$_3$, —C(O)cyclopropyl, —C(O)CH$_3$, —N(H)SO$_2$-cyclopropyl, —N(H)C(O)cyclopropyl, —SO$_2$N(H)CH$_2$CH$_2$CH$_3$, —SO$_2$NHcyclopropyl, or —SO$_2$CH$_2$CH$_2$CH$_3$.

Embodiment 33 relates to a compound according to any one of Embodiment 1-25, 27 or 29, wherein $T^5$ is F, Cl, CH$_2$Cl, CH$_2$F, CH$_3$, —CH$_2$CH$_3$, —CH(CH$_3$)$_2$, CH$_2$OH, —CH$_2$CH$_2$OH, —CH$_2$C(CH$_3$)$_2$OH, —CH(CH$_2$OH)$_2$, —CH$_2$CH(OH)CF$_3$, CH$_2$CF$_3$, CN, —CH$_2$CN, —OCH$_3$, —CH$_2$OCH$_3$, —CHF$_2$, —CH$_2$CHF$_2$, —CH$_2$CH(OH)CH$_2$CH$_2$Cl, —CH(CH$_2$OH)CH$_2$Cl, —CH(CH$_2$OH)CH$_2$I, or —CH$_2$C(CH$_3$)(CH$_2$OH)CH$_2$Cl.

Embodiment 34 relates to a compound according to any of Embodiments 1-25, wherein $Z^5$ is CH$_3$, F, Cl, CN, —CH$_2$CN, —CH$_2$CH$_3$, or OH.

Embodiment 35 relates to a compound according to Embodiment 1 selected from Table 1, or a pharmaceutically acceptable salt thereof.

Additionally, the formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, dimethyl sulfoxide, ethyl acetate, acetic acid, or ethanolamine.

III. Formulations and Administration

Embodiment 36 of this disclosure relates to a pharmaceutical composition comprising a compound in one of Embodiments of this disclosure, for example, a compound according to any one of Embodiments 1-35, including any subembodiments thereof, and a pharmaceutically acceptable carrier.

Embodiment 37 of this disclosure relates to a pharmaceutical composition of Embodiment 36, further comprising a second pharmaceutical agent.

Suitable dosage forms, in part, depend upon the use or the route of administration, for example, oral, transdermal, transmucosal, inhalant, or by injection (parenteral). Such dosage forms should allow the compound to reach target cells. Other factors are well known in the art, and include considerations such as toxicity and dosage forms that retard the compound or composition from exerting its effects. Techniques and formulations generally may be found in The Science and Practice of Pharmacy, 21$^{st}$ edition, Lippincott, Williams and Wilkins, Philadelphia, PA, 2005 (hereby incorporated by reference herein).

Compounds of the present disclosure (i.e. any of the compounds described in Embodiments 1-36, including any of the subembodiments thereof) can be formulated as pharmaceutically acceptable salts.

Carriers or excipients can be used to produce compositions. The carriers or excipients can be chosen to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

The compounds can be administered by different routes including intravenous, intraperitoneal, subcutaneous, intramuscular, oral, transmucosal, rectal, transdermal, or inhalant. In some embodiments, the compounds can be administered by oral administration. For oral administration, for example, the compounds can be formulated into conventional oral dosage forms such as capsules, tablets, and liquid preparations such as syrups, elixirs, and concentrated drops.

For inhalants, compounds of the disclosure may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds of the disclosure may also be used in combination with other inhaled therapies, for example corticosteroids such as fluticasone propionate, beclomethasone dipropionate, triamcinolone acetonide, budesonide, and mometasone furoate; beta agonists such as albuterol, salmeterol, and formoterol; anticholinergic agents such as ipratropium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

Pharmaceutical preparations for oral use can be obtained, for example, by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

Dragee cores are provided with suitable coatings. For this purpose, concentrated sugar solutions may be used, which may optionally contain, for example, gum arabic, talc, poly-vinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/or subcutaneous. For injection, the compounds of the disclosure are formulated in sterile liquid solutions, such as in physiologically compatible buffers or solutions, such as saline solution, Hank's solution, or Ringer's solution. In addition, the compounds may be formulated in solid form and redissolved or suspended immediately prior to use. Lyophilized forms can also be produced.

Administration can also be by transmucosal, topical, transdermal, or inhalant means. For transmucosal, topical or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

The topical compositions of this disclosure are formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In another embodiment, the carriers are those in which the active ingredient is soluble. Emulsifiers, stabilizers, humectants and antioxidants may also be included as well as agents imparting color or fragrance, if desired. Creams for topical application are formulated from a mixture of mineral oil, self-emulsifying beeswax and water in which mixture the active ingredient, dissolved in a small amount solvent (e.g. an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will, of course, be continuous rather than intermittent throughout the dosage regimen.

The amounts of various compounds to be administered can be determined by standard procedures taking into account factors such as the compound $IC_{50}$, the biological half-life of the compound, the age, size, and weight of the subject, and the indication being treated. The importance of these and other factors are well known to those of ordinary skill in the art. Generally, a dose will be between about 0.01 and 50 mg/kg, or 0.1 and 20 mg/kg of the subject being treated. Multiple doses may be used.

The compounds of the disclosure may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the disclosure or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound of the present disclosure, or at the same time as a compound of the disclosure. Use in combination also includes use with a therapy or medical procedure that is administered once or infrequently, such as surgery, along with a compound of the disclosure administered within a short time or longer time before or after the other therapy or procedure. In some embodiments, the present disclosure provides for delivery of compounds of the disclosure and one or more other drug therapeutics delivered by a different route of administration or by the same route of administration. The use in combination for any route of administration includes delivery of compounds of the disclosure and one or more other drug therapeutics delivered by the same route of administration together in any formulation, including formulations where the two compounds are chemically linked in such a way that they maintain their therapeutic activity when administered. In one aspect, the other drug therapy may be co-administered with one or more compounds of the disclosure. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of compounds of the disclosure and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

IV. Methods of Use

The methods and compounds will typically be used in therapy for human subjects. However, they may also be used to treat similar or identical indications in other animal subjects.

In certain embodiments, the patient is 60 years or older and relapsed after a first line cancer therapy. In certain embodiments, the patient is 18 years or older and is relapsed or refractory after a second line cancer therapy. In certain embodiments, the patient is 60 years or older and is primary refractory to a first line cancer therapy. In certain embodiments, the patient is 70 years or older and is previously untreated. In certain embodiments, the patient is 70 years or older and is ineligible and/or unlikely to benefit from cancer therapy.

In certain embodiments, the therapeutically effective amount used in the methods provided herein is at least 10 mg per day. In certain embodiments, the therapeutically effective amount is 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500 mg per day. In other embodiments, the therapeutically effective amount is 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500, 3000, 3500, 4000, 4500, 5000 mg per day or more. In certain embodiments, the compound is administered continuously.

In certain embodiments, provided herein is a method for treating a diseases or condition mediated by CD73 by administering to a mammal having a disease or condition at least 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500, 3000, 3500, 4000, 4500, 5000 mg per day of any of the compounds described in a compound in one of Embodiments 1-36, or a pharmaceutically acceptable salt, deuterated analog, a tautomer or a stereoisomer thereof, and wherein the compound is administered on an empty stomach.

Embodiment 38 of this disclosure relates to a method for treating a subject with a disease or condition mediated by CD73, said method comprising administering to the subject an effective amount of a compound in one of Embodiments 1-35 (or any subembodiments thereof where applicable), or a pharmaceutically acceptable salt, deuterated analog, a tautomer or a stereoisomer thereof, or a pharmaceutical composition in one of Embodiments 36-37.

Embodiment 39 of this disclosure relates to a method for treatment of a disease or condition according to Embodiment 38, wherein the disease or condition is a neoplastic disorder, a cancer, an age-related disease, an inflammatory disorder, a cognitive disorder and or a neurodegenerative disease.

Embodiment 40 of this disclosure relates a method for treatment of a disease or condition according to Embodiment 38, wherein the disease or condition is bladder cancer, colorectal cancer, gastric cancer, gall bladder cancer, glioblastoma multiforme, glioma, leukemia, lymphoma, lung cancer, breast cancer, melanoma, multiple myeloma, ovarian cancer, prostate cancer, pancreatic cancer, thyroid cancer, liver fibrosis, Alzheimer's disease, multiple sclerosis, or Parkinson's disease.

Embodiment 40(a) of this disclosure relates a method for treatment of a disease or condition according to Embodiment 38, wherein the disease or condition is bladder cancer, colorectal cancer, gastric cancer, gall bladder cancer, glioblastoma multiforme, glioma, leukemia, lymphoma, lung cancer, breast cancer, melanoma, multiple myeloma, ovarian cancer, prostate cancer, pancreatic cancer, thyroid cancer, lung fibrosis, liver fibrosis, Alzheimer's disease, multiple sclerosis, or Parkinson's disease.

Embodiment 41 of this disclosure relates to a method for treatment of a disease or condition according to Embodiment 40, wherein the lymphoma is adult T-cell lymphoma, AIDS-related lymphoma, anaplastic large cell lymphoma, angioimmunoblastic T-cell lymphoma, B-cell lymphoma, Burkitt's lymphoma, cutaneous T-cell lymphoma, diffuse large B-cell lymphoma, enteropathy-associated T-cell lymphoma, follicular lymphoma, hepatosplenic T-cell lymphoma, Hodgkin's lymphoma, non-Hodgkin's lymphoma, MALT lymphoma, mantle cell lymphoma, marginal zone B-cell lymphoma, primary effusion lymphoma, or T-cell lymphoma.

Embodiment 42 of this disclosure relates to a method for treatment of a disease or condition according to Embodiment 40, wherein the leukemia is adult T-cell leukemia, aggressive NK-cell leukemia, B-cell chronic lymphocytic leukemia, acute monocytic leukemia, acute promyelocytic leukemia, B-cell prolymphocytic leukemia, acute eosinophilic leukemia, acute erythroid leukemia, acute lymphoblastic leukemia, acute megakaryoblastic leukemia, acute lymphocytic leukemia, acute myeloid leukemia, chronic lymphocytic leukemia, or mast cell leukemia.

Embodiment 43 of this disclosure relates to a method for treatment of a disease or condition according to Embodiment 38, wherein the disease or condition is renal cancer, small-cell lung cancer, non-small cell lung cancer, acute myeloid leukemia, multiple myeloma, diffuse large B-cell lymphoma, breast cancer or prostate cancer.

Subembodiments of Embodiment 43

Embodiment 43(a) of this disclosure relates a method for treatment of a disease or condition according to Embodiment 43, wherein the disease or condition is renal cancer.

Embodiment 43(b) of this disclosure relates a method for treatment of a disease or condition according to Embodiment 43, wherein the disease or condition is small-cell lung cancer.

Embodiment 43(c) of this disclosure relates a method for treatment of a disease or condition according to Embodiment 43, wherein the disease or condition is non-small cell lung cancer.

Embodiment 43(d) of this disclosure relates a method for treatment of a disease or condition according to Embodiment 43, wherein the disease or condition is acute myeloid leukemia.

Embodiment 43(e) of this disclosure relates a method for treatment of a disease or condition according to Embodiment 43, wherein the disease or condition is multiple myeloma.

Embodiment 43(f) of this disclosure relates a method for treatment of a disease or condition according to Embodiment 43, wherein the disease or condition is diffuse large B-cell lymphoma.

Embodiment 43(g) of this disclosure relates a method for treatment of a disease or condition according to Embodiment 43, wherein the disease or condition is breast cancer.

Embodiment 43(h) of this disclosure relates a method for treatment of a disease or condition according to Embodiment 43, wherein the disease or condition is prostate cancer.

V. Combination Therapy

CD73 modulators may be usefully combined with another pharmacologically active compound, or with two or more other pharmacologically active compounds, particularly in the treatment of cancer. In one embodiment, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer.

Combination with Other Adenosine Axis Blockade Agents Such as Agents Against CD39, CD38, A2AR or A2BR:

Under physiological conditions, ATP and $NAD^+$ in biological fluids and extracellular space is low (30-100 nM), while their intracellular concentration is in mM range. Upon cell activation, stress, hypoxia and tissue damage, they are released from the cells. The excess of extracellular ATP is rapidly hydrolyzed by ectonucleotidases such as CD39 or ectonucleotide pyrophosphatase/phosphdiesterases (ie. ENPP1) to generate ADP and finally AMP. Alternatively AMP can be generated from extracellular nicotinamide adenine dinucleotide (NAD+) by the coordinated action of the ecto-NAD-glucohydrolase CD38 and the ENPP1. AMP is further hydrolyzed to adenosine primarily by CD73 and, less efficiently, by alkaline phosphatase. Adenosine activates signaling pathway through G-protein coupled receptors A1, A2a, A2b and A3. Upon engagement of A2a or A2b receptor that are upregulated in response to immune cell activation, adenosine triggers the increase of intracellular cAMP and leads to a profound suppression of immune function. Preclinical studies support targeting multiple points of the adenosinergic pathway may provide significant therapeutic benefit for cancer treatment. Perrot, I. et al. Blocking Antibodies Targeting the CD39/CD73 Immunosuppressive Pathway Unleash Immune Responses in Combination Cancer Therapies. *Cell Rep.* 27, 2411-2425.e9 (2019), Young, A. et al. Co-inhibition of CD73 and A2AR Adenosine Signaling Improves Anti-tumor Immune Responses. *Cancer Cell* 30, 391-403 (2016).

Combination with Immune Checkpoint Blockade:

Both anti-PD-1 and anti-CTLA4 checkpoint blockade can synergize with anti-CD73 or anti-A2a therapy. Allard, B. et al. Targeting CD73 Enhances the Antitumor Activity of Anti-PD-1 and Anti-CTLA-4 mAbs. *Clin. Cancer Res.* 19, 5626-5636 (2013); Hay, C. M. et al. Targeting CD73 in the tumor microenvironment with MEDI9447. Oncoimmunology 5, 1-10 (2016); Willingham, S. B. et al. A2AR Antagonism with CPI-444 Induces Antitumor Responses and Augments Efficacy to Anti-PD-(L) 1 and Anti-CTLA-4 in Preclinical Models. 6, 22-25 (2018); Waickman, A. T. & Powell, J. D. NIH Public Access. 61, 917-926 (2013); Beavis, P. A. et al. Adenosine Receptor 2A Blockade Increases the Efficacy of Anti-PD-1 through Enhanced Antitumor T-cell Responses. 3, (2015); Mittal, D. et al. Antimetastatic Effects of Blocking PD-1 and the Adenosine A2A Receptor. 3, 3652-3659 (2014). The synergistic effect was shown to promote growth delay and even complete rejection in some tumor models in a CD8+ T cell and IFN-gamma dependent manner. Allard, B. et al. Targeting CD73 Enhances the Antitumor Activity of Anti-PD-1 and Anti-CTLA-4 mAbs. *Clin Cancer Res.* 19, 5626-5636 (2013); Hay, C. M. et al. Targeting CD73 in the tumor microenvironment with MEDI9447. Oncoimmunology 5, 1-10 (2016); Willingham, S. B. et al. A2AR Antagonism with CPI-444 Induces Antitumor Responses and Augments Efficacy to Anti-PD-(L) 1 and Anti-CTLA-4 in Preclinical Models. 6, 22-25 (2018); Beavis, P. A. et al. Adenosine Receptor 2A Blockade Increases the Efficacy of Anti-PD-1 through Enhanced Antitumor T-cell Responses. 3, (2015). Potentially CD73 inhibitor can synergize with other reagents that target T cell-associated inhibitory molecules such as PDL1, LAG-3, TIGIT, TIM-3, VISTA, B7-H3 etc.

Combination with Agonists of TNFA Super Family Member:

Agonist antibodies against Tumor necrosis factor receptor (TNFR) superfamily members such as 4-1BB, GITR and OX40 on the surface of antigen-primed T cells are in various stages of pre-clinical and clinical trials. However they exhibited limited therapeutic benefit as single agents. CD73 expression on T cells sustained by TGF-beta in the tumor microenviroment hindered therapeutic activity of these agonist antibodies. CD73 inhibitors could overcome resistance to and enhance efficacy of TNFR agonists.

Combination with Targeted Therapy:

High expression of CD73 in breast cancers are associated with resistance to Trastuzumab, an anti-HER2/ErbB2 mAb. Turcotte, M. et al. CD73 promotes resistance to HER2/ErbB2 antibody therapy. *Cancer Res.* 77, 5652-5663 (2017). Blocking CD73 was shown to enhance activity of anti-ErbB2 mAb to treat breast tumors as well as lung metastases. Id.

Elevated expression of CD73 was observed in melanoma patients harboring BRAF-mutant tumors. A2AR antagonist was shown to enhance the efficacy of BRAF and MEK inhibition in mice bearing BRAF-mutant tumors. Young, A. et al. Targeting adenosine in BRAF-mutant melanoma reduces tumor growth and metastasis. Cancer Res. 77, 4684-4696 (2017). Similarly CD73 inhibitor could improve the therapeutic benefit of BRAF and MEK inhibitors.

CD73 are overexpressed in NSCLCs harboring EGFR mutations. Inoue, Y. et al. Prognostic impact of CD73 and A2A adenosine receptor expression in non-small-cell lung cancer. Oncotarget 8, 8738-8751 (2017). Similarly CD73 inhibitor could improve the therapeutic benefit of BRAF and MEK inhibitors. CD73 is overexpressed in non-small cell lung cancers (NSCLCs) harboring EGFR mutations (Inoue, Y. et al. Prognostic impact of CD73 and A2A adenosine receptor expression in non-small-cell lung cancer. Oncotarget 8, 8738-8751 (2017)) and its expression is positively correlated with EGFR expression in NSCLC, liver, breast cancer and glioblastoma. Zhu, J. et al. CD73/NT5E is a target of miR-30a-5p and plays an important role in the pathogenesis of non-small cell lung cancer. *Mol. Cancer* 16, 1-15 (2017); Shali, S. et al. Ecto-5'-nucleotidase (CD73) is a potential target of hepatocellular carcinoma. *J. Cell. Physiol.* 234, 10248-10259 (2019); Zhi, X. et al. Potential Prognostic Biomarker CD73 Regulates Epidermal Growth Factor Receptor Expression in Human Breast Cancer. *IUBMB Life.* 64, 911-920 (2012); Ludwig, H. et al. Expression of CD 73 (ecto-5'-nucleotidase) in 165 glioblastomas by immunohistochemistry and electronmicroscopic histochemistry *Anticancer Res.* 19, 1747-52 (1999). CD73 was found to promote EGFR expression in several types of cancer cells including NSCLC, liver and breast cancer cells. Zhu, J. et al. CD73/NT5E is a target of miR-30a-5p and plays an important role in the pathogenesis of non-small cell lung cancer. *Mol. Cancer* 16, 1-15 (2017); Shali, S. et al. Ecto-5'-nucleotidase (CD73) is a potential target of hepatocellular carcinoma. *J. Cell. Physiol.* 234, 10248-10259 (2019); Zhi, X. et al. Potential Prognostic Biomarker CD73 Regulates Epidermal Growth Factor Receptor Expression in Human Breast Cancer. *IUBMB Life.* 64, 911-920 (2012). Previous studies have shown that inhibition of CD73 decreased the proliferation of NSCLC and liver cancer cells (Zhu, J. et al. CD73/NT5E is a target of miR-30a-5p and plays an important role in the pathogenesis of non-small cell lung cancer. *Mol. Cancer* 16, 1-15 (2017); Shali, S. et al. Ecto-5'-nucleotidase (CD73) is a potential target of hepatocellular carcinoma. *J. Cell. Physiol.* 234, 10248-10259 (2019)) and the migration and invasion of breast cancer cells. Zhi, X. et al. Potential Prognostic Biomarker CD73 Regulates Epidermal Growth Factor Receptor Expression in Human Breast Cancer. *IUBMB Life* 64, 911-920 (2012). CD73 inhibition could potentially improve therapeutic outcomes of EGFR inhibitors in these cancers. Combination of CD73 inhibitor with EGFR inhibitor could produce a better therapeutic benefit than single agents.

Combination with Irradiation and Chemotherapy:

Radiotherapy and chemotherapy can induce ATP release from cancer cells. They also enhance the expression of CD73 and other members in adenosine axis. The activity of CD73/adenosine system in tumor microenviroment is not only linked to increased tumor growth and tumor immune escape but is also involved in in radiation-induced adverse late effects such as lung fibrosis. Wirsdorfer, F. et al. Extracellular adenosine production by ecto-50-nucleotidase (CD73) enhances radiation-induced lung fibrosis. *Cancer Res.* 76, 3045-3056 (2016). Blocking CD73 activity can enhance anti-tumor efficacy of radiotherapy (Wennerberg, E. et al. Adenosine regulates radiation therapy-induced anti-tumor immunity. *J. Immunother. Cancer* 3, P378 (2015); Wennerberg, E. et al. Adenosine generation limits radiation-induced tumor immunogenicity by abrogating recruitment and activation of CD103+DCs. *J. Immunol.* 198, 154.6 (2017)) and chemotherapeutic reagent such as Doxorubincin, Paclitaxel (Loi, S. et al. CD73 promotes anthracycline resistance and poor prognosis in triple negative breast cancer. doi:10.1073/pnas.1222251110.), and Mitoxantrone and also decrease radiotherapy induced late toxicity to normal tissues (Wirsdorfer, F. et al. Extracellular adenosine production by ecto-50-nucleotidase (CD73) enhances radiation-induced lung fibrosis. *Cancer Res.* 76, 3045-3056 (2016); de Leve, S. et al. The CD73/Ado System-A New Player in RT Induced Adverse Late Effects. *Cancers (Basel)* 11, 1578 (2019)), therefore improve the therapeutic gain of radiotherapy and chemotherapy.

Combination with Adoptive T Cell Transfer or DC Vaccine:

Adoptive T cell transfer (tumor infiltrating lymphocyte therapy and CAR-T therapy) yielded unprecedented clinical response against certain types of malignancies. Synergy has been demonstrated between CD73 blockade and adoptive T cell transfer in mice. Wang, L. et al. CD73 has distinct roles in nonhematopoietic and hematopoietic cells to promote tumor growth in mice. *J. Clin. Invest.* 121, 2371-2382 (2011); Jin, D. et al. CD73 on tumor cells impairs anti-tumor T cell responses: a novel mechanism of tumor-induced immune suppression. *Cancer Res.* 70, 2245-2255 (2011). This was explained by boosting the homing of the adoptively transferred tumor-specific T cells at the tumor sites by CD73 blockade. Wang, L. et al. CD73 has distinct roles in nonhematopoietic and hematopoietic cells to promote tumor growth in mice. *J. Clin. Invest.* 121, 2371-2382 (2011).

Dendritic cells (DCs) vaccination that aims to induce tumor-specific effector T cells with immunological memory is a promising approach for cancer immunotherapy. Its combination with other therapies that target immunosuppressive mechanisms are needed to improve the outcomes. Targeting CD73 was shown to improve the efficacy of DC vaccines via the induction of tumor-specific T-cell activity. Arab, S. et al. Increased efficacy of a dendritic cell-based therapeutic cancer vaccine with adenosine receptor antagonist and CD73 inhibitor. *Tumor Biol.* 1-8 (2017) doi: 10.1177/1010428317695021.

In another embodiment, the present disclosure provides methods for treating a disease or condition mediated by CD73 by administering to the subject an effective amount of a composition including any one or more compound(s) as described herein in combination with one or more other suitable therapies for treating the disease.

Liver Fibrosis

Hepatic fibrosis is developed as a response to chronic inflammation and ongoing liver injury due to alcohol or virus infection. This pathological process is driven by activation and accumulation of myofibrablasts. CD73 is upregulated in hepatic stellate cells, portal fibroblasts and in fibrous septa as a result of myofibroblast differentiation. Fausther, M. et al. Activated hepatic stellate cells upregulate transcription of ecto-5'-nucleotidase/CD73 via specific SP1 and SMAD promoter elements. *Am. J. Physiol. —Gastrointest. Liver Physiol.* 303, (2012). CD73 deficient mice are protected from the development of liver fibrosis suggesting its role and adenosine generation in fibrogenesis. Peng, Z. et al. Ecto-5'-nucleotidase (CD73)-mediated extracellular adenosine production plays a critical role in hepatic fibrosis. *FASEB J.* 22, 2263-2272 (2008). CD73 might be useful in the prevention of liver fibrosis.

Multiple Sclerosis (MS)

MS is an autoimmune disease that affects the CNS. In a MS animal model, experimental autoimmune encephalomyelitis (EAE), myelin antigen specific CD4+ T cells was shown to play a role in inducing CNS inflammation, demyelination and neurodegeneration. Despite CD73 is well known for its central role in immunosuppression, CD73−/− mice were highly resistant to EAE induction. Mills, J. H. et al. CD73 is required for efficient entry of lymphocytes into the central nervous system during experimental autoimmune encephalomyelitis. *Proc. Natl. Acad. Sci. U.S.A* 105, 9325-9330 (2008). This was explained by more profound role of CD73 and adenosine in CNS lymphocyte infiltration during EAE induction than their role in modulation of neuroinflammation. Id. CD73 inhibition might be useful for treating MS and other neuroinflammatory disease.

Embodiment 44 of this disclosure relates to the method according to any one of Embodiments 38-43, or any sub-embodiments thereof, further comprising administering one or more additional therapeutic agents.

Embodiment 45 of this disclosure relates to the method according Embodiment 44, wherein the one or more of i) an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from the group consisting of azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an immunotherapy agent selected from a PD-1 or PD-L1 inhibitor; v) a hormone or hormone antagonist selected from the group consisting of enzalutamide, abiraterone, anastrozole, androgens, buserelin, diethylstilbestrol, exemestane, flutamide, fulvestrant, goserelin, idoxifene, letrozole, leuprolide, magestrol, raloxifene, tamoxifen, and toremifene; vi) a taxane selected from DJ-927, docetaxel, TPI 287, paclitaxel and DHA-paclitaxel; vii) a retinoid selected from alitretinoin, bexarotene, fenretinide, isotretinoin, and tretinoin; viii) an alkaloid selected from etoposide, homoharringtonine, teniposide, vinblastine, vincristine, vindesine, and vinorelbine; ix) an antiangiogenic agent selected from AE-941 (GW786034, Neovastat), ABT-510, 2-methoxyestradiol, lenalidomide, and thalidomide; x) a topoisomerase inhibitor selected from amsacrine, edotecarin, exatecan, irinotecan, SN-38 (7-ethyl-10-hydroxycamptothecin), rubitecan, topotecan, and 9-aminocamptothecin; xi) a kinase inhibitor selected from erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib, trametinib, cobimetinib selumetinib and vatalanib; xii) a targeted signal transduction inhibitor selected from bortezomib, geldanamycin, and rapamycin; xiii) a biological response modifier selected from imiquimod, interferon-α and interleukin-2; xiv) an IDO inhibitor; and xv) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, a mTOR inhibitor, a PI3K inhibitor, a Cdk4 inhibitor, an Akt inhibitor, a Hsp90 inhibitor, a farnesyltransferase inhibitor or an aromatase inhibitor (anastrozole letrozole exemestane); xvi) a Mek inhibitor; xvii) a tyrosine kinase inhibitor; xviii) a c-Kit mutant inhibitor, xix) an EGFR inhibitor, a PD-1 inhibitor, or xx) an epigenetic modulator.

Embodiment 46 of this disclosure relates to the method according Embodiment 45, wherein the or more additional therapeutic agents is a PD-1 or PD-L1 inhibitor.

Embodiment 47 of this disclosure relates to the method according Embodiment 46, wherein the PD-1 or PD-L1 inhibitor is nivolumab, pembrolizumab, cemiplimab, atezolizumab, avelumab, or durvalumab.

Embodiment 47(a) of this disclosure relates to the method according Embodiment 46, wherein the PD-1 or PD-L1 inhibitor is nivolumab, pembrolizumab, cemiplimab, atezolizumab, avelumab, durvalumab, or zimberelimab.

Embodiment 48 of this disclosure relates to the method according Embodiment 44, wherein the one or more additional therapeutic agents is a PD-1 inhibitor and the disease or condition is colorectal cancer.

Embodiment 49 of this disclosure relates to the method according Embodiment 44, comprising administering a first and a second additional therapeutic agents.

Embodiment 50 of this disclosure relates to the method according Embodiment 49, wherein the first additional therapeutic agent is a PD-1 inhibitor, the second additional therapeutic agent is a chemotherapeutic agent, and the disease or condition is an adenocarcinoma.

Embodiment 50(a) of this disclosure relates to the method according Embodiment 50, wherein the adenocarcinoma is metastatic pancreatic ductal adenocarcinomas.

In another embodiment, the present disclosure provides a method of treating a cancer in a subject in need thereof by administering to the subject an effective amount of a composition including any one or more compound(s) as described herein in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, .gamma.-ray, or electron, proton, neutron, or alpha. particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexatin lutetium), surgery, or bone marrow and stem cell transplantation.

VI. Kits

In another aspect, the present disclosure provides kits that include one or more compounds as described in any one of a compound in one of Embodiments 1-35, or a pharmaceutically acceptable salt, deuterated analog, a tautomer or a stereoisomer thereof, or a pharmaceutical composition in one of Embodiments 36-37. In some embodiments, the compound or composition is packaged, e.g., in a vial, bottle, flask, which may be further packaged, e.g., within a box, envelope, or bag. The compound or composition may be approved by the U.S. Food and Drug Administration or similar regulatory agency for administration to a mammal, e.g., a human. The compound or composition may be approved for administration to a mammal, e.g., a human, for a CD73 mediated disease or condition. The kits described herein may include written instructions for use and/or other indication that the compound or composition is suitable or approved for administration to a mammal, e.g., a human, for a CD73 mediated disease or condition. The compound or composition may be packaged in unit dose or single dose form, e.g., single dose pills, capsules, or the like.

VI. Binding Assays

The methods of the present disclosure can involve assays that are able to detect the binding of compounds to a target molecule. Such binding is at a statistically significant level, with a confidence level of at least 90%, or at least 95, 97, 98, 99% or greater confidence level that the assay signal represents binding to the target molecule, i.e., is distinguished from background. In some embodiments, controls are used to distinguish target binding from non-specific binding. A large variety of assays indicative of binding are known for different target types and can be used for this disclosure.

Binding compounds can be characterized by their effect on the activity of the target molecule. Thus, a "low activity" compound has an inhibitory concentration ($IC_{50}$) or effective concentration ($EC_{50}$) of greater than 1 µM under standard conditions. By "very low activity" is meant an $IC_{50}$ or $EC_{50}$ of above 100 µM under standard conditions. By "extremely low activity" is meant an $IC_{50}$ or $EC_{50}$ of above 1 mM under standard conditions. By "moderate activity" is meant an $IC_{50}$ or $EC_{50}$ of 200 nM to 1 µM under standard conditions. By "moderately high activity" is meant an $IC_{50}$ or $EC_{50}$ of 1 nM to 200 nM. By "high activity" is meant an $IC_{50}$ or $EC_{50}$ of below 1 nM under standard conditions. The $IC_{50}$ or $EC_{50}$ is defined as the concentration of compound at which 50% of the activity of the target molecule (e.g. enzyme or other protein) activity being measured is lost or gained relative to the range of activity observed when no compound is present. Activity can be measured using methods known to those of ordinary skill in the art, e.g., by measuring any detectable product or signal produced by occurrence of an enzymatic reaction, or other activity by a protein being measured.

By "background signal" in reference to a binding assay is meant the signal that is recorded under standard conditions for the particular assay in the absence of a test compound, molecular scaffold, or ligand that binds to the target molecule. Persons of ordinary skill in the art will realize that accepted methods exist and are widely available for determining background signal.

By "standard deviation" is meant the square root of the variance. The variance is a measure of how spread out a distribution is. It is computed as the average squared deviation of each number from its mean. For example, for the numbers 1, 2, and 3, the mean is 2 and the variance is:

$$\sigma^2 = \frac{(1-2)^2 + (2-2)^2 + (3-2)^2}{3} = 0.667.$$

Surface Plasmon Resonance

Binding parameters can be measured using surface plasmon resonance, for example, with a BIAcore® chip (Biacore, Japan) coated with immobilized binding components. Surface plasmon resonance is used to characterize the microscopic association and dissociation constants of reaction between an sFv or other ligand directed against target molecules. Such methods are generally described in the following references which are incorporated herein by reference. Vely F. et al., (2000) BIAcore® analysis to test phosphopeptide-SH2 domain interactions, Methods in Molecular Biology. 121:313-21; Liparoto et al., (1999) Biosensor analysis of the interleukin-2 receptor complex, Journal of Molecular Recognition. 12:316-21; Lipschultz et al., (2000) Experimental design for analysis of complex kinetics using surface plasmon resonance, Methods. 20(3): 310-8; Malmqvist., (1999) BIACORE: an affinity biosensor system for characterization of biomolecular interactions, Biochemical Society Transactions 27:335-40; Alfthan, (1998) Surface plasmon resonance biosensors as a tool in antibody engineering, Biosensors & Bioelectronics. 13:653-63; Fivash et al., (1998) BIAcore for macromolecular interaction, Current Opinion in Biotechnology. 9:97-101; Price et al.; (1998) Summary report on the ISOBM TD-4 Workshop: analysis of 56 monoclonal antibodies against the MUC1 mucin. Tumour Biology 19 Suppl 1:1-20; Malmqvist et al, (1997) Biomolecular interaction analysis: affinity biosensor technologies for functional analysis of proteins, Current Opinion in Chemical Biology. 1:378-83; O'Shannessy et al., (1996) Interpretation of deviations from pseudo-first-order kinetic behavior in the characterization of ligand binding by biosensor technology, Analytical Biochemistry. 236:275-83; Malmborg et al., (1995) BIAcore as a tool in antibody engineering, Journal of Immunological Methods. 183:7-13; Van Regenmortel, (1994) Use of biosensors to characterize recombinant proteins, Developments in Biological Standardization. 83:143-51; and O'Shannessy, (1994) Determination of kinetic rate and equilibrium binding constants for macromolecular interactions: a critique of the surface plasmon resonance literature, Current Opinions in Biotechnology. 5:65-71.

BIAcore® uses the optical properties of surface plasmon resonance (SPR) to detect alterations in protein concentration bound to a dextran matrix lying on the surface of a gold/glass sensor chip interface, a dextran biosensor matrix. In brief, proteins are covalently bound to the dextran matrix at a known concentration and a ligand for the protein is injected through the dextran matrix. Near infrared light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (e.g. by ligand binding to the bound protein) a shift occurs in the resonance angle. This angle shift can be measured and is expressed as resonance units (RUs) such that 1000 RUs is equivalent to a change in surface protein concentration of 1 $ng/mm^2$. These changes are displayed with respect to time along the y-axis of a sensorgram, which depicts the association and dissociation of any biological reaction.

High Throughput Screening (HTS) Assays

HTS typically uses automated assays to search through large numbers of compounds for a desired activity. Typically HTS assays are used to find new drugs by screening for chemicals that act on a particular enzyme or molecule. For example, if a chemical inactivates an enzyme it might prove to be effective in preventing a process in a cell which causes a disease. High throughput methods enable researchers to assay thousands of different chemicals against each target molecule very quickly using robotic handling systems and automated analysis of results.

As used herein, "high throughput screening" or "HTS" refers to the rapid in vitro screening of large numbers of compounds (libraries); generally tens to hundreds of thousands of compounds, using robotic screening assays. Ultra-high-throughput Screening (uHTS) generally refers to the high-throughput screening accelerated to greater than 100,000 tests per day.

To achieve high-throughput screening, it is advantageous to house samples on a multicontainer carrier or platform. A multicontainer carrier facilitates measuring reactions of a plurality of candidate compounds simultaneously. Multi-well microplates may be used as the carrier. Such multi-well microplates, and methods for their use in numerous assays, are both known in the art and commercially available.

Screening assays may include controls for purposes of calibration and confirmation of proper manipulation of the components of the assay. Blank wells that contain all of the reactants but no member of the chemical library are usually included. As another example, a known inhibitor (or activator) of an enzyme for which modulators are sought, can be incubated with one sample of the assay, and the resulting decrease (or increase) in the enzyme activity used as a comparator or control. It will be appreciated that modulators can also be combined with the enzyme activators or inhibitors to find modulators which inhibit the enzyme activation or repression that is otherwise caused by the presence of the known the enzyme modulator.

Measuring Enzymatic and Binding Reactions During Screening Assays

Techniques for measuring the progression of enzymatic and binding reactions, e.g., in multicontainer carriers, are known in the art and include, but are not limited to, the following.

Spectrophotometric and spectrofluorometric assays are well known in the art. Examples of such assays include the use of colorimetric assays for the detection of peroxides, as described in Gordon, A. J. and Ford, R. A., (1972) The Chemist's Companion: A Handbook Of Practical Data, Techniques, And References, John Wiley and Sons, N.Y., Page 437.

Fluorescence spectrometry may be used to monitor the generation of reaction products. Fluorescence methodology is generally more sensitive than the absorption methodology. The use of fluorescent probes is well known to those skilled in the art. For reviews, see Bashford et al., (1987) Spectrophotometry and Spectrofluorometry: A Practical Approach, pp. 91-114, IRL Press Ltd.; and Bell, (1981) Spectroscopy In Biochemistry, Vol. I, pp. 155-194, CRC Press.

In spectrofluorometric methods, enzymes are exposed to substrates that change their intrinsic fluorescence when processed by the target enzyme. Typically, the substrate is nonfluorescent and is converted to a fluorophore through one or more reactions. As a non-limiting example, SMase activity can be detected using the Amplex® Red reagent (Molecular Probes, Eugene, OR). In order to measure sphingomyelinase activity using Amplex® Red, the following reactions occur. First, SMase hydrolyzes sphingomyelin to yield ceramide and phosphorylcholine. Second, alkaline phosphatase hydrolyzes phosphorylcholine to yield choline. Third, choline is oxidized by choline oxidase to betaine. Finally, $H_2O_2$, in the presence of horseradish peroxidase, reacts with Amplex® Red to produce the fluorescent product, Resorufin, and the signal therefrom is detected using spectrofluorometry.

Fluorescence polarization (FP) is based on a decrease in the speed of molecular rotation of a fluorophore that occurs upon binding to a larger molecule, such as a receptor protein, allowing for polarized fluorescent emission by the bound ligand. FP is empirically determined by measuring the vertical and horizontal components of fluorophore emission following excitation with plane polarized light. Polarized emission is increased when the molecular rotation of a fluorophore is reduced. A fluorophore produces a larger polarized signal when it is bound to a larger molecule (i.e. a receptor), slowing molecular rotation of the fluorophore. The magnitude of the polarized signal relates quantitatively to the extent of fluorescent ligand binding. Accordingly, polarization of the "bound" signal depends on maintenance of high affinity binding.

FP is a homogeneous technology and reactions are very rapid, taking seconds to minutes to reach equilibrium. The reagents are stable, and large batches may be prepared, resulting in high reproducibility. Because of these properties, FP has proven to be highly automatable, often performed with a single incubation with a single, premixed, tracer-receptor reagent. For a review, see Owicki et al., (1997), Application of Fluorescence Polarization Assays in High-Throughput Screening, Genetic Engineering News, 17:27.

FP is particularly desirable since its readout is independent of the emission intensity (Checovich, W. J., et al., (1995) Nature 375:254-256; Dandliker, W. B., et al., (1981) Methods in Enzymology 74:3-28) and is thus insensitive to the presence of colored compounds that quench fluorescence emission. FP and FRET (see below) are well-suited for identifying compounds that block interactions between sphingolipid receptors and their ligands. See, for example, Parker et al., (2000) Development of high throughput screening assays using fluorescence polarization: nuclear receptor-ligand-binding and kinase/phosphatase assays, J Biomol Screen 5:77-88.

Fluorophores derived from sphingolipids that may be used in FP assays are commercially available. For example, Molecular Probes (Eugene, OR) currently sells sphingomyelin and one ceramide flurophores. These are, respectively, N-(4,4-difluoro-5,7-dimethyl-4-bora-3a,4a-diaza-s-indacene-3-pentanoyl)sphingosyl phosphocholine (BODIPY® FL C5-sphingomyelin); N-(4,4-difluoro-5,7-dimethyl-4-bora-3a,4a-diaza-s-indacene-3-dodecanoyl)sphingosyl phosphocholine (BODIPY® FL C12-sphingomyelin); and N-(4,4-difluoro-5,7-dimethyl-4-bora-3a,4a-diaza-s-indacene-3-pentanoyl)sphingosine (BODIPY® FL C5-ceramide). U.S. Pat. No. 4,150,949, (Immunoassay for gentamicin), discloses fluorescein-labelled gentamicins, including fluoresceinthiocarbanyl gentamicin. Additional fluorophores may be prepared using methods well known to the skilled artisan.

Exemplary normal-and-polarized fluorescence readers include the POLARION® fluorescence polarization system (Tecan A G, Hombrechtikon, Switzerland). General multiwell plate readers for other assays are available, such as the VERSAMAX® reader and the SPECTRAMAX® multiwell plate spectrophotometer (both from Molecular Devices).

Fluorescence resonance energy transfer (FRET) is another useful assay for detecting interaction and has been described. See, e.g., Heim et al., (1996) Curr. Biol. 6:178-182; Mitra et al., (1996) Gene 173:13-17; and Selvin et al., (1995) Meth. Enzymol. 246:300-345. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a fMAX multiwell fluorometer (Molecular Devices, Sunnyvale Calif.).

Scintillation proximity assay (SPA) is a particularly useful assay for detecting an interaction with the target molecule. SPA is widely used in the pharmaceutical industry and has been described (Hanselman et al., (1997) J. Lipid Res. 38:2365-2373; Kahl et al., (1996) Anal. Biochem. 243:282-283; Undenfriend et al., (1987) Anal. Biochem. 161:494-500). See also U.S. Pat. Nos. 4,626,513 and 4,568,649, and European Patent No. 0,154,734. One commercially available system uses FLASHPLATE® scintillant-coated plates (NEN Life Science Products, Boston, MA).

The target molecule can be bound to the scintillator plates by a variety of well-known means. Scintillant plates are available that are derivatized to bind to fusion proteins such as GST, His6 or Flag fusion proteins. Where the target molecule is a protein complex or a multimer, one protein or subunit can be attached to the plate first, then the other components of the complex added later under binding conditions, resulting in a bound complex.

In a typical SPA assay, the gene products in the expression pool will have been radiolabeled and added to the wells, and allowed to interact with the solid phase, which is the immobilized target molecule and scintillant coating in the wells. The assay can be measured immediately or allowed to reach equilibrium. Either way, when a radiolabel becomes sufficiently close to the scintillant coating, it produces a signal detectable by a device such as a TOPCOUNT NXT® microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed. If too many signals are obtained, salt or other modifiers can be added directly to the assay plates until the desired specificity is obtained (Nichols et al., (1998) Anal. Biochem. 257:112-119).

General Synthesis

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein.

The compounds of this disclosure may contain one or more asymmetric or chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, supercritical fluid chromathography, chiral seed crystals, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance, California, USA), Emka-Chemce or Sigma (St. Louis, Missouri, USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

It will also be appreciated that in each of the schemes, the addition of any substituent may result in the production of a number of isomeric products (including, but not limited to, enantiomers or one or more diastereomers) any or all of which may be isolated and purified using conventional techniques. When enantiomerically pure or enriched compounds are desired, chiral chromatography and/or enantiomerically pure or enriched starting materials may be employed as conventionally used in the art or as described in the Examples.

Compounds of the present disclosure may be synthesized in accordance with the general reaction schemes and/or examples described below. The general schemes may be altered by substitution of the starting materials with other materials having similar structures to result in corresponding products. The structure of the desired product will generally make apparent to a person of skill in the art the required starting materials.

Scheme 1 provides exemplary synthetic routes for the synthesis of compounds provided herein (e.g., a compound of Formula I). A compound of Formula I, or other formulas or compounds disclosed herein, is typically prepared by first providing the core Formula X(a) and then attaching the desired substituents using suitable conditions (e.g., conjugate addition; carbonate, carbamate, or urea formation; or cross coupling).

In some embodiments, synthesis of a compound of Formula I proceeds according to Scheme 1.

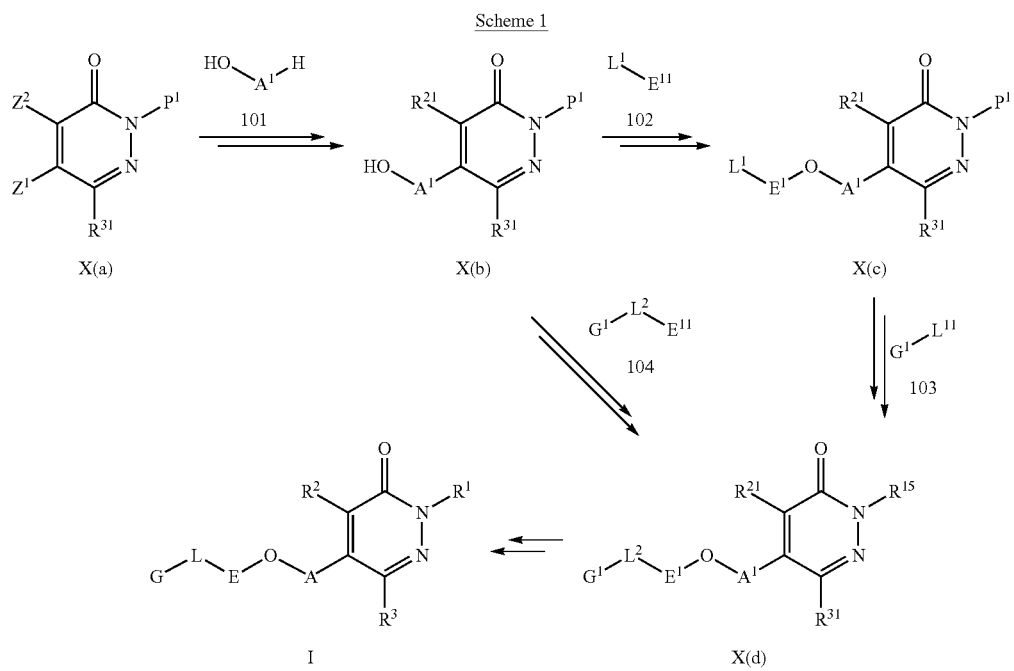

In Scheme 1, A, E, G, L, $R^1$, $R^2$, and $R^3$ are as defined in Formula I. In Scheme 1, a compound of Formula X(a) is converted into a compound of Formula X(b). The compound of Formula X(b) may then be converted into a compound of Formula X(d), optionally via Formula X(c), which may be converted into a compound of Formula I. $A^1$, $E^1$, $E^{11}$, $G^1$, $L^1$, $L^2$, $L^{11}$, $P^1$, $R^{15}$, $R^{21}$, $R^{31}$, $Z^1$, and $Z^2$ are as described below.

In Scheme 1, each of $Z^1$ and $Z^2$ is independently a leaving group, e.g., a halide or a suitable coupling partner, or $Z^2$ is $R^{21}$. For example, $Z^1$ and/or $Z^2$ may be a chloride or a bromide. As a coupling partner, $Z^1$ or $Z^2$ may be activated in situ, e.g., by a reduced zinc reagent such as zinc metal. A compound of Formula X(a) may be reacted with compound 101 under conjugate addition conditions.

In Scheme 1, $P^1$ is H, $R^{15}$, or an N-protecting group. For example, $P^1$ may be an N-protecting group that forms an aminal or amidal with the parent structure (e.g., $P^1$ may be a tetrahydropyran such as tetrahydro-2H-pyran-2-yl ("THP")). Where $P^1$ is H, $R^{15}$ may be added by conventional means, for example, by nucleophilic addition of the parent structure to a halide such as a primary halide (e.g., where $R^{15}$ is a protected precursor of $R^1$, a halide such as 2-(2-bromoethoxy)tetrahydro-2H-pyran). Where $P^1$ comprises a pyran, the pyran may be removed by conventional pyran deprotection conditions, for example, as described herein or as known in the art. Where $P^1$ is not H, $P^1$ may be added by conventional means, for example, by protection group chemistry according to a process described herein or as known in the art. For example, $P^1$ may be added by acid catalyzed addition of the parent structure to a dihydro-2H-pyran.

In Scheme 1, $R^{15}$ is $R^1$ or a derivative of $R^1$ such as a protected derivative of $R^1$. In some embodiments, $R^{15}$ is a hydroxyl-protected derivative of $R^1$. For example, the hydroxyl-protected derivative of $R^1$ may include a silyl ether, an acetate, a benzyl, a benzoyl, an acetonide, or a tetrahydropyranyl derivative (e.g., where $R^1$ is ethan-2-ol, $R^{15}$ may be 2-((tetrahydro-2H-pyran-2-yl)oxy)ethyl). In some embodiments, $R^{15}$ comprises a protected diol corresponding to a diol at $R^1$ (e.g., where $R^1$ comprises a vicinal diol, $R^{15}$ may comprise a dioxolane).

In Scheme 1, $A^1$ is A or a derivative thereof. The derivative of A at A1 may further include a substituent group from which A may be derived by oxidation, reduction, and/or protection (e.g., $A^1$ may comprise a cyano substituent where A comprises an amide). For example, $A^1$ may be a pyrrolidin-1-yl such as (R)-3-hydroxypyrrolidin-1-yl or (3S,4S)-3-hydroxy-4-fluoropyrrolidin-1-yl.

In Scheme 1, $E^1$ is E or a derivative thereof, or $E^1$ may be H. The derivative of E at $E^1$ may comprise a leaving group or a suitable coupling partner (e.g., $E^1$ may comprise a halo such as a bromo or an iodo). The derivative of E at $E^1$ may further include a substituent group from which E may be derived by oxidation, reduction, and/or protection (e.g., $E^1$ may comprise a cyano substituent where E comprises an amide). The compound of Formula X(b) may be reacted with compound 102 or compound 104 under nucleophilic aromatic substitution conditions or copper coupling conditions as described herein or as known in the art. In some embodiments, $E^1$ may comprise a phenyl, pyridazin-4-yl, pyrimidin-4-yl, pyrimidin-6-yl, pyridin-2-yl, pyridin-3-yl, or pyridin-4-yl. In some embodiments, $L^1$-$E^{11}$ is 4-bromopyridin-2-yl, 4-bromo-5-chloro-2-fluoro-pyridine, 3-bromo-5-iodo-pyridine, 1-bromo-3-iodobenzene, 5-bromo-3-chloro-pyridazine, or 4,6-dichloropyrimidine. When compound X(b) is convered directly to Formula X(d), Formula X(b) may be reacted with compound 104. In such embodiments, $G^1$-$L^2$-$E^{11}$ may be 4-(2-fluoro-4-pyridyl)-3,5-dimethyl-isoxazole or 4-(6-chloropyridazin-4-yl)-3, 5-dimethyl-isoxazole.

In Scheme 1, $E^{11}$ is a derivative of $E^1$ suitable for appending $E^1$ to the parent structure of Formula X(b) by reaction with compound 102 or compound 104. For example, a compound of Formula X(b) may be reacted with compound 102 or compound 104 under nucleophilic displacement conditions, for example, nucleophilic aromatic substitution conditions.

In Scheme 1, each of $L^1$ and $L^2$ is independently a portion or a derivative of L, or $L^1$ may be H, or $L^2$ may be L. The portion or the derivative of L at $L^1$ may include a hydrogen atom at the point of attachment for the remainder of L or for $G^1$ (e.g., where L includes an oxygen or a nitrogen atom as connected to the parent structure, $A^1$-$L^1$ may be a corresponding hydroxyl, amine, or —C(O)NH$_2$). The portion or the derivative of L at $L^1$ may comprise a protecting group at the point of attachment for $G^1$ (e.g., a hydroxyl protecting group such as a p-nitrophenoxycarbonyl or a tetrahydropyran, or an amine protecting group such as a tert-butoxycarbonyl). In some embodiments, $L^1$ or L2 may be absent.

In Scheme 1, $L^{11}$ is a derivative of $L^2$ suitable for appending $L^2$ to the parent structure of Formula X(c) by reaction with compound 103. $L^{11}$ may be a suitable coupling partner or leaving group (e.g., a boronic acid, boronic ester such as a 4,4,5,5-tetramethyl-1,3,2-dioxaborolan-2-yl, a pseudohalide, or a halide such as a chloro, bromo, or an iodo). For example, a compound of Formula X(c) may be reacted with compound 103 under nucleophilic displacement conditions, for example, nucleophilic aromatic substitution conditions, or under coupling conditions such as palladium coupling conditions or copper coupling conditions. In some embodiments, $L^{11}$ is hydrogen.

In Scheme 1, $G^1$ is G or a derivative of G. The derivative of G may comprise one or more moieties suitable for appending Ti, $T^2$, $T^3$, $T^4$, $T^5$, and/or $T^6$ ("$T^1$-$T^6$"), and/or the derivative of G may comprise a nitrogen or oxygen protecting group (e.g., a THP). Thus, the derivative of G may comprise an amine (e.g., a cyclic amine where G comprises a piperidinyl, piperazinyl, or pyrrolidinyl) or a protected amine (e.g., comprising a tert-butoxycarbonyl protecting group). Conversion of $G^1$ to G may comprise a displacement reaction at a carbonyl or sulfonyl portion of $T^1$-$T^6$ to form a carbonate, carbamate, urea, or sulfonamide (e.g., where Gi comprises an amine, the amine of $G^1$ may be added to a sulfamoyl chloride or an acyl chloride corresponding to $T^1$-$T^6$). Conversion of $G^1$ to G may alternatively comprise a nculeophilic displacement reaction (e.g., Sn1 or Sn2 type reaction) at a portion of $T^1$-$T^6$. For example, where $T^1$-$T^6$ comprises a alpha-carbonyl, reaction may proceed by an Sn2 displacement of a pseudohalide (e.g., a sulfonate such as (3-cyanobicyclo[1.1.1]pentan-1-yl)methyl 4-methylbenzenesulfonate) or a halide (e.g., a bromo such as tert-butyl 2-bromoacetate).

In Scheme 1, $R^{21}$ is H, or a protected derivative of $R^2$, or a suitable coupling partner (e.g., a pseudohalide or a halide such as chloro, bromo, or iodo), or $R^{21}$ is $R^2$.

In Scheme 1, $R^{31}$ is $R^3$.

Conjugate Addition Conditions

Where appropriate, for example, where compound 101 (OH-$A^1$-H) is added to the compound of Formula X(a), a conjugate addition reaction may be conducted. The conjugate addition reaction is conducted under nucleophilic addition conditions (e.g., in the presence of a base such as triethylamine, N,N-diisopropyl-N-ethylamine or a carbonate, e.g., potassium carbonate), in a suitable solvent (e.g., a polar aprotic solvent, tetrahydrofuran, DMF, etc.), optionally under an inert atmosphere. The reaction is typically conducted at a temperature of about 20 to 100° C., for about 10 minutes to about 7 days. When the reaction is substantially complete, the product is isolated by conventional means. In some embodiments, compound 101 is (R)-pyrrolidin-3-ol or (3S,4S)-4-fluoropyrrolidin-3-ol, or a salt thereof.

Nucleophilic Aromatic Substitution Conditions

Where appropriate, for example, where compound 102 ($L^1$-$E^{11}$) is added to the compound of Formula X(b), a nucleophilic aromatic substitution reaction may be conducted. The nucleophilic aromatic substitution reaction is conducted under nucleophilic addition conditions (e.g., in the presence of a base such as sodium hydride or cesium carbonate), in a suitable solvent (e.g., a polar aprotic solvent, 1,4-dioxane, tetrahydrofuran, DMF, etc.), optionally under an inert atmosphere. The reaction is typically conducted at a temperature of about 20 to 120° C., for about 10 minutes to about 7 days. The conditions may comprise a discrete deprotonation step (e.g., where the base is sodium hydride). When the reaction is substantially complete, the product is isolated by conventional means. In some embodiments, compound 102 is a 2-fluoropyridine, 3-fluoropyridine, or 4-fluoropyridine (e.g., 4-bromo-5-chloro-2-fluoro-pyridine).

Palladium Coupling Conditions

Where appropriate, e.g., the compound of Formula X(a), Formula X(b), Formula X(c), or Formula X(d), compound 102, compound 103, or compound 104, in which any of $Z^1$, $Z^2$, $E^{11}$, $L^1$, $L^{11}$, or $G^1$ comprises a suitable coupling partner, for example, a pseudohalide or a halide (e.g., chloro), or a zinc reagent (e.g., zinc cyanide), is reacted under standard metal-catalyzed cross coupling conditions (e.g., using a palladium catalyst) in a suitable solvent (e.g., toluene, N,N-dimethylacetamide, dioxane, acetonitrile, water, etc.), optionally under an inert atmosphere. The coupling reaction is carried out in an inert solvent, for example aqueous 1,4-dioxane or aqueous N,N-dimethylformamide, in the presence of a mild base, for example pyridine, potassium carbonate, sodium carbonate, sodium bicarbonate, or sodium tert-butoxide. The reaction is typically conducted in the presence of a metal catalyst, for example tris(dibenzylideneacetone)dipalladium(0), dichlorobis(triphenylphosphine) palladium(II), or dichloro 1,1'-bis(diphenylphosphino)ferrocene palladium(II), ruphos palladacycle GEN 4, optionally with an appropriate ligand (e.g., 1,1'-bis(diphenylphosphino)ferrocene), optionally under microwave irradiation, at a temperature of about 60 to 160° C., for about 10 minutes to about 24 hours. The reaction may be sealed. When the reaction is substantially complete, the product is isolated by conventional means.

Copper Coupling Conditions

Where appropriate, e.g., the compound of Formula X(b) in which $E^1$ or $Z^2$ includes a suitable coupling partner, for example, a halide (e.g., chloro, bromo, or iodo) is reacted to form Formula X(c) or X(d) under copper-catalyzed cross coupling conditions in a suitable solvent, optionally under an inert atmosphere. The coupling reaction is carried out in an inert solvent, for example toluene or DMF, in the presence of a mild base, for example cesium carbonate, optionally in a sealed vessel. The reaction is typically conducted in the presence of a copper catalyst (e.g., copper (I) iodide (cuprous iodide)), optionally with an appropriate ligand (e.g., 3,4,7,8-tetramethyl-1,10-phenanthroline), at a temperature of about 60 to 150° C., for about 10 minutes to about 24 hours. When the reaction is substantially complete, the product is isolated by conventional means.

Nucleophilic Aromatic Substitution Conditions

Where appropriate, for example, where a compound of Formula X(d) is converted into a compound of Formula (I), a nucleophilic displacement reaction may be conducted. The nucleophilic displacement reaction is conducted under nucleophilic addition conditions (e.g., in the presence of a base such as sodium hydride, sodium tert-butoxide, or cesium carbonate), in a suitable solvent (e.g., a polar aprotic solvent, 1,4-dioxane, tetrahydrofuran, DMF, etc.), optionally under an inert atmosphere. The reaction is typically conducted at a temperature of about 20 to 160° C., for about 10 minutes to about 7 days. The conditions may comprise a discrete deprotonation step (e.g., where the base is sodium hydride), which may proceed at −78° C. to 0° C. When the reaction is substantially complete, the product is isolated by conventional means. In some embodiments, the electrophile corresponding to $T^1$-$T^6$ is a primary pseudohalide (e.g., a phenylsulfonyl) or halide (e.g., a bromo).

Pyran Deprotection Conditions

Where appropriate, e.g., where the compound of Formula X(c) or X(d) comprises a pyran protecting group, for example, at $P^1$ or $R^{15}$, the compound may be reacted to form $R^{15}$ or $R^1$ under standard acid-catalyzed deprotection conditions (e.g., using a Lewis acid or a protic acid) in a suitable solvent (e.g., 1,4-dioxane, dichloromethane, ethyl acetate, acetonitrile, water, methanol, ethanol, etc.), optionally under an inert atmosphere. The reaction is typically conducted in the presence of an acid catalyst, for example HCl or trifluoroacetic acid, at a temperature of about 0 to 100° C., for about 10 minutes to about 24 hours. When the reaction is substantially complete, the product is isolated by conventional means. In some embodiments, the starting material for the pyran deprotection may be carried over from a previous step without purification.

A person of skill in the art will appreciate that any of a compound of Formula X(a), X(b), or X(c) may be available from a commercial supplier for a particular embodiment. Alternative synthesis of a compound of Formula X(a), X(b), or X(c) may be as described herein or as known to those of skill in the art.

Intermediate 1

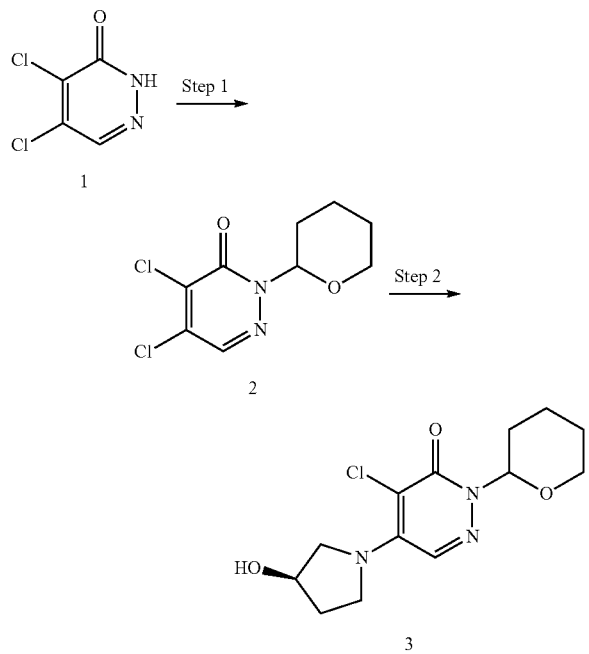

Step 1: Preparation of 4,5-dichloro-2-(tetrahydro-2H-pyran-2-yl)pyridazin-3(2H)-one 2: 4,5-Dichloropyridazin-3(2H)-one (1, 30 g, 182 mmol) and tosic acid (1.6 g, 9.1 mmol) were combined in a 250 mL flask and tetrahydrofuran (100 mL) was added. 3,4-Dihydro-2H-pyran (18.4 g, 218 mmol) was then added via syringe and the reaction was heated to reflux for 15 hours. LCMS analysis indicated conversion to product and remaining starting material. The reaction was concentrated onto 50 g of silica gel and purified by normal phase flash column chromatography (120 g column, 0-100% ethyl acetate in hexanes) to provide 4,5-dichloro-2-(tetrahydro-2H-pyran-2-yl)pyridazin-3(2H)-one (2). MS (ESI) $[M+H^+-THP]^+$=248.9.

Step 2: Preparation of 4-chloro-5-((R)-3-hydroxypyrrolidin-1-yl)-2-(tetrahydro-2H-pyran-2-yl)pyridazin-3(2H)-one 3: To a 250 mL round bottom flask were added 4,5-dichloro-2-(tetrahydro-2H-pyran-2-yl)pyridazin-3(2H)-one (2, 9.35 g, 37.5 mmol) and (R)-pyrrolidin-3-ol hydrochloride (5.6 g, 45.0 mmol). Potassium carbonate (15.6 g, 113 mmol) and N,N-dimethylformamide (100 mL) were then added and the reaction was stirred at room temperature for 15 hours. LCMS analysis indicated conversion to desired product. The reaction was concentrated onto 40 g of silica gel and purified by normal phase flash column chromatography (40 g column, 0-100% ethyl acetate in hexanes) to provide 4-chloro-5-((R)-3-hydroxypyrrolidin-1-yl)-2-(tetrahydro-2H-pyran-2-yl)pyridazin-3(2H)-one (3). MS (ESI) $[M+H^+]^+$=300.2.

Intermediate 2

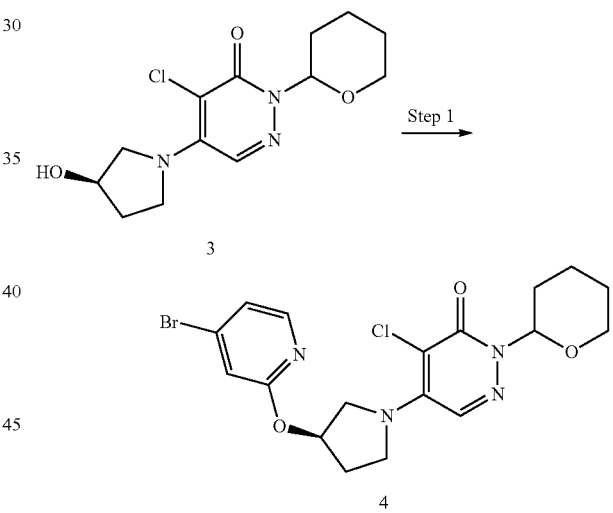

Step 1: Preparation of 5-((R)-3-((4-bromopyridin-2-yl)oxy)pyrrolidin-1-yl)-4-chloro-2-(tetrahydro-2H-pyran-2-yl)pyridazin-3(2H)-one 4: To a 250 mL round bottom flask were added 4-chloro-5-((R)-3-hydroxypyrrolidin-1-yl)-2-(tetrahydro-2H-pyran-2-yl)pyridazin-3(2H)-one (3, 4.0 g, 13.3 mmol), 4-bromo-2-fluoro-pyridine (2.8 g, 16.0 mmol), cesium carbonate (8.7 g, 26.7 mmol), and N,N-dimethylformamide (50 mL). The reaction was stirred at 80° C. for 18 hours in an oil bath. LCMS analysis indicated conversion to desired product. The reaction was concentrated onto 20 g of silica gel and purified by normal phase flash column chromatography (120 g silica gel column, 0 to 100% ethyl acetate in hexanes) to give 5-((R)-3-((4-bromopyridin-2-yl)oxy)pyrrolidin-1-yl)-4-chloro-2-(tetrahydro-2H-pyran-2-yl)pyridazin-3(2H)-one (4). MS (ESI) $[M+H^+]^+$=455.1.

Example 1

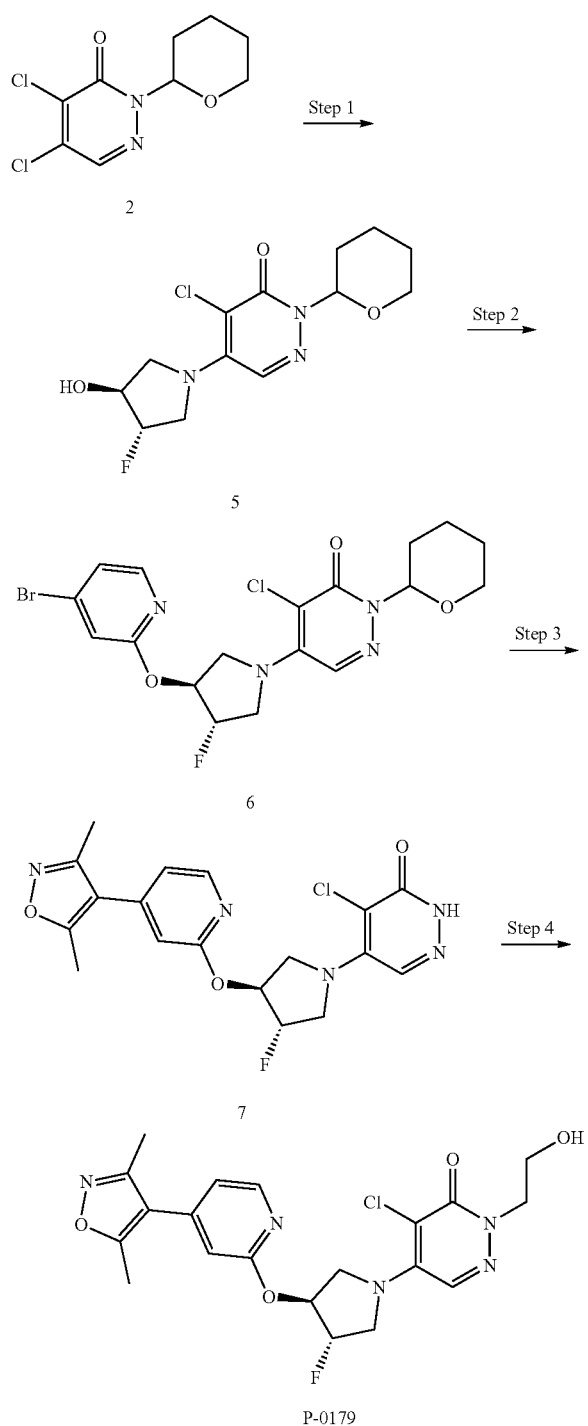

Step 1: Preparation of 4-chloro-5-((3S,4S)-3-fluoro-4-hydroxypyrrolidin-1-yl)-2-(tetrahydro-2H-pyran-2-yl)pyridazin-3(2H)-one 5: To a 250 mL round bottom flask were added 4,5-dichloro-2-(tetrahydro-2H-pyran-2-yl)pyridazin-3(2H)-one (2, 7.2 g, 28.9 mmol) and (3S,4S)-4-fluoropyrrolidin-3-ol hydrochloride (4.5 g, 31.8 mmol). Potassium carbonate (16.0 g, 116 mmol) and N,N-dimethylformamide (100 mL) were then added and the reaction was stirred at room temperature for 15 hours. LCMS analysis indicated conversion to desired product. The reaction was concentrated onto 40 g of silica gel and purified by normal phase flash column chromatography (120 g column, 0-100% ethyl acetate in hexanes) to provide 4-chloro-5-((3S,4S)-3-fluoro-4-hydroxypyrrolidin-1-yl)-2-(tetrahydro-2H-pyran-2-yl)pyridazin-3(2H)-one (5). MS (ESI) [M+H$^+$-THP]$^+$=234.1.

Step 2: Preparation of 5-[(3S,4S)-3-[(4-bromo-2-pyridyl)oxy]-4-fluoro-pyrrolidin-1-yl]-4-chloro-2-tetrahydropyran-2-yl-pyridazin-3-one 6: To a 250 mL round bottom flask were added 4-chloro-5-[(3S,4S)-3-fluoro-4-hydroxy-pyrrolidin-1-yl-2-tetrahydropyran-2-yl-pyridazin-3-one (5, 4.0 g, 12.6 mmol), 4-bromo-2-fluoro-pyridine (2.7 g, 15.1 mmol), cesium carbonate (8.2 g, 25.2 mmol), and N,N-dimethylformamide (50 ml). The reaction was stirred at 80° C. for 18 hours in an oil bath. LCMS analysis indicated conversion to the desired product. The reaction was concentrated onto 20 g of silica gel and purified by normal phase chromatography (120 g silica gel column, 0 to 100% ethyl acetate in hexanes) to give 5-[(3S,4S)-3-[(4-bromo-2-pyridyl)oxy]-4-fluoro-pyrrolidin-1-yl]-4-chloro-2-tetrahydropyran-2-yl-pyridazin-3-one (6). MS (ESI) [M+H$^+$]$^+$=473.0.

Step 3: Preparation of 4-chloro-5-((3S,4S)-3-((4-(3,5-dimethylisoxazol-4-yl)pyridin-2-yl)oxy)-4-fluoropyrrolidin-1-yl)pyridazin-3(2H)-one 7: In a 250 mL round bottom flask, to 5-((3S,4S)-3-((4-bromopyridin-2-yl)oxy)-4-fluoropyrrolidin-1-yl)-4-chloro-2-(tetrahydro-2H-pyran-2-yl)pyridazin-3(2H)-one (6, 4.6 g, 9.8 mmol), 3,5-dimethyl-4-(4,4,5,5-tetramethyl-1,3,2-dioxaborolan-2-yl)isoxazole (3.3 g, 14.7 mmol), and dichloro(1,1-bis(diphenylphosphino)ferrocene)palladium(II) acetone adduct (772 mg, 0.98 mmol) in 1,4-dioxane (90 ml) was added 1 M potassium carbonate in water (29 ml). The reaction mixture was immediately heated at 100° C. in an oil bath which was preheated to 100° C. The reaction was stirred for two hours at temperature. The reaction was cooled to room temperature and concentrated onto 20 g of silica gel. The reaction was purified by normal phase flash column chromatography (120 g silica column, 0 to 100% ethyl acetate in hexanes) to give the intermediate product. This material was then dissolved in 20 mL of dichloromethane and hydrochloric acid (4 M in 1,4-dioxane, 20 mL, 80 mmol) was added and the reaction was stirred at room temperature for 30 minutes. The reaction was concentrated to give 4-chloro-5-((3S,4S)-3-((4-(3,5-dimethylisoxazol-4-yl)pyridin-2-yl)oxy)-4-fluoropyrrolidin-1-yl)pyridazin-3(2H)-one (7). MS (ESI) [M+H$^+$]$^+$=406.2.

Step 4: Preparation of 4-chloro-5-((3S,4S)-3-((4-(3,5-dimethylisoxazol-4-yl)pyridin-2-yl)oxy)-4-fluoropyrrolidin-1-yl)-2-(2-hydroxyethyl)pyridazin-3(2H)-one (P-0179): 4-chloro-5-((3S,4S)-3-((4-(3,5-dimethylisoxazol-4-yl)pyridin-2-yl)oxy)-4-fluoropyrrolidin-1-yl)pyridazin-3(2H)-one (7, 4.0 g, 9.9 mmol) was dissolved in N,N-dimethylformamide (40 mL) and potassium carbonate (2.7 g, 19.7 mmol) was added. 2-(2-Bromoethoxy)tetrahydro-2H-pyran (2.7 g, 12.8 mmol) was then added and the reaction was stirred at 60° C. for 15 hours. LCMS indicated conversion to 4-chloro-5-((3S,4S)-3-((4-(3,5-dimethylisoxazol-4-yl)pyridin-2-yl)oxy)-4-fluoropyrrolidin-1-yl)-2-(2-((tetrahydro-2H-pyran-2-yl)oxy)ethyl)pyridazin-3(2H)-one. The solid potassium carbonate was filtered off and the crude reaction was mixed with hydrochloric acid (4 M in 1,4-dioxane, 20 mL, 80 mmol). The reaction was stirred at room temperature for two hours. The reaction was quenched with 20 mL of methanol and concentrated onto 60 g of silica gel. This material was then purified by reverse phase flash chromatography (415 g C$_{18}$ column; 0-45% B; A: 99.9% H$_2$O, 0.1% HCO$_2$H; B: 99.9% CH$_3$CN, 0.1% HCO$_2$H). This purification provided still impure product. The material was then purified by normal phase chromatography (40 g silica gel column, 0-100% ethyl acetate in hexanes). This purification provided 4-chloro-5-((3S,4S)-3-((4-(3,5-dimethylisoxazol-4-yl)pyridin-2-yl)oxy)-4-fluoropyrrolidin-1-yl)-2-(2-hydroxyethyl)pyridazin-3(2H)-one (P-0179). MS (ESI) [M+H$^+$]$^+$=450.1.

Example 2

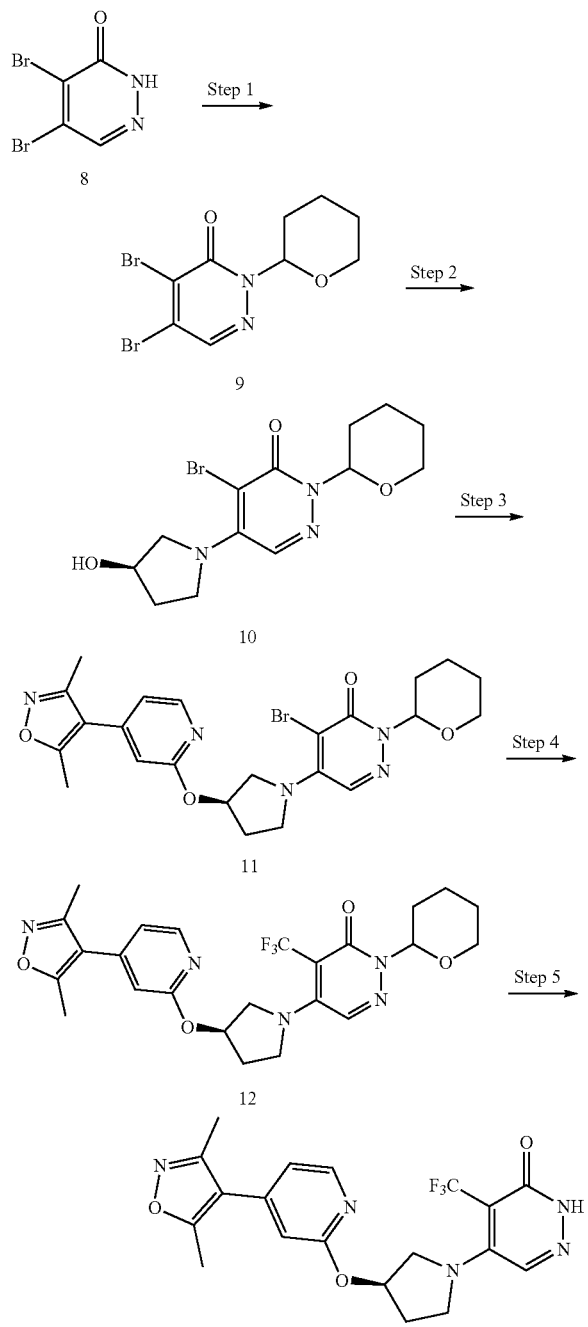

Step 1: Preparation of 4,5-dibromo-2-(tetrahydro-2H-pyran-2-yl)pyridazin-3(2H)-one 9: A screw-cap reaction vessel was charged with 4,5-dibromo-1H-pyridazin-6-one (8, 1.00 g, 3.95 mmol), 3,4-dihydro-2H-pyran (1.00 g, 11.9 mmol), DCE (25 ml) and PTSA monohydrate (0.195 g, 1.03 mmol). The reaction vessel was sealed and allowed to stir in an oil bath at 70° C. for 16 hours. The reaction was then cooled and extracted with ethyl acetate and water, filtering two times to remove particulates. The organic layer was separated, dried over magnesium sulfate, and filtered. The volatiles were removed by rotary evaporation and the resulting residues were purified by silica gel flash column chromatography (40 g silica gel column, 0 to 60% ethyl acetate in hexanes). This purification provided 4,5-dibromo-2-(tetrahydro-2H-pyran-2-yl)pyridazin-3(2H)-one (9). MS (ESI) [M+H$^+$]$^+$=338.8.

Step 2: Preparation of 4-bromo-5-((R)-3-hydroxypyrrolidin-1-yl)-2-(tetrahydro-2H-pyran-2-yl)pyridazin-3(2H)-one 10: To a round bottom flask charged 4,5-dibromo-2-(tetrahydro-2H-pyran-2-yl)pyridazin-3(2H)-one (9, 0.43 g, 1.27 mmol) were added (3R)-pyrrolidin-3-ol hydrochloride (0.189 g, 1.53 mmol) followed by N,N-dimethylformamide (10 ml). To this solution was added triethylamine (0.27 ml, 1.91 mmol). The reaction was allowed to stir at room temperature for four days. All volatiles were removed under reduced pressure and the resulting residue was extracted with ethyl acetate and water. The water layer was extracted an additional four times until the aqueous layer no longer contained product by TLC. The combined organic layers were dried over magnesium sulfate and filtered. The volatiles were removed by rotary evaporation and the resulting residue was purified by silica gel flash column chromatography (24 g silica gel column, 0 to 6% methanol in dichloromethane). This purification provided 4-bromo-5-((R)-3-hydroxypyrrolidin-1-yl)-2-(tetrahydro-2H-pyran-2-yl)pyridazin-3(2H)-one (10). MS (ESI) [M+H$^+$]$^+$=344.0.

Step 3: Preparation of 4-bromo-5-[(3R)-3-[[4-(3,5-dimethylisoxazol-4-yl)-2-pyridyl]oxy]pyrrolidin-1-yl]-2-tetrahydropyran-2-yl-pyridazin-3-one 11: To 4-bromo-5-((R)-3-hydroxypyrrolidin-1-yl)-2-(tetrahydro-2H-pyran-2-yl)pyridazin-3(2H)-one (10, 195 mg, 0.567 mmol) in 1,4-dioxane (10 ml) was added sodium hydride (60% in mineral oil, 25 mg, 0.62 mmol). After gas evolution ceased, 4-(2-fluoro-4-pyridyl)-3,5-dimethyl-isoxazole (122 mg, 0.635 mmol) was added and the reaction was allowed to stir under an argon atmosphere in an oil bath at 60° C. for six hours followed by 80° C. for an additional 17 hours. The reaction volatiles were removed under reduced pressure and the resulting residue was dry-loaded onto silica from THF/MeOH and purified by silica gel flash column chromatography (24 g column, 50 to 100% ethyl acetate in hexanes). This purification provided 4-bromo-5-[(3R)-3-[[4-(3,5-dimethylisoxazol-4-yl)-2-pyridyl]oxy]pyrrolidin-1-yl]-2-tetrahydropyran-2-yl-pyridazin-3-one (11). MS (ESI) [M+H$^+$]$^+$=515.5.

Step 4: Preparation of 5-[(3R)-3-[[4-(3,5-dimethylisoxazol-4-yl)-2-pyridyl]oxy]pyrrolidin-1-yl]-2-tetrahydropyran-2-yl-4-(trifluoromethyl)pyridazin-3-one 12: To methyl 2,2-difluoro-2-fluorosulfonyl-acetate (79 mg, 0.41 mmol) and 4-bromo-5-[(3R)-3-[[4-(3,5-dimethylisoxazol-4-yl)-2-pyridyl]oxy]pyrrolidin-1-yl]-2-tetrahydropyran-2-yl-pyridazin-3-one (11, 101 mg, 0.196 mmol) in N,N-dimethylformamide (2 ml) was added copper (I) iodide (122 mg, 0.383 mmol). The mixture was heated at 100° C. for 15 hours. The reaction was allowed to cool and was diluted with THF. The THF insoluble material was allowed to settle and the soluble fraction was dry-loaded onto silica gel and purified by silica gel flash column chromatography (12 g silica gel column, 0 to 100% ethyl acetate in hexanes). This purification provided 5-[(3R)-3-[[4-(3,5-dimethylisoxazol-4-yl)-2-pyridyl]oxy]pyrrolidin-1-yl]-2-tetrahydropyran-2-yl-4-(trifluoromethyl)pyridazin-3-one (12). MS (ESI) [M+H⁺]⁺=506.1.

Step 5: Preparation of (R)-5-(3-((4-(3,5-dimethylisoxazol-4-yl)pyridin-2-yl)oxy)pyrrolidin-1-yl)-4-(trifluoromethyl)pyridazin-3(2H)-one (P-0053): To a round bottom flask charged with 5-[(3R)-3-[[4-(3,5-dimethylisoxazol-4-yl)-2-pyridyl]oxy]pyrrolidin-1-yl]-2-tetrahydropyran-2-yl-4-(trifluoromethyl)pyridazin-3-one (12, 6.0 mg, 0.01 mmol) were added dichloromethane (5 ml) followed by trifluoroacetic acid (0.5 ml, 6.53 mmol). The solution was allowed to stir at ambient temperature for 2 hours. The volatiles were removed under reduced pressure to provide (R)-5-(3-((4-(3,5-dimethylisoxazol-4-yl)pyridin-2-yl)oxy)pyrrolidin-1-yl)-4-(trifluoromethyl)pyridazin-3(2H)-one (P-0053). MS (ESI) [M+H⁺]⁺=422.0.

Example 3

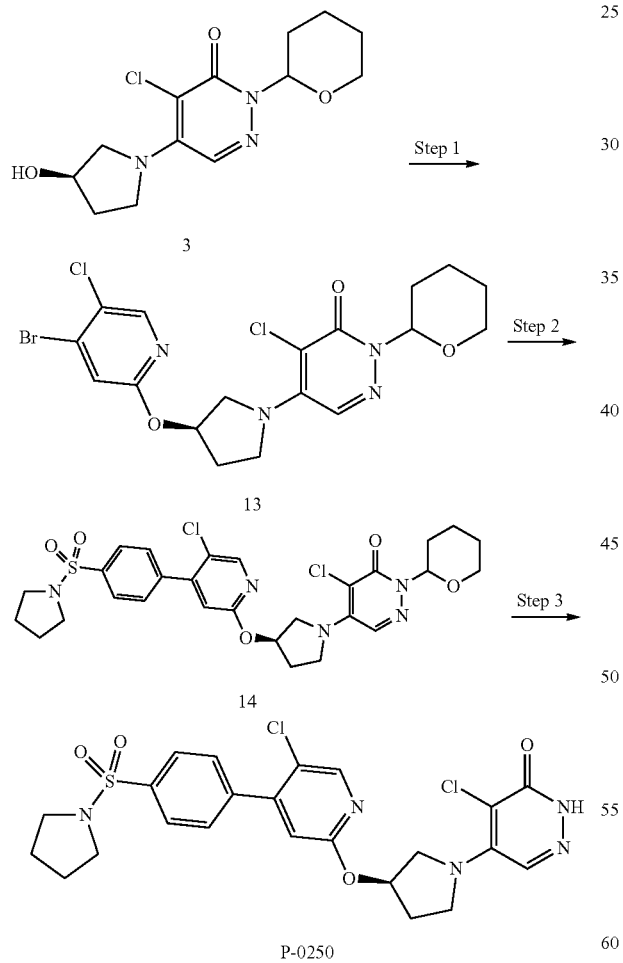

Step 1: Preparation of 5-((R)-3-((4-bromo-5-chloropyridin-2-yl)oxy)pyrrolidin-1-yl)-4-chloro-2-(tetrahydro-2H-pyran-2-yl)pyridazin-3(2H)-one 13: In a vial, to 4-chloro-5-[(3R)-3-hydroxypyrrolidin-1-yl]-2-tetrahydropyran-2-yl-pyridazin-3-one (3, 0.30 g, 1.0 mmol) and cesium carbonate (1.27 g, 4.0 mmol) in N,N-dimethylformamide (5 ml) was added 4-bromo-5-chloro-2-fluoro-pyridine (0.27 g, 1.28 mmol). The reaction mixture was stirred at room temperature for 3 days. The reaction was filtered to remove the cesium carbonate. The volatiles were removed under vacuum. This material was directly loaded onto silica gel and purified by normal phase flash column chromatography (12 g silica gel column, 0 to 100% ethyl acetate in hexanes). This purification provided 5-((R)-3-((4-bromo-5-chloropyridin-2-yl)oxy)pyrrolidin-1-yl)-4-chloro-2-(tetrahydro-2H-pyran-2-yl)pyridazin-3(2H)-one (13). MS (ESI) [M+H⁺]⁺=488.8.

Step 2: Preparation of 4-chloro-5-((R)-3-((5-chloro-4-(4-(pyrrolidin-1-ylsulfonyl)phenyl)pyridin-2-yl)oxy)pyrrolidin-1-yl)-2-(tetrahydro-2H-pyran-2-yl)pyridazin-3(2H)-one 14: In a 10 mL microwave vial, to 5-[(3R)-3-[(4-bromo-5-chloro-2-pyridyl)oxy]pyrrolidin-1-yl]-4-chloro-2-tetrahydropyran-2-yl-pyridazin-3-one (13, 50 mg, 0.1 mmol), (4-pyrrolidin-1-ylsulfonylphenyl)boronic acid (40 mg, 0.16 mmol), and dichloro(1,1-bis(diphenylphosphino)ferrocene) palladium(II) acetone adduct (15 mg, 0.019 mmol) in 1,4-dioxane (2 ml) was added 1 M potassium carbonate in water (1 ml, 1 mmol). The reaction mixture was immediately heated at 100° C. in an oil bath which was preheated to 100° C. The reaction was stirred at temperature for five minutes. To the cooled reaction mixture were added water and ethyl acetate. The organic layer was separated and washed with water and brine before being dried over magnesium sulfate. The volatiles were removed under vacuum onto 5 g of silica gel. The crude material was then purified by normal phase flash column chromatography (12 g silica gel column, 0 to 100% ethyl acetate in dichloromethane). This purification provided 4-chloro-5-[(3R)-3-[[5-chloro-4-(4-pyrrolidin-1-ylsulfonylphenyl)-2-pyridyl]oxy]pyrrolidin-1-yl]-2-tetrahydropyran-2-yl-pyridazin-3-one (14). MS (ESI) [M+H⁺]⁺=620.0.

Step 3: Preparation of (R)-4-chloro-5-(3-((5-chloro-4-(4-(pyrrolidin-1-ylsulfonyl)phenyl)pyridin-2-yl)oxy)pyrrolidin-1-yl)pyridazin-3(2H)-one (P-0250): In a 40 mL vial, to 4-chloro-5-[(3R)-3-[[5-chloro-4-(4-pyrrolidin-1-ylsulfonylphenyl)-2-pyridyl]oxy]pyrrolidin-1-yl]-2-tetrahydropyran-2-yl-pyridazin-3-one (14, 40 mg, 0.064 mmol) in 1,4-dioxane (2 ml) was added hydrochloric acid (4 M in 1,4-dioxane, 9 mL, 36 mmol). The reaction mixture was stirred at room temperature for 2 hours. The volatiles were removed under vacuum. The crude material was directly purified by preparatory HPLC (C18 column; 0-60% B; A: 99.9% H₂O, 0.1% HCO₂H; B: 99.9% CH₃CN, 0.1% HCO₂H). This purification provided (R)-4-chloro-5-(3-((5-chloro-4-(4-(pyrrolidin-1-ylsulfonyl)phenyl)pyridin-2-yl)oxy)pyrrolidin-1-yl)pyridazin-3(2H)-one (P-0250). MS (ESI) [M+H⁺]⁺=535.9.

Example 4

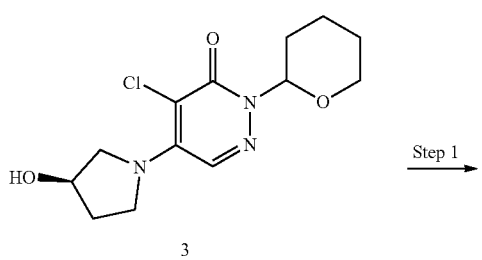

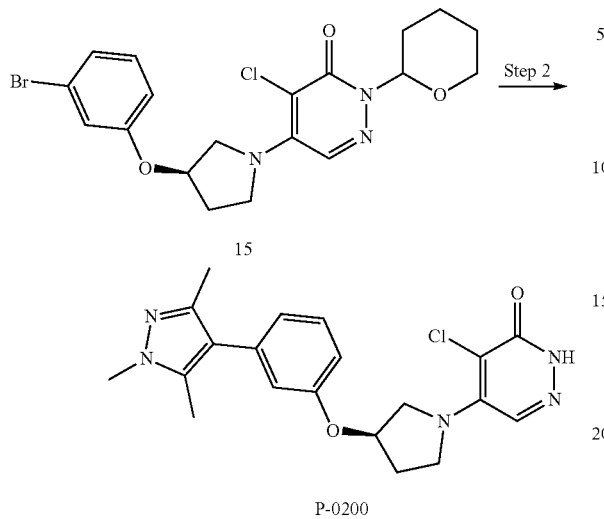

P-0200

Example 5

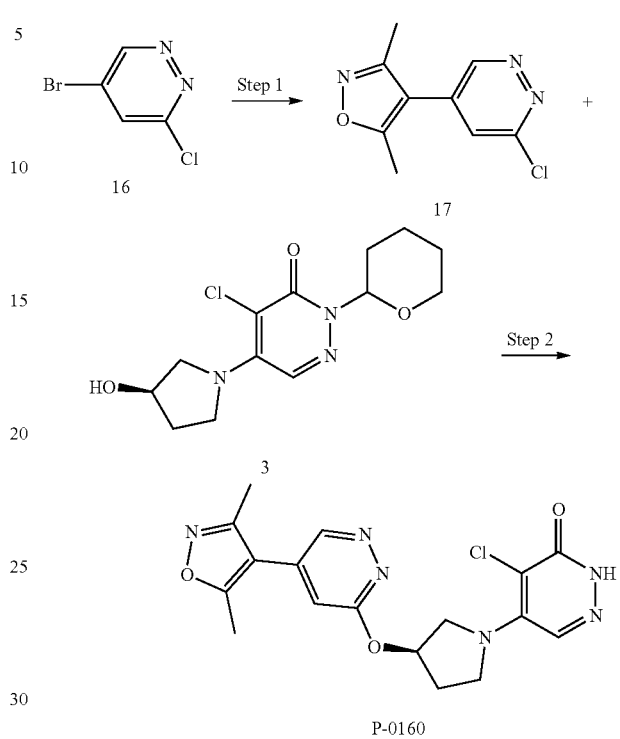

P-0160

Step 1: Preparation of 5-[(3R)-3-(3-bromophenoxy)pyrrolidin-1-yl]-4-chloro-2-tetrahydropyran-2-yl-pyridazin-3-one 15: To a 20 mL microwave vial were added 4-chloro-5-[(3R)-3-hydroxypyrrolidin-1-yl]-2-tetrahydropyran-2-yl-pyridazin-3-one (3, 0.30 g, 1.0 mmol), 1-bromo-3-iodobenzene (0.19 ml, 1.5 mmol), cuprous iodide (10 mg, 0.05 mmol), 3,4,7,8-tetramethyl-1,10-phenanthroline (24 mg, 0.1 mmol), cesium carbonate (489 mg, 1.5 mmol), and toluene (5 ml). The vial was sealed, degassed, and stirred at 120° C. for 18 hours under nitrogen atmosphere. The reaction mixture was poured over brine and extracted with ethyl acetate. The organic layer was dried over anhydrous sodium sulfate, filtered, and evaporated onto silica gel. The reaction was purified by normal phase flash column chromatography (24 g silica gel column, 0 to 100% ethyl acetate in hexanes) to give 5-[(3R)-3-(3-bromophenoxy)pyrrolidin-1-yl]-4-chloro-2-tetrahydropyran-2-yl-pyridazin-3-one (15). MS (ESI) [M+H$^+$]$^+$=453.9.

Step 2: Preparation of (R)-4-chloro-5-(3-(3-(1,3,5-trimethyl-1H-pyrazol-4-yl)phenoxy)pyrrolidin-1-yl)pyridazin-3 (2H)-one (P-0200): To a 5 mL microwave vial were added 5-[(3R)-3-(3-bromophenoxy)pyrrolidin-1-yl]-4-chloro-2-tetrahydropyran-2-yl-pyridazin-3-one (15, 0.15 g, 0.33 mmol), 1,3,5-trimethyl-4-(4,4,5,5-tetramethyl-1,3,2-dioxaborolan-2-yl)pyrazole (0.12 g, 0.50 mmol), dichloro(1,1-bis(diphenylphosphino) ferrocene)palladium(II) acetone adduct (0.026 g, 0.033 mmol), aqueous potassium carbonate (1 M, 0.66 ml, 0.66 mmol), and 1,4-dioxane (2 ml). The vial was sealed and irradiated at 100° C. for 30 minutes. The reaction was filtered, evaporated onto silica gel, and purified by reverse phase flash column chromatography (30 g C18 column; 0-70% B; A: 99.9% H$_2$O, 0.1% HCO$_2$H; B: 99.9% CH$_3$CN, 0.1% HCO$_2$H). This purification gave the THP protected intermediate. The protected intermediate was dissolved in dichloromethane (2 mL) and treated with hydrochloric acid (4 M in 1,4-dioxane, 0.80 ml, 3.2 mmol). The reaction was stirred at room temperature for 2 hours and evaporated to dryness to give (R)-4-chloro-5-(3-(3-(1,3,5-trimethyl-1H-pyrazol-4-yl)phenoxy)pyrrolidin-1-yl) pyridazin-3(2H)-one (P-0200). MS (ESI) [M+H$^+$]$^+$=400.0.

Step 1: Preparation of 4-(6-chloropyridazin-4-yl)-3,5-dimethylisoxazole 17: To a 5 mL microwave vial were added 5-bromo-3-chloro-pyridazine (16, 0.1 g, 0.52 mmol), 3,5-dimethyl-4-(4,4,5,5-tetramethyl-1,3,2-dioxaborolan-2-yl) isoxazole (0.14 g, 0.62 mmol), dichloro(1,1-bis(diphenylphosphino) ferrocene)palladium(II) acetone adduct (0.04 g, 0.05 mmol), 1 M aqueous potassium carbonate (1.03 ml), and 1,4-dioxane (2 ml). The vial was sealed, degassed, and irradiated at 100° C. for 30 minutes. The reaction was evaporated onto silica gel and purified by reverse phase flash column chromatography (30 g C18 column; 0-70% B; A: 99.9% H$_2$O, 0.1% HCO$_2$H; B: 99.9% CH$_3$CN, 0.1% HCO$_2$H) to give 4-(6-chloropyridazin-4-yl)-3,5-dimethyl-isoxazole (17). MS (ESI) [M+H$^+$]$^+$=210.0.

Step 2: Preparation of (R)-4-chloro-5-(3-((5-(3,5-dimethylisoxazol-4-yl)pyridazin-3-yl)oxy)pyrrolidin-1-yl) pyridazin-3(2H)-one (P-0160): To a 20 mL scintillation vial were added 4-chloro-5-[(3R)-3-hydroxypyrrolidin-1-yl]-2-tetrahydropyran-2-yl-pyridazin-3-one (3, 0.10 g, 0.33 mmol), 4-(6-chloropyridazin-4-yl)-3,5-dimethyl-isoxazole (17, 0.070 g, 0.33 mmol), and N,N-dimethylformamide (5 mL). Sodium hydride (60% in mineral oil, 16 mg, 0.67 mmol) was added and the reaction was stirred at room temperature for 2 hours. The reaction was evaporated onto silica gel and purified by reverse phase flash column chromatography (30 g C18 column; 0-70% B; A: 99.9% H$_2$O, 0.1% HCO$_2$H; B: 99.9% CH$_3$CN, 0.1% HCO$_2$H) to provide the THP protected intermediate. The THP protected intermediate was dissolved in dichloromethane (5 mL), treated with hydrochloric acid (4 M in 1,4-dioxane, 0.83 mL, 3.3 mmol), and stirred at room temperature for 2 hours. The reaction was evaporated onto silica gel and purified by reverse phase flash column chromatography (30 g C18 column; 0-50% B; A: 99.9% H$_2$O, 0.1% HCO$_2$H; B: 99.9%

CH₃CN, 0.1% HCO₂H) to give (R)-4-chloro-5-(3-((5-(3,5-dimethylisoxazol-4-yl)pyridazin-3-yl)oxy)pyrrolidin-1-yl)pyridazin-3(2H)-one (P-0160). MS (ESI) [M+H⁺]⁺=389.0.

Example 6

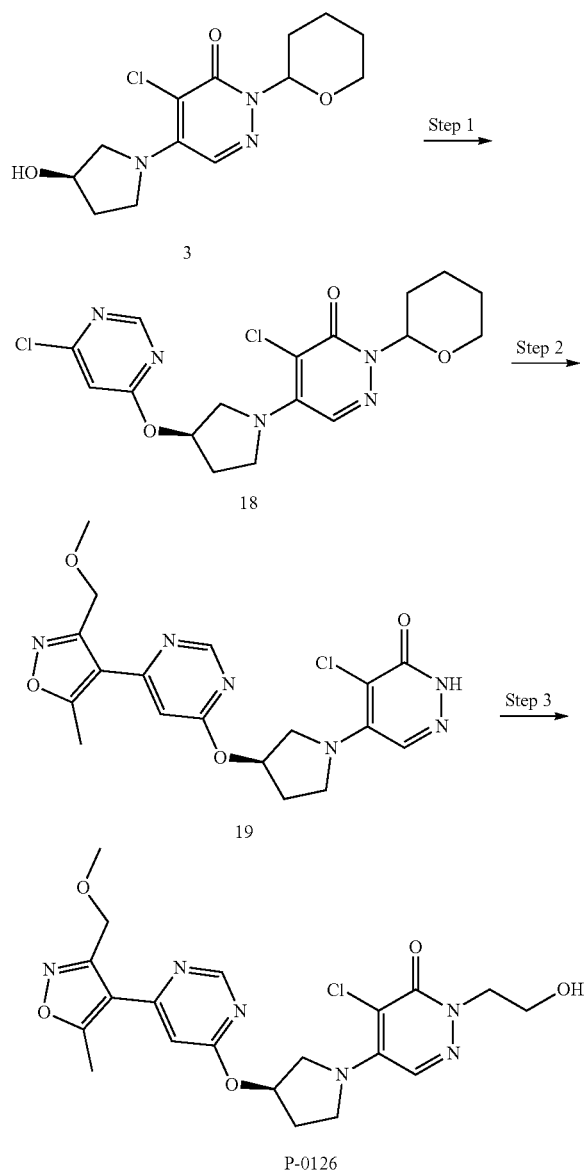

P-0126

Step 1: Preparation of 4-chloro-5-((R)-3-((6-chloropyrimidin-4-yl)oxy)pyrrolidin-1-yl)-2-(tetrahydro-2H-pyran-2-yl)pyridazin-3(2H)-one 18: In a 250 mL round bottom flask were combined 4-chloro-5-[(3R)-3-hydroxypyrrolidin-1-yl]-2-tetrahydropyran-2-yl-pyridazin-3-one (3, 3.0 g, 10.0 mmol), 4,6-dichloropyrimidine (2.98 g, 20.0 mmol), and N,N-dimethylformamide (100 mL). The reaction mixture was cooled to 0° C. and sodium hydride (60% in mineral oil, 0.48 g, 20.0 mmol) was added in portions. The reaction was stirred while slowly warming to room temperature over 2 hours. The reaction was poured into cold saturated ammonium chloride and extracted with ethyl acetate. The organic layer was washed with brine, filtered, and evaporated onto silica gel. The product was isolated by normal phase flash column chromatography (40 g silica gel column, 0 to 100% ethyl acetate in hexanes) to give 4-chloro-5-[(3R)-3-(6-chloropyrimidin-4-yl) oxypyrrolidin-1-yl]-2-tetrahydropyran-2-yl-pyridazin-3-one (18). MS (ESI) [M+H⁺]⁺=412.0.

Step 2: Preparation of (R)-4-chloro-5-(3-((6-(3-(methoxymethyl)-5-methylisoxazol-4-yl)pyrimidin-4-yl)oxy)pyrrolidin-1-yl)pyridazin-3(2H)-one 19: In a 5 mL microwave vial were combined 4-chloro-5-[(3R)-3-(6-chloropyrimidin-4-yl) oxypyrrolidin-1-yl]-2-tetrahydropyran-2-yl-pyridazin-3-one (18, 0.10 g, 0.24 mmol), [3-(methoxymethyl)-5-methyl-isoxazol-4-yl]boronic acid (0.050 g, 0.29 mmol), dichloro (1,1-bis(diphenylphosphino)ferrocene)palladium(II) acetone adduct (0.020 g, 0.02 mmol), 1 M aqueous potassium carbonate (0.49 mL, 0.49 mmol), and 1,4-dioxane (3 mL). The vial was placed under nitrogen atmosphere and irradiated at 100° C. for 40 minutes. The reaction was evaporated onto silica gel and the THP-protected intermediate was isolated by reverse phase flash column chromatography (30 g C18 column; 0-70% B; A: 99.9% H₂O, 0.1% HCO₂H; B: 99.9% CH₃CN, 0.1% HCO₂H). The intermediate was dissolved in dichloromethane (5 mL), treated with hydrochloric acid (4 M in 1,4-dioxane, 0.61 mL, 2.4 mmol), and stirred at room temperature for 2 hours. The reaction mixture was evaporated to dryness, dissolved in N,N-dimethylformamide (2 mL), and purified by reverse phase column chromatography (30 g C₁₈ column; 0-50% B; A: 99.9% H₂O, 0.1% HCO₂H; B: 99.9% CH₃CN, 0.1% HCO₂H) to give (R)-4-chloro-5-(3-((6-(3-(methoxymethyl)-5-methylisoxazol-4-yl)pyrimidin-4-yl)oxy)pyrrolidin-1-yl)pyridazin-3(2H)-one (19). MS (ESI) [M+H⁺]⁺=419.0.

Step 3: Preparation of (R)-4-chloro-2-(2-hydroxyethyl)-5-(3-((6-(3-(methoxymethyl)-5-methylisoxazol-4-yl)pyrimidin-4-yl)oxy)pyrrolidin-1-yl)pyridazin-3(2H)-one (P-0126): In a 20 mL scintillation vial were combined (R)-4-chloro-5-(3-((6-(3-(methoxymethyl)-5-methylisoxazol-4-yl)pyrimidin-4-yl)oxy)pyrrolidin-1-yl)pyridazin-3 (2H)-one (19, 0.040 g, 0.080 mmol), N,N-dimethylformamide (3 mL), potassium carbonate (0.020 g, 0.17 mmol), and 2-(2-bromoethoxy)tetrahydro-2H-pyran (0.030 ml, 0.17 mmol). The reaction was stirred at 70° C. for 3 hours. The reaction was cooled to room temperature and hydrochloric acid (4 M in 1,4-dioxane, 0.42 mL, 1.68 mmol) was added and the reaction was stirred for 2 hours. The reaction mixture was evaporated onto silica gel and the product was isolated by reverse phase flash column chromatography (30 g C18 column; 0-50% B; A: 99.9% H₂O, 0.1% HCO₂H; B: 99.9% CH₃CN, 0.1% HCO₂H) to give (R)-4-chloro-2-(2-hydroxyethyl)-5-(3-((6-(3-(methoxymethyl)-5-methylisoxazol-4-yl)pyrimidin-4-yl)oxy)pyrrolidin-1-yl)pyridazin-3(2H)-one (P-0126). MS (ESI) [M+H⁺]⁺=463.0.

Example 7

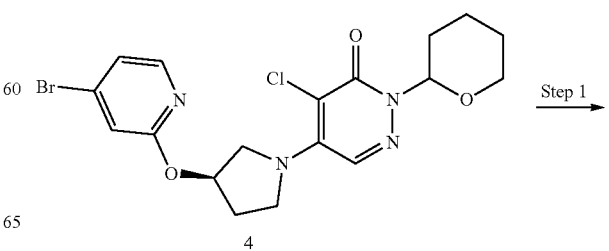

4

Example 8

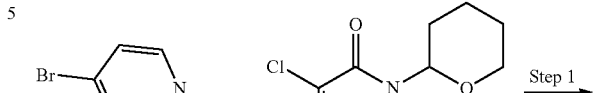

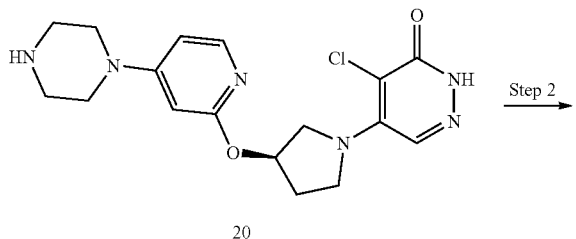

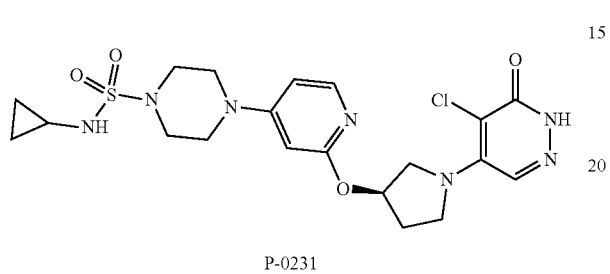

P-0231

Step 1: Preparation of (R)-4-chloro-5-(3-((4-(piperazin-1-yl)pyridin-2-yl)oxy)pyrrolidin-1-yl)pyridazin-3(2H)-one 20: To a dry 5 mL microwave vial were added 5-[(3R)-3-[(4-bromo-2-pyridyl)oxy]pyrrolidin-1-yl]-4-chloro-2-tetrahydropyran-2-yl-pyridazin-3-one (4, 0.30 g, 0.66 mmol), tert-butyl piperazine-1-carboxylate (0.25 g, 1.32 mmol), (2-dicyclohexylphosphino-2',4',6'-triisopropyl-1,1'-biphenyl)[2-(2-aminoethyl)phenyl)]palladium(II) chloride (0.050 g, 0.07 mmol), cesium carbonate (0.32 g, 0.99 mmol), and 1,4-dioxane (5 mL). The vial was sealed and heated to 80° C. for 12 hours in an oil bath. The reaction was evaporated onto silica gel and purified by reverse phase flash column chromatography (50 g C18 column; 0-70% B; A: 99.9% $H_2O$, 0.1% $HCO_2H$; B: 99.9% $CH_3CN$, 0.1% $HCO_2H$) to give the bis-protected intermediate. This material was dissolved in dichloromethane (5 mL) and treated with hydrochloric acid (4 M in 1,4-dioxane, 0.82 ml, 3.3 mmol). After stirring at room temperature for 2 hours, the reaction was evaporated to dryness to give (R)-4-chloro-5-(3-((4-(piperazin-1-yl)pyridin-2-yl)oxy)pyrrolidin-1-yl)pyridazin-3(2H)-one (20). MS (ESI) $[M+H^+]^+=377.0$.

Step 2: Preparation of (R)-4-(2-((1-(5-chloro-6-oxo-1,6-dihydropyridazin-4-yl)pyrrolidin-3-yl)oxy)pyridin-4-yl)-N-cyclopropylpiperazine-1-sulfonamide (P-0231): To a 20 mL scintillation vial were added (R)-4-chloro-5-(3-((4-(piperazin-1-yl)pyridin-2-yl)oxy)pyrrolidin-1-yl)pyridazin-3(2H)-one (20, 0.050 g, 0.11 mmol), pyridine (0.88 ml, 10.9 mmol), and N-cyclopropylsulfamoyl chloride (0.020 g, 0.13 mmol). The reaction was stirred at room temperature for 2 hours. The reaction was evaporated onto silica gel and purified by reverse phase flash column chromatography (30 g C18 column; 0-50% B; A: 99.9% $H_2O$, 0.1% $HCO_2H$; B: 99.9% $CH_3CN$, 0.1% $HCO_2H$) to give (R)-4-(2-((1-(5-chloro-6-oxo-1,6-dihydropyridazin-4-yl)pyrrolidin-3-yl)oxy)pyridin-4-yl)-N-cyclopropylpiperazine-1-sulfonamide (P-0231). MS (ESI) $[M+H^+]^+=496.0$.

Step 1: Preparation of 5-((R)-3-((4-(4-amino-2-fluorophenyl)pyridin-2-yl)oxy)pyrrolidin-1-yl)-4-chloro-2-(tetrahydro-2H-pyran-2-yl)pyridazin-3(2H)-one 21: In a 20 mL microwave vial, to 5-[(3R)-3-[(4-bromo-2-pyridyl)oxy]pyrrolidin-1-yl]-4-chloro-2-tetrahydropyran-2-yl-pyridazin-3-one (4, 0.50 g, 1.1 mmol), 3-fluoro-4-(4,4,5,5-tetramethyl-1,3,2-dioxaborolan-2-yl)aniline (0.46 g, 1.9 mmol), and dichloro(1,1-bis(diphenylphosphino)ferrocene)palladium (II) acetone adduct (0.15 g, 0.19 mmol) in 1,4-dioxane (10 mL) was added 1 M aqueous potassium carbonate (5 mL). The reaction mixture was immediately heated at 100° C. in an oil bath which was preheated to 100° C. The reaction was completed in less than 5 minutes. The reaction was concentrated onto 10 g of silica gel and purified by reverse phase flash column chromatography (50 g C18 column; 0-60% B; A: 99.9% $H_2O$, 0.1% $HCO_2H$; B: 99.9% $CH_3CN$, 0.1% $HCO_2H$) to give 5-((R)-3-((4-(4-amino-2-fluorophenyl)pyridin-2-yl)oxy)pyrrolidin-1-yl)-4-chloro-2-(tetrahydro-2H-pyran-2-yl)pyridazin-3(2H)-one (21). MS (ESI) $[M+H^+]^+=486.0$.

Step 2: Preparation of (R)—N-(4-(2-((1-(5-chloro-6-oxo-1,6-dihydropyridazin-4-yl)pyrrolidin-3-yl)oxy)pyridin-4-yl)-3-fluorophenyl)benzamide (P-0216): 5-((R)-3-((4-(4-amino-2-fluorophenyl)pyridin-2-yl)oxy)pyrrolidin-1-yl)-4-chloro-2-(tetrahydro-2H-pyran-2-yl)pyridazin-3(2H)-one (21, 40 mg, 0.082 mmol) was dissolved in dichloromethane (2 mL) and triethylamine (25 mg, 0.25 mmol) was added. While stirring vigorously at room temperature, benzoyl chloride (14 mg, 0.099 mmol) was added in one portion and the reaction was stirred at room temperature for 2 hours. To the crude reaction was added hydrochloric acid (4 M in 1,4-dioxane, 2 mL, 8 mmol) and the mixture was stirred at room temperature for 30 minutes. The reaction was then concentrated onto 10 g of silica gel and purified by reverse phase chromatography (50 g C18 column; 0-60% B; A: 99.9% $H_2O$, 0.1% $HCO_2H$; B: 99.9% $CH_3CN$, 0.1%

HCO₂H). This purification provided (R)—N-(4-(2-((1-(5-chloro-6-oxo-1,6-dihydropyridazin-4-yl)pyrrolidin-3-yl)oxy)pyridin-4-yl)-3-fluorophenyl)benzamide (P-0216). MS (ESI) [M+H⁺]⁺=506.0.

Example 9

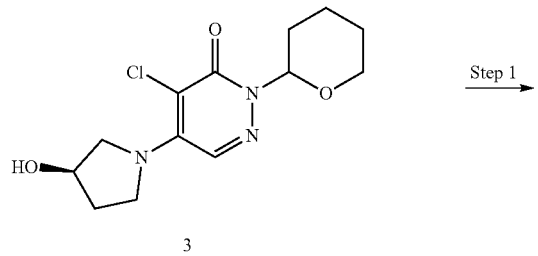

3

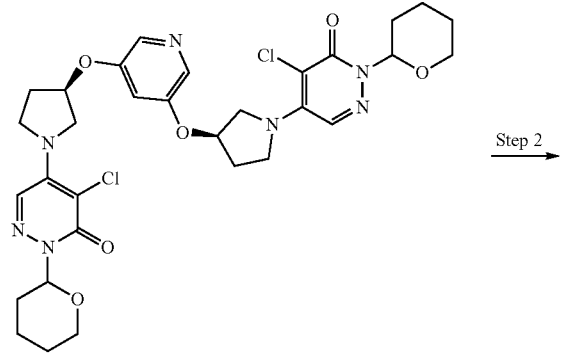

22

P-0165

Step 1: Preparation of 5,5'-((3R,3'R)-(pyridine-3, 5-diylbis(oxy))bis(pyrrolidine-3,1-diyl))bis(4-chloro-2-(tetrahydro-2H-pyran-2-yl)pyridazin-3(2H)-one) 22: In a vial, to 4-chloro-5-[(3R)-3-hydroxypyrrolidin-1-yl]-2-tetrahydropyran-2-yl-pyridazin-3-one (3, 500 mg, 1.67 mmol), cuprous iodide (20.0 mg, 0.11 mmol), and 3,4,7,8-tetramethyl-1,10-phenanthroline (0.04 ml, 0.17 mmol) in N,N-dimethylformamide (5 mL) were added 3-bromo-5-iodopyridine (500 mg, 1.76 mmol) and cesium carbonate (850 mg, 2.61 mmol). The reaction mixture was heated to 100° C. for 16 hours. Three products were detected including a small amount of the desired product. The crude reaction was filtered and concentrated onto silica gel. This material was then purified by normal phase flash column chromatography (24 g silica gel column, 0 to 100% ethyl acetate in dichloromethane gradient). This purification provided 5,5'-((3R, 3'R)-(pyridine-3, 5-diylbis(oxy))bis(pyrrolidine-3,1-diyl)) bis(4-chloro-2-(tetrahydro-2H-pyran-2-yl)pyridazin-3(2H)-one) (22). MS (ESI) [M+H⁺]⁺=674.1.

Step 2: Preparation of 5,5'-((3R,3'R)-(pyridine-3,5-diylbis(oxy))bis(pyrrolidine-3,1-diyl))bis(4-chloropyridazin-3(2H)-one) (P-0165): In a 40 mL vial, to 5,5'-((3R,3'R)-(pyridine-3, 5-diylbis(oxy))bis(pyrrolidine-3,1-diyl))bis(4-chloro-2-(tetrahydro-2H-pyran-2-yl)pyridazin-3(2H)-one) (22, 40 mg, 0.060 mmol) in 1,4-dioxane (2 mL) was added hydrochloric acid (4 M in 1,4-dioxane, 6 mL, 24 mmol). The reaction mixture was stirred at room temperature for 2 hours. The volatiles were removed under reduced pressure and the material was dissolved in 2 mL of N,N-dimethylformamide. This material was then purified by reverse phase flash column chromatography (30 g C18 column; 0-50% B; A: 99.9% H₂O, 0.1% HCO₂H; B: 99.9% CH₃CN, 0.1% HCO₂H). This purification provided 5,5'-((3R,3'R)-(pyridine-3,5-diylbis(oxy))bis(pyrrolidine-3,1-diyl))bis(4-chloropyridazin-3(2H)-one) (P-0165). MS (ESI) [M+H⁺]⁺=505.9.

Example 10

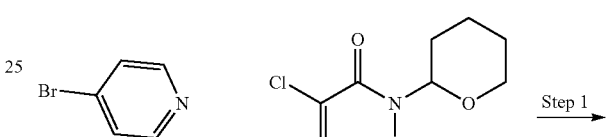

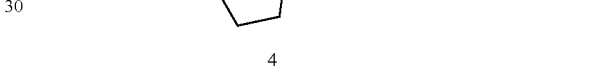

4

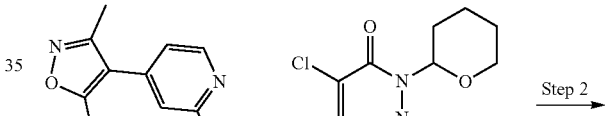

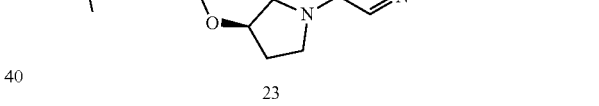

23

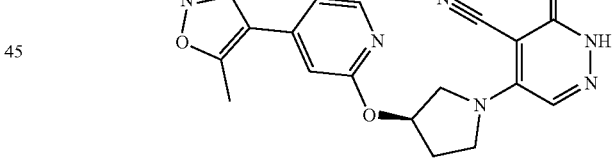

P-0065

Step 1: Preparation of 4-chloro-5-((R)-3-((4-(3,5-dimethylisoxazol-4-yl)pyridin-2-yl)oxy)pyrrolidin-1-yl)-2-(tetrahydro-2H-pyran-2-yl)pyridazin-3(2H)-one 23: In a 10 mL microwave vial, to 5-[(3R)-3-[(4-bromo-2-pyridyl)oxy]pyrrolidin-1-yl]-4-chloro-2-tetrahydropyran-2-yl-pyridazin-3-one (4, 0.20 g, 0.44 mmol), 3,5-dimethyl-4-(4,4,5,5-tetramethyl-1,3,2-dioxaborolan-2-yl)isoxazole (0.20 g, 0.90 mmol), and dichloro(1,1-bis(diphenylphosphino)ferrocene)palladium(II) acetone adduct (0.050 g, 0.060 mmol) in 1,4-dioxane (4 mL) was added 1 M aqueous potassium carbonate (2 mL, 2.0 mmol). The reaction mixture was immediately heated at 100° C. in an oil bath which was preheated to 100° C. The reaction was complete in less than 5 minutes. The reaction mixture was poured into water and extracted with ethyl acetate. The organic layer was washed with water and brine, then dried over magnesium sulfate. The organic layer was concentrated onto silica gel and purified by normal phase flash column chromatography (12 g silica gel column, 0 to 100% ethyl acetate in dichloromethane gradient). This purification provided 4-chloro-5-((R)-3-((4-(3,5-dimethylisoxazol-4-yl)pyridin-2-yl)oxy)pyrrolidin-1-yl)-2-(tetrahydro-2H-pyran-2-yl)pyridazin-3(2H)-one (23). MS (ESI) [M+H$^+$]$^+$=472.3.

Step 2: Preparation of (R)-5-(3-((4-(3,5-dimethylisoxazol-4-yl)pyridin-2-yl)oxy)pyrrolidin-1-yl)-3-oxo-2,3-dihydropyridazine-4-carbonitrile (P-0065): In a vial, to 4-chloro-5-((R)-3-((4-(3,5-dimethylisoxazol-4-yl)pyridin-2-yl)oxy)pyrrolidin-1-yl)-2-(tetrahydro-2H-pyran-2-yl)pyridazin-3(2H)-one (23, 156 mg, 0.33 mmol) was added N,N-dimethylacetamide (5 mL). The solution was degassed by bubbling with argon. To this solution were added zinc dust (10 mg, 0.15 mmol), 1,1'-bis(diphenylphosphino)ferrocene (16 mg, 0.030 mmol), tris(dibenzylideneacetone)dipalladium(0) (15 mg, 0.030 mmol), and zinc cyanide (50 mg, 0.43 mmol) at room temperature under argon. The mixture was heated at 120° C. for 20 hours. After cooling to room temperature, the reaction mixture was poured into aqueous sodium bicarbonate (saturated) and extracted with ethyl acetate. The organic layer was washed with water and brine, then dried over magnesium sulfate. This solution was concentrated onto silica gel and purified by normal phase flash column chromatography (12 g silica gel column, 0 to 80% ethyl acetate in dichloromethane gradient followed by a 0 to 10% methanol in dichloromethane gradient). The crude THP protected product was collected and the residue was dissolved in 1,4-dioxane (2 mL) and hydrochloric acid (4 M in 1,4-dioxane, 8 mL, 32 mmol) was added. The mixture was stirred at room temperature for 2 hours. The reaction was concentrated and then dissolved in 2 mL of N,N-dimethylformamide. This solution was purified by reverse phase flash column chromatography (30 g C18 column; 0-50% B; A: 99.9% H$_2$O, 0.1% HCO$_2$H; B: 99.9% CH$_3$CN, 0.1% HCO$_2$H) to provide (R)-5-(3-((4-(3,5-dimethylisoxazol-4-yl)pyridin-2-yl)oxy)pyrrolidin-1-yl)-3-oxo-2,3-dihydropyridazine-4-carbonitrile (P-0065). MS (ESI) [M+H$^+$]$^+$=379.3.

Example 11

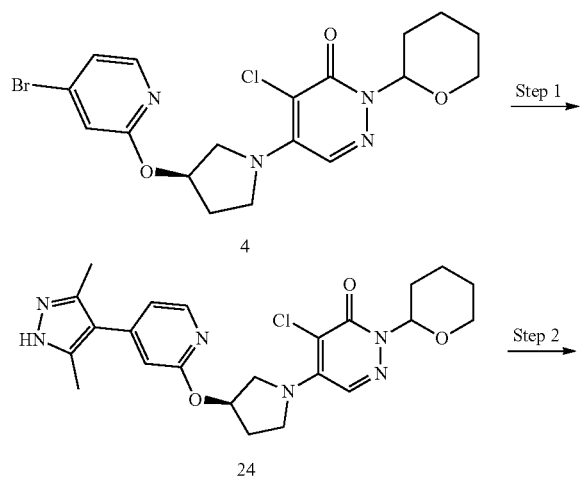

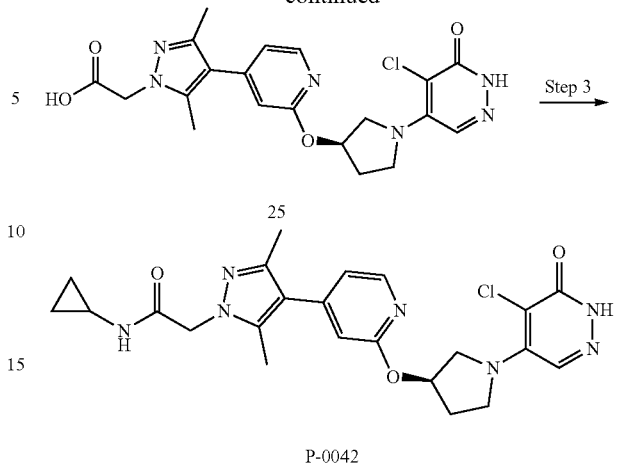

Step 1: Preparation of 4-chloro-5-[(3R)-3-[[4-(3,5-dimethyl-1H-pyrazol-4-yl)-2-pyridyl]oxy]pyrrolidin-1-yl]-2-tetrahydropyran-2-yl-pyridazin-3-one 24: In a 250 mL round bottom flask, to 5-[(3R)-3-[(4-bromo-2-pyridyl)oxy]pyrrolidin-1-yl]-4-chloro-2-tetrahydropyran-2-yl-pyridazin-3-one (4, 2.0 g, 4.39 mmol), 3,5-dimethyl-4-(4,4,5,5-tetramethyl-1,3,2-dioxaborolan-2-yl)-1H-pyrazole (1.46 g, 6.6 mmol), and dichloro(1,1-bis(diphenylphosphino)ferrocene) palladium(II) acetone adduct (0.35 g, 0.44 mmol) in 1,4-dioxane (50 ml) was added 1 M aqueous potassium carbonate (13 mL, 13 mmol). The reaction mixture was immediately heated at 100° C. in the oil bath which was preheated to 100° C. The reaction was stirred at 100° C. for 4 hours. The reaction was concentrated onto 50 g of silica gel and purified by reverse phase flash column chromatography (150 g C18 column; 0-50% B; A: 99.9% H$_2$O, 0.1% HCO$_2$H; B: 99.9% CH$_3$CN, 0.1% HCO$_2$H). This purification provided 4-chloro-5-[(3R)-3-[[4-(3, 5-dimethyl-1H-pyrazol-4-yl)-2-pyridyl]oxy]pyrrolidin-1-yl]-2-tetrahydropyran-2-yl-pyridazin-3-one (24). MS (ESI) [M+H$^+$]$^+$=471.3.

Step 2: Preparation of 2-[4-[2-[(3R)-1-(5-chloro-6-oxo-1H-pyridazin-4-yl)pyrrolidin-3-yl]oxy-4-pyridyl]-3,5-dimethyl-pyrazol-1-yl]acetic acid 25: 4-chloro-5-[(3R)-3-[[4-(3,5-dimethyl-1H-pyrazol-4-yl)-2-pyridyl]oxy]pyrrolidin-1-yl]-2-tetrahydropyran-2-yl-pyridazin-3-one (24, 250 mg, 0.53 mmol) and tert-butyl 2-bromoacetate (207 mg, 1.1 mmol) were dissolved in N,N-dimethylformamide (5 mL) and sodium hydride was added (60% in mineral oil, 42 mg, 1.1 mmol). The reaction was stirred at room temperature for 15 hours overnight. The reaction was concentrated onto 10 g of silica gel and purified by normal phase flash column chromatography (12 g silica gel column, 0 to 100% ethyl acetate in hexanes). This purification gave the intermediate bis-protected product. This material was dissolved in 20 mL of dichloromethane and hydrochloric acid (4 M in 1,4-dioxane, 5 mL, 20 mmol) was added. The reaction was stirred at room temperature for 30 minutes. The reaction was concentrated to give 2-[4-[2-[(3R)-1-(5-chloro-6-oxo-1H-pyridazin-4-yl)pyrrolidin-3-yl]oxy-4-pyridyl]-3,5-dimethyl-pyrazol-1-yl]acetic acid (25). MS (ESI) [M+H$^+$]$^+$=445.2.

Step 3: Preparation of (R)-2-(4-(2-((1-(5-chloro-6-oxo-1,6-dihydropyridazin-4-yl)pyrrolidin-3-yl)oxy)pyridin-4-yl)-3,5-dimethyl-1H-pyrazol-1-yl)-N-cyclopropylacetamide P-0042: 2-[4-[2-[(3R)-1-(5-chloro-6-oxo-1H-pyridazin-4- yl)pyrrolidin-3-yl]oxy-4-pyridyl]-3,5-dimethyl-pyrazol-1-yl]acetic acid (25, 50 mg, 0.112 mmol) was dissolved in N,N-dimethylformamide (1 mL) and HBTU (55 mg, 0.10 mmol) and cyclopropylamine (26 mg, 0.45 mmol) were added. While stirring vigorously at room temperature, triethylamine (45 mg, 0.45 mmol) was added in one portion and the reaction was stirred for 15 hours overnight. The reaction was then directly purified by reverse phase flash column chromatography (50 g C$_{18}$ column; 0-50% B; A: 99.9% H$_2$O, 0.1% HCO$_2$H; B: 99.9% CH$_3$CN, 0.1% HCO$_2$H). This purification provided (R)-2-(4-(2-((1-(5-chloro-6-oxo-1,6-dihydropyridazin-4-yl)pyrrolidin-3-yl)oxy)pyridin-4-yl)-3,5-dimethyl-1H-pyrazol-1-yl)-N-cyclopropylacetamide (P-0042). MS (ESI) [M+H$^+$]$^+$=484.3.

Example 12

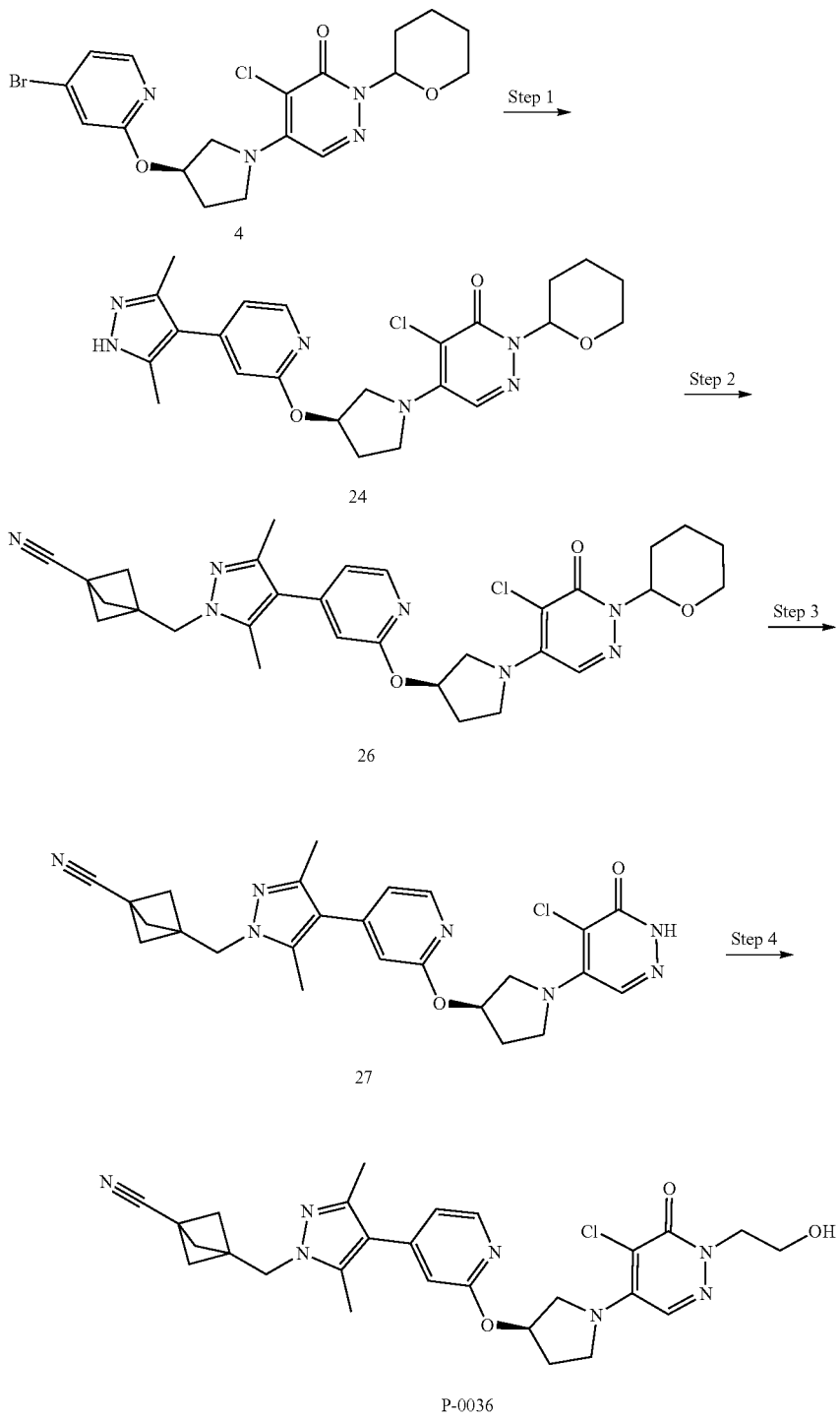

Step 1: Preparation of 4-chloro-5-[(3R)-3-[[4-(3,5-dimethyl-1H-pyrazol-4-yl)-2-pyridyl]oxy]pyrrolidin-1-yl]-2-tetrahydropyran-2-yl-pyridazin-3-one 24: In a 250 mL round bottom flask, to 5-[(3R)-3-[(4-bromo-2-pyridyl)oxy]pyrrolidin-1-yl]-4-chloro-2-tetrahydropyran-2-yl-pyridazin-3-one (4, 2.0 g, 4.39 mmol), 3,5-dimethyl-4-(4,4,5,5-tetramethyl-1,3,2-dioxaborolan-2-yl)-1H-pyrazole (1.46 g, 6.6 mmol), and dichloro(1,1-bis(diphenylphosphino)ferrocene)palladium(II) acetone adduct (0.35 g, 0.44 mmol) in 1,4-dioxane (50 ml) was added 1 M aqueous potassium carbonate (13 mL, 13 mmol). The reaction mixture was immediately heated at 100° C. in the oil bath which was preheated to 100° C. The reaction was stirred at 100° C. for 4 hours. The reaction was concentrated onto 50 g of silica gel and purified by reverse phase flash column chromatography (150 g C18 column; 0-50% B; A: 99.9% H$_2$O, 0.1% HCO$_2$H; B: 99.9% CH$_3$CN, 0.1% HCO$_2$H). This purification provided 4-chloro-5-[(3R)-3-[[4-(3, 5-dimethyl-1H-pyrazol-4-yl)-2-pyridyl]oxy]pyrrolidin-1-yl]-2-tetrahydropyran-2-yl-pyridazin-3-one (24). MS (ESI) [M+H$^+$]$^+$=471.3.

Step 2: Preparation of 3-((4-(2-(((3R)-1-(5-chloro-6-oxo-1-(tetrahydro-2H-pyran-2-yl)-1,6-dihydropyridazin-4-yl)pyrrolidin-3-yl)oxy)pyridin-4-yl)-3, 5-dimethyl-1H-pyrazol-1-yl)methyl)bicyclo[1.1.1]pentane-1-carbonitrile 26: In a vial, to 4-chloro-5-[(3R)-3-[[4-(3,5-dimethyl-1H-pyrazol-4-yl)-2-pyridyl]oxy]pyrrolidin-1-yl]-2-tetrahydropyran-2-yl-pyridazin-3-one (24, 0.060 g, 0.13 mmol) in N,N-dimethylformamide (2 mL) was added sodium hydride (60% in mineral oil, 0.010 g, 0.34 mmol). The reaction was stirred at room temperature for 15 minutes. At this time, (3-cyanobicyclo[1.1.1]pentan-1-yl)methyl 4-methylbenzenesulfonate (0.060 g, 0.22 mmol) was added and the reaction was stirred at room temperature for 16 hours. The reaction was filtered to remove insoluble material and concentrated onto silica gel. This material was then purified by normal phase flash column chromatography (12 g silica gel column, 0 to 100% ethyl acetate in dichloromethane gradient). This purification provided 3-((4-(2-(((3R)-1-(5-chloro-6-oxo-1-(tetrahydro-2H-pyran-2-yl)-1,6-dihydropyridazin-4-yl)pyrrolidin-3-yl)oxy)pyridin-4-yl)-3,5-dimethyl-1H-pyrazol-1-yl)methyl)bicyclo[1.1.1]pentane-1-carbonitrile (26). MS (ESI) [M+H$^+$]$^+$=576.3.

Step 3: Preparation of (R)-3-((4-(2-((1-(5-chloro-6-oxo-1,6-dihydropyridazin-4-yl)pyrrolidin-3-yl)oxy)pyridin-4-yl)-3, 5-dimethyl-1H-pyrazol-1-yl)methyl)bicyclo[1.1.1]pentane-1-carbonitrile 27: In a 40 mL vial, to 3-((4-(2-(((3R)-1-(5-chloro-6-oxo-1-(tetrahydro-2H-pyran-2-yl)-1, 6-dihydropyridazin-4-yl)pyrrolidin-3-yl)oxy)pyridin-4-yl)-3, 5-dimethyl-1H-pyrazol-1-yl)methyl)bicyclo[1.1.1]pentane-1-carbonitrile (26, 48 mg, 0.080 mmol) in dichloromethane (10 mL) was added trifluoroacetic acid (1 mL). The reaction mixture was stirred at room temperature for 2 hours. The reaction was concentrated under reduced pressure and dissolved in 2 mL of N,N-dimethylformamide. This solution was then purified by reverse phase flash column chromatography (30 g C18 column; 0-50% B; A: 99.9% H$_2$O, 0.1% HCO$_2$H; B: 99.9% CH$_3$CN, 0.1% HCO$_2$H). This purification provided (R)-3-((4-(2-((1-(5-chloro-6-oxo-1,6-dihydropyridazin-4-yl)pyrrolidin-3-yl)oxy)pyridin-4-yl)-3, 5-dimethyl-1H-pyrazol-1-yl)methyl)bicyclo[1.1.1]pentane-1-carbonitrile (27). MS (ESI) [M+H$^+$]$^+$=492.3.

Step 4: Preparation of (R)-3-((4-(2-((1-(5-chloro-1-(2-hydroxyethyl)-6-oxo-1,6-dihydropyridazin-4-yl)pyrrolidin-3-yl)oxy)pyridin-4-yl)-3,5-dimethyl-1H-pyrazol-1-yl)methyl)bicyclo[1.1.1]pentane-1-carbonitrile (P-0036): In a vial, to (R)-3-((4-(2-((1-(5-chloro-6-oxo-1,6-dihydropyridazin-4-yl)pyrrolidin-3-yl)oxy)pyridin-4-yl)-3, 5-dimethyl-1H-pyrazol-1-yl)methyl)bicyclo[1.1.1]pentane-1-carbonitrile (27, 18 mg, 0.040 mmol) in N,N-dimethylformamide (2 mL) were added potassium carbonate (0.15 g, 1.1 mmol) and 2-(2-bromoethoxy)tetrahydropyran (50 mg, 0.24 mmol). The reaction mixture was heated to 60° C. for 16 hours. The reaction was filtered to remove insoluble material and concentrated under reduced pressure. To this material was added dichloromethane (8 mL) and trifluoroacetic acid (1 mL). The reaction mixture was stirred at room temperature for 2 hours. The reaction was concentrated under reduced pressure and dissolved in 2 mL of N,N-dimethylformamide. This solution was purified by reverse phase flash column chromatography (30 g C18 column; 0-50% B; A: 99.9% H$_2$O, 0.1% HCO$_2$H; B: 99.9% CH$_3$CN, 0.1% HCO$_2$H). This purification provided (R)-3-((4-(2-((1-(5-chloro-1-(2-hydroxyethyl)-6-oxo-1,6-dihydropyridazin-4-yl)pyrrolidin-3-yl)oxy)pyridin-4-yl)-3, 5-dimethyl-1H-pyrazol-1-yl)methyl)bicyclo[1.1.1]pentane-1-carbonitrile (P-0036). MS (ESI) [M+H$^+$]$^+$=536.3.

Example 13

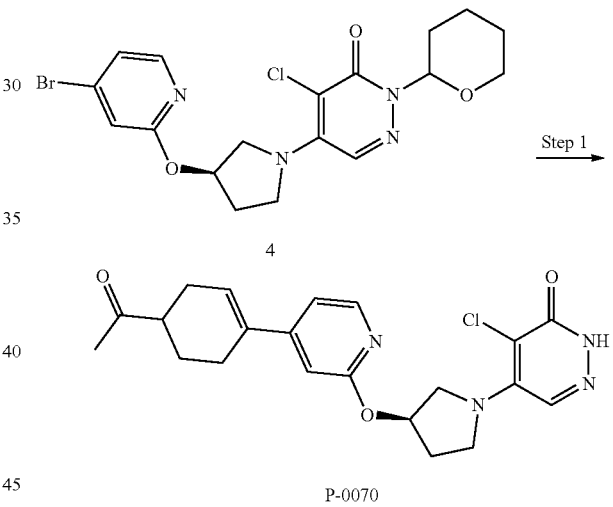

Step 1: Preparation of 5-((3R)-3-((4-(4-acetylcyclohex-1-en-1-yl)pyridin-2-yl)oxy)pyrrolidin-1-yl)-4-chloropyridazin-3(2H)-one (P-0070): To a mixture of 5-[(3R)-3-[(4-bromo-2-pyridyl)oxy]pyrrolidin-1-yl]-4-chloro-2-tetrahydropyran-2-yl-pyridazin-3-one (4, 0.10 g, 0.22 mmol), 1-[4-(4,4,5,5-tetramethyl-1,3,2-dioxaborolan-2-yl)cyclohex-3-en-1-yl]ethanone (0.080 g, 0.33 mmol), and dichloro(1,1-bis(diphenylphosphino)ferrocene)palladium (II) acetone adduct (0.020 g, 0.020 mmol) in a small glass vial was added 1,4-dioxane (3 mL). The vial was capped and purged with nitrogen for 5 minutes and then heated at 100° C. in an oil bath. Aqueous potassium carbonate (1 M, 0.44 mL, 0.44 mmol) was added and the mixture was heated at 100° C. for 150 minutes. The crude reaction was concentrated onto celite and purified by normal phase flash column chromatography (12 g silica gel column, 0 to 80% ethyl acetate in hexanes gradient). This purification provided the intermediate THP protected product. This material was dissolved in dichloromethane (3 mL) and treated with hydrochloric acid (1 M in ethyl acetate, 2.2 mL, 2.2 mmol).

The reaction was then stirred at room temperature for 2 hours. The reaction was concentrated and re-dissolved in acetonitrile/water (1:1, 4 mL) and then purified by reverse phase flash column chromatography (30 g C18 column; 5-100% B; A: 99.9% H₂O, 0.1% HCO₂H; B: 99.9% CH₃CN, 0.1% HCO₂H). This purification provided 5-((3R)-3-((4-(4-acetylcyclohex-1-en-1-yl)pyridin-2-yl)oxy)pyrrolidin-1-yl)-4-chloropyridazin-3(2H)-one (P-0070). MS (ESI) [M+H⁺]⁺=415.3.

Example 14

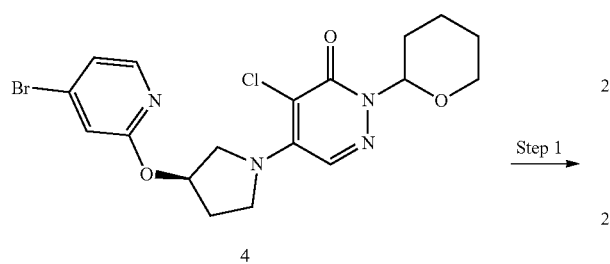

4

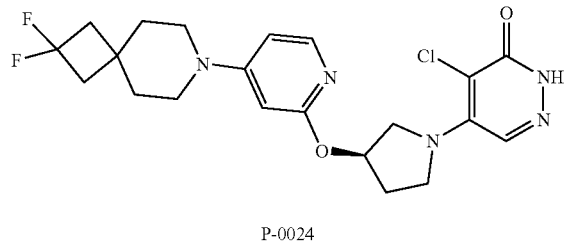

P-0024

Step 1: Preparation of (R)-4-chloro-5-(3-((4-(2,2-difluoro-7-azaspiro[3.5]nonan-7-yl)pyridin-2-yl)oxy)pyrrolidin-1-yl)pyridazin-3(2H)-one (P-0024): 5-[(3R)-3-[(4-bromo-2-pyridyl)oxy]pyrrolidin-1-yl]-4-chloro-2-tetrahydropyran-2-yl-pyridazin-3-one (4, 0.10 g, 0.22 mmol), 2,2-difluoro-7-azaspiro[3.5]nonane hydrochloride (0.070 g, 0.33 mmol), ruphos palladacycle GEN 4 (0.040 g, 0.040 mmol), sodium tert-butoxide (0.060 g, 0.66 mmol), and toluene (2 mL) were added to a microwave vial. The vial was then capped, purged with nitrogen, and heated in a microwave reactor to 150° C. for 45 minutes. The crude reaction was concentrated onto celite and purified by reverse phase flash column chromatography (30 g C₁₈ column; 5-80% B; A: 99.9% H₂O, 0.1% HCO₂H; B: 99.9% CH₃CN, 0.1% HCO₂H). This purification provided the intermediate THP protected product. This material was dissolved in dichloromethane (2 mL) and treated with hydrochloric acid (1 M in ethyl acetate, 1.0 mL, 1.0 mmol). The reaction was then stirred at room temperature for 90 minutes. The reaction was concentrated and re-dissolved in acetonitrile/water (1:1, 2 mL) and then purified by reverse phase flash column chromatography (30 g C18 column; 5-80% B; A: 99.9% H₂O, 0.1% HCO₂H; B: 99.9% CH₃CN, 0.1% HCO₂H). This purification provided (R)-4-chloro-5-(3-((4-(2,2-difluoro-7-azaspiro[3.5]nonan-7-yl)pyridin-2-yl)oxy)pyrrolidin-1-yl)pyridazin-3(2H)-one (P-0024). MS (ESI) [M+H⁺]⁺=452.2.

Example 15

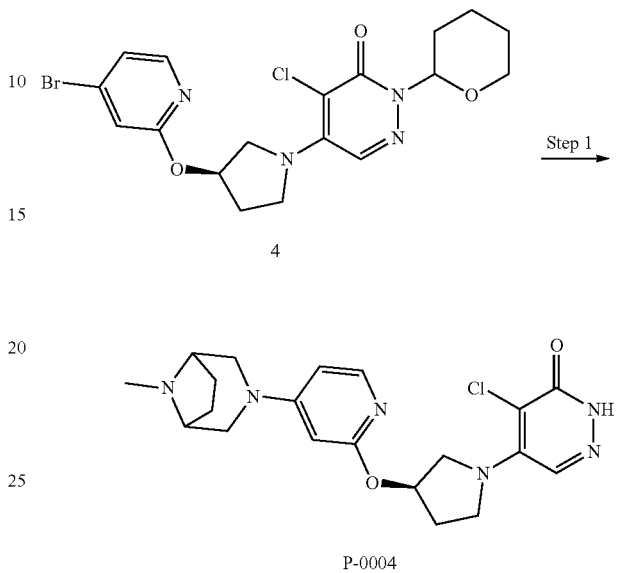

Step 1: Preparation of 4-chloro-5-((3R)-3-((4-(8-methyl-3,8-diazabicyclo[3.2.1]octan-3-yl)pyridin-2-yl)oxy)pyrrolidin-1-yl)pyridazin-3(2H)-one (P-0004): 5-[(3R)-3-[(4-bromo-2-pyridyl)oxy]pyrrolidin-1-yl]-4-chloro-2-tetrahydropyran-2-yl-pyridazin-3-one (4, 0.10 g, 0.22 mmol), 8-methyl-3,8-diazabicyclo[3.2.1]octane hydrochloride (0.054 g, 0.33 mmol), sodium tert-butoxide (0.084 g, 0.88 mmol), ruphos palladacycle GEN 4 (0.037 g, 0.044 mmol), and toluene (2 mL) were added to a microwave vial. The vial was then capped, purged with nitrogen, and heated in a microwave reactor to 150° C. for 30 minutes. The crude reaction was concentrated onto celite and purified by reverse phase flash column chromatography (30 g C18 column; 5-80% B; A: 99.9% H₂O, 0.1% HCO₂H; B: 99.9% CH₃CN, 0.1% HCO₂H). This purification provided the intermediate THP protected product. This material was dissolved in dichloromethane (1 mL) and treated with hydrochloric acid (1 M in ethyl acetate, 0.5 mL, 0.5 mmol). The reaction was then stirred at room temperature for 60 minutes. The reaction was concentrated and re-dissolved in acetonitrile/water (1:1, 2 mL) and then purified by reverse phase flash column chromatography (15 g C18 column; 5-80% B; A: 99.9% H₂O, 0.1% HCO₂H; B: 99.9% CH₃CN, 0.1% HCO₂H). This purification provided 4-chloro-5-((3R)-3-((4-(8-methyl-3,8-diazabicyclo[3.2.1]octan-3-yl)pyridin-2-yl)oxy)pyrrolidin-1-yl)pyridazin-3(2H)-one (P-0004). MS (ESI) [M+H⁺]⁺=417.3.

All compounds in Table 1 listed below can be made according to the synthetic examples described in this disclosure, and by making any necessary substitutions of starting materials that the skilled artisan would be able to obtain either commercially or otherwise.

TABLE 1

| P# | Structure | Name | (MH)+ |
|---|---|---|---|
| P-0001 | 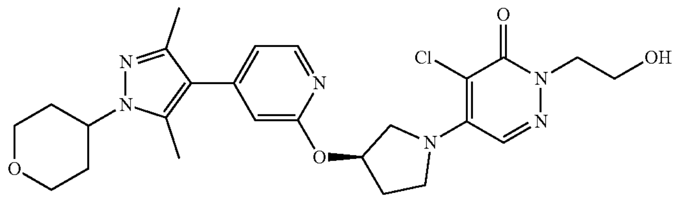 [SMILES: Cc1nn(C2CCOCC2)c(C)c1-c1ccnc(O[C@@H]2CCN(c3cnn(CCO)c(=O)c3Cl)C2)c1] | butyl (R)-(1-(5-chloro-6-oxo-1,6-dihydropyridazin-4-yl)pyrrolidin-3-yl)carbamate | 515.3 |
| P-0002 | 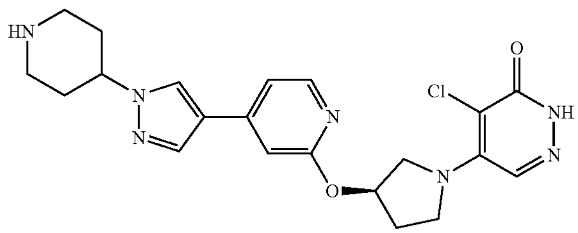 [SMILES: O=c1[nH]ncc(N2CC[C@@H](Oc3cc(-c4cnn(C5CCNCC5)c4)ccn3)C2)c1Cl] | (R)-4-chloro-5-(3-((4-(1-(piperidin-4-yl)-1H-pyrazol-4-yl)pyridin-2-yl)oxy)pyrrolidin-1-yl)pyridazin-3(2H)-one | 442.3 |
| P-0003 | 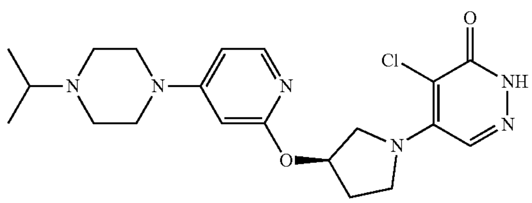 [SMILES: CC(C)N1CCN(c2ccnc(O[C@@H]3CCN(c4cn[nH]c(=O)c4Cl)C3)c2)CC1] | (R)-4-chloro-5-(3-((4-(4-isopropylpiperazin-1-yl)pyridin-2-yl)oxy)pyrrolidin-1-yl)pyridazin-3(2H)-one | 419.3 |
| P-0004 | 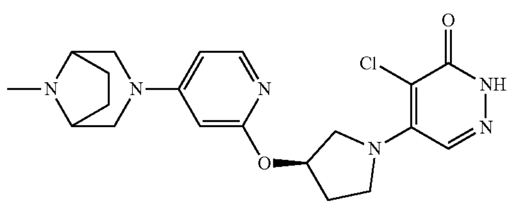 [SMILES: CN1C2CCC1CN(c1ccnc(O[C@@H]3CCN(c4cn[nH]c(=O)c4Cl)C3)c1)C2] | 4-chloro-5-((3R)-3-((4-(8-methyl-3,8-diazabicyclo[3.2.1]octan-3-yl)pyridin-2-yl)oxy)pyrrolidin-1-yl)pyridazin-3(2H)-one | 417.3 |
| P-0005 | 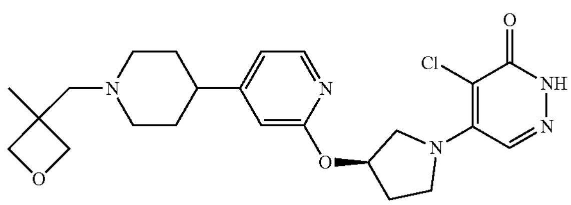 [SMILES: CC1(CN2CCC(c3ccnc(O[C@@H]4CCN(c5cn[nH]c(=O)c5Cl)C4)c3)CC2)COC1] | (R)-4-chloro-5-(3-((4-(1-((3-methyloxetan-3-yl)methyl)piperidin-4-yl)pyridin-2-yl)oxy)pyrrolidin-1-yl)pyridazin-3(2H)-one | 460.3 |
| P-0006 | 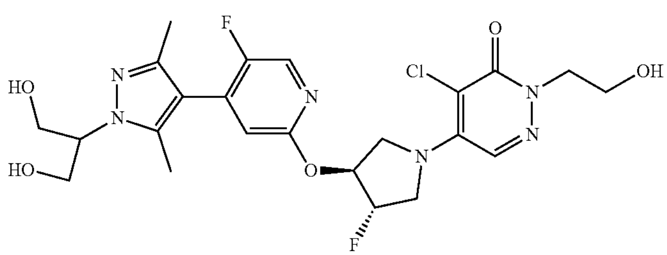 [SMILES: Cc1nn(C(CO)CO)c(C)c1-c1cc(O[C@H]2CN(c3cnn(CCO)c(=O)c3Cl)C[C@@H]2F)ncc1F] | 4-chloro-5-((3S,4S)-3-((4-(1-(1,3-dihydroxypropan-2-yl)-3,5-dimethyl-1H-pyrazol-4-yl)-5-fluoropyridin-2-yl)oxy)-4-fluoropyrrolidin-1-yl)-2-(2-hydroxyethyl)pyridazin-3(2H)-one | 541.2 |
| P-0007 | 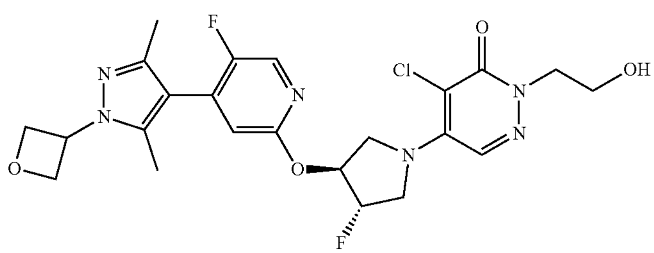 [SMILES: Cc1nn(C2COC2)c(C)c1-c1cc(O[C@H]2CN(c3cnn(CCO)c(=O)c3Cl)C[C@@H]2F)ncc1F] | 4-chloro-5-((3S,4S)-3-((4-(3,5-dimethyl-1-(oxetan-3-yl)-1H-pyrazol-4-yl)-5-fluoropyridin-2-yl)oxy)-4-fluoropyrrolidin-1-yl)-2-(2-hydroxyethyl)pyridazin-3(2H)-one | 523.3 |

TABLE 1-continued

| P# | Structure | Name | (MH)+ |
|---|---|---|---|
| P-0008 | 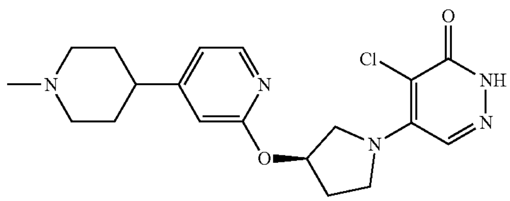 [SMILES: CN1CCC(c2ccnc(O[C@@H]3CCN(c4cn[nH]c(=O)c4Cl)C3)c2)CC1] | (R)-4-chloro-5-(3-((4-(1-methylpiperidin-4-yl)pyridin-2-yl)oxy)pyrrolidin-1-yl)pyridazin-3(2H)-one | 390.3 |
| P-0009 | 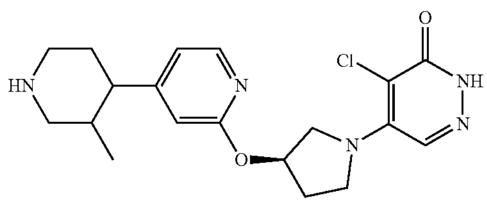 [SMILES: CC1CNCCC1c1ccnc(O[C@@H]2CCN(c3cn[nH]c(=O)c3Cl)C2)c1] | 4-chloro-5-((3R)-3-((4-(3-methylpiperidin-4-yl)pyridin-2-yl)oxy)pyrrolidin-1-yl)pyridazin-3(2H)-one | 390.3 |
| P-0010 | 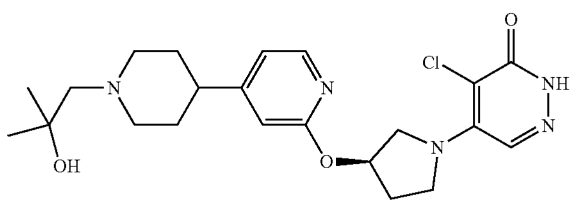 [SMILES: CC(C)(O)CN1CCC(c2ccnc(O[C@@H]3CCN(c4cn[nH]c(=O)c4Cl)C3)c2)CC1] | (R)-4-chloro-5-(3-((4-(1-(2-hydroxy-2-methylpropyl)piperidin-4-yl)pyridin-2-yl)oxy)pyrrolidin-1-yl)pyridazin-3(2H)-one | 448.3 |
| P-0011 | 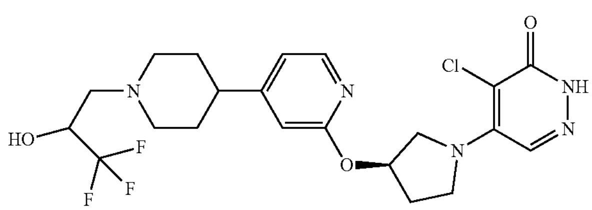 [SMILES: O=c1[nH]ncc(N2CC[C@@H](Oc3cc(C4CCN(CC(O)C(F)(F)F)CC4)ccn3)C2)c1Cl] | 4-chloro-5-((3R)-3-((4-(1-(3,3,3-trifluoro-2-hydroxypropyl)piperidin-4-yl)pyridin-2-yl)oxy)pyrrolidin-1-yl)pyridazin-3(2H)-one | 488.2 |
| P-0012 | 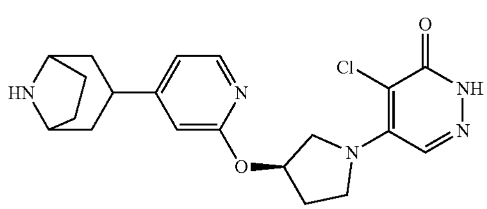 [SMILES: O=c1[nH]ncc(N2CC[C@@H](Oc3cc(C4CC5CCC(C4)N5)ccn3)C2)c1Cl] | 5-((3R)-3-((4-(8-azabicyclo[3.2.1]octan-3-yl)pyridin-2-yl)oxy)pyrrolidin-1-yl)-4-chloropyridazin-3(2H)-one | 402.3 |
| P-0013 | 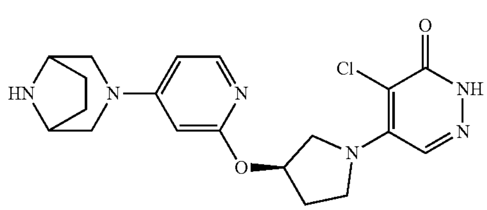 [SMILES: O=c1[nH]ncc(N2CC[C@@H](Oc3cc(N4CC5CCC(C4)N5)ccn3)C2)c1Cl] | 5-((3R)-3-((4-(3,8-diazabicyclo[3.2.1]octan-3-yl)pyridin-2-yl)oxy)pyrrolidin-1-yl)-4-chloropyridazin-3(2H)-one | 403.3 |
| P-0014 | 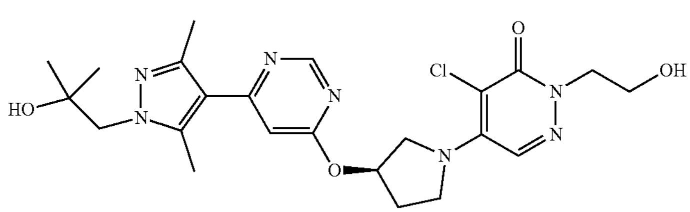 [SMILES: Cc1nn(CC(C)(C)O)c(C)c1-c1cc(O[C@@H]2CCN(c3cnn(CCO)c(=O)c3Cl)C2)ncn1] | (R)-4-chloro-5-(3-((6-(1-(2-hydroxy-2-methylpropyl)-3,5-dimethyl-1H-pyrazol-4-yl)pyrimidin-4-yl)oxy)pyrrolidin-1-yl)-2-(2-hydroxyethyl)pyridazin-3(2H)-one | 504.3 |

TABLE 1-continued

| P# | Structure | Name | (MH)+ |
|---|---|---|---|
| P-0015 | 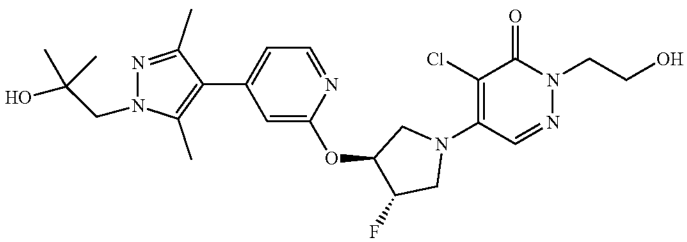 [SMILES: Cc1nn(CC(C)(C)O)c(C)c1-c1ccnc(O[C@H]2CN(c3cnn(CCO)c(=O)c3Cl)C[C@@H]2F)c1] | 4-chloro-5-((3S,4S)-3-fluoro-4-((4-(1-(2-hydroxy-2-methylpropyl)-3,5-dimethyl-1H-pyrazol-4-yl)pyridin-2-yl)oxy)pyrrolidin-1-yl)-2-(2-hydroxyethyl)pyridazin-3(2H)-one | 521.2 |
| P-0016 | 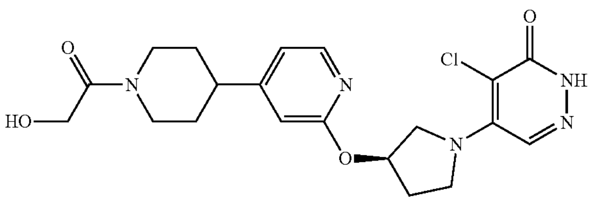 [SMILES: O=C(CO)N1CCC(c2ccnc(O[C@@H]3CCN(c4cn[nH]c(=O)c4Cl)C3)c2)CC1] | (R)-4-chloro-5-(3-((4-(1-(2-hydroxyacetyl)piperidin-4-yl)pyridin-2-yl)oxy)pyrrolidin-1-yl)pyridazin-3(2H)-one | 434.3 |
| P-0017 | 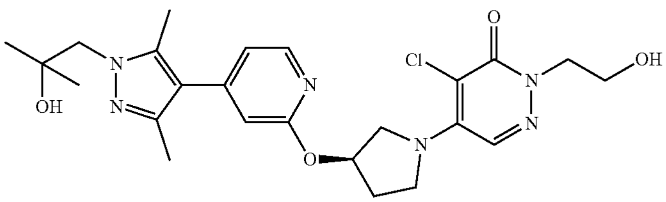 [SMILES: Cc1nn(CC(C)(C)O)c(C)c1-c1ccnc(O[C@@H]2CCN(c3cnn(CCO)c(=O)c3Cl)C2)c1] | (R)-4-chloro-5-(3-((4-(1-(2-hydroxy-2-methylpropyl)-3,5-dimethyl-1H-pyrazol-4-yl)pyridin-2-yl)oxy)pyrrolidin-1-yl)-2-(2-hydroxyethyl)pyridazin-3(2H)-one | 503.3 |
| P-0018 | 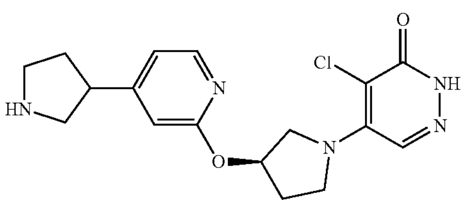 | 4-chloro-5-((3R)-3-((4-(pyrrolidin-3-yl)pyridin-2-yl)oxy)pyrrolidin-1-yl)pyridazin-3(2H)-one | 362.2 |
| P-0019 | 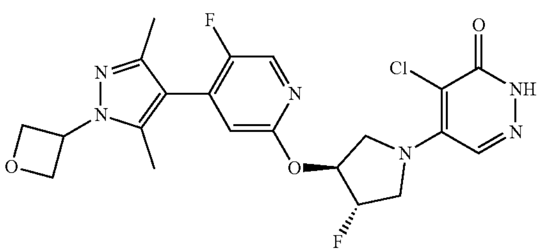 [SMILES: Cc1nn(C2COC2)c(C)c1-c1cc(O[C@H]2CN(c3cn[nH]c(=O)c3Cl)C[C@@H]2F)ncc1F] | 4-chloro-5-((3S,4S)-3-((4-(3,5-dimethyl-1-(oxetan-3-yl)-1H-pyrazol-4-yl)-5-fluoropyridin-2-yl)oxy)-4-fluoropyrrolidin-1-yl)pyridazin-3(2H)-one | 479.2 |
| P-0020 | 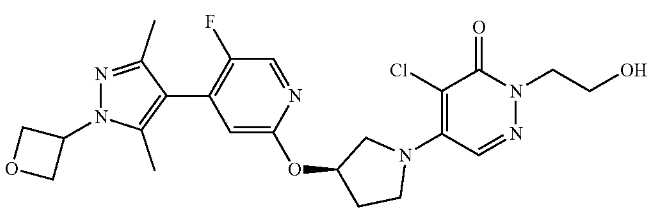 [SMILES: Cc1nn(C2COC2)c(C)c1-c1cc(O[C@@H]2CCN(c3cnn(CCO)c(=O)c3Cl)C2)ncc1F] | (R)-4-chloro-5-(3-((4-(3,5-dimethyl-1-(oxetan-3-yl)-1H-pyrazol-4-yl)-5-fluoropyridin-2-yl)oxy)pyrrolidin-1-yl)-2-(2-hydroxyethyl)pyridazin-3(2H)-one | 505.2 |
| P-0021 | 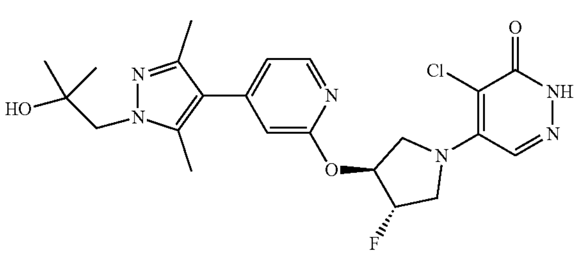 [SMILES: Cc1nn(CC(C)(C)O)c(C)c1-c1ccnc(O[C@H]2CN(c3cn[nH]c(=O)c3Cl)C[C@@H]2F)c1] | 4-chloro-5-((3S,4S)-3-fluoro-4-((4-(1-(2-hydroxy-2-methylpropyl)-3,5-dimethyl-1H-pyrazol-4-yl)pyridin-2-yl)oxy)pyrrolidin-1-yl)pyridazin-3(2H)-one | 477.2 |

TABLE 1-continued

| P# | Structure | Name | (MH)+ |
|---|---|---|---|
| P-0022 | 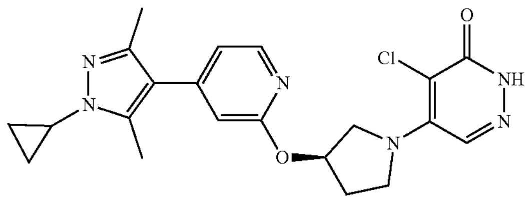 [SMILES: Cc1nn(C2CC2)c(C)c1-c1ccnc(O[C@@H]2CCN(c3cn[nH]c(=O)c3Cl)C2)c1] | (R)-4-chloro-5-(3-((4-(1-cyclopropyl-3,5-dimethyl-1H-pyrazol-4-yl)pyridin-2-yl)oxy)pyrrolidin-1-yl)pyridazin-3(2H)-one | 427.3 |
| P-0023 | 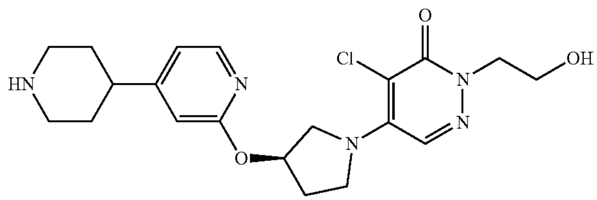 [SMILES: O=c1c(Cl)c(N2CC[C@@H](Oc3cc(C4CCNCC4)ccn3)C2)cnn1CCO] | (R)-4-chloro-2-(2-hydroxyethyl)-5-(3-((4-(piperidin-4-yl)pyridin-2-yl)oxy)pyrrolidin-1-yl)pyridazin-3(2H)-one | 420.3 |
| P-0024 | 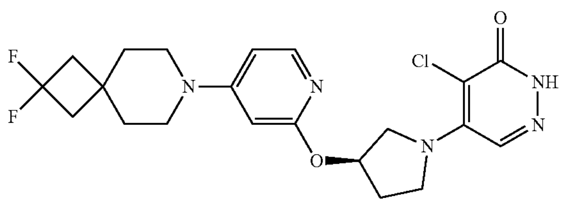 [SMILES: O=c1[nH]ncc(N2CC[C@@H](Oc3cc(N4CCC5(CC4)CC(F)(F)C5)ccn3)C2)c1Cl] | (R)-4-chloro-5-(3-((4-(2,2-difluoro-7-azaspiro[3.5]nonan-7-yl)pyridin-2-yl)oxy)pyrrolidin-1-yl)pyridazin-3(2H)-one | 452.2 |
| P-0025 | 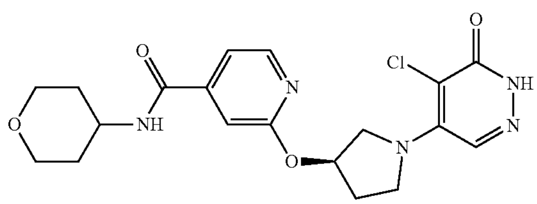 [SMILES: O=C(NC1CCOCC1)c1ccnc(O[C@@H]2CCN(c3cn[nH]c(=O)c3Cl)C2)c1] | (R)-2-((1-(5-chloro-6-oxo-1,6-dihydropyridazin-4-yl)pyrrolidin-3-yl)oxy)-N-(tetrahydro-2H-pyran-4-yl)isonicotinamide | 420.0 |
| P-0026 | 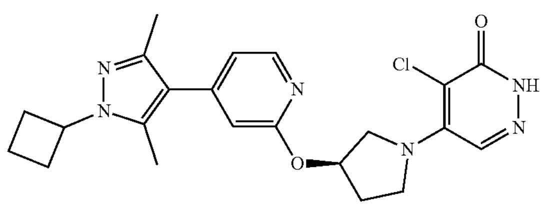 [SMILES: Cc1nn(C2CCC2)c(C)c1-c1ccnc(O[C@@H]2CCN(c3cn[nH]c(=O)c3Cl)C2)c1] | (R)-4-chloro-5-(3-((4-(1-cyclobutyl-3,5-dimethyl-1H-pyrazol-4-yl)pyridin-2-yl)oxy)pyrrolidin-1-yl)pyridazin-3(2H)-one | 441.4 |
| P-0027 | 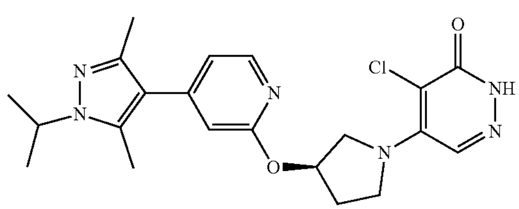 [SMILES: Cc1nn(C(C)C)c(C)c1-c1ccnc(O[C@@H]2CCN(c3cn[nH]c(=O)c3Cl)C2)c1] | (R)-4-chloro-5-(3-((4-(1-isopropyl-3,5-dimethyl-1H-pyrazol-4-yl)pyridin-2-yl)oxy)pyrrolidin-1-yl)pyridazin-3(2H)-one | 429.4 |
| P-0028 | 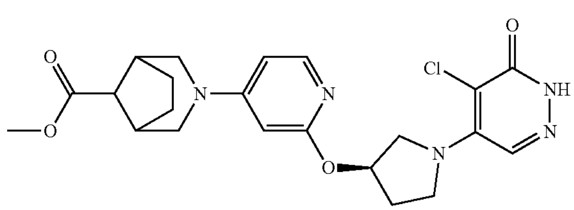 [SMILES: COC(=O)C1C2CCC1CN(c1ccnc(O[C@@H]3CCN(c4cn[nH]c(=O)c4Cl)C3)c1)C2] | methyl 3-(2-(((R)-1-(5-chloro-6-oxo-1,6-dihydropyridazin-4-yl)pyrrolidin-3-yl)oxy)pyridin-4-yl)-3-azabicyclo[3.2.1]octane-8-carboxylate | 460.3 |

TABLE 1-continued

| P# | Structure | Name | (MH)+ |
|---|---|---|---|
| P-0029 | 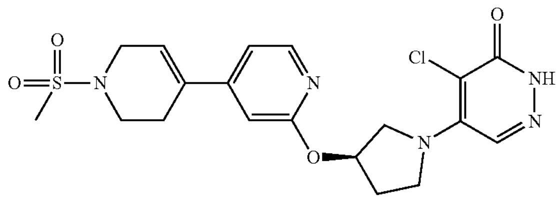 [SMILES: CS(=O)(=O)N1CC=C(c2ccnc(O[C@@H]3CCN(c4cn[nH]c(=O)c4Cl)C3)c2)CC1] | (R)-4-chloro-5-(3-((1'-(methylsulfonyl)-1',2',3',6'-tetrahydro-[4,4'-bipyridin]-2-yl)oxy)pyrrolidin-1-yl)pyridazin-3(2H)-one | 452.2 |
| P-0030 | 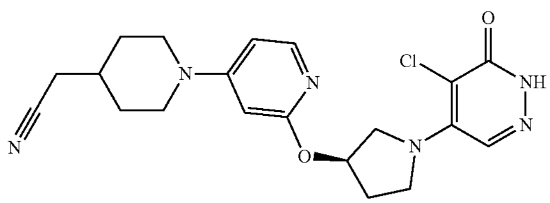 [SMILES: N#CCC1CCN(c2ccnc(O[C@@H]3CCN(c4cn[nH]c(=O)c4Cl)C3)c2)CC1] | (R)-2-(1-(2-((1-(5-chloro-6-oxo-1,6-dihydropyridazin-4-yl)pyrrolidin-3-yl)oxy)pyridin-4-yl)piperidin-4-yl)acetonitrile | 415.3 |
| P-0031 | 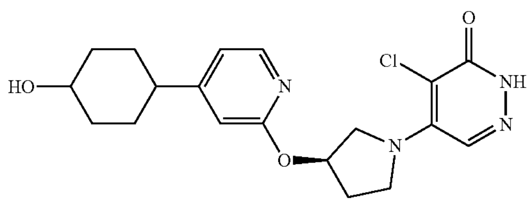 [SMILES: O=c1[nH]ncc(N2CC[C@@H](Oc3cc(C4CCC(O)CC4)ccn3)C2)c1Cl] | (R)-4-chloro-5-(3-((4-(4-hydroxycyclohexyl)pyridin-2-yl)oxy)pyrrolidin-1-yl)pyridazin-3(2H)-one | 391.3 |
| P-0032 | 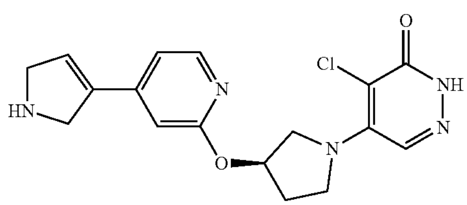 [SMILES: O=c1[nH]ncc(N2CC[C@@H](Oc3cc(C4=CCNC4)ccn3)C2)c1Cl] | (R)-4-chloro-5-(3-((4-(2,5-dihydro-1H-pyrrol-3-yl)pyridin-2-yl)oxy)pyrrolidin-1-yl)pyridazin-3(2H)-one | 360.2 |
| P-0033 | 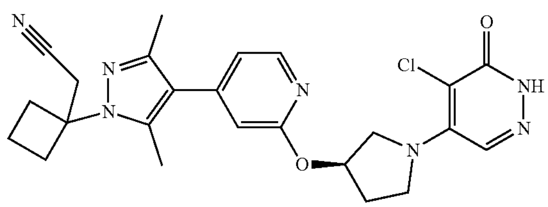 [SMILES: Cc1nn(C2(CC#N)CCC2)c(C)c1-c1ccnc(O[C@@H]2CCN(c3cn[nH]c(=O)c3Cl)C2)c1] | (R)-2-(3-(4-(2-((1-(5-chloro-6-oxo-1,6-dihydropyridazin-4-yl)pyrrolidin-3-yl)oxy)pyridin-4-yl)-3,5-dimethyl-1H-pyrazol-1-yl)oxetan-3-yl)acetonitrile | 482.3 |
| P-0034 | 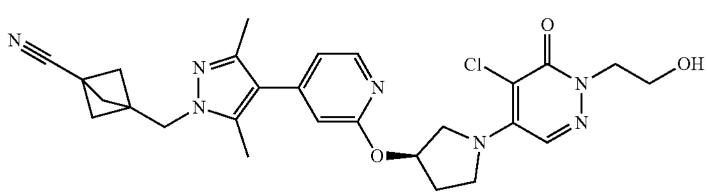 [SMILES: Cc1nn(CC23CC(C#N)(C2)C3)c(C)c1-c1ccnc(O[C@@H]2CCN(c3cnn(CCO)c(=O)c3Cl)C2)c1] | (R)-3-((4-(2-((1-(5-chloro-1-(2-hydroxyethyl)-6-oxo-1,6-dihydropyridazin-4-yl)pyrrolidin-3-yl)oxy)pyridin-4-yl)-3,5-dimethyl-1H-pyrazol-1-yl)methyl)bicyclo[1.1.1]pentane-1-carbonitrile | 536.3 |
| P-0035 | 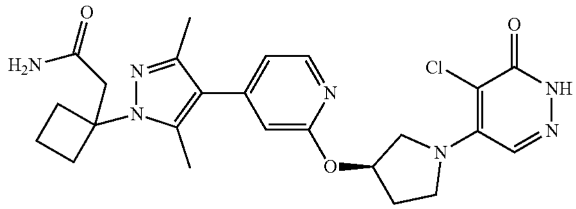 [SMILES: Cc1nn(C2(CC(N)=O)CCC2)c(C)c1-c1ccnc(O[C@@H]2CCN(c3cn[nH]c(=O)c3Cl)C2)c1] | (R)-2-(1-(4-(2-((1-(5-chloro-6-oxo-1,6-dihydropyridazin-4-yl)pyrrolidin-3-yl)oxy)pyridin-4-yl)-3,5-dimethyl-1H-pyrazol-1-yl)cyclobutyl)acetamide | 498.3 |

TABLE 1-continued

| P# | Structure | Name | (MH)+ |
|---|---|---|---|
| P-0036 | 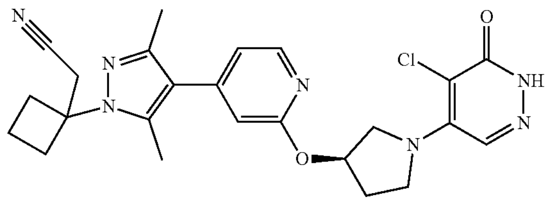 [SMILES: Cc1nn(C2(CC#N)CCC2)c(C)c1-c1ccnc(O[C@@H]2CCN(c3cn[nH]c(=O)c3Cl)C2)c1] | (R)-2-(1-(4-(2-((1-(5-chloro-6-oxo-1,6-dihydropyridazin-4-yl)pyrrolidin-3-yl)oxy)pyridin-4-yl)-3,5-dimethyl-1H-pyrazol-1-yl)cyclobutyl)acetonitrile | 480.3 |
| P-0037 | 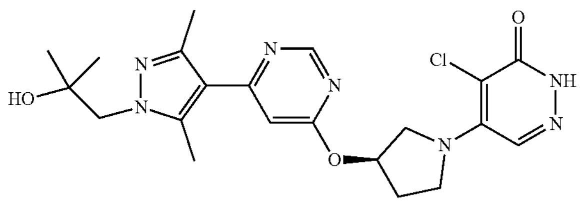 [SMILES: Cc1nn(CC(C)(C)O)c(C)c1-c1cc(O[C@@H]2CCN(c3cn[nH]c(=O)c3Cl)C2)ncn1] | (R)-4-chloro-5-(3-((6-(1-(2-hydroxy-2-methylpropyl)-3,5-dimethyl-1H-pyrazol-4-yl)pyrimidin-4-yl)oxy)pyrrolidin-1-yl)pyridazin-3(2H)-one | 460.3 |
| P-0038 | 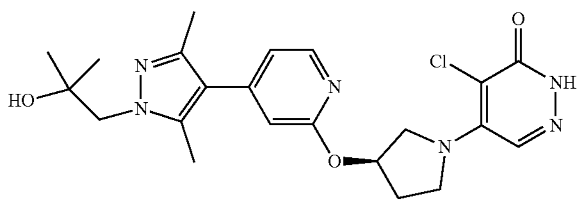 | (R)-4-chloro-5-(3-((4-(1-(2-hydroxy-2-methylpropyl)-3,5-dimethyl-1H-pyrazol-4-yl)pyridin-2-yl)oxy)pyrrolidin-1-yl)pyridazin-3(2H)-one | 459.3 |
| P-0039 | 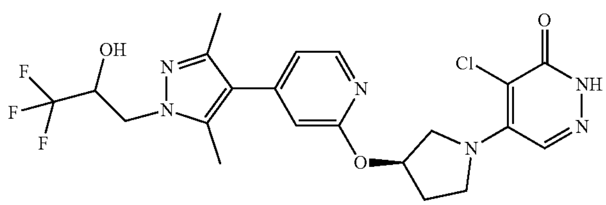 [SMILES: Cc1nn(CC(O)C(F)(F)F)c(C)c1-c1ccnc(O[C@@H]2CCN(c3cn[nH]c(=O)c3Cl)C2)c1] | 4-chloro-5-((3R)-3-((4-(3,5-dimethyl-1-(3,3,3-trifluoro-2-hydroxypropyl)-1H-pyrazol-4-yl)pyridin-2-yl)oxy)pyrrolidin-1-yl)pyridazin-3(2H)-one | 499.3 |
| P-0040 | 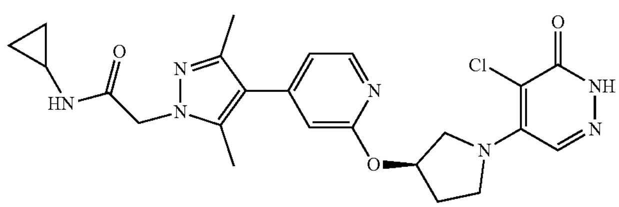 [SMILES: Cc1nn(CC(=O)NC2CC2)c(C)c1-c1ccnc(O[C@@H]2CCN(c3cn[nH]c(=O)c3Cl)C2)c1] | (R)-2-(4-(2-((1-(5-chloro-6-oxo-1,6-dihydropyridazin-4-yl)pyrrolidin-3-yl)oxy)pyridin-4-yl)-3,5-dimethyl-1H-pyrazol-1-yl)-N-cyclopropylacetamide | 484.4 |
| P-0041 | 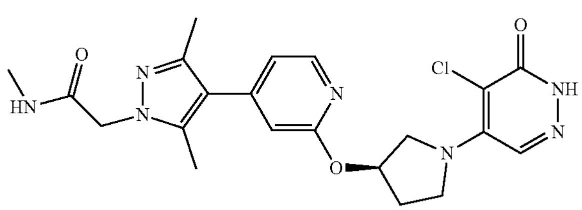 [SMILES: CNC(=O)Cn1nc(C)c(-c2ccnc(O[C@@H]3CCN(c4cn[nH]c(=O)c4Cl)C3)c2)c1C] | (R)-2-(4-(2-((1-(5-chloro-6-oxo-1,6-dihydropyridazin-4-yl)pyrrolidin-3-yl)oxy)pyridin-4-yl)-3,5-dimethyl-1H-pyrazol-1-yl)-N-methylacetamide | 458.4 |
| P-0042 | 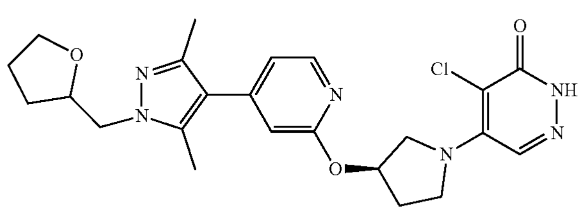 [SMILES: Cc1nn(CC2CCCO2)c(C)c1-c1ccnc(O[C@@H]2CCN(c3cn[nH]c(=O)c3Cl)C2)c1] | 4-chloro-5-((3R)-3-((4-(3,5-dimethyl-1-((tetrahydrofuran-2-yl)methyl)-1H-pyrazol-4-yl)pyridin-2-yl)oxy)pyrrolidin-1-yl)pyridazin-3(2H)-one | 471.4 |

TABLE 1-continued

| P# | Structure | Name | (MH)+ |
|---|---|---|---|
| P-0043 | 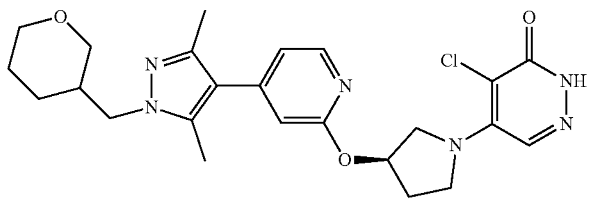 [SMILES: Cc1nn(CC2CCCOC2)c(C)c1-c1ccnc(O[C@@H]2CCN(c3cn[nH]c(=O)c3Cl)C2)c1] | 4-chloro-5-((3R)-3-((4-(3,5-dimethyl-1-((tetrahydro-2H-pyran-3-yl)methyl)-1H-pyrazol-4-yl)pyridin-2-yl)oxy)pyrrolidin-1-yl)pyridazin-3(2H)-one | 485.4 |
| P-0044 | 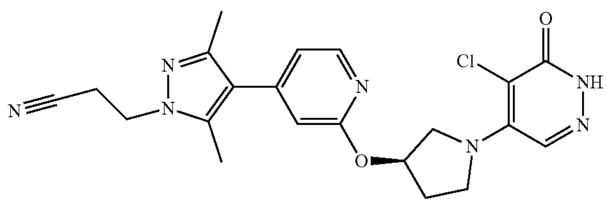 [SMILES: Cc1nn(CCC#N)c(C)c1-c1ccnc(O[C@@H]2CCN(c3cn[nH]c(=O)c3Cl)C2)c1] | (R)-3-(4-(2-((1-(5-chloro-6-oxo-1,6-dihydropyridazin-4-yl)pyrrolidin-3-yl)oxy)pyridin-4-yl)-3,5-dimethyl-1H-pyrazol-1-yl)propanenitrile | 440.4 |
| P-0045 | 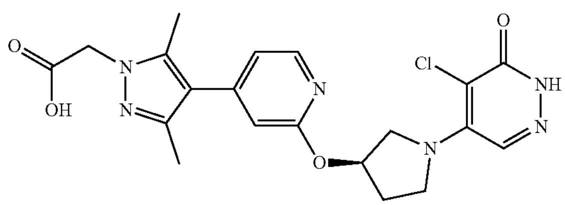 [SMILES: Cc1nn(CC(=O)O)c(C)c1-c1ccnc(O[C@@H]2CCN(c3cn[nH]c(=O)c3Cl)C2)c1] | (R)-2-(4-(2-((1-(5-chloro-6-oxo-1,6-dihydropyridazin-4-yl)pyrrolidin-3-yl)oxy)pyridin-4-yl)-3,5-dimethyl-1H-pyrazol-1-yl)acetic acid | 445.2 |
| P-0046 | 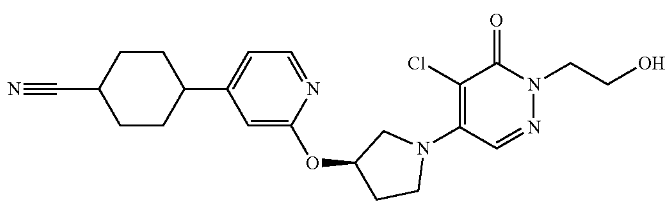 [SMILES: N#CC1CCC(c2ccnc(O[C@@H]3CCN(c4cnn(CCO)c(=O)c4Cl)C3)c2)CC1] | (R)-4-(2-((1-(5-chloro-1-(2-hydroxyethyl)-6-oxo-1,6-dihydropyridazin-4-yl)pyrrolidin-3-yl)oxy)pyridin-4-yl)cyclohexane-1-carbonitrile | 444.3 |
| P-0047 | 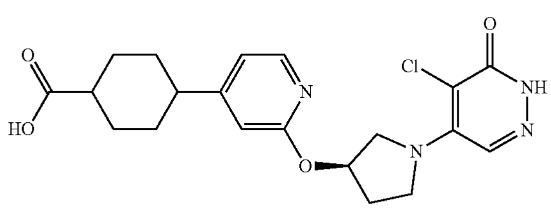 | (R)-4-(2-((1-(5-chloro-6-oxo-1,6-dihydropyridazin-4-yl)pyrrolidin-3-yl)oxy)pyridin-4-yl)cyclohexane-1-carboxylic acid | 419.3 |
| P-0048 | 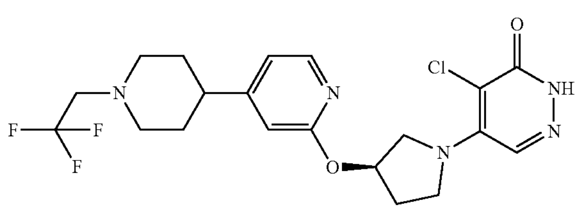 [SMILES: O=c1[nH]ncc(N2CC[C@@H](Oc3cc(C4CCN(CC(F)(F)F)CC4)ccn3)C2)c1Cl] | (R)-4-chloro-5-(3-((4-(1-(2,2,2-trifluoroethyl)piperidin-4-yl)pyridin-2-yl)oxy)pyrrolidin-1-yl)pyridazin-3(2H)-one | 458.3 |
| P-0049 | 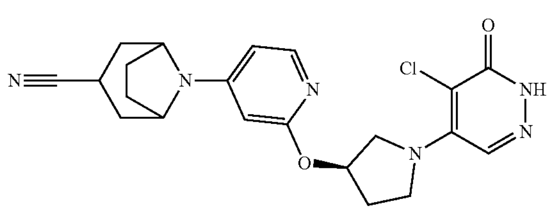 [SMILES: N#CC1CC2CCC(C1)N2c1ccnc(O[C@@H]2CCN(c3cn[nH]c(=O)c3Cl)C2)c1] | 8-(2-(((R)-1-(5-chloro-6-oxo-1,6-dihydropyridazin-4-yl)pyrrolidin-3-yl)oxy)pyridin-4-yl)-8-azabicyclo[3.2.1]octane-3-carbonitrile | 427.2 |

TABLE 1-continued

| P# | Structure | Name | (MH)+ |
|---|---|---|---|
| P-0050 | 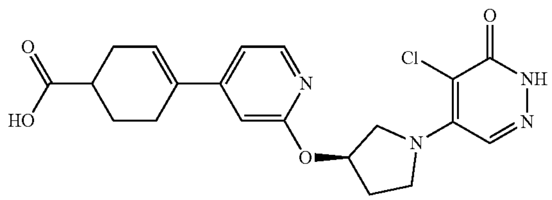 [SMILES: O=C(O)C1CC=C(c2ccnc(O[C@@H]3CCN(c4cn[nH]c(=O)c4Cl)C3)c2)CC1] | 4-(2-(((R)-1-(5-chloro-6-oxo-1,6-dihydropyridazin-4-yl)pyrrolidin-3-yl)oxy)pyridin-4-yl)cyclohex-3-ene-1-carboxylic acid | 417.2 |
| P-0051 | 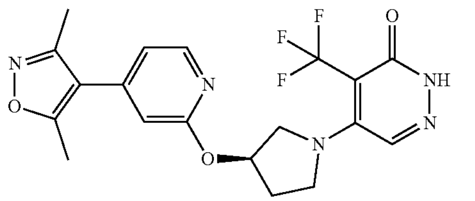 [SMILES: Cc1noc(C)c1-c1ccnc(O[C@@H]2CCN(c3cn[nH]c(=O)c3C(F)(F)F)C2)c1] | (R)-5-(3-((4-(3,5-dimethylisoxazol-4-yl)pyridin-2-yl)oxy)pyrrolidin-1-yl)-4-(trifluoromethyl)pyridazin-3(2H)-one | 422.0 |
| P-0052 | 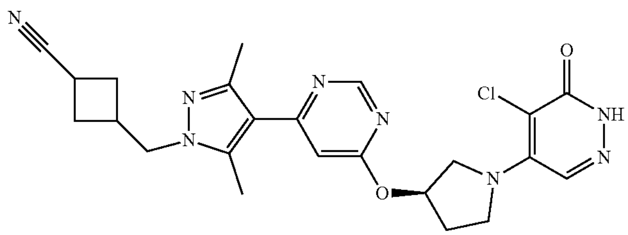 [SMILES: Cc1nn(CC2CC(C#N)C2)c(C)c1-c1cc(O[C@@H]2CCN(c3cn[nH]c(=O)c3Cl)C2)ncn1] | (R)-3-((4-(6-((1-(5-chloro-6-oxo-1,6-dihydropyridazin-4-yl)pyrrolidin-3-yl)oxy)pyrimidin-4-yl)-3,5-dimethyl-1H-pyrazol-1-yl)methyl)cyclobutane-1-carbonitrile | 481.0 |
| P-0053 | 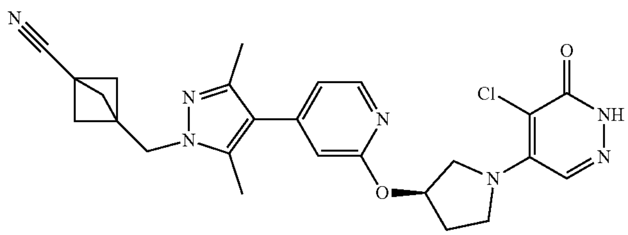 [SMILES: Cc1nn(CC23CC(C#N)(C2)C3)c(C)c1-c1ccnc(O[C@@H]2CCN(c3cn[nH]c(=O)c3Cl)C2)c1] | (R)-3-((4-(2-((1-(5-chloro-6-oxo-1,6-dihydropyridazin-4-yl)pyrrolidin-3-yl)oxy)pyridin-4-yl)-3,5-dimethyl-1H-pyrazol-1-yl)methyl)bicyclo[1.1.1]pentane-1-carbonitrile | 492.3 |
| P-0054 | 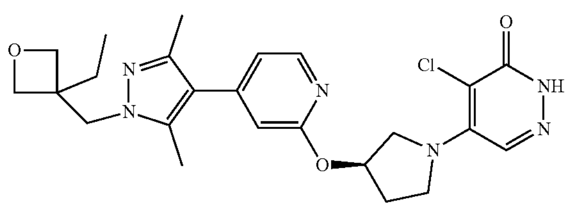 [SMILES: CCC1(Cn2nc(C)c(-c3ccnc(O[C@@H]4CCN(c5cn[nH]c(=O)c5Cl)C4)c3)c2C)COC1] | (R)-4-chloro-5-(3-((4-(1-((3-ethyloxetan-3-yl)methyl)-3,5-dimethyl-1H-pyrazol-4-yl)pyridin-2-yl)oxy)pyrrolidin-1-yl)pyridazin-3(2H)-one | 485.3 |
| P-0055 | 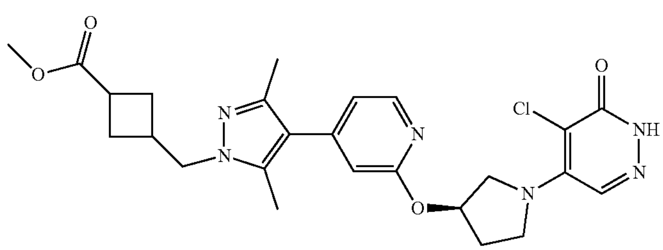 [SMILES: COC(=O)C1CC(Cn2nc(C)c(-c3ccnc(O[C@@H]4CCN(c5cn[nH]c(=O)c5Cl)C4)c3)c2C)C1] | methyl (R)-3-((4-(2-((1-(5-chloro-6-oxo-1,6-dihydropyridazin-4-yl)pyrrolidin-3-yl)oxy)pyridin-4-yl)-3,5-dimethyl-1H-pyrazol-1-yl)methyl)cyclobutane-1-carboxylate | 513.3 |
| P-0056 | 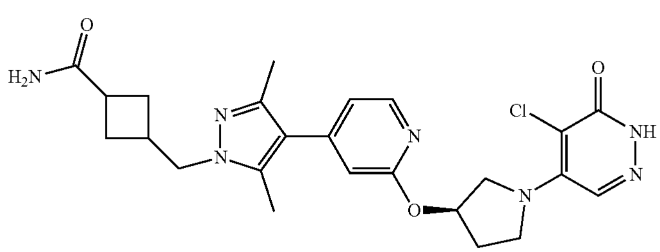 [SMILES: Cc1nn(CC2CC(C(N)=O)C2)c(C)c1-c1ccnc(O[C@@H]2CCN(c3cn[nH]c(=O)c3Cl)C2)c1] | (R)-3-((4-(2-((1-(5-chloro-6-oxo-1,6-dihydropyridazin-4-yl)pyrrolidin-3-yl)oxy)pyridin-4-yl)-3,5-dimethyl-1H-pyrazol-1-yl)methyl)cyclobutane-1-carboxamide | 498.3 |

TABLE 1-continued

| P# | Structure | Name | (MH)+ |
|---|---|---|---|
| P-0057 | 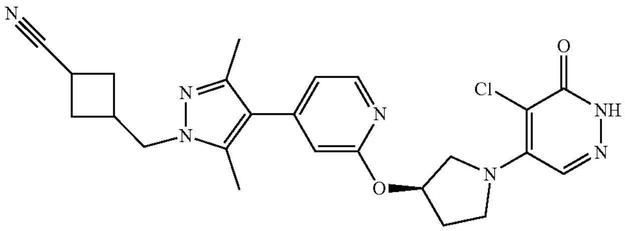 [SMILES: Cc1nn(CC2CC(C#N)C2)c(C)c1-c1ccnc(O[C@@H]2CCN(c3cn[nH]c(=O)c3Cl)C2)c1] | (R)-3-((4-(2-((1-(5-chloro-6-oxo-1,6-dihydropyridazin-4-yl)pyrrolidin-3-yl)oxy)pyridin-4-yl)-3,5-dimethyl-1H-pyrazol-1-yl)methyl)cyclobutane-1-carbonitrile | 480.3 |
| P-0058 | 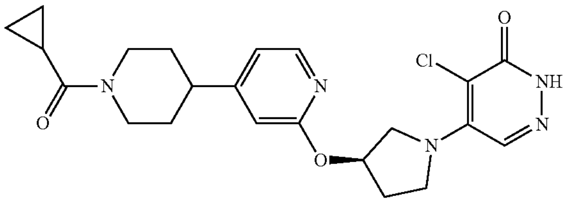 [SMILES: O=C(C1CC1)N1CCC(c2ccnc(O[C@@H]3CCN(c4cn[nH]c(=O)c4Cl)C3)c2)CC1] | (R)-4-chloro-5-(3-((4-(1-(cyclopropanecarbonyl)piperidin-4-yl)pyridin-2-yl)oxy)pyrrolidin-1-yl)pyridazin-3(2H)-one | 444.3 |
| P-0059 | 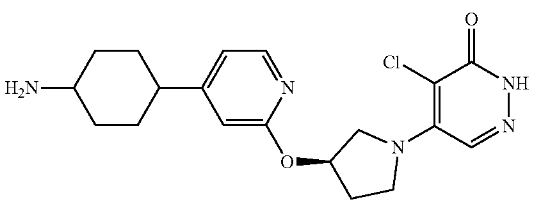 [SMILES: NC1CCC(c2ccnc(O[C@@H]3CCN(c4cn[nH]c(=O)c4Cl)C3)c2)CC1] | (R)-5-(3-((4-(4-aminocyclohexyl)pyridin-2-yl)oxy)pyrrolidin-1-yl)-4-chloropyridazin-3(2H)-one | 390.2 |
| P-0060 | 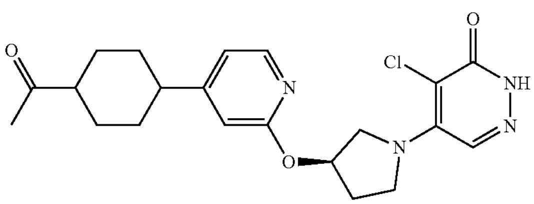 [SMILES: CC(=O)C1CCC(c2ccnc(O[C@@H]3CCN(c4cn[nH]c(=O)c4Cl)C3)c2)CC1] | (R)-5-(3-((4-(4-acetylcyclohexyl)pyridin-2-yl)oxy)pyrrolidin-1-yl)-4-chloropyridazin-3(2H)-one | 417.2 |
| P-0061 | 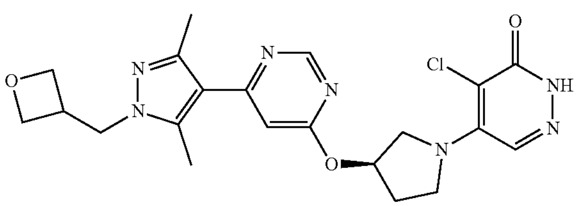 [SMILES: Cc1nn(CC2COC2)c(C)c1-c1cc(O[C@@H]2CCN(c3cn[nH]c(=O)c3Cl)C2)ncn1] | (R)-4-chloro-5-(3-((6-(3,5-dimethyl-1-(oxetan-3-ylmethyl)-1H-pyrazol-4-yl)pyrimidin-4-yl)oxy)pyrrolidin-1-yl)pyridazin-3(2H)-one | 458.3 |
| P-0062 | 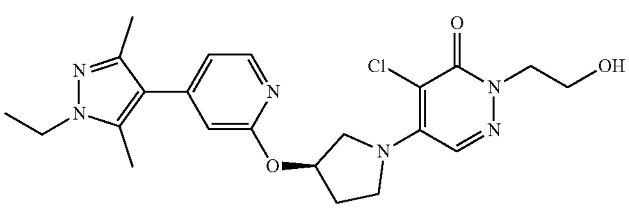 [SMILES: CCn1nc(C)c(-c2ccnc(O[C@@H]3CCN(c4cnn(CCO)c(=O)c4Cl)C3)c2)c1C] | (R)-4-chloro-5-(3-((4-(1-ethyl-3,5-dimethyl-1H-pyrazol-4-yl)pyridin-2-yl)oxy)pyrrolidin-1-yl)-2-(2-hydroxyethyl)pyridazin-3(2H)-one | 459.3 |
| P-0063 | 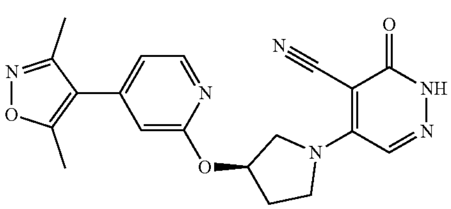 [SMILES: Cc1noc(C)c1-c1ccnc(O[C@@H]2CCN(c3cn[nH]c(=O)c3C#N)C2)c1] | (R)-5-(3-((4-(3,5-dimethylisoxazol-4-yl)pyridin-2-yl)oxy)pyrrolidin-1-yl)-3-oxo-2,3-dihydropyridazine-4-carbonitrile | 379.3 |

TABLE 1-continued

| P# | Structure | Name | (MH)+ |
|---|---|---|---|
| P-0064 | 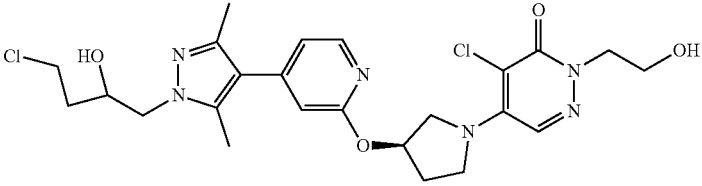 [SMILES: Cc1nn(CC(O)CCCl)c(C)c1-c1ccnc(O[C@@H]2CCN(c3cnn(CCO)c(=O)c3Cl)C2)c1] | 4-chloro-5-((3R)-3-((4-(1-(4-chloro-2-hydroxybutyl)-3,5-dimethyl-1H-pyrazol-4-yl)pyridin-2-yl)oxy)pyrrolidin-1-yl)-2-(2-hydroxyethyl)pyridazin-3(2H)-one | 537.2 |
| P-0065 | 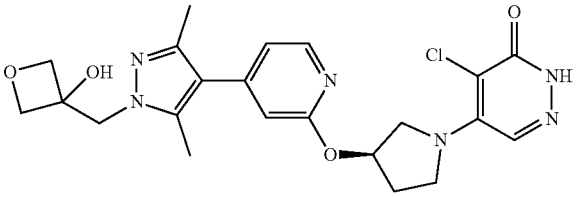 [SMILES: Cc1nn(CC2(O)COC2)c(C)c1-c1ccnc(O[C@@H]2CCN(c3cn[nH]c(=O)c3Cl)C2)c1] | (R)-4-chloro-5-(3-((4-(1-((3-hydroxyoxetan-3-yl)methyl)-3,5-dimethyl-1H-pyrazol-4-yl)pyridin-2-yl)oxy)pyrrolidin-1-yl)pyridazin-3(2H)-one | 473.2 |
| P-0066 | 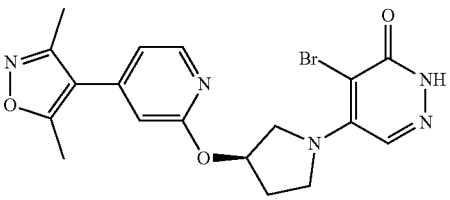 [SMILES: Cc1noc(C)c1-c1ccnc(O[C@@H]2CCN(c3cn[nH]c(=O)c3Br)C2)c1] | (R)-4-bromo-5-(3-((4-(3,5-dimethylisoxazol-4-yl)pyridin-2-yl)oxy)pyrrolidin-1-yl)pyridazin-3(2H)-one | 431.9 |
| P-0067 | 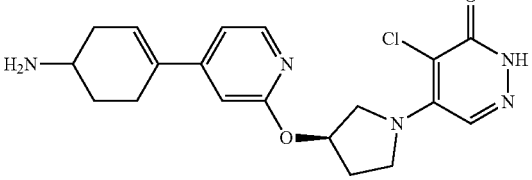 | 5-((3R)-3-((4-(4-aminocyclohex-1-en-1-yl)pyridin-2-yl)oxy)pyrrolidin-1-yl)-4-chloropyridazin-3(2H)-one | 388.3 |
| P-0068 | 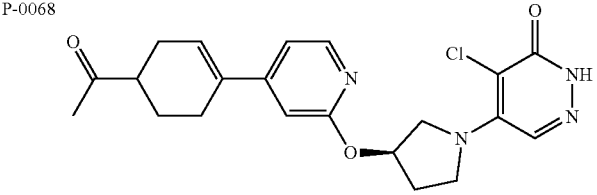 | 5-((3R)-3-((4-(4-acetylcyclohex-1-en-1-yl)pyridin-2-yl)oxy)pyrrolidin-1-yl)-4-chloropyridazin-3(2H)-one | 415.3 |
| P-0069 | 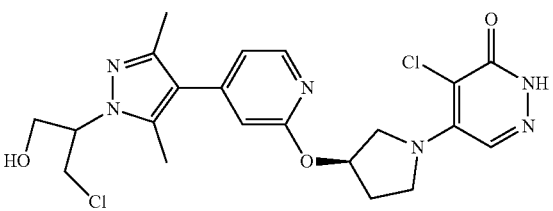 [SMILES: Cc1nn(C(CO)CCl)c(C)c1-c1ccnc(O[C@@H]2CCN(c3cn[nH]c(=O)c3Cl)C2)c1] | 4-chloro-5-((3R)-3-((4-(1-(1-chloro-3-hydroxypropan-2-yl)-3,5-dimethyl-1H-pyrazol-4-yl)pyridin-2-yl)oxy)pyrrolidin-1-yl)pyridazin-3(2H)-one | 479.2 |
| P-0070 | 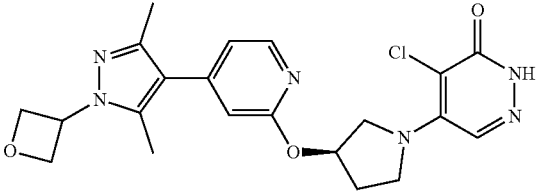 [SMILES: Cc1nn(C2COC2)c(C)c1-c1ccnc(O[C@@H]2CCN(c3cn[nH]c(=O)c3Cl)C2)c1] | (R)-4-chloro-5-(3-((4-(3,5-dimethyl-1-(oxetan-3-yl)-1H-pyrazol-4-yl)pyridin-2-yl)oxy)pyrrolidin-1-yl)pyridazin-3(2H)-one | 443.3 |

TABLE 1-continued

| P# | Structure | Name | (MH)+ |
|---|---|---|---|
| P-0071 | 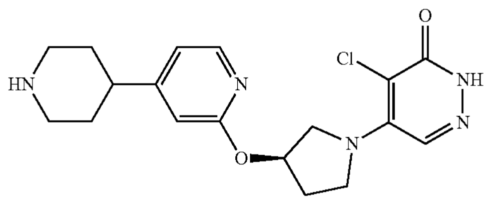 [SMILES: O=c1[nH]ncc(N2CC[C@@H](Oc3cc(C4CCNCC4)ccn3)C2)c1Cl] | (R)-4-chloro-5-(3-((4-(piperidin-4-yl)pyridin-2-yl)oxy)pyrrolidin-1-yl)pyridazin-3(2H)-one | 376.3 |
| P-0072 | 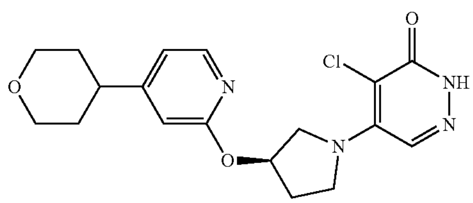 [SMILES: O=c1[nH]ncc(N2CC[C@@H](Oc3cc(C4CCOCC4)ccn3)C2)c1Cl] | (R)-4-chloro-5-(3-((4-(tetrahydro-2H-pyran-4-yl)pyridin-2-yl)oxy)pyrrolidin-1-yl)pyridazin-3(2H)-one | 377.3 |
| P-0073 | 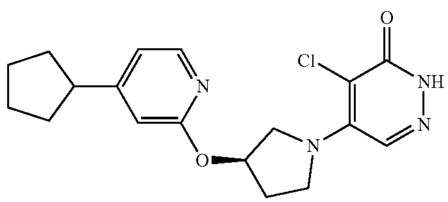 [SMILES: O=c1[nH]ncc(N2CC[C@@H](Oc3cc(C4CCCC4)ccn3)C2)c1Cl] | (R)-4-chloro-5-(3-((4-cyclopentylpyridin-2-yl)oxy)pyrrolidin-1-yl)pyridazin-3(2H)-one | 361.2 |
| P-0074 | 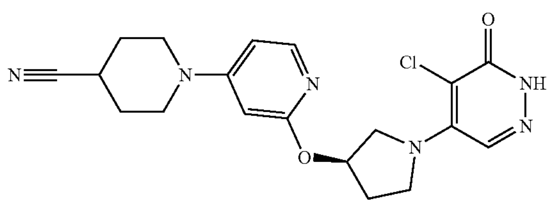 [SMILES: N#CC1CCN(c2ccnc(O[C@@H]3CCN(c4cn[nH]c(=O)c4Cl)C3)c2)CC1] | (R)-1-(2-((1-(5-chloro-6-oxo-1,6-dihydropyridazin-4-yl)pyrrolidin-3-yl)oxy)pyridin-4-yl)piperidine-4-carbonitrile | 401.2 |
| P-0075 | 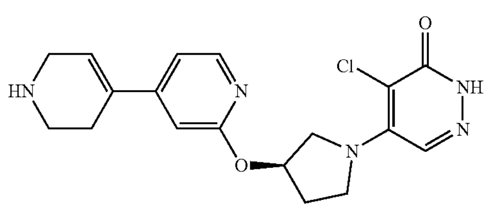 [SMILES: O=c1[nH]ncc(N2CC[C@@H](Oc3cc(C4=CCNCC4)ccn3)C2)c1Cl] | (R)-4-chloro-5-(3-((1',2',3',6'-tetrahydro-[4,4'-bipyridin]-2-yl)oxy)pyrrolidin-1-yl)pyridazin-3(2H)-one | 374.2 |
| P-0076 | 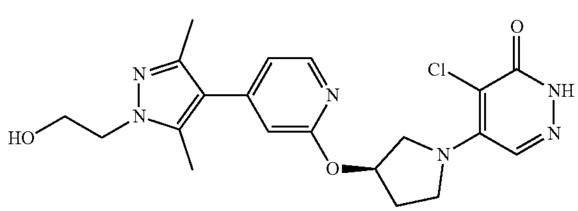 [SMILES: Cc1nn(CCO)c(C)c1-c1ccnc(O[C@@H]2CCN(c3cn[nH]c(=O)c3Cl)C2)c1] | (R)-4-chloro-5-(3-((4-(1-(2-hydroxyethyl)-3,5-dimethyl-1H-pyrazol-4-yl)pyridin-2-yl)oxy)pyrrolidin-1-yl)pyridazin-3(2H)-one | 431.3 |
| P-0077 | 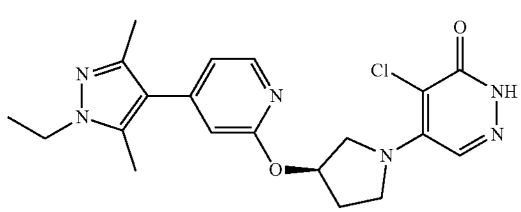 [SMILES: CCn1nc(C)c(-c2ccnc(O[C@@H]3CCN(c4cn[nH]c(=O)c4Cl)C3)c2)c1C] | (R)-4-chloro-5-(3-((4-(1-ethyl-3,5-dimethyl-1H-pyrazol-4-yl)pyridin-2-yl)oxy)pyrrolidin-1-yl)pyridazin-3(2H)-one | 415.3 |

TABLE 1-continued

| P# | Structure | Name | (MH)+ |
| --- | --- | --- | --- |
| P-0078 | 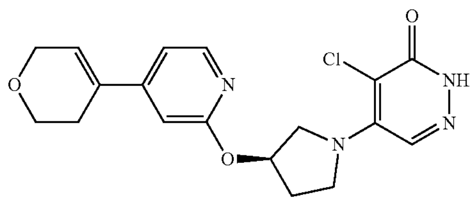 [SMILES: O=c1[nH]ncc(N2CC[C@@H](Oc3cc(C4=CCOCC4)ccn3)C2)c1Cl] | (R)-4-chloro-5-(3-((4-(3,6-dihydro-2H-pyran-4-yl)pyridin-2-yl)oxy)pyrrolidin-1-yl)pyridazin-3(2H)-one | 375.2 |
| P-0079 | 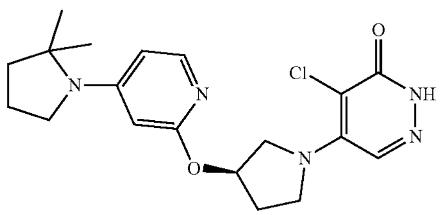 [SMILES: CC1(C)CCCN1c1ccnc(O[C@@H]2CCN(c3cn[nH]c(=O)c3Cl)C2)c1] | (R)-4-chloro-5-(3-((4-(2,2-dimethylpyrrolidin-1-yl)pyridin-2-yl)oxy)pyrrolidin-1-yl)pyridazin-3(2H)-one | 390.3 |
| P-0080 | 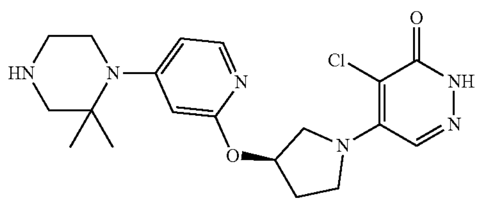 [SMILES: CC1(C)CNCCN1c1ccnc(O[C@@H]2CCN(c3cn[nH]c(=O)c3Cl)C2)c1] | (R)-4-chloro-5-(3-((4-(2,2-dimethylpiperazin-1-yl)pyridin-2-yl)oxy)pyrrolidin-1-yl)pyridazin-3(2H)-one | 405.2 |
| P-0081 | 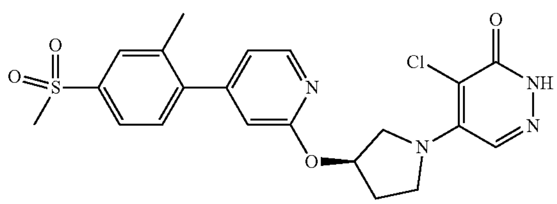 [SMILES: Cc1cc(S(C)(=O)=O)ccc1-c1ccnc(O[C@@H]2CCN(c3cn[nH]c(=O)c3Cl)C2)c1] | (R)-4-chloro-5-(3-((4-(2-methyl-4-(methylsulfonyl)phenyl)pyridin-2-yl)oxy)pyrrolidin-1-yl)pyridazin-3(2H)-one | 461.1 |
| P-0082 | 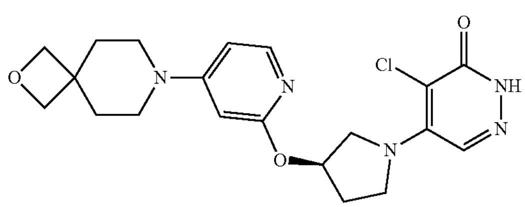 [SMILES: O=c1[nH]ncc(N2CC[C@@H](Oc3cc(N4CCC5(CC4)COC5)ccn3)C2)c1Cl] | (R)-5-(3-((4-(2-oxa-7-azaspiro[3.5]nonan-7-yl)pyridin-2-yl)oxy)pyrrolidin-1-yl)-4-chloropyridazin-3(2H)-one | 418.2 |
| P-0083 | 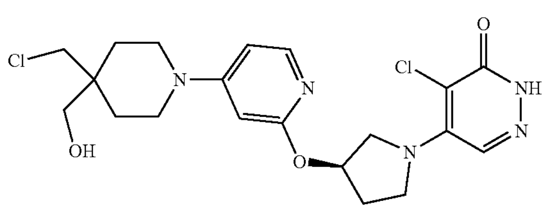 [SMILES: O=c1[nH]ncc(N2CC[C@@H](Oc3cc(N4CCC(CO)(CCl)CC4)ccn3)C2)c1Cl] | (R)-4-chloro-5-(3-((4-(4-(chloromethyl)-4-(hydroxymethyl)piperidin-1-yl)pyridin-2-yl)oxy)pyrrolidin-1-yl)pyridazin-3(2H)-one | 454.0 |
| P-0084 | 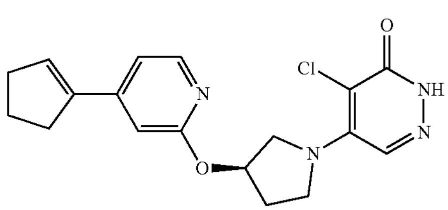 [SMILES: O=c1[nH]ncc(N2CC[C@@H](Oc3cc(C4=CCCC4)ccn3)C2)c1Cl] | (R)-4-chloro-5-(3-((4-(cyclopent-1-en-1-yl)pyridin-2-yl)oxy)pyrrolidin-1-yl)pyridazin-3(2H)-one | 359.1 |

TABLE 1-continued

| P# | Structure | Name | (MH)+ |
|---|---|---|---|
| P-0085 | 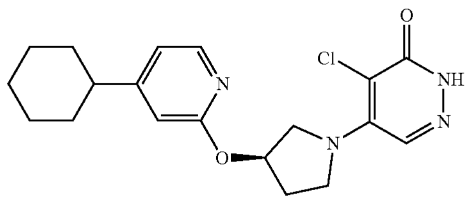 | (R)-4-chloro-5-(3-((4-cyclohexylpyridin-2-yl)oxy)pyrrolidin-1-yl)pyridazin-3(2H)-one | 375.2 |
| P-0086 | 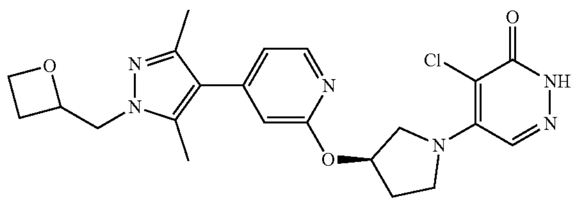 [SMILES: Cc1nn(CC2CCO2)c(C)c1-c1ccnc(O[C@@H]2CCN(c3cn[nH]c(=O)c3Cl)C2)c1] | 4-chloro-5-((3R)-3-((4-(3,5-dimethyl-1-(oxetan-2-ylmethyl)-1H-pyrazol-4-yl)pyridin-2-yl)oxy)pyrrolidin-1-yl)pyridazin-3(2H)-one | 457.1 |
| P-0087 | 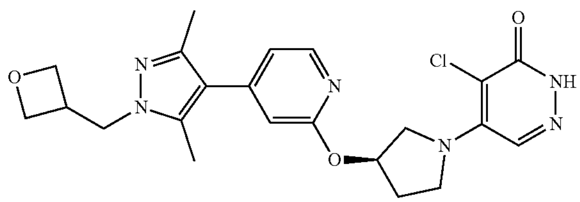 [SMILES: Cc1nn(CC2COC2)c(C)c1-c1ccnc(O[C@@H]2CCN(c3cn[nH]c(=O)c3Cl)C2)c1] | (R)-4-chloro-5-(3-((4-(3,5-dimethyl-1-(oxetan-3-ylmethyl)-1H-pyrazol-4-yl)pyridin-2-yl)oxy)pyrrolidin-1-yl)pyridazin-3(2H)-one | 457.1 |
| P-0088 | 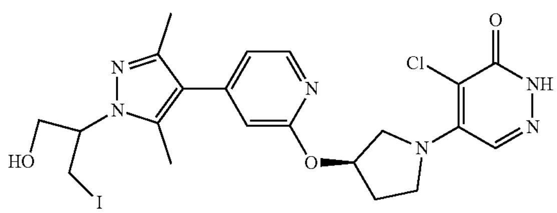 [SMILES: Cc1nn(C(CO)CI)c(C)c1-c1ccnc(O[C@@H]2CCN(c3cn[nH]c(=O)c3Cl)C2)c1] | 4-chloro-5-((3R)-3-((4-(1-(1-hydroxy-3-iodopropan-2-yl)-3,5-dimethyl-1H-pyrazol-4-yl)pyridin-2-yl)oxy)pyrrolidin-1-yl)pyridazin-3(2H)-one | 570.9 |
| P-0089 | 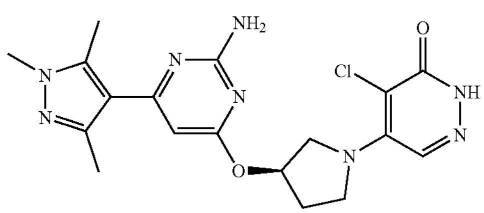 [SMILES: Cc1nn(C)c(C)c1-c1cc(O[C@@H]2CCN(c3cn[nH]c(=O)c3Cl)C2)nc(N)n1] | (R)-5-(3-((2-amino-6-(1,3,5-trimethyl-1H-pyrazol-4-yl)pyrimidin-4-yl)oxy)pyrrolidin-1-yl)-4-chloropyridazin-3(2H)-one | 417.2 |
| P-0090 | 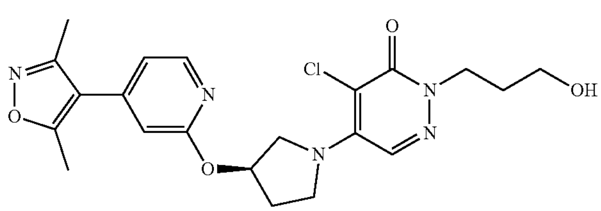 [SMILES: Cc1noc(C)c1-c1ccnc(O[C@@H]2CCN(c3cnn(CCCO)c(=O)c3Cl)C2)c1] | (R)-4-chloro-5-(3-((4-(3,5-dimethylisoxazol-4-yl)pyridin-2-yl)oxy)pyrrolidin-1-yl)-2-(3-hydroxypropyl)pyridazin-3(2H)-one | 446.1 |
| P-0091 | 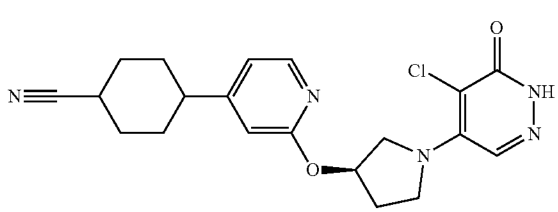 [SMILES: N#CC1CCC(c2ccnc(O[C@@H]3CCN(c4cn[nH]c(=O)c4Cl)C3)c2)CC1] | (R)-4-(2-((1-(5-chloro-6-oxo-1,6-dihydropyridazin-4-yl)pyrrolidin-3-yl)oxy)pyridin-4-yl)cyclohexane-1-carbonitrile | 400.1 |

TABLE 1-continued

| P# | Structure | Name | (MH)+ |
|---|---|---|---|
| P-0092 | 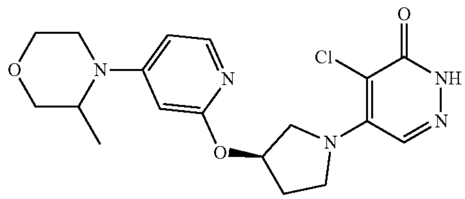 [SMILES: CC1COCCN1c1ccnc(O[C@@H]2CCN(c3cn[nH]c(=O)c3Cl)C2)c1] | 4-chloro-5-((3R)-3-((4-(3-methylmorpholino)pyridin-2-yl)oxy)pyrrolidin-1-yl)pyridazin-3(2H)-one | 392.1 |
| P-0093 | 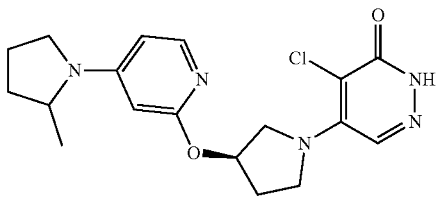 [SMILES: CC1CCCN1c1ccnc(O[C@@H]2CCN(c3cn[nH]c(=O)c3Cl)C2)c1] | 4-chloro-5-((3R)-3-((4-(2-methylpyrrolidin-1-yl)pyridin-2-yl)oxy)pyrrolidin-1-yl)pyridazin-3(2H)-one | 376.1 |
| P-0094 | 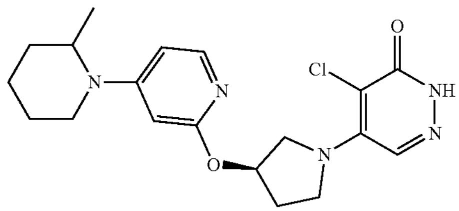 [SMILES: CC1CCCCN1c1ccnc(O[C@@H]2CCN(c3cn[nH]c(=O)c3Cl)C2)c1] | 4-chloro-5-((3R)-3-((4-(2-methylpiperidin-1-yl)pyridin-2-yl)oxy)pyrrolidin-1-yl)pyridazin-3(2H)-one | 390.1 |
| P-0095 | 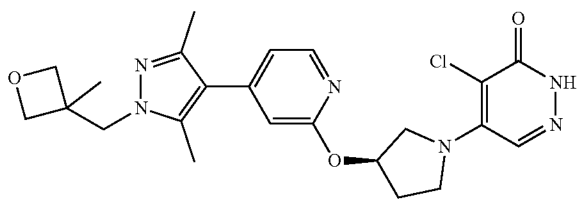 | (R)-4-chloro-5-(3-((4-(3,5-dimethyl-1-((3-methyloxetan-3-yl)methyl)-1H-pyrazol-4-yl)pyridin-2-yl)oxy)pyrrolidin-1-yl)pyridazin-3(2H)-one | 471.1 |
| P-0096 | 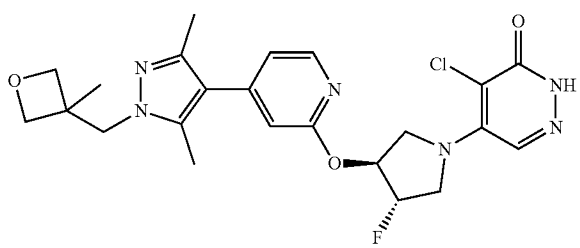 [SMILES: Cc1nn(CC2(C)COC2)c(C)c1-c1ccnc(O[C@H]2CN(c3cn[nH]c(=O)c3Cl)C[C@@H]2F)c1] | 4-chloro-5-((3S,4S)-3-((4-(3,5-dimethyl-1-((3-methyloxetan-3-yl)methyl)-1H-pyrazol-4-yl)pyridin-2-yl)oxy)-4-fluoropyrrolidin-1-yl)pyridazin-3(2H)-one | 489.1 |
| P-0097 | 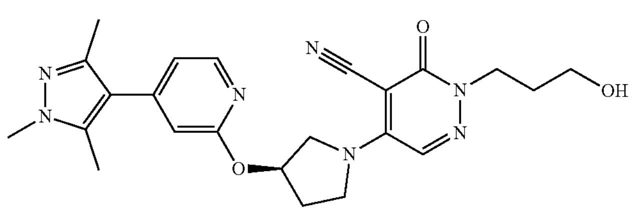 [SMILES: Cc1nn(C)c(C)c1-c1ccnc(O[C@@H]2CCN(c3cnn(CCCO)c(=O)c3C#N)C2)c1] | (R)-2-(3-hydroxypropyl)-3-oxo-5-(3-((4-(1,3,5-trimethyl-1H-pyrazol-4-yl)pyridin-2-yl)oxy)pyrrolidin-1-yl)-2,3-dihydropyridazine-4-carbonitrile | 450.2 |
| P-0098 | 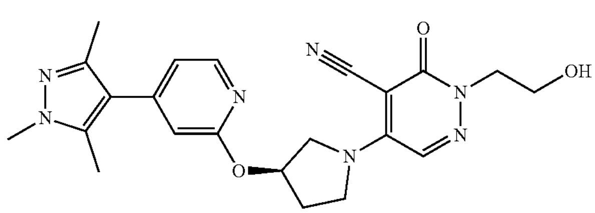 [SMILES: Cc1nn(C)c(C)c1-c1ccnc(O[C@@H]2CCN(c3cnn(CCO)c(=O)c3C#N)C2)c1] | (R)-2-(2-hydroxyethyl)-3-oxo-5-(3-((4-(1,3,5-trimethyl-1H-pyrazol-4-yl)pyridin-2-yl)oxy)pyrrolidin-1-yl)-2,3-dihydropyridazine-4-carbonitrile | 436.2 |

TABLE 1-continued

| P# | Structure | Name | (MH)+ |
|---|---|---|---|
| P-0099 | 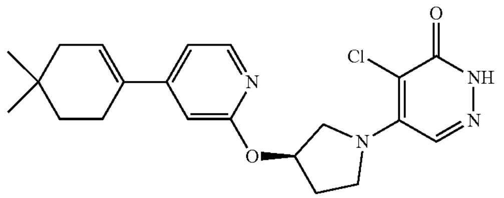 [SMILES: CC1(C)CC=C(c2ccnc(O[C@@H]3CCN(c4cn[nH]c(=O)c4Cl)C3)c2)CC1] | (R)-4-chloro-5-(3-((4-(4,4-dimethylcyclohex-1-en-1-yl)pyridin-2-yl)oxy)pyrrolidin-1-yl)pyridazin-3(2H)-one | 401.1 |
| P-0100 | 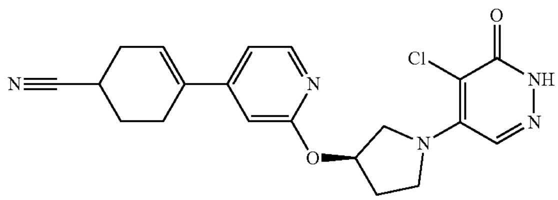 [SMILES: N#CC1CC=C(c2ccnc(O[C@@H]3CCN(c4cn[nH]c(=O)c4Cl)C3)c2)CC1] | 4-(2-(((R)-1-(5-chloro-6-oxo-1,6-dihydropyridazin-4-yl)pyrrolidin-3-yl)oxy)pyridin-4-yl)cyclohex-3-ene-1-carbonitrile | (M + H)+ |
| P-0101 | 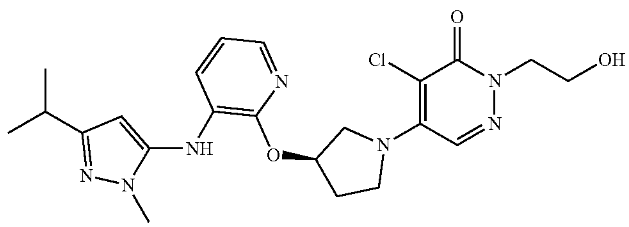 [SMILES: CC(C)c1cc(Nc2cccnc2O[C@@H]2CCN(c3cnn(CCO)c(=O)c3Cl)C2)n(C)n1] | (R)-4-chloro-2-(2-hydroxyethyl)-5-(3-((3-((3-isopropyl-1-methyl-1H-pyrazol-5-yl)amino)pyridin-2-yl)oxy)pyrrolidin-1-yl)pyridazin-3(2H)-one | 474.0 |
| P-0102 | 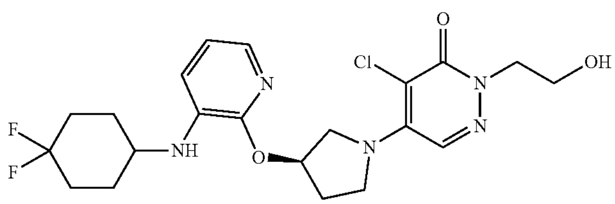 [SMILES: O=c1c(Cl)c(N2CC[C@@H](Oc3ncccc3NC3CCC(F)(F)CC3)C2)cnn1CCO] | (R)-4-chloro-5-(3-((3-((4,4-difluorocyclohexyl)amino)pyridin-2-yl)oxy)pyrrolidin-1-yl)-2-(2-hydroxyethyl)pyridazin-3(2H)-one | 470.0 |
| P-0103 | 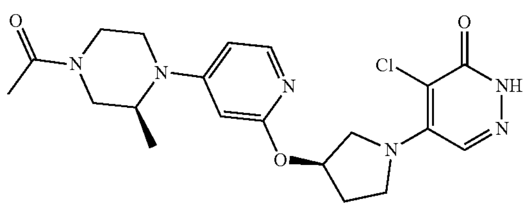 [SMILES: CC(=O)N1CCN(c2ccnc(O[C@@H]3CCN(c4cn[nH]c(=O)c4Cl)C3)c2)[C@@H](C)C1] | 5-((R)-3-((4-((S)-4-acetyl-2-methylpiperazin-1-yl)pyridin-2-yl)oxy)pyrrolidin-1-yl)-4-chloropyridazin-3(2H)-one | 433.0 |
| P-0104 | 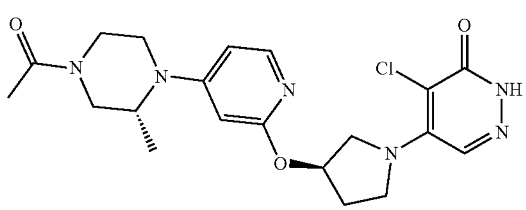 [SMILES: CC(=O)N1CCN(c2ccnc(O[C@@H]3CCN(c4cn[nH]c(=O)c4Cl)C3)c2)[C@H](C)C1] | 5-((R)-3-((4-((R)-4-acetyl-2-methylpiperazin-1-yl)pyridin-2-yl)oxy)pyrrolidin-1-yl)-4-chloropyridazin-3(2H)-one | 432.9 |
| P-0105 | 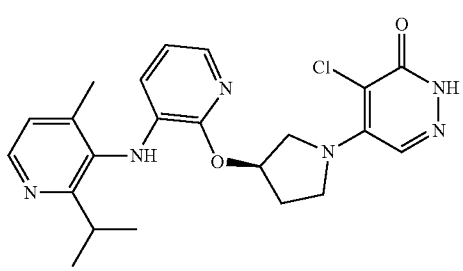 [SMILES: Cc1ccnc(C(C)C)c1Nc1cccnc1O[C@@H]1CCN(c2cn[nH]c(=O)c2Cl)C1] | (R)-4-chloro-5-(3-((3-((2-isopropyl-4-methylpyridin-3-yl)amino)pyridin-2-yl)oxy)pyrrolidin-1-yl)pyridazin-3(2H)-one | 441.0 |

TABLE 1-continued

| P# | Structure | Name | (MH)+ |
|---|---|---|---|
| P-0106 | 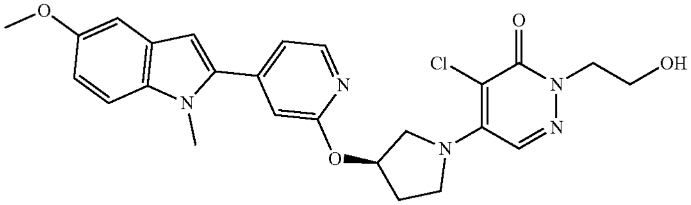 [SMILES: COc1ccc2c(c1)cc(-c1ccnc(O[C@@H]3CCN(c4cnn(CCO)c(=O)c4Cl)C3)c1)n2C] | (R)-4-chloro-2-(2-hydroxyethyl)-5-(3-((4-(5-methoxy-1-methyl-1H-indol-2-yl)pyridin-2-yl)oxy)pyrrolidin-1-yl)pyridazin-3(2H)-one | 496.0 |
| P-0107 | 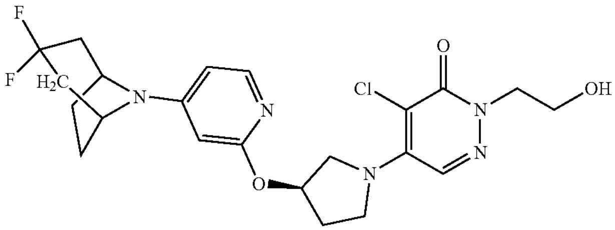 [SMILES: O=c1c(Cl)c(N2CC[C@@H](Oc3cc(N4C5CCC4CC(F)(F)C5)ccn3)C2)cnn1CCO] | 4-chloro-5-((R)-3-((4-((1R,5S)-3,3-difluoro-8-azabicyclo[3.2.1]octan-8-yl)pyridin-2-yl)oxy)pyrrolidin-1-yl)-2-(2-hydroxyethyl)pyridazin-3(2H)-one | 482.0 |
| P-0108 | 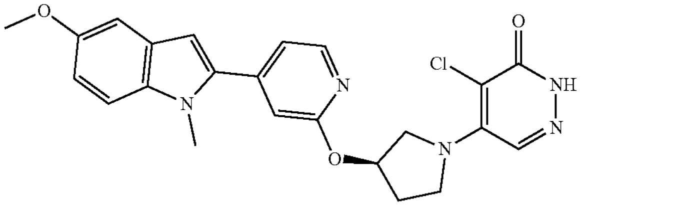 [SMILES: COc1ccc2c(c1)cc(-c1ccnc(O[C@@H]3CCN(c4cn[nH]c(=O)c4Cl)C3)c1)n2C] | (R)-4-chloro-5-(3-((4-(5-methoxy-1-methyl-1H-indol-2-yl)pyridin-2-yl)oxy)pyrrolidin-1-yl)pyridazin-3(2H)-one | 452.0 |
| P-0109 | 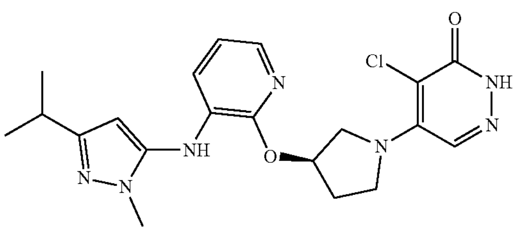 [SMILES: CC(C)c1cc(Nc2cccnc2O[C@@H]2CCN(c3cn[nH]c(=O)c3Cl)C2)n(C)n1] | (R)-4-chloro-5-(3-((3-((3-isopropyl-1-methyl-1H-pyrazol-5-yl)amino)pyridin-2-yl)oxy)pyrrolidin-1-yl)pyridazin-3(2H)-one | 430.0 |
| P-0110 | 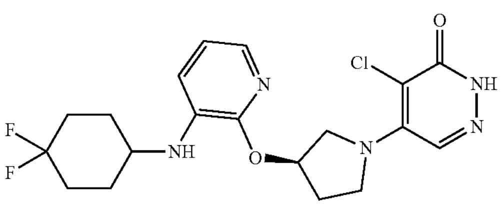 [SMILES: O=c1[nH]ncc(N2CC[C@@H](Oc3ncccc3NC3CCC(F)(F)CC3)C2)c1Cl] | (R)-4-chloro-5-(3-((3-((4,4-difluorocyclohexyl)amino)pyridin-2-yl)oxy)pyrrolidin-1-yl)pyridazin-3(2H)-one | 426.0 |
| P-0111 | 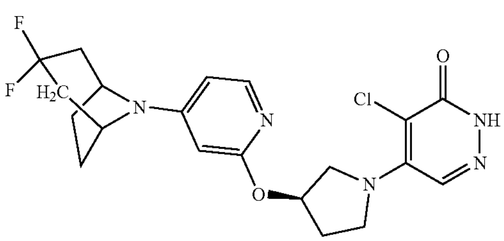 [SMILES: O=c1[nH]ncc(N2CC[C@@H](Oc3cc(N4C5CCC4CC(F)(F)C5)ccn3)C2)c1Cl] | 4-chloro-5-((R)-3-((4-((1R,5S)-3,3-difluoro-8-azabicyclo[3.2.1]octan-8-yl)pyridin-2-yl)oxy)pyrrolidin-1-yl)pyridazin-3(2H)-one | 437.9 |
| P-0112 | 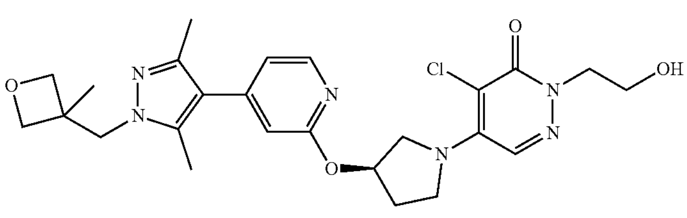 [SMILES: Cc1nn(CC2(C)COC2)c(C)c1-c1ccnc(O[C@@H]2CCN(c3cnn(CCO)c(=O)c3Cl)C2)c1] | (R)-4-chloro-5-(3-((4-(3,5-dimethyl-1-((3-methyloxetan-3-yl)methyl)-1H-pyrazol-4-yl)pyridin-2-yl)oxy)pyrrolidin-1-yl)-2-(2-hydroxyethyl)pyridazin-3(2H)-one | 515.0 |

TABLE 1-continued

| P# | Structure | Name | (MH)+ |
|---|---|---|---|
| P-0113 | 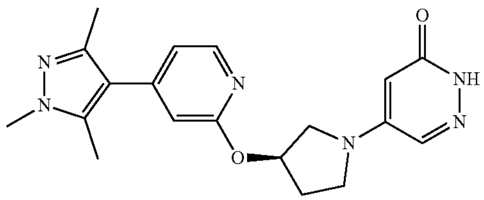 [SMILES: Cc1nn(C)c(C)c1-c1ccnc(O[C@@H]2CCN(c3cn[nH]c(=O)c3)C2)c1] | (R)-5-(3-((4-(1,3,5-trimethyl-1H-pyrazol-4-yl)pyridin-2-yl)oxy)pyrrolidin-1-yl)pyridazin-3(2H)-one | 367.2 |
| P-0114 | 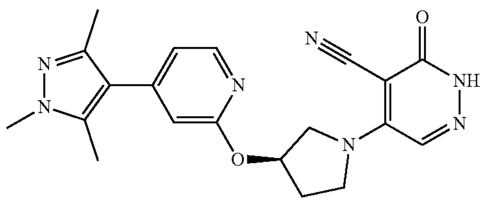 [SMILES: Cc1nn(C)c(C)c1-c1ccnc(O[C@@H]2CCN(c3cn[nH]c(=O)c3C#N)C2)c1] | (R)-3-oxo-5-(3-((4-(1,3,5-trimethyl-1H-pyrazol-4-yl)pyridin-2-yl)oxy)pyrrolidin-1-yl)-2,3-dihydropyridazine-4-carbonitrile | 392.0 |
| P-0115 | 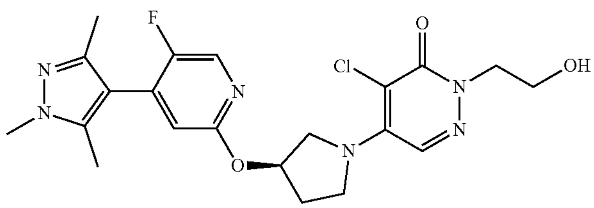 [SMILES: Cc1nn(C)c(C)c1-c1cc(O[C@@H]2CCN(c3cnn(CCO)c(=O)c3Cl)C2)ncc1F] | (R)-4-chloro-5-(3-((5-fluoro-4-(1,3,5-trimethyl-1H-pyrazol-4-yl)pyridin-2-yl)oxy)pyrrolidin-1-yl)-2-(2-hydroxyethyl)pyridazin-3(2H)-one | 463.1 |
| P-0116 | 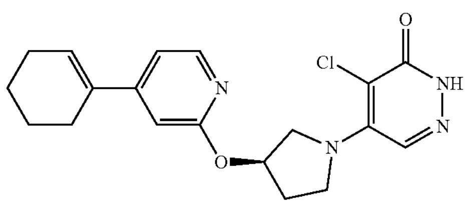 [SMILES: O=c1[nH]ncc(N2CC[C@@H](Oc3cc(C4=CCCCC4)ccn3)C2)c1Cl] | (R)-4-chloro-5-(3-((4-(cyclohex-1-en-1-yl)pyridin-2-yl)oxy)pyrrolidin-1-yl)pyridazin-3(2H)-one | 373.1 |
| P-0117 | 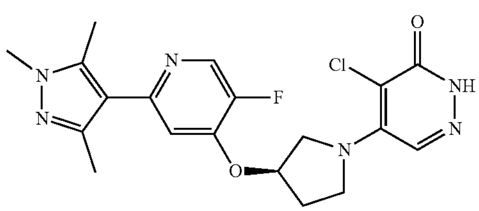 [SMILES: Cc1nn(C)c(C)c1-c1cc(O[C@@H]2CCN(c3cn[nH]c(=O)c3Cl)C2)c(F)cn1] | (R)-4-chloro-5-(3-((5-fluoro-2-(1,3,5-trimethyl-1H-pyrazol-4-yl)pyridin-4-yl)oxy)pyrrolidin-1-yl)pyridazin-3(2H)-one | 419.3 |
| P-0118 | 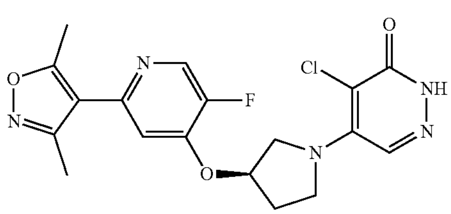 [SMILES: Cc1noc(C)c1-c1cc(O[C@@H]2CCN(c3cn[nH]c(=O)c3Cl)C2)c(F)cn1] | (R)-4-chloro-5-(3-((2-(3,5-dimethylisoxazol-4-yl)-5-fluoropyridin-4-yl)oxy)pyrrolidin-1-yl)pyridazin-3(2H)-one | 406.2 |
| P-0119 | 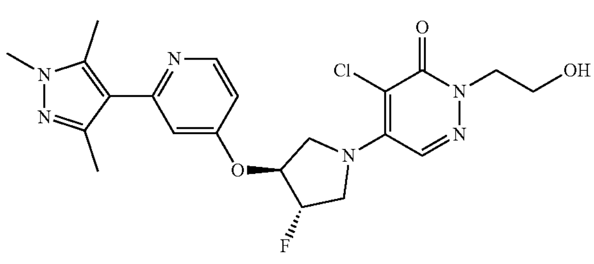 [SMILES: Cc1nn(C)c(C)c1-c1cc(O[C@H]2CN(c3cnn(CCO)c(=O)c3Cl)C[C@@H]2F)ccn1] | 4-chloro-5-(((3S,4S)-3-fluoro-4-((2-(1,3,5-trimethyl-1H-pyrazol-4-yl)pyridin-4-yl)oxy)pyrrolidin-1-yl)-2-(2-hydroxyethyl)pyridazin-3(2H)-one | 463.2 |

TABLE 1-continued

| P# | Structure | Name | (MH)+ |
|---|---|---|---|
| P-0120 | 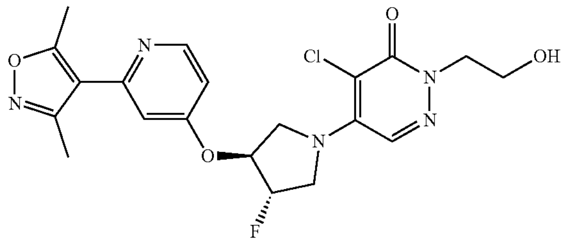 [SMILES: Cc1noc(C)c1-c1cc(O[C@H]2CN(c3cnn(CCO)c(=O)c3Cl)C[C@@H]2F)ccn1] | 4-chloro-5-((3S,4S)-3-((2-(3,5-dimethylisoxazol-4-yl)pyridin-4-yl)oxy)-4-fluoropyrrolidin-1-yl)-2-(2-hydroxyethyl)pyridazin-3(2H)-one | 450.1 |
| P-0121 | 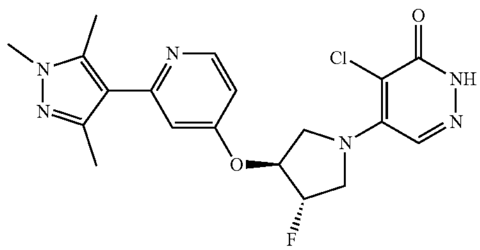 [SMILES: Cc1nn(C)c(C)c1-c1cc(O[C@H]2CN(c3cn[nH]c(=O)c3Cl)C[C@@H]2F)ccn1] | 4-chloro-5-((3S,4S)-3-fluoro-4-((2-(1,3,5-trimethyl-1H-pyrazol-4-yl)pyridin-4-yl)oxy)pyrrolidin-1-yl)pyridazin-3(2H)-one | 419.2 |
| P-0122 | 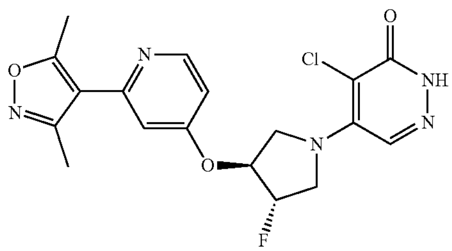 [SMILES: Cc1noc(C)c1-c1cc(O[C@H]2CN(c3cn[nH]c(=O)c3Cl)C[C@@H]2F)ccn1] | 4-chloro-5-((3S,4S)-3-((2-(3,5-dimethylisoxazol-4-yl)pyridin-4-yl)oxy)-4-fluoropyrrolidin-1-yl)pyridazin-3(2H)-one | 406.2 |
| P-0123 | 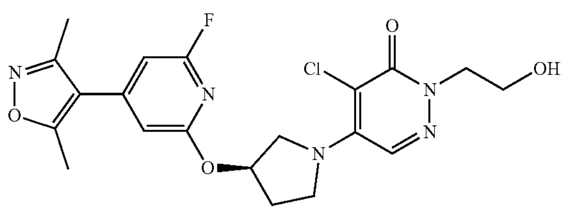 [SMILES: Cc1noc(C)c1-c1cc(F)nc(O[C@@H]2CCN(c3cnn(CCO)c(=O)c3Cl)C2)c1] | (R)-4-chloro-5-(3-((4-(3,5-dimethylisoxazol-4-yl)-6-fluoropyridin-2-yl)oxy)pyrrolidin-1-yl)-2-(2-hydroxyethyl)pyridazin-3(2H)-one | 450.0 |
| P-0124 | 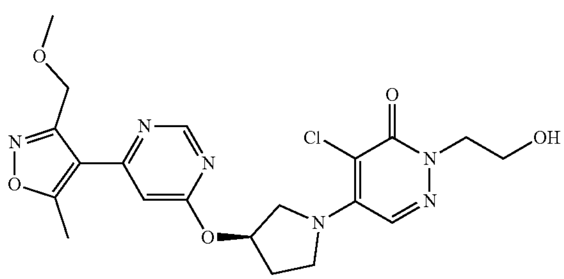 [SMILES: COCc1noc(C)c1-c1cc(O[C@@H]2CCN(c3cnn(CCO)c(=O)c3Cl)C2)ncn1] | (R)-4-chloro-2-(2-hydroxyethyl)-5-(3-((6-(3-(methoxymethyl)-5-methylisoxazol-4-yl)pyrimidin-4-yl)oxy)pyrrolidin-1-yl)pyridazin-3(2H)-one | 463.0 |
| P-0125 | 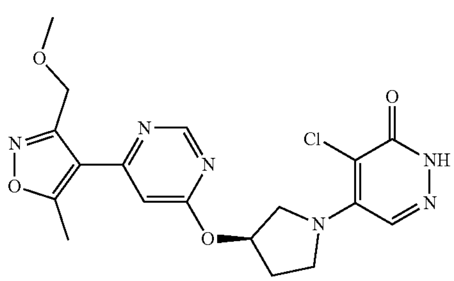 [SMILES: COCc1noc(C)c1-c1cc(O[C@@H]2CCN(c3cn[nH]c(=O)c3Cl)C2)ncn1] | (R)-4-chloro-5-(3-((6-(3-(methoxymethyl)-5-methylisoxazol-4-yl)pyrimidin-4-yl)oxy)pyrrolidin-1-yl)pyridazin-3(2H)-one | 419.0 |

TABLE 1-continued

| P# | Structure | Name | (MH)+ |
|---|---|---|---|
| P-0126 | 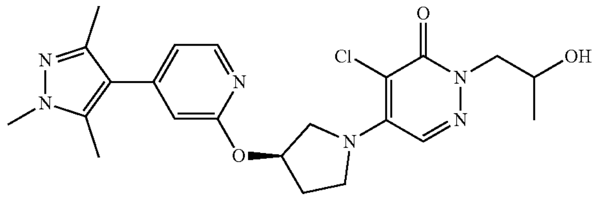 | 4-chloro-2-(2-hydroxypropyl)-5-((R)-3-((4-(1,3,5-trimethyl-1H-pyrazol-4-yl)pyridin-2-yl)oxy)pyrrolidin-1-yl)pyridazin-3(2H)-one | 459.1 |
| P-0127 | 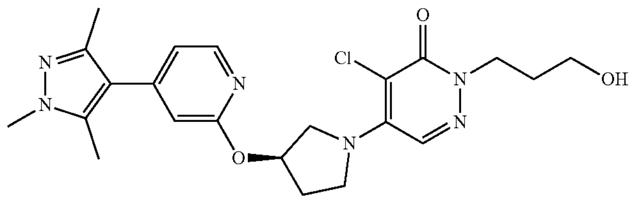 [SMILES: Cc1nn(C)c(C)c1-c1ccnc(O[C@@H]2CCN(c3cnn(CCCO)c(=O)c3Cl)C2)c1] | (R)-4-chloro-2-(3-hydroxypropyl)-5-(3-((4-(1,3,5-trimethyl-1H-pyrazol-4-yl)pyridin-2-yl)oxy)pyrrolidin-1-yl)pyridazin-3(2H)-one | 459.1 |
| P-0128 | 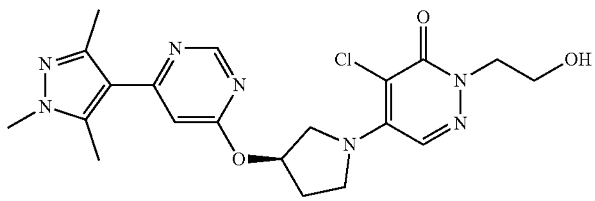 [SMILES: Cc1nn(C)c(C)c1-c1cc(O[C@@H]2CCN(c3cnn(CCO)c(=O)c3Cl)C2)ncn1] | (R)-4-chloro-2-(2-hydroxyethyl)-5-(3-((6-(1,3,5-trimethyl-1H-pyrazol-4-yl)pyrimidin-4-yl)oxy)pyrrolidin-1-yl)pyridazin-3(2H)-one | 446.3 |
| P-0129 | 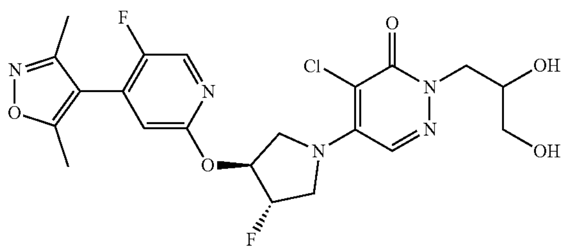 [SMILES: Cc1noc(C)c1-c1cc(O[C@H]2CN(c3cnn(CC(O)CO)c(=O)c3Cl)C[C@@H]2F)ncc1F] | 4-chloro-2-(2,3-dihydroxypropyl)-5-((3S,4S)-3-((4-(3,5-dimethylisoxazol-4-yl)-5-fluoropyridin-2-yl)oxy)-4-fluoropyrrolidin-1-yl)pyridazin-3(2H)-one | 498.0 |
| P-0130 | 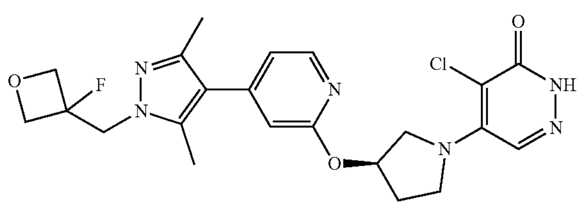 [SMILES: Cc1nn(CC2(F)COC2)c(C)c1-c1ccnc(O[C@@H]2CCN(c3cn[nH]c(=O)c3Cl)C2)c1] | (R)-4-chloro-5-(3-((4-(1-((3-fluorooxetan-3-yl)methyl)-3,5-dimethyl-1H-pyrazol-4-yl)pyridin-2-yl)oxy)pyrrolidin-1-yl)pyridazin-3(2H)-one | 475.0 |
| P-0131 | 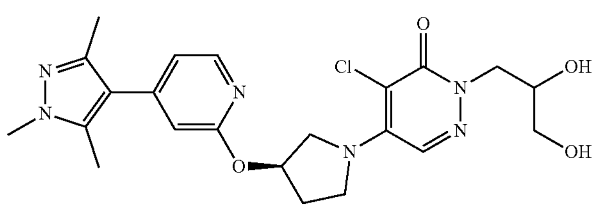 [SMILES: Cc1nn(C)c(C)c1-c1ccnc(O[C@@H]2CCN(c3cnn(CC(O)CO)c(=O)c3Cl)C2)c1] | 4-chloro-2-(2,3-dihydroxypropyl)-5-((R)-3-((4-(1,3,5-trimethyl-1H-pyrazol-4-yl)pyridin-2-yl)oxy)pyrrolidin-1-yl)pyridazin-3(2H)-one | 474.9 |
| P-0132 | 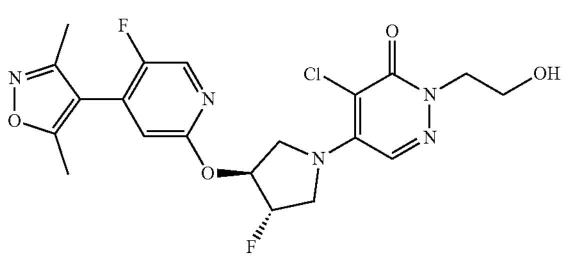 [SMILES: Cc1noc(C)c1-c1cc(O[C@H]2CN(c3cnn(CCO)c(=O)c3Cl)C[C@@H]2F)ncc1F] | 4-chloro-5-((3S,4S)-3-((4-(3,5-dimethylisoxazol-4-yl)-5-fluoropyridin-2-yl)oxy)-4-fluoropyrrolidin-1-yl)-2-(2-hydroxyethyl)pyridazin-3(2H)-one | 468.3 |

TABLE 1-continued

| P# | Structure | Name | (MH)+ |
|---|---|---|---|
| P-0133 | 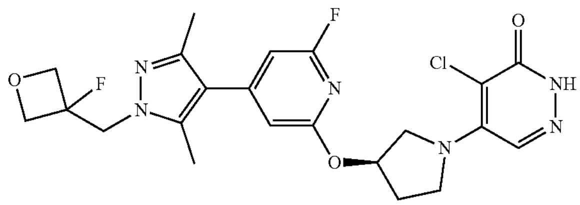 [SMILES: Cc1nn(CC2(F)COC2)c(C)c1-c1cc(F)nc(O[C@@H]2CCN(c3cn[nH]c(=O)c3Cl)C2)c1] | (R)-4-chloro-5-(3-((6-fluoro-4-(1-((3-fluorooxetan-3-yl)methyl)-3,5-dimethyl-1H-pyrazol-4-yl)pyridin-2-yl)oxy)pyrrolidin-1-yl)pyridazin-3(2H)-one | 493.0 |
| P-0134 | 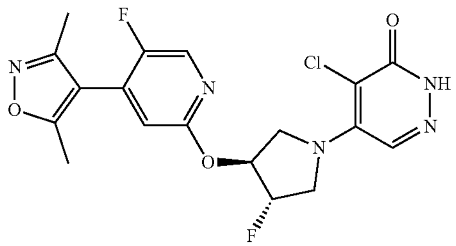 [SMILES: Cc1noc(C)c1-c1cc(O[C@H]2CN(c3cn[nH]c(=O)c3Cl)C[C@@H]2F)ncc1F] | 4-chloro-5-((3S,4S)-3-((4-(3,5-dimethylisoxazol-4-yl)-5-fluoropyridin-2-yl)oxy)-4-fluoropyrrolidin-1-yl)pyridazin-3(2H)-one | 424.1 |
| P-0135 | 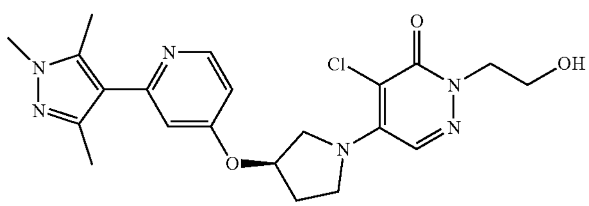 [SMILES: Cc1nn(C)c(C)c1-c1cc(O[C@@H]2CCN(c3cnn(CCO)c(=O)c3Cl)C2)ccn1] | (R)-4-chloro-2-(2-hydroxyethyl)-5-(3-((2-(1,3,5-trimethyl-1H-pyrazol-4-yl)pyridin-4-yl)oxy)pyrrolidin-1-yl)pyridazin-3(2H)-one | 445.1 |
| P-0136 | 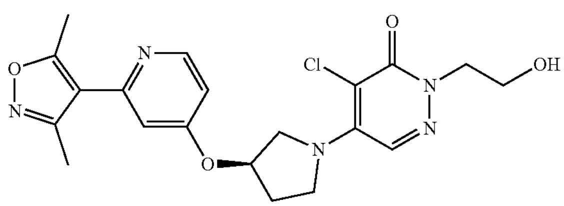 [SMILES: Cc1noc(C)c1-c1cc(O[C@@H]2CCN(c3cnn(CCO)c(=O)c3Cl)C2)ccn1] | (R)-4-chloro-5-(3-((2-(3,5-dimethylisoxazol-4-yl)pyridin-4-yl)oxy)pyrrolidin-1-yl)-2-(2-hydroxyethyl)pyridazin-3(2H)-one | 432.2 |
| P-0137 | 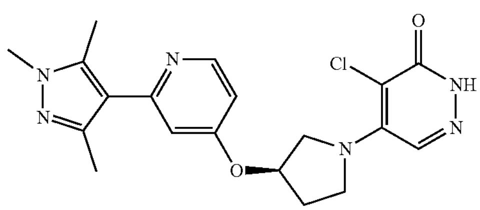 [SMILES: Cc1nn(C)c(C)c1-c1cc(O[C@@H]2CCN(c3cn[nH]c(=O)c3Cl)C2)ccn1] | (R)-4-chloro-5-(3-((2-(1,3,5-trimethyl-1H-pyrazol-4-yl)pyridin-4-yl)oxy)pyrrolidin-1-yl)pyridazin-3(2H)-one | 401.199 |
| P-0138 | 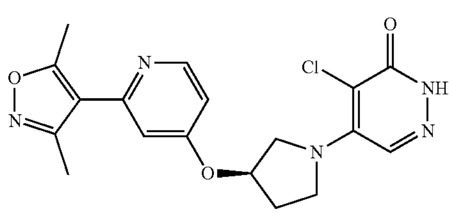 [SMILES: Cc1noc(C)c1-c1cc(O[C@@H]2CCN(c3cn[nH]c(=O)c3Cl)C2)ccn1] | (R)-4-chloro-5-(3-((2-(3,5-dimethylisoxazol-4-yl)pyridin-4-yl)oxy)pyrrolidin-1-yl)pyridazin-3(2H)-one | 388.2 |
| P-0139 | 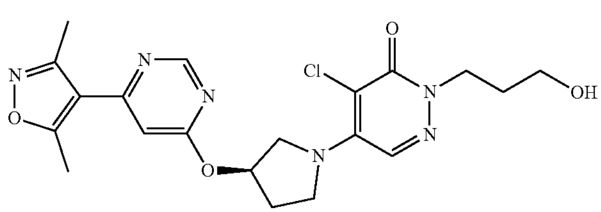 [SMILES: Cc1noc(C)c1-c1cc(O[C@@H]2CCN(c3cnn(CCCO)c(=O)c3Cl)C2)ncn1] | (R)-4-chloro-5-(3-((6-(3,5-dimethylisoxazol-4-yl)pyrimidin-4-yl)oxy)pyrrolidin-1-yl)-2-(3-hydroxypropyl)pyridazin-3(2H)-one | 447.0 |

TABLE 1-continued

| P# | Name | (MH)+ |
|---|---|---|
| P-0140 | 4-chloro-2-(2,3-dihydroxypropyl)-5-((R)-3-((6-(3,5-dimethylisoxazol-4-yl)pyrimidin-4-yl)oxy)pyrrolidin-1-yl)pyridazin-3(2H)-one | 463.0 |
| P-0141 | (R)-2-(2-aminoethyl)-4-chloro-5-(3-((6-(3,5-dimethylisoxazol-4-yl)pyrimidin-4-yl)oxy)pyrrolidin-1-yl)pyridazin-3(2H)-one | 432.3 |
| P-0142 | 4-chloro-5-((3S,4S)-3-fluoro-4-((4-(1,3,5-trimethyl-1H-pyrazol-4-yl)pyridin-2-yl)oxy)pyrrolidin-1-yl)-2-(2-hydroxyethyl)pyridazin-3(2H)-one | 463.3 |
| P-0143 | (R)-4-chloro-2-(2-hydroxyethyl)-5-(3-((4-(1,3,5-trimethyl-1H-pyrazol-4-yl)pyridin-2-yl)oxy)pyrrolidin-1-yl)pyridazin-3(2H)-one | 444.95 |
| P-0144 | 4-chloro-5-((3S,4S)-3-fluoro-4-((6-(1,3,5-trimethyl-1H-pyrazol-4-yl)pyrimidin-4-yl)oxy)pyrrolidin-1-yl)-2-(2-hydroxyethyl)pyridazin-3(2H)-one | 463.9599 |
| P-0145 | 4-chloro-5-((3S,4S)-3-((6-(3,5-dimethylisoxazol-4-yl)pyrimidin-4-yl)oxy)-4-fluoropyrrolidin-1-yl)-2-(2-hydroxyethyl)pyridazin-3(2H)-one | 451.0 |
| P-0146 | (R)-4-chloro-5-(3-((4-(3,5-dimethylisoxazol-4-yl)-5-fluoropyridin-2-yl)oxy)pyrrolidin-1-yl)-2-(2-hydroxyethyl)pyridazin-3(2H)-one | 450.1 |

TABLE 1-continued

| P# | Structure | Name | (MH)+ |
|---|---|---|---|
| P-0147 | 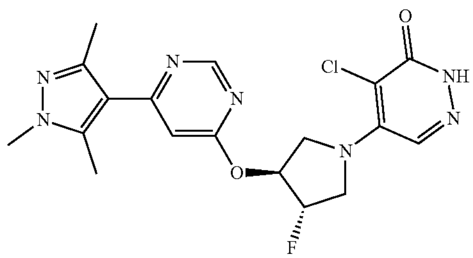 [SMILES: Cc1nn(C)c(C)c1-c1cc(O[C@H]2CN(c3cn[nH]c(=O)c3Cl)C[C@@H]2F)ncn1] | 4-chloro-5-((3S,4S)-3-fluoro-4-((6-(1,3,5-trimethyl-1H-pyrazol-4-yl)pyrimidin-4-yl)oxy)pyrrolidin-1-yl)pyridazin-3(2H)-one | 420.0 |
| P-0148 | 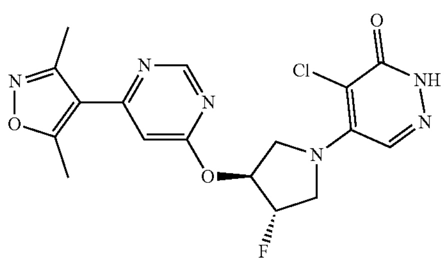 [SMILES: Cc1noc(C)c1-c1cc(O[C@H]2CN(c3cn[nH]c(=O)c3Cl)C[C@@H]2F)ncn1] | 4-chloro-5-((3S,4S)-3-((6-(3,5-dimethylisoxazol-4-yl)pyrimidin-4-yl)oxy)-4-fluoropyrrolidin-1-yl)pyridazin-3(2H)-one | 407.0 |
| P-0149 | 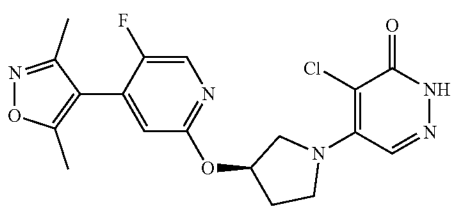 [SMILES: Cc1noc(C)c1-c1cc(O[C@@H]2CCN(c3cn[nH]c(=O)c3Cl)C2)ncc1F] | (R)-4-chloro-5-(3-((4-(3,5-dimethylisoxazol-4-yl)-5-fluoropyridin-2-yl)oxy)pyrrolidin-1-yl)pyridazin-3(2H)-one | 406.0 |
| P-0150 | 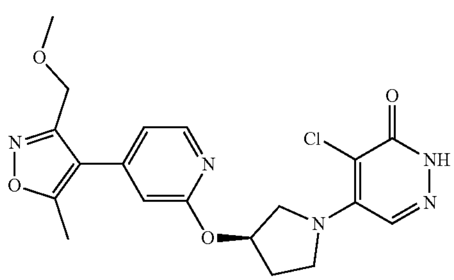 [SMILES: COCc1noc(C)c1-c1ccnc(O[C@@H]2CCN(c3cn[nH]c(=O)c3Cl)C2)c1] | (R)-4-chloro-5-(3-((4-(3-(methoxymethyl)-5-methylisoxazol-4-yl)pyridin-2-yl)oxy)pyrrolidin-1-yl)pyridazin-3(2H)-one | 418.0 |
| P-0151 | 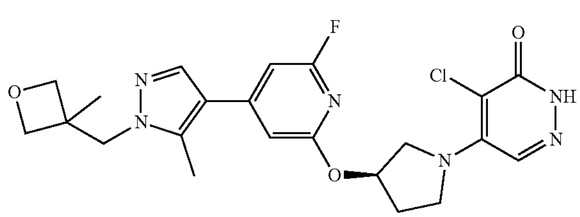 [SMILES: Cc1c(-c2cc(F)nc(O[C@@H]3CCN(c4cn[nH]c(=O)c4Cl)C3)c2)cnn1CC1(C)COC1] | (R)-4-chloro-5-(3-((6-fluoro-4-(5-methyl-1-((3-methyloxetan-3-yl)methyl)-1H-pyrazol-4-yl)pyridin-2-yl)oxy)pyrrolidin-1-yl)pyridazin-3(2H)-one | 475.9 |
| P-0152 | 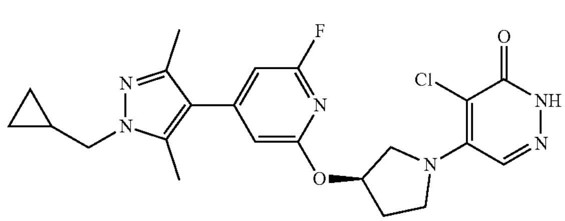 [SMILES: Cc1nn(CC2CC2)c(C)c1-c1cc(F)nc(O[C@@H]2CCN(c3cn[nH]c(=O)c3Cl)C2)c1] | (R)-4-chloro-5-(3-((4-(1-(cyclopropylmethyl)-3,5-dimethyl-1H-pyrazol-4-yl)-6-fluoropyridin-2-yl)oxy)pyrrolidin-1-yl)pyridazin-3(2H)-one | 459.0 |

TABLE 1-continued

| P# | Structure | Name | (MH)+ |
|---|---|---|---|
| P-0153 | 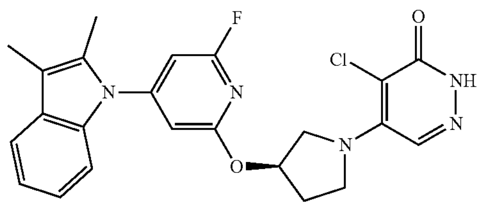 [SMILES: Cc1c(C)n(-c2cc(F)nc(O[C@@H]3CCN(c4cn[nH]c(=O)c4Cl)C3)c2)c2ccccc12] | (R)-4-chloro-5-(3-((4-(2,3-dimethyl-1H-indol-1-yl)-6-fluoropyridin-2-yl)oxy)pyrrolidin-1-yl)pyridazin-3(2H)-one | 454.0 |
| P-0154 | 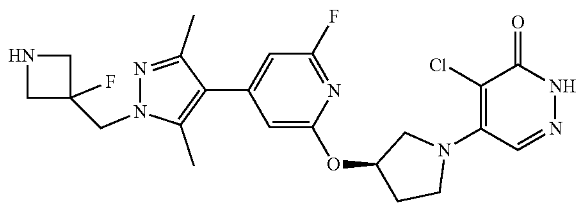 [SMILES: Cc1nn(CC2(F)CNC2)c(C)c1-c1cc(F)nc(O[C@@H]2CCN(c3cn[nH]c(=O)c3Cl)C2)c1] | (R)-4-chloro-5-(3-((6-fluoro-4-(1-((3-fluoroazetidin-3-yl)methyl)-3,5-dimethyl-1H-pyrazol-4-yl)pyridin-2-yl)oxy)pyrrolidin-1-yl)pyridazin-3(2H)-one | 492.0 |
| P-0155 | 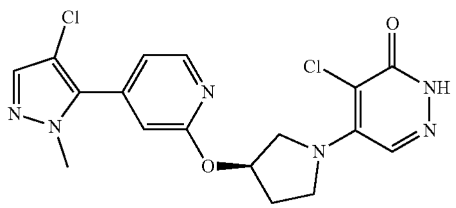 [SMILES: Cn1ncc(Cl)c1-c1ccnc(O[C@@H]2CCN(c3cn[nH]c(=O)c3Cl)C2)c1] | (R)-4-chloro-5-(3-((4-(4-chloro-1-methyl-1H-pyrazol-5-yl)pyridin-2-yl)oxy)pyrrolidin-1-yl)pyridazin-3(2H)-one | 407.0 |
| P-0156 | 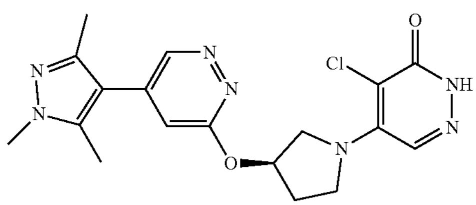 [SMILES: Cc1nn(C)c(C)c1-c1cnnc(O[C@@H]2CCN(c3cn[nH]c(=O)c3Cl)C2)c1] | (R)-4-chloro-5-(3-((5-(1,3,5-trimethyl-1H-pyrazol-4-yl)pyridazin-3-yl)oxy)pyrrolidin-1-yl)pyridazin-3(2H)-one | 402.0 |
| P-0157 | 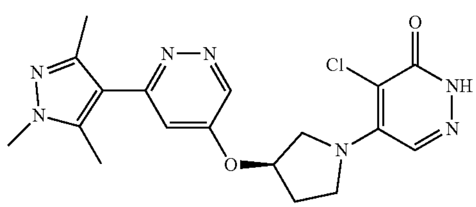 [SMILES: Cc1nn(C)c(C)c1-c1cc(O[C@@H]2CCN(c3cn[nH]c(=O)c3Cl)C2)cnn1] | (R)-4-chloro-5-(3-((6-(1,3,5-trimethyl-1H-pyrazol-4-yl)pyridazin-4-yl)oxy)pyrrolidin-1-yl)pyridazin-3(2H)-one | 402.0 |
| P-0158 | 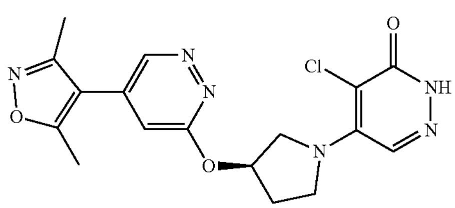 [SMILES: Cc1noc(C)c1-c1cnnc(O[C@@H]2CCN(c3cn[nH]c(=O)c3Cl)C2)c1] | (R)-4-chloro-5-(3-((5-(3,5-dimethylisoxazol-4-yl)pyridazin-3-yl)oxy)pyrrolidin-1-yl)pyridazin-3(2H)-one | 389.0 |
| P-0159 | 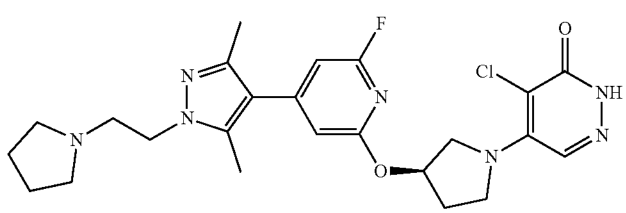 [SMILES: Cc1nn(CCN2CCCC2)c(C)c1-c1cc(F)nc(O[C@@H]2CCN(c3cn[nH]c(=O)c3Cl)C2)c1] | (R)-4-chloro-5-(3-((4-(3,5-dimethyl-1-(2-(pyrrolidin-1-yl)ethyl)-1H-pyrazol-4-yl)-6-fluoropyridin-2-yl)oxy)pyrrolidin-1-yl)pyridazin-3(2H)-one | 502.0 |

TABLE 1-continued

| P# | Structure | Name | (MH)+ |
|---|---|---|---|
| P-0160 | 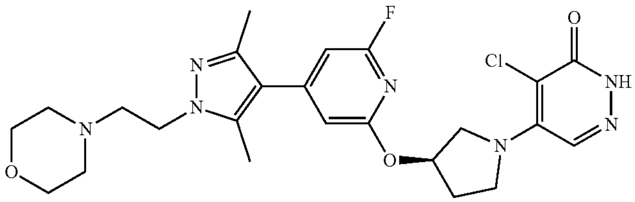 [SMILES: Cc1nn(CCN2CCOCC2)c(C)c1-c1cc(F)nc(O[C@@H]2CCN(c3cn[nH]c(=O)c3Cl)C2)c1] | (R)-4-chloro-5-(3-((4-(3,5-dimethyl-1-(2-morpholinoethyl)-1H-pyrazol-4-yl)-6-fluoropyridin-2-yl)oxy)pyrrolidin-1-yl)pyridazin-3(2H)-one | 517.95 |
| P-0161 | 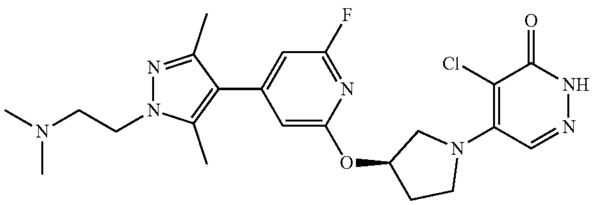 [SMILES: Cc1nn(CCN(C)C)c(C)c1-c1cc(F)nc(O[C@@H]2CCN(c3cn[nH]c(=O)c3Cl)C2)c1] | (R)-4-chloro-5-(3-((4-(1-(2-(dimethylamino)ethyl)-3,5-dimethyl-1H-pyrazol-4-yl)-6-fluoropyridin-2-yl)oxy)pyrrolidin-1-yl)pyridazin-3(2H)-one | 476.0 |
| P-0162 | 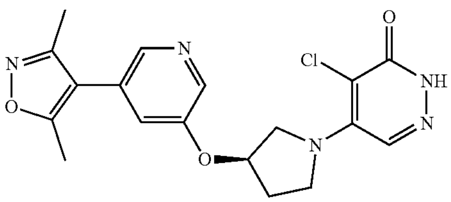 [SMILES: Cc1noc(C)c1-c1cncc(O[C@@H]2CCN(c3cn[nH]c(=O)c3Cl)C2)c1] | (R)-4-chloro-5-(3-((5-(3,5-dimethylisoxazol-4-yl)pyridin-3-yl)oxy)pyrrolidin-1-yl)pyridazin-3(2H)-one | 388.0 |
| P-0163 | 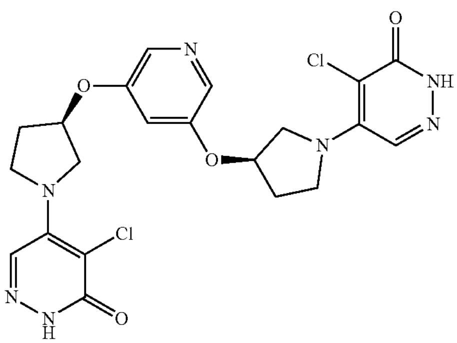 [SMILES: O=c1[nH]ncc(N2CC[C@@H](Oc3cncc(O[C@@H]4CCN(c5cn[nH]c(=O)c5Cl)C4)c3)C2)c1Cl] | 5,5'-((3R,3'R)-(pyridine-3,5-diylbis(oxy))bis(pyrrolidine-3,1-diyl))bis(4-chloropyridazin-3(2H)-one) | 506.0 |
| P-0164 | 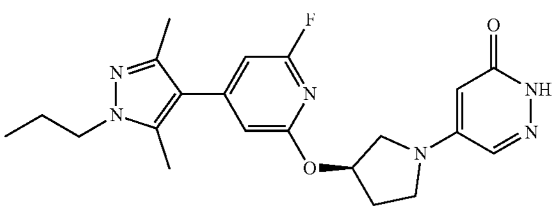 [SMILES: CCCn1nc(C)c(-c2cc(F)nc(O[C@@H]3CCN(c4cn[nH]c(=O)c4)C3)c2)c1C] | (R)-5-(3-((4-(3,5-dimethyl-1-propyl-1H-pyrazol-4-yl)-6-fluoropyridin-2-yl)oxy)pyrrolidin-1-yl)pyridazin-3(2H)-one | 413.1 |
| P-0165 | 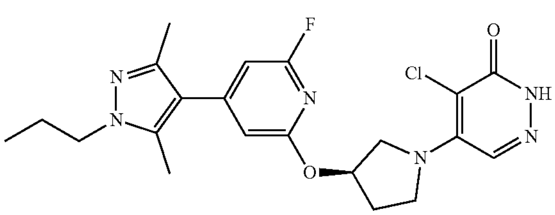 [SMILES: CCCn1nc(C)c(-c2cc(F)nc(O[C@@H]3CCN(c4cn[nH]c(=O)c4Cl)C3)c2)c1C] | (R)-4-chloro-5-(3-((4-(3,5-dimethyl-1-propyl-1H-pyrazol-4-yl)-6-fluoropyridin-2-yl)oxy)pyrrolidin-1-yl)pyridazin-3(2H)-one | 447.0 |
| P-0166 | 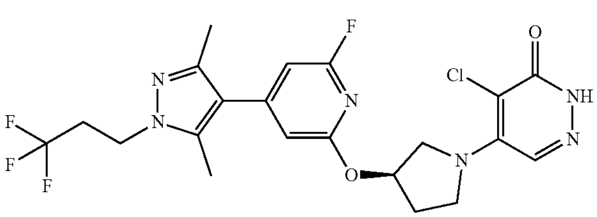 [SMILES: Cc1nn(CCC(F)(F)F)c(C)c1-c1cc(F)nc(O[C@@H]2CCN(c3cn[nH]c(=O)c3Cl)C2)c1] | (R)-4-chloro-5-(3-((4-(3,5-dimethyl-1-(3,3,3-trifluoropropyl)-1H-pyrazol-4-yl)-6-fluoropyridin-2-yl)oxy)pyrrolidin-1-yl)pyridazin-3(2H)-one | 500.95 |

TABLE 1-continued

| P# | Structure | Name | (MH)+ |
|---|---|---|---|
| P-0167 | 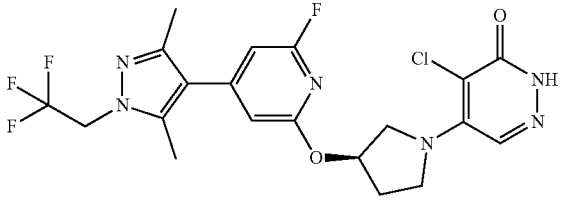 [SMILES: Cc1nn(CC(F)(F)F)c(C)c1-c1cc(F)nc(O[C@@H]2CCN(c3cn[nH]c(=O)c3Cl)C2)c1] | (R)-4-chloro-5-(3-((4-(3,5-dimethyl-1-(2,2,2-trifluoroethyl)-1H-pyrazol-4-yl)-6-fluoropyridin-2-yl)oxy)pyrrolidin-1-yl)pyridazin-3(2H)-one | 487.0 |
| P-0168 | 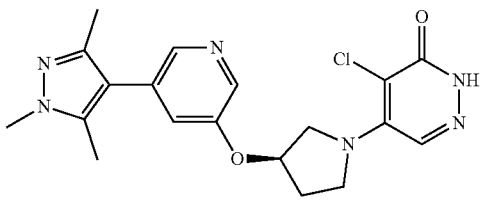 [SMILES: Cc1nn(C)c(C)c1-c1cncc(O[C@@H]2CCN(c3cn[nH]c(=O)c3Cl)C2)c1] | (R)-4-chloro-5-(3-((5-(1,3,5-trimethyl-1H-pyrazol-4-yl)pyridin-3-yl)oxy)pyrrolidin-1-yl)pyridazin-3(2H)-one | 401.0 |
| P-0169 | 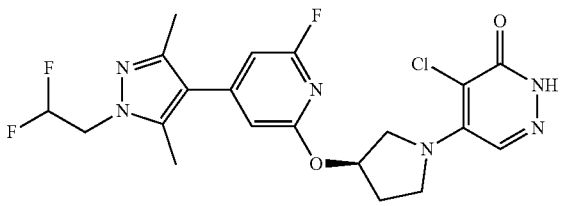 [SMILES: Cc1nn(CC(F)F)c(C)c1-c1cc(F)nc(O[C@@H]2CCN(c3cn[nH]c(=O)c3Cl)C2)c1] | (R)-4-chloro-5-(3-((4-(1-(2,2-difluoroethyl)-3,5-dimethyl-1H-pyrazol-4-yl)-6-fluoropyridin-2-yl)oxy)pyrrolidin-1-yl)pyridazin-3(2H)-one | 469.0 |
| P-0170 | 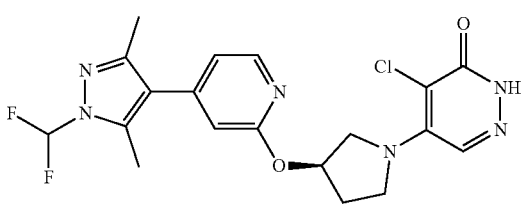 | (R)-4-chloro-5-(3-((4-(1-(difluoromethyl)-3,5-dimethyl-1H-pyrazol-4-yl)pyridin-2-yl)oxy)pyrrolidin-1-yl)pyridazin-3(2H)-one | 437.0 |
| P-0171 | 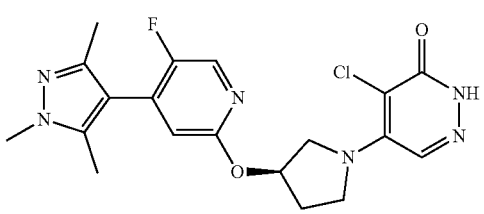 [SMILES: Cc1nn(C)c(C)c1-c1cc(O[C@@H]2CCN(c3cn[nH]c(=O)c3Cl)C2)ncc1F] | (R)-4-chloro-5-(3-((5-fluoro-4-(1,3,5-trimethyl-1H-pyrazol-4-yl)pyridin-2-yl)oxy)pyrrolidin-1-yl)pyridazin-3(2H)-one | 419.0 |
| P-0172 | 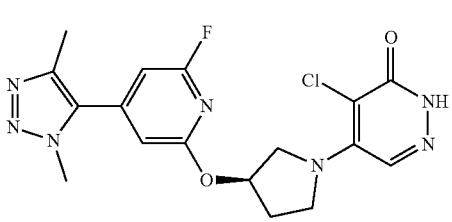 [SMILES: Cc1nnn(C)c1-c1cc(F)nc(O[C@@H]2CCN(c3cn[nH]c(=O)c3Cl)C2)c1] | (R)-4-chloro-5-(3-((4-(1,4-dimethyl-1H-1,2,3-triazol-5-yl)-6-fluoropyridin-2-yl)oxy)pyrrolidin-1-yl)pyridazin-3(2H)-one | 406.1 |
| P-0173 | 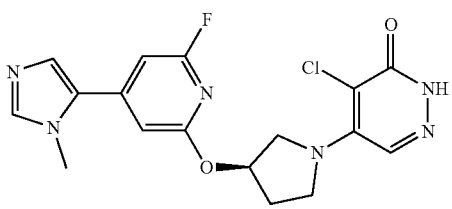 [SMILES: Cn1cncc1-c1cc(F)nc(O[C@@H]2CCN(c3cn[nH]c(=O)c3Cl)C2)c1] | (R)-4-chloro-5-(3-((6-fluoro-4-(1-methyl-1H-imidazol-5-yl)pyridin-2-yl)oxy)pyrrolidin-1-yl)pyridazin-3(2H)-one | 391.1 |

TABLE 1-continued

| P# | Structure | Name | (MH)+ |
|---|---|---|---|
| P-0174 | 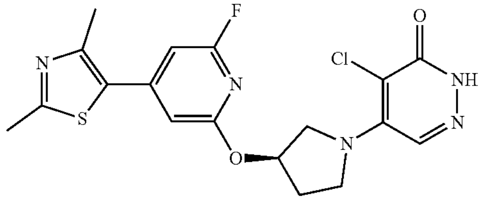 [SMILES: Cc1nc(C)c(-c2cc(F)nc(O[C@@H]3CCN(c4cn[nH]c(=O)c4Cl)C3)c2)s1] | (R)-4-chloro-5-(3-((4-(2,4-dimethylthiazol-5-yl)-6-fluoropyridin-2-yl)oxy)pyrrolidin-1-yl)pyridazin-3(2H)-one | 422.0 |
| P-0175 | 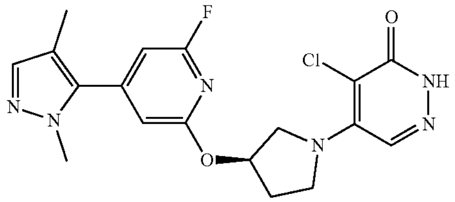 [SMILES: Cc1cnn(C)c1-c1cc(F)nc(O[C@@H]2CCN(c3cn[nH]c(=O)c3Cl)C2)c1] | (R)-4-chloro-5-(3-((4-(1,4-dimethyl-1H-pyrazol-5-yl)-6-fluoropyridin-2-yl)oxy)pyrrolidin-1-yl)pyridazin-3(2H)-one | 405.1 |
| P-0176 | 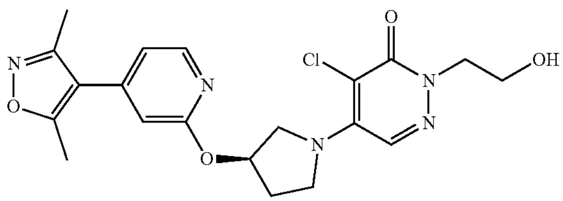 [SMILES: Cc1noc(C)c1-c1ccnc(O[C@@H]2CCN(c3cnn(CCO)c(=O)c3Cl)C2)c1] | (R)-4-chloro-5-(3-((4-(3,5-dimethylisoxazol-4-yl)pyridin-2-yl)oxy)pyrrolidin-1-yl)-2-(2-hydroxyethyl)pyridazin-3(2H)-one | 432.4 |
| P-0177 | 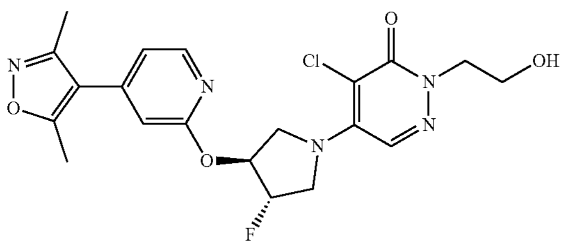 [SMILES: Cc1noc(C)c1-c1ccnc(O[C@H]2CN(c3cnn(CCO)c(=O)c3Cl)C[C@@H]2F)c1] | 4-chloro-5-((3S,4S)-3-((4-(3,5-dimethylisoxazol-4-yl)pyridin-2-yl)oxy)-4-fluoropyrrolidin-1-yl)-2-(2-hydroxyethyl)pyridazin-3(2H)-one | 450.2 |
| P-0178 | 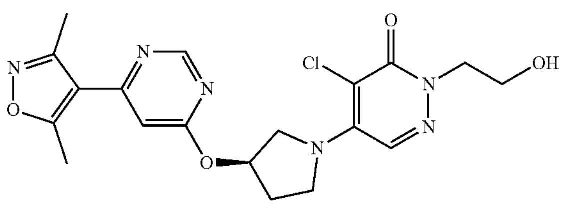 [SMILES: Cc1noc(C)c1-c1cc(O[C@@H]2CCN(c3cnn(CCO)c(=O)c3Cl)C2)ncn1] | (R)-4-chloro-5-(3-((6-(3,5-dimethylisoxazol-4-yl)pyrimidin-4-yl)oxy)pyrrolidin-1-yl)-2-(2-hydroxyethyl)pyridazin-3(2H)-one | 433.0 |
| P-0179 | 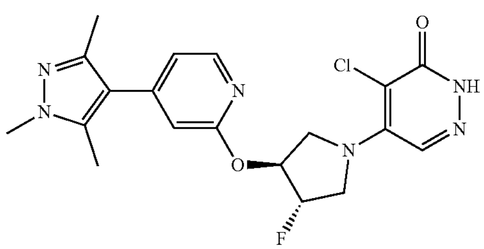 [SMILES: Cc1nn(C)c(C)c1-c1ccnc(O[C@H]2CN(c3cn[nH]c(=O)c3Cl)C[C@@H]2F)c1] | 4-chloro-5-((3S,4S)-3-fluoro-4-((4-(1,3,5-trimethyl-1H-pyrazol-4-yl)pyridin-2-yl)oxy)pyrrolidin-1-yl)pyridazin-3(2H)-one | 419.0 |
| P-0180 | 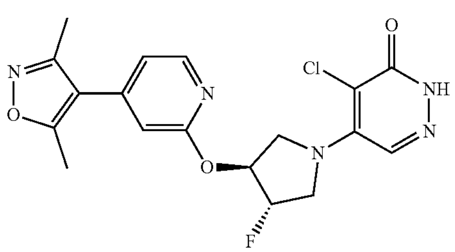 [SMILES: Cc1noc(C)c1-c1ccnc(O[C@H]2CN(c3cn[nH]c(=O)c3Cl)C[C@@H]2F)c1] | 4-chloro-5-((3S,4S)-3-((4-(3,5-dimethylisoxazol-4-yl)pyridin-2-yl)oxy)-4-fluoropyrrolidin-1-yl)pyridazin-3(2H)-one | 406.0 |

TABLE 1-continued

| P# | Structure | Name | (MH)+ |
|---|---|---|---|
| P-0181 | 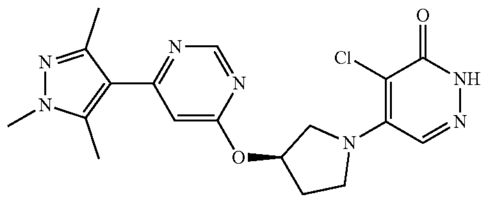 [SMILES: Cc1nn(C)c(C)c1-c1cc(O[C@@H]2CCN(c3cn[nH]c(=O)c3Cl)C2)ncn1] | (R)-4-chloro-5-(3-((6-(1,3,5-trimethyl-1H-pyrazol-4-yl)pyrimidin-4-yl)oxy)pyrrolidin-1-yl)pyridazin-3(2H)-one | 402.0 |
| P-0182 | 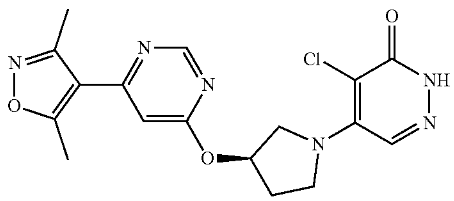 [SMILES: Cc1noc(C)c1-c1cc(O[C@@H]2CCN(c3cn[nH]c(=O)c3Cl)C2)ncn1] | (R)-4-chloro-5-(3-((6-(3,5-dimethylisoxazol-4-yl)pyrimidin-4-yl)oxy)pyrrolidin-1-yl)pyridazin-3(2H)-one | 389.0 |
| P-0183 | 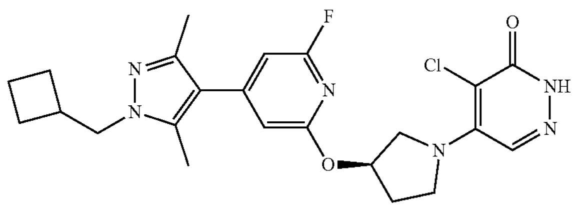 [SMILES: Cc1nn(CC2CCC2)c(C)c1-c1cc(F)nc(O[C@@H]2CCN(c3cn[nH]c(=O)c3Cl)C2)c1] | (R)-4-chloro-5-(3-((4-(1-(cyclobutylmethyl)-3,5-dimethyl-1H-pyrazol-4-yl)-6-fluoropyridin-2-yl)oxy)pyrrolidin-1-yl)pyridazin-3(2H)-one | 473.0 |
| P-0184 | 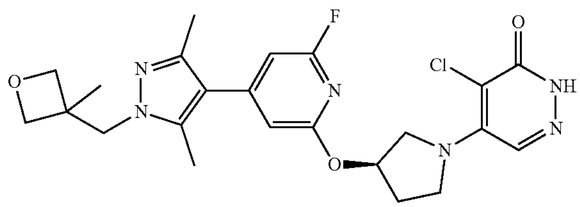 | (R)-4-chloro-5-(3-((4-(3,5-dimethyl-1-((3-methyloxetan-3-yl)methyl)-1H-pyrazol-4-yl)-6-fluoropyridin-2-yl)oxy)pyrrolidin-1-yl)pyridazin-3(2H)-one | 489.3 |
| P-0185 | 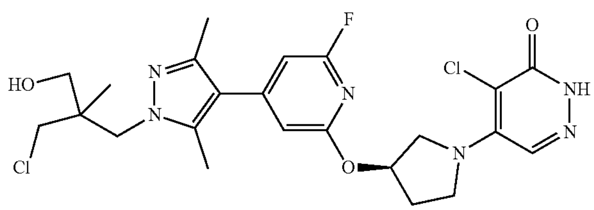 [SMILES: Cc1nn(CC(C)(CO)CCl)c(C)c1-c1cc(F)nc(O[C@@H]2CCN(c3cn[nH]c(=O)c3Cl)C2)c1] | 4-chloro-5-((3R)-3-((4-(1-(3-chloro-2-(hydroxymethyl)-2-methylpropyl)-3,5-dimethyl-1H-pyrazol-4-yl)-6-fluoropyridin-2-yl)oxy)pyrrolidin-1-yl)pyridazin-3(2H)-one | 525.0 |
| P-0186 | 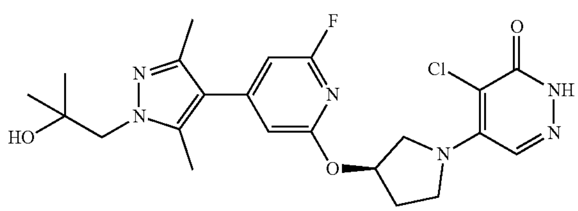 [SMILES: Cc1nn(CC(C)(C)O)c(C)c1-c1cc(F)nc(O[C@@H]2CCN(c3cn[nH]c(=O)c3Cl)C2)c1] | (R)-4-chloro-5-(3-((6-fluoro-4-(1-(2-hydroxy-2-methylpropyl)-3,5-dimethyl-1H-pyrazol-4-yl)pyridin-2-yl)oxy)pyrrolidin-1-yl)pyridazin-3(2H)-one | 477.0 |
| P-0187 | 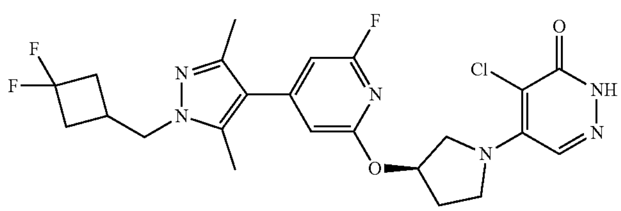 [SMILES: Cc1nn(CC2CC(F)(F)C2)c(C)c1-c1cc(F)nc(O[C@@H]2CCN(c3cn[nH]c(=O)c3Cl)C2)c1] | (R)-4-chloro-5-(3-((4-(1-((3,3-difluorocyclobutyl)methyl)-3,5-dimethyl-1H-pyrazol-4-yl)-6-fluoropyridin-2-yl)oxy)pyrrolidin-1-yl)pyridazin-3(2H)-one | 509.0 |

TABLE 1-continued

| P# | Name | (MH)+ |
|---|---|---|
| P-0188 | 4-chloro-5-((3S,4S)-3-((4-(3,5-dimethylisoxazol-4-yl)-6-fluoropyridin-2-yl)oxy)-4-fluoropyrrolidin-1-yl)-2-(2-hydroxyethyl)pyridazin-3(2H)-one | 468.0 |
| P-0189 | 4-chloro-5-((3S,4S)-3-((4-(3,5-dimethylisoxazol-4-yl)-6-fluoropyridin-2-yl)oxy)-4-fluoropyrrolidin-1-yl)pyridazin-3(2H)-one | 424.0 |
| P-0190 | 4-chloro-5-((3S,4S)-3-fluoro-4-((6-fluoro-4-(1,3,5-trimethyl-1H-pyrazol-4-yl)pyridin-2-yl)oxy)pyrrolidin-1-yl)-2-(2-hydroxyethyl)pyridazin-3(2H)-one | 481.3 |
| P-0191 | 4-chloro-5-((3S,4S)-3-fluoro-4-((6-fluoro-4-(1,3,5-trimethyl-1H-pyrazol-4-yl)pyridin-2-yl)oxy)pyrrolidin-1-yl)pyridazin-3(2H)-one | 437.0 |
| P-0192 | (R)-4-chloro-5-(3-((6-fluoro-4-(1-(2-hydroxyethyl)-3,5-dimethyl-1H-pyrazol-4-yl)pyridin-2-yl)oxy)pyrrolidin-1-yl)pyridazin-3(2H)-one | 449.0 |
| P-0193 | (R)-4-chloro-5-(3-((4-(3,5-dimethyl-1H-pyrazol-4-yl)-6-fluoropyridin-2-yl)oxy)pyrrolidin-1-yl)pyridazin-3(2H)-one | 405.0 |

TABLE 1-continued

| P# | Structure | Name | (MH)+ |
|---|---|---|---|
| P-0194 | 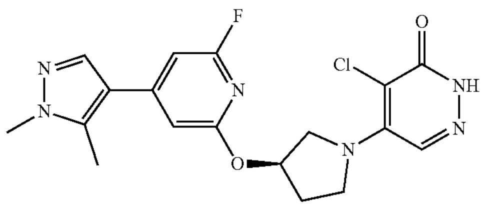 [SMILES: Cc1c(-c2cc(F)nc(O[C@@H]3CCN(c4cn[nH]c(=O)c4Cl)C3)c2)cnn1C] | (R)-4-chloro-5-(3-((4-(1,5-dimethyl-1H-pyrazol-4-yl)-6-fluoropyridin-2-yl)oxy)pyrrolidin-1-yl)pyridazin-3(2H)-one | 405.0 |
| P-0195 | 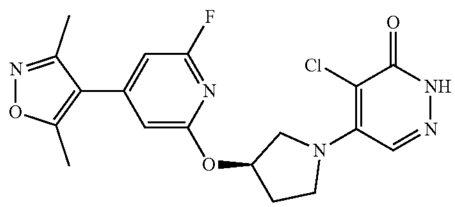 [SMILES: Cc1noc(C)c1-c1cc(F)nc(O[C@@H]2CCN(c3cn[nH]c(=O)c3Cl)C2)c1] | (R)-4-chloro-5-(3-((4-(3,5-dimethylisoxazol-4-yl)-6-fluoropyridin-2-yl)oxy)pyrrolidin-1-yl)pyridazin-3(2H)-one | 406.0 |
| P-0196 | 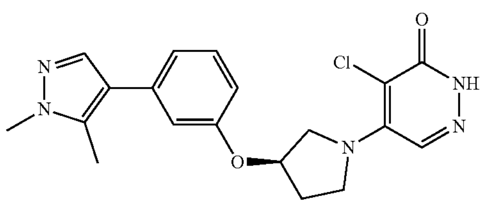 [SMILES: Cc1c(-c2cccc(O[C@@H]3CCN(c4cn[nH]c(=O)c4Cl)C3)c2)cnn1C] | (R)-4-chloro-5-(3-(3-(1,5-dimethyl-1H-pyrazol-4-yl)phenoxy)pyrrolidin-1-yl)pyridazin-3(2H)-one | 386.0 |
| P-0197 | 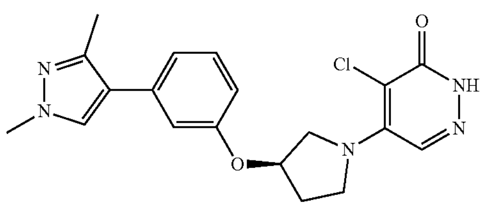 [SMILES: Cc1nn(C)cc1-c1cccc(O[C@@H]2CCN(c3cn[nH]c(=O)c3Cl)C2)c1] | (R)-4-chloro-5-(3-(3-(1,3-dimethyl-1H-pyrazol-4-yl)phenoxy)pyrrolidin-1-yl)pyridazin-3(2H)-one | 386.0 |
| P-0198 | 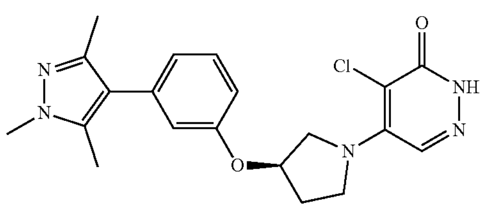 [SMILES: Cc1nn(C)c(C)c1-c1cccc(O[C@@H]2CCN(c3cn[nH]c(=O)c3Cl)C2)c1] | (R)-4-chloro-5-(3-(3-(1,3,5-trimethyl-1H-pyrazol-4-yl)phenoxy)pyrrolidin-1-yl)pyridazin-3(2H)-one | 400.0 |
| P-0199 | 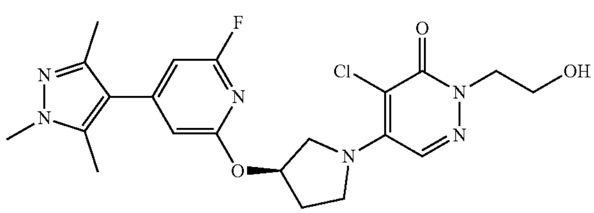 [SMILES: Cc1nn(C)c(C)c1-c1cc(F)nc(O[C@@H]2CCN(c3cnn(CCO)c(=O)c3Cl)C2)c1] | (R)-4-chloro-5 (3-((6-fluoro-4-(1,3,5-trimethyl-1H-pyrazol-4-yl)pyridin-2-yl)oxy)pyrrolidin-1-yl)-2-(2-hydroxyethyl)pyridazin-3(2H)-one | 463.9 |
| P-0200 | 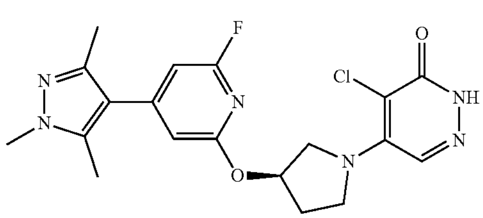 [SMILES: Cc1nn(C)c(C)c1-c1cc(F)nc(O[C@@H]2CCN(c3cn[nH]c(=O)c3Cl)C2)c1] | (R)-4-chloro-5-(3-((6-fluoro-4-(1,3,5-trimethyl-1H-pyrazol-4-yl)pyridin-2-yl)oxy)pyrrolidin-1-yl)pyridazin-3(2H)-one | |

TABLE 1-continued

| P# | Structure | Name | (MH)+ |
|---|---|---|---|
| P-0201 | 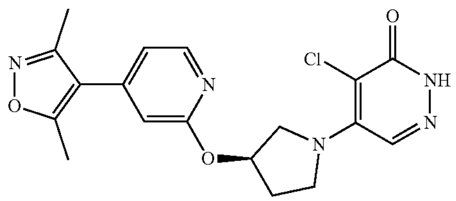 | (R)-4-chloro-5-(3-((4-(3,5-dimethylisoxazol-4-yl)pyridin-2-yl)oxy)pyrrolidin-1-yl)pyridazin-3(2H)-one | 388.0 |
| P-0202 | 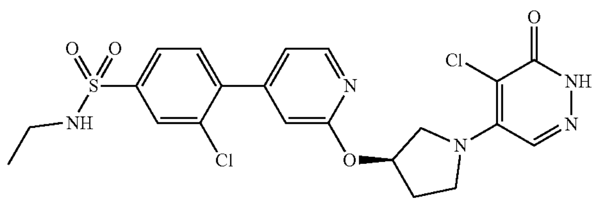 [SMILES: CCNS(=O)(=O)c1ccc(-c2ccnc(O[C@@H]3CCN(c4cn[nH]c(=O)c4Cl)C3)c2)c(Cl)c1] | (R)-3-chloro-4-(2-((1-(5-chloro-6-oxo-1,6-dihydropyridazin-4-yl)pyrrolidin-3-yl)oxy)pyridin-4-yl)-N-ethylbenzenesulfonamide | 509.9 |
| P-0203 | 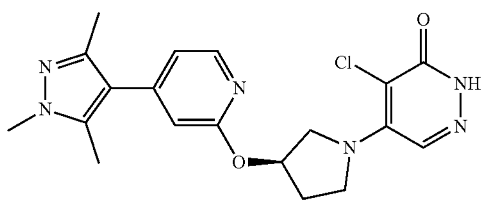 [SMILES: Cc1nn(C)c(C)c1-c1ccnc(O[C@@H]2CCN(c3cn[nH]c(=O)c3Cl)C2)c1] | (R)-4-chloro-5-(3-((4-(1,3,5-trimethyl-1H-pyrazol-4-yl)pyridin-2-yl)oxy)pyrrolidin-1-yl)pyridazin-3(2H)-one | 401.1 |
| P-0204 | 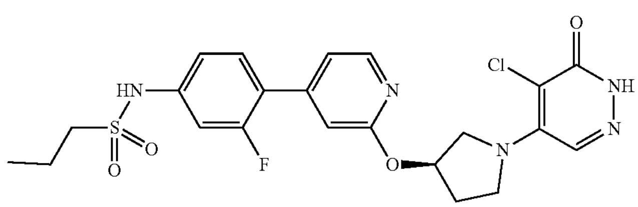 [SMILES: CCCS(=O)(=O)Nc1ccc(-c2ccnc(O[C@@H]3CCN(c4cn[nH]c(=O)c4Cl)C3)c2)c(F)c1] | (R)-N-(4-(2-((1-(5-chloro-6-oxo-1,6-dihydropyridazin-4-yl)pyrrolidin-3-yl)oxy)pyridin-4-yl)-3-fluorophenyl)propane-1-sulfonamide | 508.0 |
| P-0205 | 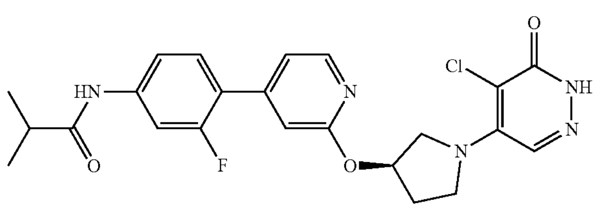 [SMILES: CC(C)C(=O)Nc1ccc(-c2ccnc(O[C@@H]3CCN(c4cn[nH]c(=O)c4Cl)C3)c2)c(F)c1] | (R)-N-(4-(2-((1-(5-chloro-6-oxo-1,6-dihydropyridazin-4-yl)pyrrolidin-3-yl)oxy)pyridin-4-yl)-3-fluorophenyl)isobutyramide | 472.0 |
| P-0206 | 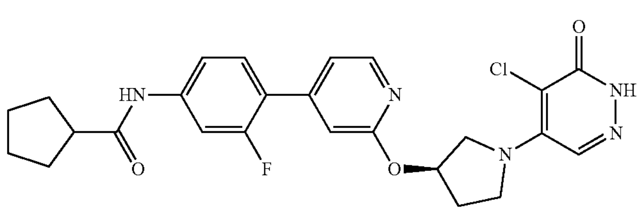 [SMILES: O=C(Nc1ccc(-c2ccnc(O[C@@H]3CCN(c4cn[nH]c(=O)c4Cl)C3)c2)c(F)c1)C1CCCC1] | (R)-N-(4-(2-((1-(5-chloro-6-oxo-1,6-dihydropyridazin-4-yl)pyrrolidin-3-yl)oxy)pyridin-4-yl)-3-fluorophenyl)cyclopentanecarboxamide | 498.0 |
| P-0207 | 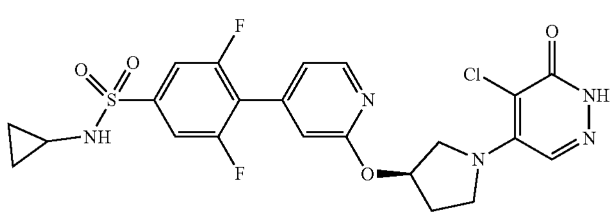 [SMILES: O=c1[nH]ncc(N2CC[C@@H](Oc3cc(-c4c(F)cc(S(=O)(=O)NC5CC5)cc4F)ccn3)C2)c1Cl] | (R)-4-(2-((1-(5-chloro-6-oxo-1,6-dihydropyridazin-4-yl)pyrrolidin-3-yl)oxy)pyridin-4-yl)-N-cyclopropyl-3,5-difluorobenzenesulfonamide | 523.9 |

TABLE 1-continued

| P# | Structure | Name | (MH)+ |
|---|---|---|---|
| P-0208 | 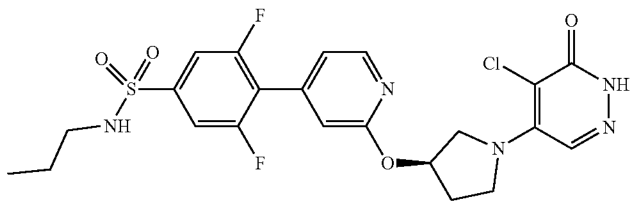 [SMILES: CCCNS(=O)(=O)c1cc(F)c(-c2ccnc(O[C@@H]3CCN(c4cn[nH]c(=O)c4Cl)C3)c2)c(F)c1] | (R)-4-(2-((1-(5-chloro-6-oxo-1,6-dihydropyridazin-4-yl)pyrrolidin-3-yl)oxy)pyridin-4-yl)-3,5-difluoro-N-propylbenzenesulfonamide | 526.0 |
| P-0209 | 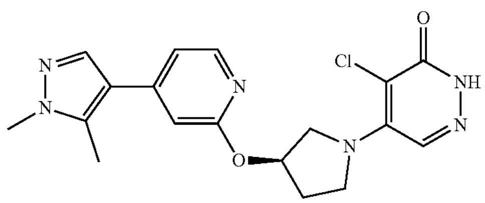 [SMILES: Cc1c(-c2ccnc(O[C@@H]3CCN(c4cn[nH]c(=O)c4Cl)C3)c2)cnn1C] | (R)-4-chloro-5-(3-((4-(1,5-dimethyl-1H-pyrazol-4-yl)pyridin-2-yl)oxy)pyrrolidin-1-yl)pyridazin-3(2H)-one | 387.1 |
| P-0210 | 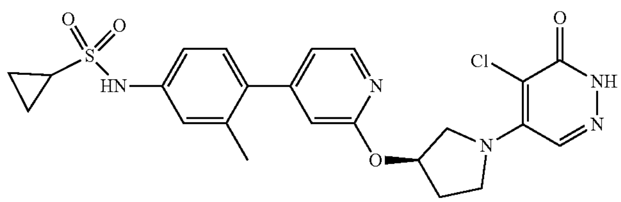 [SMILES: Cc1cc(NS(=O)(=O)C2CC2)ccc1-c1ccnc(O[C@@H]2CCN(c3cn[nH]c(=O)c3Cl)C2)c1] | (R)-N-(4-(2-((1-(5-chloro-6-oxo-1,6-dihydropyridazin-4-yl)pyrrolidin-3-yl)oxy)pyridin-4-yl)-3-methylphenyl)cyclopropane-sulfonamide | 502.0 |
| P-0211 | 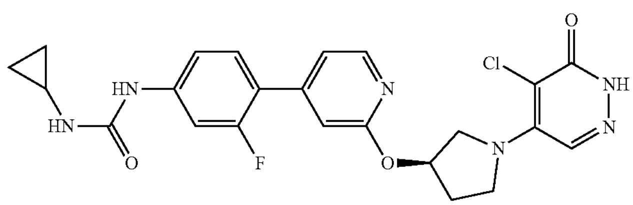 [SMILES: O=C(Nc1ccc(-c2ccnc(O[C@@H]3CCN(c4cn[nH]c(=O)c4Cl)C3)c2)c(F)c1)NC1CC1] | (R)-1-(4-(2-((1-(5-chloro-6-oxo-1,6-dihydropyridazin-4-yl)pyrrolidin-3-yl)oxy)pyridin-4-yl)-3-fluorophenyl)-3-cyclopropylurea | 485.0 |
| P-0212 | 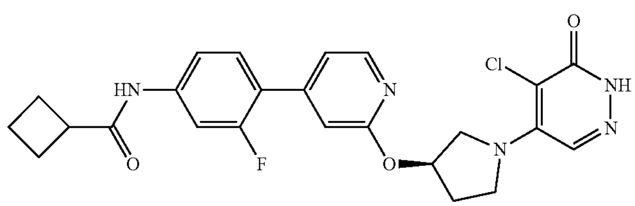 [SMILES: O=C(Nc1ccc(-c2ccnc(O[C@@H]3CCN(c4cn[nH]c(=O)c4Cl)C3)c2)c(F)c1)C1CCC1] | (R)-N-(4-(2-((1-(5-chloro-6-oxo-1,6-dihydropyridazin-4-yl)pyrrolidin-3-yl)oxy)pyridin-4-yl)-3-fluorophenyl)cyclobutane-carboxamide | 484.0 |
| P-0213 | 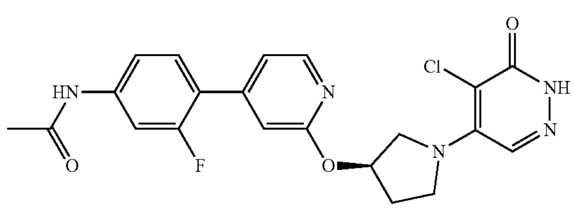 [SMILES: CC(=O)Nc1ccc(-c2ccnc(O[C@@H]3CCN(c4cn[nH]c(=O)c4Cl)C3)c2)c(F)c1] | (R)-N-(4-(2-((1-(5-chloro-6-oxo-1,6-dihydropyridazin-4-yl)pyrrolidin-3-yl)oxy)pyridin-4-yl)-3-fluorophenyl)acetamide | 444.0 |
| P-0214 | 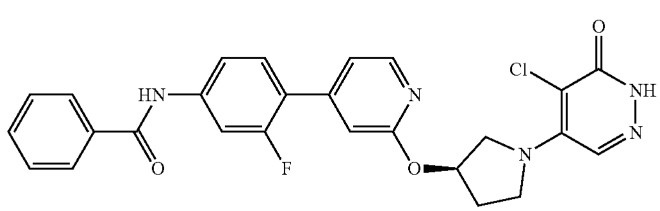 [SMILES: O=C(Nc1ccc(-c2ccnc(O[C@@H]3CCN(c4cn[nH]c(=O)c4Cl)C3)c2)c(F)c1)c1ccccc1] | (R)-N-(4-(2-((1-(5-chloro-6-oxo-1,6-dihydropyridazin-4-yl)pyrrolidin-3-yl)oxy)pyridin-4-yl)-3-fluorophenyl)benzamide | 506.0 |

TABLE 1-continued

| P# | Structure | Name | (MH)+ |
|---|---|---|---|
| P-0215 | 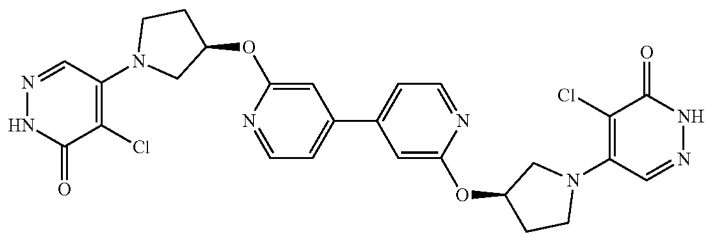 [SMILES: O=c1[nH]ncc(N2CC[C@@H](Oc3cc(-c4ccnc(O[C@@H]5CCN(c6cn[nH]c(=O)c6Cl)C5)c4)ccn3)C2)c1Cl] | 5,5'-((3R,3'R)-([4,4'-bipyridine]-2,2'-diylbis(oxy))bis(pyrrolidine-3,1-diyl))bis(4-chloropyridazin-3(2H)-one) | 583.0 |
| P-0216 | 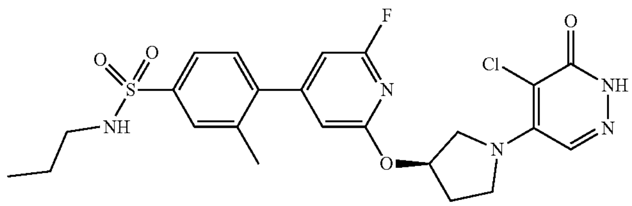 [SMILES: CCCNS(=O)(=O)c1ccc(-c2cc(F)nc(O[C@@H]3CCN(c4cn[nH]c(=O)c4Cl)C3)c2)c(C)c1] | (R)-4-(2-((1-(5-chloro-6-oxo-1,6-dihydropyridazin-4-yl)pyrrolidin-3-yl)oxy)-6-fluoropyridin-4-yl)-3-methyl-N-propylbenzenesulfonamide | 522.0 |
| P-0217 | 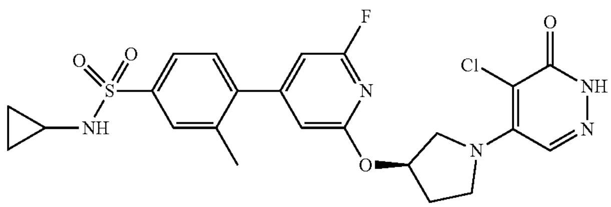 [SMILES: Cc1cc(S(=O)(=O)NC2CC2)ccc1-c1cc(F)nc(O[C@@H]2CCN(c3cn[nH]c(=O)c3Cl)C2)c1] | (R)-4-(2-((1-(5-chloro-6-oxo-1,6-dihydropyridazin-4-yl)pyrrolidin-3-yl)oxy)-6-fluoropyridin-4-yl)-N-cyclopropyl-3-methylbenzenesulfonamide | 522.0 |
| P-0218 | 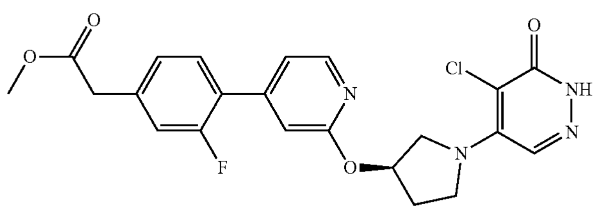 [SMILES: COC(=O)Cc1ccc(-c2ccnc(O[C@@H]3CCN(c4cn[nH]c(=O)c4Cl)C3)c2)c(F)c1] | methyl (R)-2-(4-(2-((1-(5-chloro-6-oxo-1,6-dihydropyridazin-4-yl)pyrrolidin-3-yl)oxy)pyridin-4-yl)-3-fluorophenyl)acetate | 459.0 |
| P-0219 | 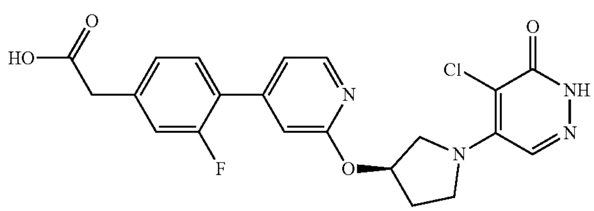 [SMILES: O=C(O)Cc1ccc(-c2ccnc(O[C@@H]3CCN(c4cn[nH]c(=O)c4Cl)C3)c2)c(F)c1] | (R)-2-(4-(2-((1-(5-chloro-6-oxo-1,6-dihydropyridazin-4-yl)pyrrolidin-3-yl)oxy)pyridin-4-yl)-3-fluorophenyl)acetic acid | 444.95 |
| P-0220 | 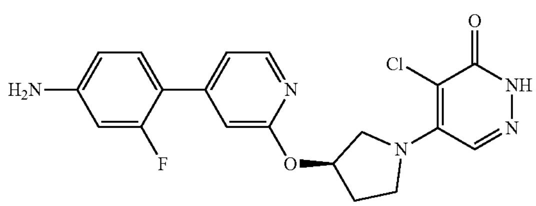 [SMILES: Nc1ccc(-c2ccnc(O[C@@H]3CCN(c4cn[nH]c(=O)c4Cl)C3)c2)c(F)c1] | (R)-5-(3-((4-(4-amino-2-fluorophenyl)pyridin-2-yl)oxy)pyrrolidin-1-yl)-4-chloropyridazin-3(2H)-one | 402.1 |
| P-0221 | 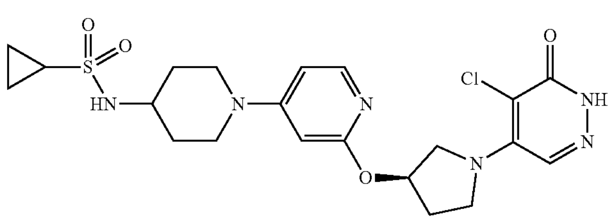 [SMILES: O=c1[nH]ncc(N2CC[C@@H](Oc3cc(N4CCC(NS(=O)(=O)C5CC5)CC4)ccn3)C2)c1Cl] | (R)-N-(1-(2-((1-(5-chloro-6-oxo-1,6-dihydropyridazin-4-yl)pyrrolidin-3-yl)oxy)pyridin-4-yl)piperidin-4-yl)cyclopropanesulfonamide | 495.0 |

TABLE 1-continued

| P# | Structure | Name | (MH)+ |
|---|---|---|---|
| P-0222 | 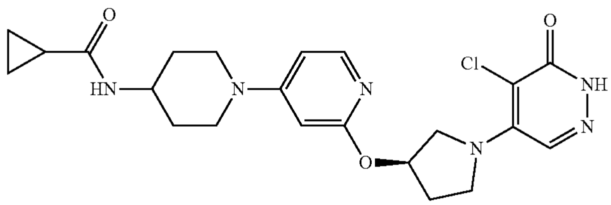 [SMILES: O=C(NC1CCN(c2ccnc(O[C@@H]3CCN(c4cn[nH]c(=O)c4Cl)C3)c2)CC1)C1CC1] | (R)-N-(1-(2-((1-(5-chloro-6-oxo-1,6-dihydropyridazin-4-yl)pyrrolidin-3-yl)oxy)pyridin-4-yl)piperidin-4-yl)cyclopropanecarboxamide | 459.0 |
| P-0223 | 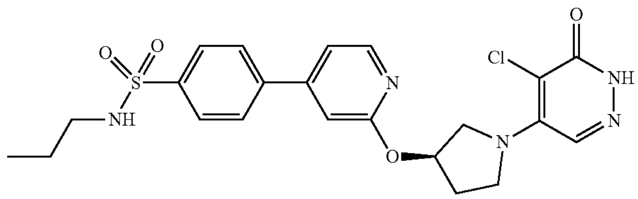 [SMILES: CCCNS(=O)(=O)c1ccc(-c2ccnc(O[C@@H]3CCN(c4cn[nH]c(=O)c4Cl)C3)c2)cc1] | (R)-4-(2-((1-(5-chloro-6-oxo-1,6-dihydropyridazin-4-yl)pyrrolidin-3-yl)oxy)pyridin-4-yl)-N-propylbenzenesulfonamide | 490.0 |
| P-0224 | 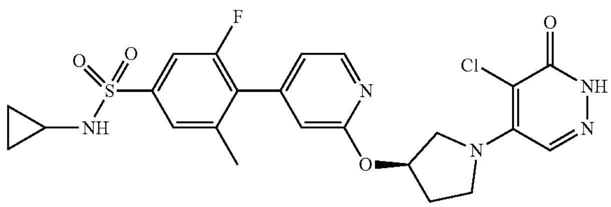 [SMILES: Cc1cc(S(=O)(=O)NC2CC2)cc(F)c1-c1ccnc(O[C@@H]2CCN(c3cn[nH]c(=O)c3Cl)C2)c1] | (R)-4-(2-((1-(5-chloro-6-oxo-1,6-dihydropyridazin-4-yl)pyrrolidin-3-yl)oxy)pyridin-4-yl)-N-cyclopropyl-3-fluoro-5-methylbenzenesulfonamide | 520.0 |
| P-0225 | 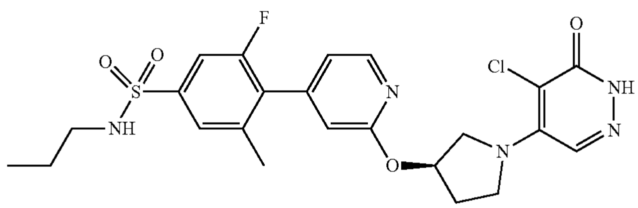 [SMILES: CCCNS(=O)(=O)c1cc(C)c(-c2ccnc(O[C@@H]3CCN(c4cn[nH]c(=O)c4Cl)C3)c2)c(F)c1] | (R)-4-(2-((1-(5-chloro-6-oxo-1,6-dihydropyridazin-4-yl)pyrrolidin-3-yl)oxy)pyridin-4-yl)-3-fluoro-5-methyl-N-propylbenzenesulfonamide | 522.0 |
| P-0226 | 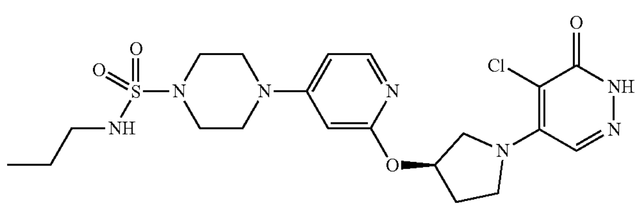 [SMILES: CCCNS(=O)(=O)N1CCN(c2ccnc(O[C@@H]3CCN(c4cn[nH]c(=O)c4Cl)C3)c2)CC1] | (R)-4-(2-((1-(5-chloro-6-oxo-1,6-dihydropyridazin-4-yl)pyrrolidin-3-yl)oxy)pyridin-4-yl)-N-propylpiperazine-1-sulfonamide | 498.0 |
| P-0227 | 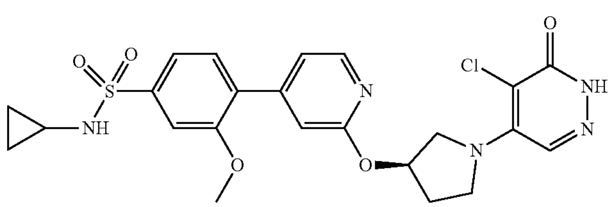 [SMILES: COc1cc(S(=O)(=O)NC2CC2)ccc1-c1ccnc(O[C@@H]2CCN(c3cn[nH]c(=O)c3Cl)C2)c1] | (R)-4-(2-((1-(5-chloro-6-oxo-1,6-dihydropyridazin-4-yl)pyrrolidin-3-yl)oxy)pyridin-4-yl)-N-cyclopropyl-3-methoxybenzenesulfonamide | 518.0 |
| P-0228 | 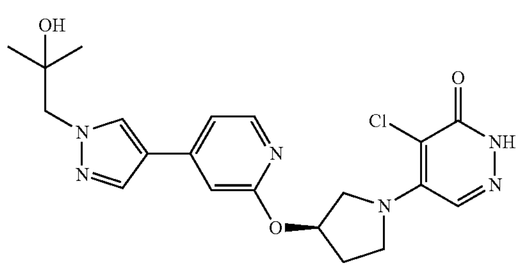 [SMILES: CC(C)(O)Cn1cc(-c2ccnc(O[C@@H]3CCN(c4cn[nH]c(=O)c4Cl)C3)c2)cn1] | (R)-4-chloro-5-(3-((4-(1-(2-hydroxy-2-methylpropyl)-1H-pyrazol-4-yl)pyridin-2-yl)oxy)pyrrolidin-1-yl)pyridazin-3(2H)-one | 431.1 |

TABLE 1-continued

| P# | Structure | Name | (MH)+ |
|---|---|---|---|
| P-0229 | 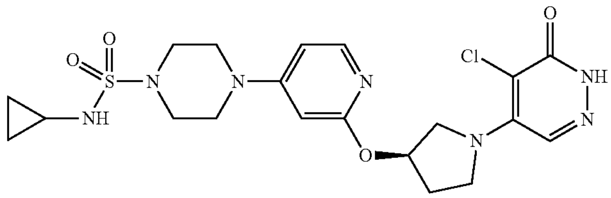 [SMILES: O=c1[nH]ncc(N2CC[C@@H](Oc3cc(N4CCN(S(=O)(=O)NC5CC5)CC4)ccn3)C2)c1Cl] | (R)-4-(2-((1-(5-chloro-6-oxo-1,6-dihydropyridazin-4-yl)pyrrolidin-3-yl)oxy)pyridin-4-yl)-N-cyclopropylpiperazine-1-sulfonamide | 496.0 |
| P-0230 | 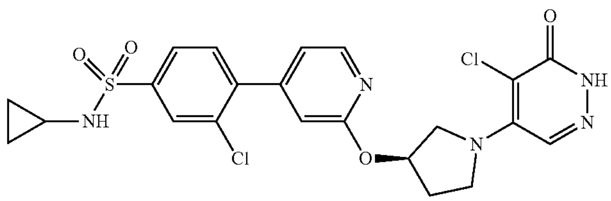 | (R)-3-chloro-4-(2-((1-(5-chloro-6-oxo-1,6-dihydropyridazin-4-yl)pyrrolidin-3-yl)oxy)pyridin-4-yl)-N-cyclopropylbenzenesulfonamide | 521.9 |
| P-0231 | 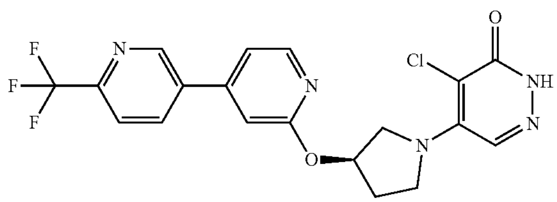 [SMILES: O=c1[nH]ncc(N2CC[C@@H](Oc3cc(-c4ccc(C(F)(F)F)nc4)ccn3)C2)c1Cl] | (R)-4-chloro-5-(3-((6-(trifluoromethyl)-[3,4'-bipyridin]-2'-yl)oxy)pyrrolidin-1-yl)pyridazin-3(2H)-one | 437.95 |
| P-0232 | 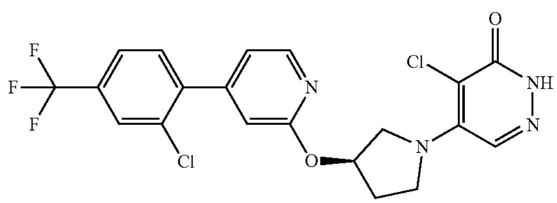 [SMILES: O=c1[nH]ncc(N2CC[C@@H](Oc3cc(-c4ccc(C(F)(F)F)cc4Cl)ccn3)C2)c1Cl] | (R)-4-chloro-5-(3-((4-(2-chloro-4-(trifluoromethyl)phenyl)pyridin-2-yl)oxy)pyrrolidin-1-yl)pyridazin-3(2H)-one | 470.9 |
| P-0233 | 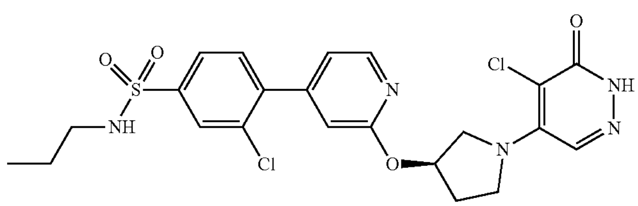 [SMILES: CCCNS(=O)(=O)c1ccc(-c2ccnc(O[C@@H]3CCN(c4cn[nH]c(=O)c4Cl)C3)c2)c(Cl)c1] | (R)-3-chloro-4-(2-((1-(5-chloro-6-oxo-1,6-dihydropyridazin-4-yl)pyrrolidin-3-yl)oxy)pyridin-4-yl)-N-propylbenzenesulfonamide | 523.9 |
| P-0234 | 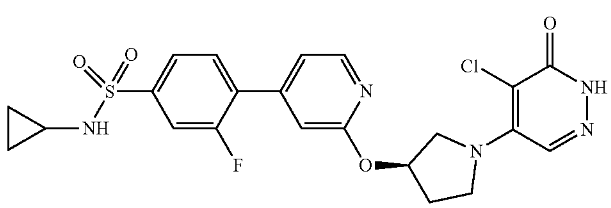 [SMILES: O=c1[nH]ncc(N2CC[C@@H](Oc3cc(-c4ccc(S(=O)(=O)NC5CC5)cc4F)ccn3)C2)c1Cl] | (R)-4-(2-((1-(5-chloro-6-oxo-1,6-dihydropyridazin-4-yl)pyrrolidin-3-yl)oxy)pyridin-4-yl)-N-cyclopropyl-3-fluorobenzenesulfonamide | 506.0 |
| P-0235 | 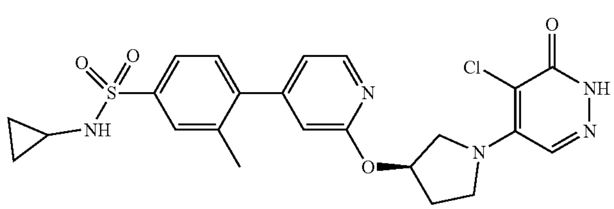 [SMILES: Cc1cc(S(=O)(=O)NC2CC2)ccc1-c1ccnc(O[C@@H]2CCN(c3cn[nH]c(=O)c3Cl)C2)c1] | (R)-4-(2-((1-(5-chloro-6-oxo-1,6-dihydropyridazin-4-yl)pyrrolidin-3-yl)oxy)pyridin-4-yl)-N-cyclopropyl-3-methylbenzenesulfonamide | 502.0 |

TABLE 1-continued

| P# | Structure | Name | (MH)+ |
|---|---|---|---|
| P-0236 | 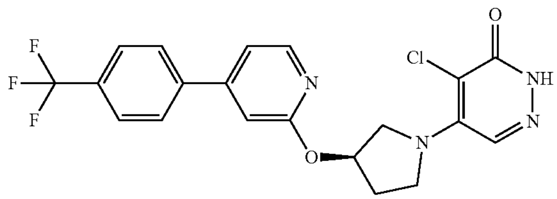 | (R)-4-chloro-5-(3-((4-(4-(trifluoromethyl)phenyl)pyridin-2-yl)oxy)pyrrolidin-1-yl)pyridazin-3(2H)-one | 437.0 |
| P-0237 | 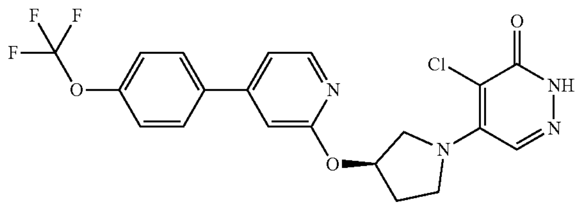 [SMILES: O=c1[nH]ncc(N2CC[C@@H](Oc3cc(-c4ccc(OC(F)(F)F)cc4)ccn3)C2)c1Cl] | (R)-4-chloro-5-(3-((4-(4-(trifluoromethoxy)phenyl)pyridin-2-yl)oxy)pyrrolidin-1-yl)pyridazin-3(2H)-one | 453.0 |
| P-0238 | 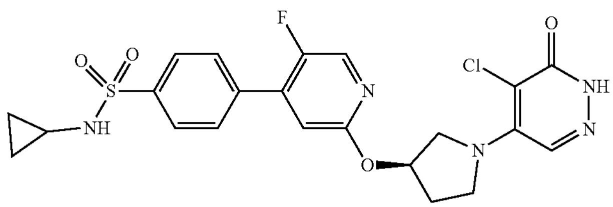 [SMILES: O=c1[nH]ncc(N2CC[C@@H](Oc3cc(-c4ccc(S(=O)(=O)NC5CC5)cc4)c(F)cn3)C2)c1Cl] | (R)-4-(2-((1-(5-chloro-6-oxo-1,6-dihydropyridazin-4-yl)pyrrolidin-3-yl)oxy)-5-fluoropyridin-4-yl)-N-cyclopropylbenzenesulfonamide | 505.9 |
| P-0239 | 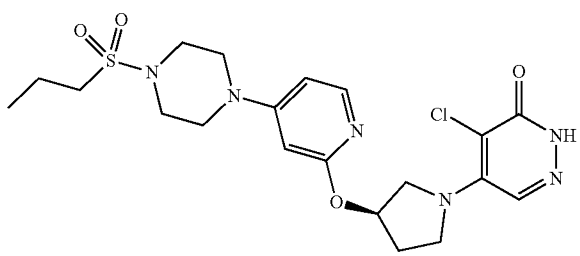 [SMILES: CCCS(=O)(=O)N1CCN(c2ccnc(O[C@@H]3CCN(c4cn[nH]c(=O)c4Cl)C3)c2)CC1] | (R)-4-chloro-5-(3-((4-(4-(propylsulfonyl)piperazin-1-yl)pyridin-2-yl)oxy)pyrrolidin-1-yl)pyridazin-3(2H)-one | 483.1 |
| P-0240 | 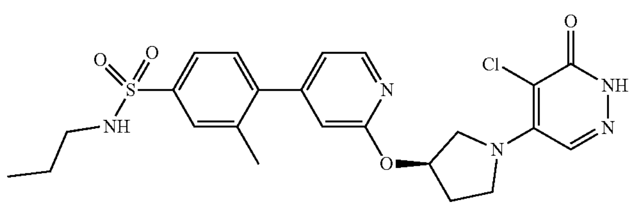 [SMILES: CCCNS(=O)(=O)c1ccc(-c2ccnc(O[C@@H]3CCN(c4cn[nH]c(=O)c4Cl)C3)c2)c(C)c1] | (R)-4-(2-((1-(5-chloro-6-oxo-1,6-dihydropyridazin-4-yl)pyrrolidin-3-yl)oxy)pyridin-4-yl)-3-methyl-N-propylbenzenesulfonamide | 504.0 |
| P-0241 | 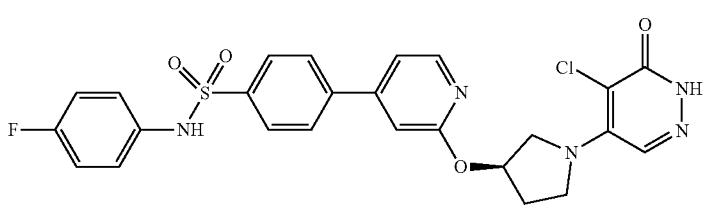 [SMILES: O=c1[nH]ncc(N2CC[C@@H](Oc3cc(-c4ccc(S(=O)(=O)Nc5ccc(F)cc5)cc4)ccn3)C2)c1Cl] | (R)-4-(2-((1-(5-chloro-6-oxo-1,6-dihydropyridazin-4-yl)pyrrolidin-3-yl)oxy)pyridin-4-yl)-N-(4-fluorophenyl)benzenesulfonamide | 541.9 |
| P-0242 | 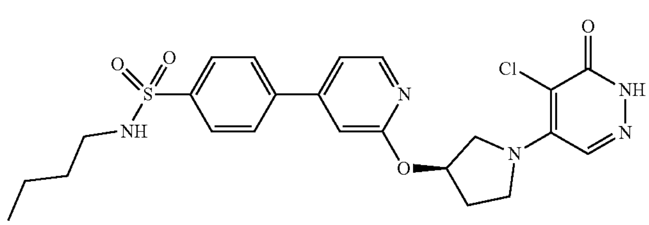 [SMILES: CCCCNS(=O)(=O)c1ccc(-c2ccnc(O[C@@H]3CCN(c4cn[nH]c(=O)c4Cl)C3)c2)cc1] | (R)-N-butyl-4-(2-((1-(5-chloro-6-oxo-1,6-dihydropyridazin-4-yl)pyrrolidin-3-yl)oxy)pyridin-4-yl)benzenesulfonamide | 504.0 |

TABLE 1-continued

| P# | Structure | Name | (MH)+ |
|---|---|---|---|
| P-0243 | 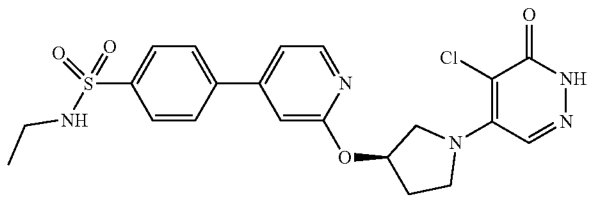 [SMILES: CCNS(=O)(=O)c1ccc(-c2ccnc(O[C@@H]3CCN(c4cn[nH]c(=O)c4Cl)C3)c2)cc1] | (R)-4-(2-((1-(5-chloro-6-oxo-1,6-dihydropyridazin-4-yl)pyrrolidin-3-yl)oxy)pyridin-4-yl)-N-ethylbenzenesulfonamide | 475.9 |
| P-0244 | 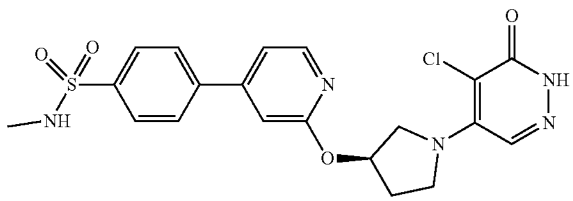 [SMILES: CNS(=O)(=O)c1ccc(-c2ccnc(O[C@@H]3CCN(c4cn[nH]c(=O)c4Cl)C3)c2)cc1] | (R)-4-(2-((1-(5-chloro-6-oxo-1,6-dihydropyridazin-4-yl)pyrrolidin-3-yl)oxy)pyridin-4-yl)-N-methylbenzenesulfonamide | 462.0 |
| P-0245 | 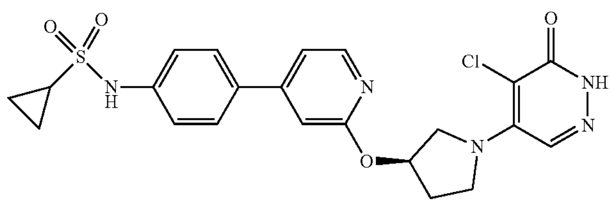 [SMILES: O=c1[nH]ncc(N2CC[C@@H](Oc3cc(-c4ccc(NS(=O)(=O)C5CC5)cc4)ccn3)C2)c1Cl] | (R)-N-(4-(2-((1-(5-chloro-6-oxo-1,6-dihydropyridazin-4-yl)pyrrolidin-3-yl)oxy)pyridin-4-yl)phenyl)cyclopropanesulfonamide | 488.0 |
| P-0246 | 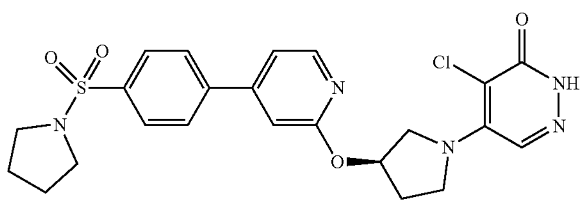 [SMILES: O=c1[nH]ncc(N2CC[C@@H](Oc3cc(-c4ccc(S(=O)(=O)N5CCCC5)cc4)ccn3)C2)c1Cl] | (R)-4-chloro-5-(3-((4-(4-(pyrrolidin-1-ylsulfonyl)phenyl)pyridin-2-yl)oxy)pyrrolidin-1-yl)pyridazin-3(2H)-one | 502.0 |
| P-0247 | 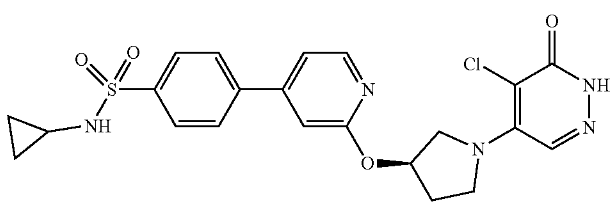 [SMILES: O=c1[nH]ncc(N2CC[C@@H](Oc3cc(-c4ccc(S(=O)(=O)NC5CC5)cc4)ccn3)C2)c1Cl] | (R)-4-(2-((1-(5-chloro-6-oxo-1,6-dihydropyridazin-4-yl)pyrrolidin-3-yl)oxy)pyridin-4-yl)-N-cyclopropylbenzenesulfonamide | 487.9 |
| P-0248 | 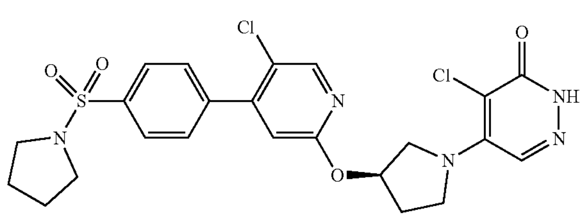 [SMILES: O=c1[nH]ncc(N2CC[C@@H](Oc3cc(-c4ccc(S(=O)(=O)N5CCCC5)cc4)c(Cl)cn3)C2)c1Cl] | (R)-4-chloro-5-(3-((5-chloro-4-(4-(pyrrolidin-1-ylsulfonyl)phenyl)pyridin-2-yl)oxy)pyrrolidin-1-yl)pyridazin-3(2H)-one | 535.9 |
| P-0249 | 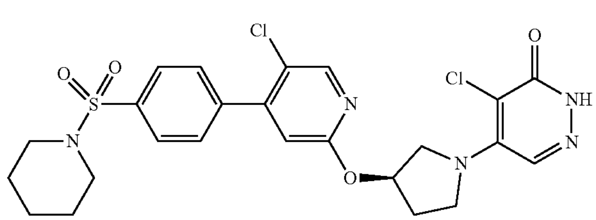 [SMILES: O=c1[nH]ncc(N2CC[C@@H](Oc3cc(-c4ccc(S(=O)(=O)N5CCCCC5)cc4)c(Cl)cn3)C2)c1Cl] | (R)-4-chloro-5-(3-((5-chloro-4-(4-(piperidin-1-ylsulfonyl)phenyl)pyridin-2-yl)oxy)pyrrolidin-1-yl)pyridazin-3(2H)-one | 549.9 |

TABLE 1-continued

| P# | Name | (MH)+ |
|---|---|---|
| P-0250 | (R)-3-(5-chloro-2-((1-(5-chloro-6-oxo-1,6-dihydropyridazin-4-yl)pyrrolidin-3-yl)oxy)pyridin-4-yl)-N-cyclopropylbenzenesulfonamide | 345.0 |
| P-0251 | (R)-4-(5-chloro-2-((1-(5-chloro-6-oxo-1,6-dihydropyridazin-4-yl)pyrrolidin-3-yl)oxy)pyridin-4-yl)-N-cyclopropylbenzenesulfonamide | 521.9 |
| P-0252 | (R)-5-(3-((4-(1H-pyrrol-1-yl)pyridin-2-yl)oxy)pyrrolidin-1-yl)-4-chloropyridazin-3(2H)-one | 358.0 |
| P-0253 | (R)-2-((1-(5-chloro-6-oxo-1,6-dihydropyridazin-4-yl)pyrrolidin-3-yl)oxy)-6-(pyrrolidin-1-yl)isonicotinonitrile | 387.0 |

Biological Examples

Biological Test Methods

The compounds of disclosure were tested using the following assays:

CD73 Enzymatic Assay

CD73 enzymatic activity was measured in a luciferase-based indirect assay using CellTiter-Glo® system from Promega. The luciferase reaction in the presence of ATP is inhibited by AMP, a primary substrate of CD73. Addition of CD73 enzyme to the reaction converts AMP to adenosine, and release the inhibition, producing a luminescent signal. Inhibition of CD73 leads to the decrease of this luminescent signal.

Human CD73 (amino acid residues 27-549) with N-Terminal His tag was purified in *E. coli*. All the assay components were prepared in 50 mM HEPEs buffer (pH 7.4) with 0.01% Tween-20. The CD73 enzymatic assay was performed using 0.4 nM CD73 and 150 μM AMP. 9.5 μL of CD73 protein and 9.5 μL of AMP were added to the wells of a 384 well plate containing 1 μL of various concentrations of test compound or DMSO vehicle and incubated for 1 hour at room temperature. 16 wells containing CD73, AMP and 5% DMSO served as high control. 16 wells containing AMP and 5% DMSO served as low control. Enzymatic reaction was stopped and AMP level was measured indirectly by adding 5 μL of CellTiter-Glo® 2.0 reagent and 5 μL of ATP with a final concentration of 1 μM. Following incubation of the plate at room temperature for 30 minutes, luminescent signal was read on a Tecan plate reader. The percentage inhibition at individual concentrations relative to high and low controls was calculated. The data were analyzed by using nonlinear regression to generate $IC_{50}$ values.

Determine Inhibitor Activity Against CD73 in Cell Based Assay

CD73 expressing CHO-K1 cell clones were generated upon stable transfection of a plasmid expressing human CD73 under the control of CMV promoter. Cells were selected in Ham's F-12K (Kaighn's) media supplemented with 10% fetal bovine serum and 1 mg/ml G418 at 37° C. in a humidified incubator supplied with 5% CO2. The assays were performed as follows. Cells were seeded in a 96 well plate in 50 μL of culture media at a density of $1\times10^4$ per well. Compound at a maximal concentration of 5 mM was serially diluted 1:3 in DMSO for a total of 8 point titration. A 2 μL aliquot of each dilution point was added to 248 μL culture media and 25 L was added to each well, providing 10 μM compound at the maximum concentration point. AMP was diluted in culture media and 25 μL was added to each well with a final concentration of 150 μM. 4 wells containing 0.2% DMSO treated cells and AMP served as high controls and 4 wells containing media only with 0.2% DMSO and AMP served as low controls. After 4 hours of incubation, 20 μL of the supernatant was transferred to a 384 well plate. AMP level in supernatant was measured indirectly by adding 5 μL of CellTiter-Glo® 2.0 reagent and 5 μL of ATP with a final concentration of 1 μM. Following incubation of plate at room temperature for 30 minutes, luminescent signal was read on a Tecan plate reader. The percentage inhibition at individual concentrations relative to high and low controls was calculated. The data were analyzed by using nonlinear regression to generate $IC_{50}$ values.

The following Table 2 provides data indicating biochemical and/or cell inhibitory activity for exemplary compounds as described herein in Table 1. In Table 2 below, activity is provided as follows: +++=0.001 μM<$IC_{50}$<10 μM; ++=10 μM<$IC_{50}$<100 μM, +=100 μM<$IC_{50}$<1000 μM.

TABLE 2

| P # | CD73 $IC_{50}$ (μM) | CHO-K1 CELL_VARIANT: CD73 $IC_{50}$ (uM) |
|---|---|---|
| P-0001 | +++ | +++ |
| P-0002 | +++ | +++ |
| P-0003 | +++ | +++ |
| P-0004 | +++ | +++ |
| P-0005 | +++ | +++ |
| P-0006 | +++ | +++ |
| P-0007 | +++ | +++ |
| P-0008 | +++ | +++ |
| P-0009 | +++ | +++ |
| P-0010 | +++ | +++ |
| P-0011 | +++ | +++ |
| P-0012 | +++ | +++ |
| P-0013 | +++ | +++ |
| P-0014 | +++ | +++ |
| P-0015 | +++ | +++ |
| P-0016 | +++ | +++ |
| P-0017 | +++ | +++ |
| P-0018 | +++ | +++ |
| P-0020 | +++ | +++ |
| P-0021 | +++ | +++ |
| P-0022 | +++ | +++ |
| P-0023 | +++ | +++ |
| P-0024 | +++ | +++ |
| P-0025 | +++ | +++ |
| P-0026 | +++ | +++ |
| P-0027 | +++ | +++ |
| P-0028 | +++ | +++ |
| P-0029 | +++ | ++ |
| P-0030 | +++ | +++ |
| P-0031 | +++ | +++ |
| P-0032 | +++ | +++ |
| P-0033 | +++ | +++ |
| P-0034 | +++ | +++ |
| P-0035 | +++ | +++ |
| P-0036 | +++ | +++ |
| P-0037 | +++ | +++ |
| P-0038 | +++ | +++ |
| P-0039 | +++ | +++ |
| P-0040 | +++ | +++ |
| P-0041 | +++ | +++ |
| P-0042 | +++ | +++ |
| P-0043 | +++ | +++ |
| P-0044 | +++ | +++ |
| P-0045 | +++ | +++ |
| P-0046 | +++ | +++ |
| P-0047 | +++ | +++ |
| P-0048 | +++ | +++ |
| P-0049 | +++ | +++ |
| P-0050 | +++ | +++ |
| P-0051 | +++ | +++ |
| P-0052 | +++ | ++ |
| P-0053 | +++ | +++ |
| P-0054 | +++ | +++ |
| P-0055 | +++ | +++ |
| P-0056 | +++ | +++ |
| P-0057 | +++ | +++ |
| P-0058 | +++ | +++ |
| P-0059 | +++ | +++ |
| P-0060 | +++ | +++ |
| P-0061 | +++ | +++ |
| P-0062 | +++ | +++ |
| P-0063 | +++ | +++ |
| P-0064 | +++ | +++ |
| P-0065 | +++ | +++ |
| P-0066 | +++ | +++ |
| P-0067 | +++ | +++ |
| P-0068 | +++ | +++ |
| P-0069 | +++ | +++ |
| P-0070 | +++ | +++ |
| P-0071 | +++ | +++ |
| P-0072 | +++ | +++ |
| P-0073 | +++ | +++ |
| P-0074 | +++ | +++ |
| P-0075 | +++ | +++ |
| P-0076 | +++ | +++ |
| P-0077 | +++ | +++ |
| P-0078 | +++ | +++ |
| P-0079 | +++ | +++ |
| P-0080 | +++ | ++ |
| P-0081 | +++ | +++ |
| P-0082 | +++ | +++ |
| P-0083 | +++ | +++ |
| P-0084 | +++ | +++ |
| P-0085 | +++ | +++ |
| P-0086 | +++ | +++ |
| P-0087 | +++ | +++ |
| P-0088 | +++ | +++ |
| P-0089 | +++ | +++ |
| P-0090 | +++ | +++ |
| P-0091 | +++ | +++ |
| P-0092 | +++ | +++ |
| P-0093 | +++ | +++ |
| P-0094 | +++ | +++ |
| P-0095 | +++ | +++ |
| P-0096 | +++ | +++ |
| P-0097 | +++ | +++ |
| P-0099 | +++ | +++ |
| P-0100 | +++ | +++ |
| P-0101 | +++ | ++ |
| P-0102 | +++ | +++ |
| P-0103 | +++ | ++ |
| P-0104 | +++ | ++ |
| P-0105 | +++ | +++ |
| P-0106 | +++ | +++ |
| P-0107 | +++ | ++ |
| P-0108 | +++ | +++ |
| P-0109 | +++ | +++ |
| P-0110- P-0111 | +++ | +++ |
| P-0111 | +++ | ++ |
| P-0112 | +++ | +++ |
| P-0113 | +++ | +++ |
| P-0114 | +++ | +++ |
| P-0115 | +++ | +++ |
| P-0116 | +++ | +++ |
| P-0117 | +++ | +++ |
| P-0118 | +++ | +++ |
| P-0119 | +++ | +++ |
| P-0120 | +++ | +++ |
| P-0121 | +++ | +++ |
| P-0122 | +++ | +++ |
| P-0123 | +++ | +++ |
| P-0124 | +++ | +++ |
| P-0125 | +++ | +++ |
| P-0126 | +++ | +++ |
| P-0127 | +++ | +++ |
| P-0128 | +++ | +++ |

TABLE 2-continued

| P # | CD73 IC$_{50}$ (μM) | CHO-K1 CELL_VARIANT: CD73 IC$_{50}$ (uM) |
|---|---|---|
| P-0129 | +++ | +++ |
| P-0130 | +++ | +++ |
| P-0131 | +++ | +++ |
| P-0132 | +++ | +++ |
| P-0133 | +++ | +++ |
| P-0134 | +++ | +++ |
| P-0135 | +++ | +++ |
| P-0136 | +++ | +++ |
| P-0137 | +++ | +++ |
| P-0138 | +++ | +++ |
| P-0139 | +++ | +++ |
| P-0140 | +++ | +++ |
| P-0141 | +++ | +++ |
| P-0142 | +++ | +++ |
| P-0143 | +++ | +++ |
| P-0144 | +++ | +++ |
| P-0145 | +++ | +++ |
| P-0146 | +++ | +++ |
| P-0147 | +++ | +++ |
| P-0148 | +++ | +++ |
| P-0149 | +++ | +++ |
| P-0150 | +++ | +++ |
| P-0151 | +++ | +++ |
| P-0152 | +++ | +++ |
| P-0153 | +++ | +++ |
| P-0154 | +++ | +++ |
| P-0155 | +++ | +++ |
| P-0156 | +++ | +++ |
| P-0157 | +++ | +++ |
| P-0158 | +++ | +++ |
| P-0159 | +++ | +++ |
| P-0160 | +++ | +++ |
| P-0161 | +++ | +++ |
| P-0162 | +++ | +++ |
| P-0163 | +++ | +++ |
| P-0164 | +++ | +++ |
| P-0165 | +++ | +++ |
| P-0166 | +++ | +++ |
| P-0167 | +++ | +++ |
| P-0168 | +++ | +++ |
| P-0169 | +++ | +++ |
| P-0170 | +++ | +++ |
| P-0171 | +++ | +++ |
| P-0172 | +++ | +++ |
| P-0173 | +++ | +++ |
| P-0174 | +++ | +++ |
| P-0175 | +++ | +++ |
| P-0176 | +++ | +++ |
| P-0177 | +++ | +++ |
| P-0178 | +++ | +++ |
| P-0179 | +++ | +++ |
| P-0180 | +++ | +++ |
| P-0181 | +++ | +++ |
| P-0182 | +++ | +++ |
| P-0183 | +++ | +++ |
| P-0184 | +++ | +++ |
| P-0185 | +++ | +++ |
| P-0186 | +++ | +++ |
| P-0187 | +++ | +++ |
| P-0188 | +++ | +++ |
| P-0189 | +++ | +++ |
| P-0190 | +++ | +++ |
| P-0191 | +++ | +++ |
| P-0192 | +++ | +++ |
| P-0193 | +++ | +++ |
| P-0194 | +++ | +++ |
| P-0195 | +++ | +++ |
| P-0196 | +++ | +++ |
| P-0197 | +++ | +++ |
| P-0198 | +++ | +++ |
| P-0199 | +++ | +++ |
| P-0200 | +++ | +++ |
| P-0201 | +++ | +++ |
| P-0202 | +++ | +++ |
| P-0203 | +++ | +++ |
| P-0204 | +++ | +++ |
| P-0205 | +++ | +++ |
| P-0206 | +++ | +++ |
| P-0207 | +++ | +++ |
| P-0208 | +++ | +++ |
| P-0209 | +++ | +++ |
| P-0210 | +++ | +++ |
| P-0211 | +++ | +++ |
| P-0212 | +++ | +++ |
| P-0213 | +++ | +++ |
| P-0214 | +++ | +++ |
| P-0215 | +++ | ++ |
| P-0216 | +++ | +++ |
| P-0217 | +++ | +++ |
| P-0218 | +++ | +++ |
| P-0219 | +++ | ++ |
| P-0220 | +++ | +++ |
| P-0221 | +++ | +++ |
| P-0222 | +++ | +++ |
| P-0223 | +++ | +++ |
| P-0224 | +++ | +++ |
| P-0225 | +++ | +++ |
| P-0226 | +++ | +++ |
| P-0227 | +++ | +++ |
| P-0228 | +++ | +++ |
| P-0229 | +++ | +++ |
| P-0230 | +++ | +++ |
| P-0231 | +++ | +++ |
| P-0232 | +++ | +++ |
| P-0233 | +++ | +++ |
| P-0234 | +++ | +++ |
| P-0235 | +++ | +++ |
| P-0236 | +++ | +++ |
| P-0237 | +++ | +++ |
| P-0238 | +++ | +++ |
| P-0239 | +++ | +++ |
| P-0240 | +++ | +++ |
| P-0241 | +++ | +++ |
| P-0242 | +++ | +++ |
| P-0243 | +++ | +++ |
| P-0244 | +++ | +++ |
| P-0245 | +++ | +++ |
| P-0246 | +++ | +++ |
| P-0247 | +++ | +++ |
| P-0248 | +++ | +++ |
| P-0249 | +++ | +++ |
| P-0250 | +++ | +++ |
| P-0251 | +++ | +++ |
| P-0252 | +++ | +++ |
| P-0253 | +++ | ++ |

All patents and other references cited herein are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, compositions and embodiments described herein are exemplary and are not intended as limitations on the scope of the disclosure. Changes therein and other uses will occur to those skilled in the art, which are encompassed within the spirit of the disclosure.

It will be readily apparent to one skilled in the art that varying substitutions and modifications may be made to the present disclosure described herein without departing from the scope and spirit of the disclosure. For example, variations can be made to provide additional compounds of this disclosure and/or various methods of administration can be used. Thus, such additional embodiments are within the scope of the present disclosure and the following claims.

The present disclosure illustratively described herein suitably may be practiced in the absence of any element, elements, limitation, or limitations which is not specifically described herein. The terms and expressions which have been employed are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the present disclosure has been specifically described by the embodiments and optional features, modification and variation of the concepts herein described may be resorted to by those skilled in the art, and that such modifications and variations are considered to be within the scope of this disclosure as defined by the appended claims.

In addition, where features or aspects of the disclosure are described in terms of a grouping of alternatives, those skilled in the art will recognize that the disclosure is also thereby described in terms of any individual member or subgroup of members of the groups described herein.

Also, unless indicated to the contrary, where various numerical values are provided for embodiments, additional embodiments are described by taking any 2 different values as the endpoints of a range. Such ranges are also within the scope of the present disclosure.

Thus, additional embodiments are within the scope of the disclosure and within the following claims.

What is claimed is:
1. A compound having Formula I:

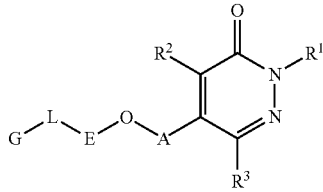

I or a pharmaceutically acceptable salt, a solvate, a tautomer, a stereoisomer, or a deuterated analog thereof, wherein:

A is a 5-6 membered aromatic ring or a 4-7 membered nitrogen containing heterocycloalkyl, wherein A is substituted with 0-3 $R^4$, provided that when ring A is a 4-7 membered nitrogen containing heterocycloalkyl, then the pyridazinone moiety of Formula I is attached to a nitrogen atom of A;

E is phenyl or a 5 or 6 membered heteroaryl, wherein E is substituted with 0-3 Q and 0-1 $R^{11}$, provided that when E is a 5 or 6 membered heteroaryl, O is not attached to a heteroatom of E;

L is absent, —C(O)N(H)—, $C_0$-$C_3$alkylene, —N(H)—, or —O—;

G is one of the following groups:
(a) cycloalkyl substituted with 0-4 $T^1$ and 0-1 $T^2$;
(b) cycloalkenyl substituted with 0-4 $T^1$ and 0-1 $T^2$;
(c) a bridged carbocyclic ring substituted with 0-4 $T^1$ and 0-1 $T^2$;
(d) a carbocyclic spiro ring containing two cycloalkyl groups joined by one common spiro carbon atom, wherein the carbocyclic spiro ring is substituted with 0-4 $T^1$ and 0-1 $T^2$;
(e) a heterocyclic spiro ring containing two cyclic groups with at least one heteroatom, wherein the two cyclic groups are joined by one common spiro carbon atom, wherein the heterocyclic spiro ring is substituted with 0-3 $T^5$, 0-1 $T^6$;
(f) phenyl substituted with 0-4 $T^1$ and 0-1 $T^4$;
(g) heterocycloalkyl substituted with 0-4 $T^5$ and 0-1 $T^6$;
(h) heterocycloalkenyl substituted with 0-4 $T^5$ and 0-1 $T^6$;
(i) a bridged heterocylic ring substituted with 0-4 $T^5$ and 0-1 $T^6$; or
(j) heteroaryl substituted with 0-3 $T^5$ and 0-1 $T^3$;

each Q is independently halogen, CN, or alkyl optionally substituted with 1-3 halogens;

each $T^1$ is independently halogen, hydroxyl, alkyl optionally substituted with 1-3 $R^b$, alkenyl optionally substituted with 1-3 $R^b$, alkynyl optionally substituted with 1-3 $R^b$, CN, cyanoalkyl, alkoxyl optionally substituted with 1-3 $R^b$, or alkoxyalkyl optionally substituted with 1-3 $R^b$;

$T^2$ is —$(CH_2)_{0-3}$—N($R^9$)$SO_2$—$R^7$, —$(CH_2)_{0-3}$—$SO_2$—$R^7$, —$(CH_2)_{0-3}$—$SO_2$N($R^9$)$R^9$, —$(CH_2)_{0-3}$—N($R^9$)$SO_2$N($R^9$)$R^9$, —$(CH_2)_{0-3}$—N($R^9$)C(O)N($R^9$)$R^9$, —$(CH_2)_{0-3}$—N($R^9$)C(O)$R^8$, —$(CH_2)_{0-3}$—N($R^9$)C(O)O$R^9$, —$(CH_2)_{0-3}$—N($R^9$)$R^9$, —$(CH_2)_{0-3}$—C(O)N($R^9$)$R^9$, —$(CH_2)_{0-3}$—C(O)O$R^9$, —$(CH_2)_{0-3}$—C(O)$R^{10}$, —$(CH_2)_{0-3}$—C(O)H, —$(CH_2)_{0-3}$—N($R^9$)C(O)$R^{10}$, —$(CH_2)_{0-3}$cycloalkyl optionally substituted with 1-4 $Z^3$, —$(CH_2)_{0-3}$-phenyl optionally substituted with 1-3 $Z^5$, or —$(CH_2)_{0-3}$heteroaryl optionally substituted with 1-3 $Z^5$;

$T^3$ is —$(CH_2)_{0-3}$—C(O)N($R^9$)$R^9$, —$(CH_2)_{0-3}$—N($R^9$)$R^9$, —$(CH_2)_{0-3}$—C(O)O$R^9$, —$(CH_2)_{0-3}$-cycloalkyl, —$(CH_2)_{0-3}$-cycloalkenyl, —$(CH_2)_{0-3}$-heterocycloalkyl, —$(CH_2)_{0-3}$-heterocycloalkenyl, —O-heterocycloalkyl optionally substituted with 4-chloropyridazin-3-one-5-yl, or —$(CH_2)_{0-3}$-bridged carbocyclic ring, wherein the —$(CH_2)_{0-3}$-cycloalkyl, —$(CH_2)_{0-3}$-cycloalkenyl, —$(CH_2)_{0-3}$-heterocycloalkyl, —$(CH_2)_{0-3}$-heterocycloalkenyl, or —$(CH_2)_{0-3}$-bridged carbocyclic are each optionally substituted with 1-3 $Z^5$ and 0-1 $Z^1$, provided that when $T^3$ is attached to a heteroatom of G, G cannot be attached to an oxygen or nitrogen atom of $T^3$;

$T^4$ is —$(CH_2)_{0-3}$C(O)O$R^9$, —$(CH_2)_{0-3}$—N($R^9$)C(O)$R^9$, —$(CH_2)_{0-3}$—N($R^9$)$SO_2$—$R^7$, —$(CH_2)_{0-3}$—$SO_2$—$R^7$, —$(CH_2)_{0-3}$—$SO_2$N($R^9$)$R^9$, —$(CH_2)_{0-3}$—N($R^9$)C(O)N(R')$R^9$, or N($R^a$)$_2$;

each $T^5$ is independently halogen, hydroxyl, alkyl optionally substituted with 1-3 $R^b$, alkenyl optionally substituted with 1-3 $R^b$, alkynyl optionally substituted with 1-3 $R^b$, CN, cyanoalkyl, alkoxyl optionally substituted with 1-3 $R^b$, or alkoxyalkyl optionally substituted with 1-3 $R^b$, provided that when $T^5$ is attached to a heteroatom of G, $T^5$ cannot be halogen, hydroxyl, CN, or alkoxyl optionally substituted with 1-3 $R^b$;

$T^6$ is —$(CH_2)_{0-3}$—N($R^9$)$SO_2$—$R^7$, —$(CH_2)_{0-3}$—$SO_2$—$R^7$, —$(CH_2)_{0-3}$—$SO_2$N($R^9$)$R^9$, —$(CH_2)_{0-3}$—N($R^9$)$SO_2$N($R^9$)$R^9$, —$(CH_2)_{0-3}$—N($R^9$)C(O)N($R^9$)$R^9$, —$(CH_2)_{0-3}$—N($R^9$)C(O)$R^9$, —$(CH_2)_{0-3}$—N($R^9$)C(O)O$R^9$, —$(CH_2)_{0-3}$—N($R^8$)$R^9$, —$(CH_2)_{0-3}$—C(O)—N($R^8$)$R^9$, —$(CH_2)_{0-3}$—C(O)O$R^9$, —$(CH_2)_{0-3}$—C(O)$R^{10}$, —$(CH_2)_{0-3}$—N($R^9$)C(O)$R^{10}$, —N(H)C(H)C═O, —$(CH_2)_{0-3}$cycloalkyl optionally substituted with 1-4 $Z^3$, —$(CH_2)_{0-2}$heterocycloalkyl optionally substituted with 1-4 $Z^3$, —$(CH_2)_{0-3}$heteroaryl optionally substituted with 1-3 $Z^5$, or 4-chloropyridazin-3-one-5-yl, provided that when $T^6$ is attached to a heteroatom of G, G cannot be attached to an oxygen or nitrogen atom of $T^6$;

$R^a$ is H or alkyl;

$R^b$ is halogen, CN, $CF_3$, or hydroxyl, provided that not more than 1 $R^b$ can be $CF_3$;

$R^1$ is $C_1$-$C_4$alkoxy$C_1$-$C_4$alkyl, $C_2$-$C_4$alkenyl substituted with 1-3 $Z^2$, or $C_2$-$C_4$alkyl substituted with 1-3 $Z^2$;

$R^2$ is H, halogen, alkyl, alkenyl, alkoxyl, haloalkyl, $CF_3$, or CN;

$R^3$ is H, halogen, alkyl, CN, or haloalkyl;

each $R^4$ is independently halogen, CN, or alkyl optionally substituted with 1-3 halogens;

$R^7$ is alkyl optionally substituted with 1-4 $Z^4$, —$C_0$-$C_3$alkyl-cycloalkyl optionally substituted with 1-4 $Z^3$, —$C_0$-$C_3$alkyl-phenyl optionally substituted with 1-4 $Z^3$, —$C_0$-$C_3$alkyl-heteroaryl optionally substituted with 1-3 $Z^5$, or —$C_0$-$C_3$alkyl-heterocycloalkyl optionally substituted with 1-3 $Z^5$;

$R^8$ is H, alkyl optionally substituted with 1-4 $Z^4$, alkenyl optionally substituted with 1-4 $Z^4$, —$C_0$-$C_3$alkyl-cycloalkyl optionally substituted with 1-4 $Z^3$, —$C_0$-$C_3$alkyl-phenyl optionally substituted with 1-4 $Z^3$, —$C_0$-$C_3$alkyl-heteroaryl optionally substituted with 1-3 $Z^5$, —$C_0$-$C_3$alkyl-heterocycloalkyl optionally substituted with 1-3 $Z^5$, or a bridged carbocyclic ring substituted with 0-5 $T^1$;

each $R^9$ is independently H or alkyl optionally substituted with 1-4 $Z^4$;

$R^{10}$ is alkyl substituted with 0-4 $Z^4$, —$C_0$-$C_3$alkyl-cycloalkyl optionally substituted with 1-4 $Z^3$, —$C_0$-$C_3$alkyl-phenyl optionally substituted with 1-4 $Z^3$, —$C_0$-$C_3$alkyl-heteroaryl optionally substituted with 1-3 $Z^5$, or —$C_0$-$C_3$alkyl-heterocycloalkyl optionally substituted with 1-3 $Z^5$;

$R^{11}$ is $NH_2$;

$Z^1$ is cyanoalkyl, —$(CH_2)_{0-2}$—C(O)$OR^9$, —$(CH_2)_{0-2}$—C(O)—N($R^8$)$R^9$, provided that when $Z^1$ is attached to a heteroatom, then $Z^1$ is not C(O)$OR^9$;

each $Z^2$ is independently hydroxyl, halogen, $NH_2$, or CN, provided that not more than 1 $Z^2$ can be $NH_2$;

each $Z^3$ is independently alkyl, halogen, haloalkyl, hydroxyl, hydroxyalkyl, alkoxyl, alkoxyalkyl, or CN;

each $Z^4$ is independently hydroxyl, halogen, alkoxyl, or CN; and each $Z^5$ is independently alkyl, haloalkyl, hydroxyl, hydroxyalkyl, halogen, alkoxyl, alkoxyalkyl, CN, or cyanoalkyl, provided that when $Z^5$ is attached to a heteroatom, then $Z^5$ is not halogen, hydroxyl, alkoxyl, or CN.

2. The compound according to claim 1, wherein ring A is azetidine, pyrrolidine, piperidine, imidazole, thiazole, or pyrazolyl.

3. The compound according to claim 1 having Formula II:

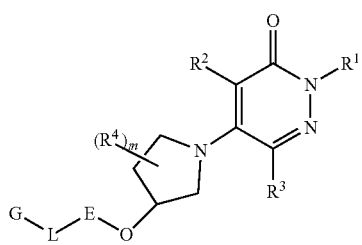

II or a pharmaceutically acceptable salt, a solvate, a tautomer, a stereoisomer, or a deuterated analog thereof, wherein L is absent, —N(H)—, or —O—; and m is 0-2.

4. The compound according to claim 1 having Formula IIIa or IIIb:

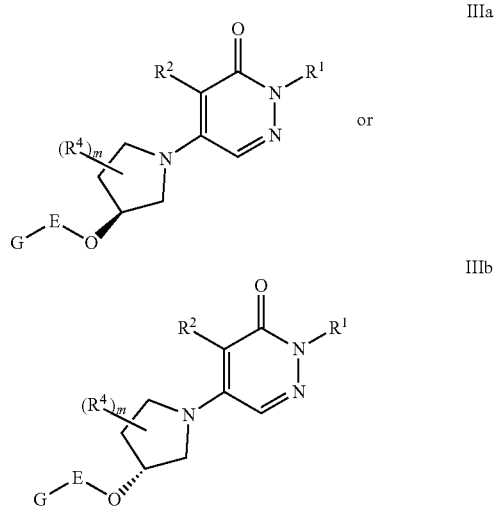

or a pharmaceutically acceptable salt, a solvate, a tautomer, a stereoisomer, or a deuterated analog thereof, wherein:

E is phenyl or a 6 membered heteroaryl, wherein E is substituted with 0-2 Q, provided that when E is a 6 membered heteroaryl, O is not attached to a heteroatom of E;

G is one of the following groups:
(a) $C_3$-$C_6$cycloalkyl substituted with 0-3 $T^1$ and 0-1 $T^2$;
(b) $C_3$-$C_6$cycloalkenyl substituted with 0-3 $T^1$ and 0-1 $T^2$;
(c) a 5-9 membered bridged carbocyclic ring substituted with 0-3 $T^1$ and 0-1 $T^2$;
(d) a 5-9 membered carbocyclic spiro ring containing two cycloalkyl groups joined by one common spiro carbon atom, wherein the carbocyclic spiro ring is substituted with 0-3 $T^1$ and 0-1 $T^2$;
(e) a 6-9 membered heterocyclic spiro ring containing two cyclic groups with at least one heteroatom, wherein the two cyclic groups are joined by one common spiro carbon atom, wherein the heterocyclic spiro ring is substituted with 0-3 $T^5$, 0-1 $T^6$;
(f) phenyl substituted with 0-3 $T^1$ and 0-1 $T^4$;
(g) a 4-6 membered heterocycloalkyl substituted with 0-3 $T^5$ and 0-1 $T^6$;
(h) a 4-6 membered heterocycloalkenyl substituted with 0-3 $T^5$ and 0-1 $T^6$;
(i) a 5-9 membered bridged heterocylic ring substituted with 0-3 $T^5$ and 0-1 $T^6$; or
(j) a 5-6 membered heteroaryl substituted with 0-3 $T^5$ and 0-1 $T^3$;

each Q is independently halogen, CN, or $C_1$-$C_3$alkyl optionally substituted with 1-3 halogens;

each $T^1$ is independently halogen, hydroxyl, $C_1$-$C_6$alkyl optionally substituted with 1-3 $R^b$, $C_2$-$C_5$alkenyl optionally substituted with 1-3 $R^b$, $C_2$-$C_5$alkynyl optionally substituted with 1-3 $R^b$, CN, $C_1$-$C_6$cyanoalkyl, $C_1$-$C_6$alkoxyl optionally substituted with 1-3 $R^b$, or $C_1$-$C_6$alkoxy$C_1$-$C_6$alkyl optionally substituted with 1-3 $R^b$;

$T^2$ is —$(CH_2)_{0-2}$—$N(R^9)SO_2$—$R^7$, —$(CH_2)_{0-2}$—$SO_2$—$R^7$, —$(CH_2)_{0-2}$—$SO_2N(R')R^9$, —$(CH_2)_{0-2}$—$N(R^9)SO_2N(R')R^9$, —$(CH_2)_{0-2}$—$N(R^9)C(O)N(R^9)R^9$, —$(CH_2)_{0-2}$—$N(R^9)C(O)R^8$, —$(CH_2)_{0-2}$—$N(R^9)C(O)OR^9$, —$(CH_2)_{0-2}$—$N(R')R^9$, —$(CH_2)_{0-2}$—$C(O)N(R')R^9$, —$(CH_2)_{0-2}$—$C(O)OR^9$, —$(CH_2)_{0-2}$—$C(O)R^{10}$, —$(CH_2)_{0-2}$—$C(O)H$, —$(CH_2)_{0-2}$—$N(R^9)C(O)R^{10}$, —$(CH_2)_{0-2}C_3$-$C_6$cycloalkyl optionally substituted with 1-4 $Z^3$, —$(CH_2)_{0-2}$-phenyl optionally substituted with 1-3 $Z^5$, or —$(CH_2)_{0-2}$-5-6 membered heteroaryl optionally substituted with 1-3 $Z^5$;

$T^3$ is —$(CH_2)_{0-2}$—$C(O)N(R')R^9$, —$(CH_2)_{0-2}$—$N(R')R^9$, —$(CH_2)_{0-2}$—$C(O)OR^9$, —$(CH_2)_{0-2}$—$C_3$-$C_6$cycloalkyl, —$(CH_2)_{0-2}$-5-6 membered heterocycloalkyl, —O-5-6 membered heterocycloalkyl optionally substituted with 4-chloropyridazin-3-one-5-yl, or —$(CH_2)_{0-2}$-5-9 membered bridged carbocyclic ring, wherein the —$(CH_2)_{0-2}$—$C_3$-$C_6$cycloalkyl, —$(CH_2)_{0-2}$-5-6 membered heterocycloalkyl, or —$(CH_2)_{0-2}$-5-9 membered bridged carbocyclic are each optionally substituted with 1-3 $Z^5$ and 0-1 $Z^1$, provided that when $T^3$ is attached to a heteroatom of G, G cannot be attached to an oxygen or nitrogen atom of $T^3$;

$T^4$ is —$(CH_2)_{0-2}C(O)OR^9$, —$(CH_2)_{0-2}$—$N(R^9)C(O)R^8$, —$(CH_2)_{0-2}$—$N(R^9)SO_2$—$R^7$, —$(CH_2)_{0-2}$—$SO_2$—$R^7$, —$(CH_2)_{0-2}$—$SO_2N(R')R^9$, —$(CH_2)_{0-2}$—$N(R^9)C(O)N(R')R^9$, or $N(R^a)_2$;

each $T^5$ is independently halogen, hydroxyl, $C_1$-$C_6$alkyl optionally substituted with 1-3 $R^b$, $C_2$-$C_6$alkenyl optionally substituted with 1-3 $R^b$, $C_2$-$C_6$alkynyl optionally substituted with 1-3 $R^b$, CN, $C_1$-$C_6$cyanoalkyl, $C_1$-$C_6$alkoxyl optionally substituted with 1-3 $R^b$, or $C_1$-$C_6$alkoxy$C_1$-$C_6$alkyl optionally substituted with 1-3 $R^b$, provided that when $T^5$ is attached to a heteroatom of G, $T^5$ cannot be halogen, hydroxyl, CN, or $C_1$-$C_6$alkoxyl optionally substituted with 1-3 $R^b$;

$T^6$ is —$(CH_2)_{0-2}$—$N(R^9)SO_2$—$R^7$, —$(CH_2)_{0-2}$—$SO_2$—$R^7$, —$(CH_2)_{0-2}$—$SO_2N(R^9)R^9$, —$(CH_2)_{0-2}$—$N(R^9)SO_2N(R')R^9$, —$(CH_2)_{0-2}$—$N(R^9)C(O)N(R')R^9$, —$(CH_2)_{0-2}$—$N(R^9)C(O)R^8$, —$(CH_2)_{0-2}$—$N(R^9)C(O)OR^9$, —$(CH_2)_{0-2}$—$N(R^9)R^9$, —$(CH_2)_{0-2}$—$C(O)$—$N(R')R^9$, —$(CH_2)_{0-2}$—$C(O)OR^9$, —$(CH_2)_{0-2}$—$C(O)R^{10}$, —$(CH_2)_{0-2}$—$N(R^9)C(O)R^{10}$, —N(H)C(H)C=O, —$(CH_2)_{0-2}$—$C_3$-$C_6$cycloalkyl optionally substituted with 1-4 $Z^3$, —$(CH_2)_{0-2}$-5-6 membered heterocycloalkyl optionally substituted with 1-4 $Z^3$, —$(CH_2)_{0-3}$-5-6 membered heteroaryl optionally substituted with 1-3 $Z^5$, or 4-chloropyridazin-3-one-5-yl, provided that when $T^6$ is attached to a heteroatom of G, G cannot be attached to an oxygen or nitrogen atom of $T^6$;

$R^a$ is H or $C_1$-$C_6$alkyl;

$R^b$ is halogen, CN, $CF_3$, or hydroxyl, provided that not more than 1 $R^b$ can be $CF_3$;

$R^2$ is H, halogen, $C_1$-$C_6$alkyl, $C_2$-$C_6$alkenyl, $C_1$-$C_6$alkoxyl, $C_1$-$C_6$haloalkyl, $CF_3$, or CN;

$R^3$ is H, halogen, $C_1$-$C_6$alkyl, CN, or $C_1$-$C_6$ haloalkyl;

each $R^4$ is independently halogen, CN, or $C_1$-$C_3$alkyl optionally substituted with 1-3 halogens;

$R^7$ is $C_1$-$C_6$alkyl optionally substituted with 1-4 $Z^4$, —$C_0$-$C_2$alkyl-$C_3$-$C_6$cycloalkyl optionally substituted with 1-4 $Z^3$, —$C_0$-$C_2$alkyl-phenyl optionally substituted with 1-4 $Z^3$, —$C_0$-$C_2$alkyl-5-6 membered heteroaryl optionally substituted with 1-3 $Z^5$, or —$C_0$-$C_2$alkyl-5-6 membered heterocycloalkyl optionally substituted with 1-3 $Z^5$;

$R^8$ is H, $C_1$-$C_6$alkyl optionally substituted with 1-4 $Z^4$, $C_2$-$C_6$alkenyl optionally substituted with 1-4 $Z^4$, —$C_0$-$C_2$alkyl-$C_3$-$C_6$cycloalkyl optionally substituted with 1-4 $Z^3$, —$C_0$-$C_2$alkyl-phenyl optionally substituted with 1-4 $Z^3$, —$C_0$-$C_2$alkyl-5-6 membered heteroaryl optionally substituted with 1-3 $Z^5$, —$C_0$-$C_2$alkyl-5-6 membered heterocycloalkyl optionally substituted with 1-3 $Z^5$, or a 5-9 membered bridged carbocylic ring substituted with 0-4 Ti;

each $R^9$ is independently H or $C_1$-$C_6$alkyl optionally substituted with 1-4 $Z^4$;

$R^{10}$ is $C_1$-$C_6$alkyl substituted with 0-4 $Z^4$, —$C_0$-$C_2$alkyl-$C_3$-$C_6$cycloalkyl optionally substituted with 1-4 $Z^3$, —$C_0$-$C_2$alkyl-phenyl optionally substituted with 1-4 $Z^3$, —$C_0$-$C_2$alkyl-5-6 membered heteroaryl optionally substituted with 1-3 $Z^5$, or —$C_0$-$C_2$alkyl-5-6 membered heterocycloalkyl optionally substituted with 1-3 $Z^5$;

$R^{11}$ is $NH_2$;

$Z^1$ is $C_1$-$C_6$cyanoalkyl, —$(CH_2)_{0-2}$—$C(O)OR^9$, —$(CH_2)_{0-2}$—$C(O)$—$N(R^8)R^9$, provided that when $Z^1$ is attached to a heteroatom, then $Z^1$ is not —$C(O)OR^9$;

each $Z^2$ is independently hydroxyl, halogen, CN;

each $Z^3$ is independently $C_1$-$C_6$alkyl, halogen, $C_1$-$C_6$haloalkyl, hydroxyl, $C_1$-$C_6$hydroxyalkyl, $C_1$-$C_6$alkoxyl, or CN;

each $Z^4$ is independently, hydroxyl, halogen, $C_1$-$C_6$alkoxyl, or CN; and each $Z^5$ is independently $C_1$-$C_6$alkyl, $C_1$-$C_6$haloalkyl, hydroxyl, $C_1$-$C_6$hydroxyalkyl, halogen, $C_1$-$C_6$alkoxyl, CN, or $C_1$-$C_6$cyanoalkyl, provided that when $Z^5$ is attached to a heteroatom, then $Z^5$ is not halogen, hydroxyl, $C_1$-$C_6$alkoxyl, or CN.

5. The compound according to claim 1, wherein:

E is phenyl or a 6 membered heteroaryl, wherein E is substituted with 0-1 Q, provided that when E is a 6 membered heteroaryl, O is not attached to a heteroatom of E;

G is one of the following groups:
(a) $C_3$-$C_6$cycloalkyl substituted with 0-2 $T^1$ and 0-1 $T^2$;
(b) $C_3$-$C_6$cycloalkenyl substituted with 0-2 $T^1$ and 0-1 $T^2$;
(c) a 5-9 membered bridged carbocyclic ring substituted with 0-2 $T^1$ and 0-1 $T^2$;
(d) a 5-9 membered carbocyclic spiro ring containing two cycloalkyl groups joined by one common spiro carbon atom, wherein the carbocyclic spiro ring is substituted with 0-2 $T^1$ and 0-1 $T^2$;
(e) a 6-9 membered heterocyclic spiro ring containing two cyclic groups with at least one heteroatom, wherein the two cyclic groups are joined by one common spiro carbon atom, wherein the heterocyclic spiro ring is substituted with 0-2 $T^5$, 0-1 $T^6$;
(f) phenyl substituted with 0-2 $T^1$ and 0-1 $T^4$;
(g) a 4-6 membered heterocycloalkyl substituted with 0-2 $T^5$ and 0-1 $T^6$;
(h) a 4-6 membered heterocycloalkenyl substituted with 0-2 $T^5$ and 0-1 $T^6$;
(i) a 5-9 membered bridged heterocylic ring substituted with 0-2 $T^5$ and 0-1 $T^6$; or
(j) a 5-6 membered heteroaryl substituted with 0-2 $T^5$ and 0-1 $T^3$;

Q is independently halogen, CN, or $C_1$-$C_4$alkyl optionally substituted with 1-3 halogens;

each $T^1$ is independently halogen, hydroxyl, $C_1$-$C_4$alkyl optionally substituted with 1-3 $R^b$, $C_2$-$C_4$alkenyl optionally substituted with 1-3 $R^b$, $C_2$-$C_4$alkynyl optionally substituted with 1-3 $R^b$, CN, $C_1$-$C_4$cyanoalkyl, $C_1$-$C_4$alkoxyl optionally substituted with 1-3 $R^b$, or $C_1$-$C_4$alkoxy$C_1$-$C_4$alkyl optionally substituted with 1-3 $R^b$;

$T^2$ is —$(CH_2)_{0-1}$—$N(R^9)SO_2$—$R^7$, —$(CH_2)_{0-1}$—$SO_2$—$R^7$, —$(CH_2)_{0-1}$—$SO_2N(R^8)R^9$, —$(CH_2)_{0-1}$—$N(R^9)SO_2N(R^9)R^9$, —$(CH_2)_{0-1}$—$N(R^9)C(O)N(R^8)R^9$, —$(CH_2)_{0-1}$—$N(R^9)C(O)R^8$, —$(CH_2)_{0-1}$—$N(R^9)C(O)OR^9$, —$(CH_2)_{0-1}$—$N(R^8)R^9$, —$(CH_2)_{0-1}$—$C(O)N(R^9)R^9$, —$(CH_2)_{0-1}$—$C(O)OR^9$, —$(CH_2)_{0-1}$—$C(O)R^{10}$, —$(CH_2)_{0-1}$—$C(O)H$, —$(CH_2)_{0-1}$—$N(R^9)C(O)R^{10}$, —$(CH_2)_{0-2}C_3$-$C_6$cycloalkyl optionally substituted with 1-3 $Z^3$, —$(CH_2)_{0-1}$-phenyl optionally substituted with 1-3 $Z^5$, or —$(CH_2)_{0-1}$-5-6 membered heteroaryl optionally substituted with 1-3 $Z^5$;

$T^3$ is —$(CH_2)_{0-2}$—$C(O)N(R^9)R^9$, —$(CH_2)_{0-2}$—$N(R^9)R^9$, —$(CH_2)_{0-2}$—$C(O)OR^9$, —$(CH_2)_{0-2}$—$C_3$-$C_6$cycloalkyl, —$(CH_2)_{0-2}$-5-6 membered heterocycloalkyl, —O-5-6 membered heterocycloalkyl optionally substituted with 4-chloropyridazin-3-one-5-yl, or —$(CH_2)_{0-2}$-5-9 membered bridged carbocyclic ring, wherein the —$(CH_2)_{0-2}$—$C_3$-$C_6$cycloalkyl, —$(CH_2)_{0-1}$-5-6 membered heterocycloalkyl, or —$(CH_2)_{0-2}$-5-9 membered bridged carbocyclic are each optionally substituted with 1-3 $Z^5$ and 0-1 $Z^1$, provided that when $T^3$ is attached to a heteroatom of G, G cannot be attached to an oxygen or nitrogen atom of $T^3$;

$T^4$ is —$(CH_2)_{0-1}C(O)OR^9$, —$(CH_2)_{0-1}$—$N(R^9)C(O)R^9$, —$(CH_2)_{0-1}$—$N(R^9)SO_2$—$R^7$, —$(CH_2)_{0-1}$—$SO_2$—$R^7$, —$(CH_2)_{0-1}$—$SO_2N(R^9)R^9$, —$(CH_2)_{0-1}$—$N(R^9)C(O)N(R^9)R^9$, or $N(R^a)$ each $T^5$ is independently halogen, hydroxyl, $C_1$-$C_4$alkyl optionally substituted with 1-3 $R^b$, $C_2$-$C_4$alkenyl optionally substituted with 1-3 $R^b$, $C_2$-$C_4$alkynyl optionally substituted with 1-3 $R^b$, CN, $C_1$-$C_4$cyanoalkyl, $C_1$-$C_4$alkoxyl optionally substituted with 1-3 $R^b$, or $C_1$-$C_4$alkoxy$C_1$-$C_4$alkyl optionally substituted with 1-3 $R^b$, provided that when $T^5$ is attached to a heteroatom of G, $T^5$ cannot be halogen, hydroxyl, CN, or $C_1$-$C_4$alkoxyl optionally substituted with 1-3 $R^b$;

$T^6$ is —$(CH_2)_{0-1}$—$N(R^9)SO_2$—$R^7$, —$(CH_2)_{0-1}$—$SO_2$—$R^7$, —$(CH_2)_{0-1}$—$SO_2N(R^9)R^9$, —$(CH_2)_{0-1}$—$N(R^9)SO_2N(R^9)R^9$, —$(CH_2)_{0-1}$—$N(R^9)C(O)N(R^9)R^9$, —$(CH_2)_{0-1}$—$N(R^9)C(O)R^9$, —$(CH_2)_{0-1}$—$N(R^9)C(O)OR^9$, —$(CH_2)_{0-1}$—$N(R^9)R^9$, —$(CH_2)_{0-1}$—$C(O)$—$N(R^9)R^9$, —$(CH_2)_{0-1}$—$C(O)OR^9$, —$(CH_2)_{0-1}$—$C(O)R^{10}$, —$(CH_2)_{0-1}$—$N(R^9)C(O)R^{10}$, —$N(H)C(H)$=O, —$(CH_2)_{0-1}$—$C_3$-$C_6$cycloalkyl optionally substituted with 1-4 $Z^3$, —$(CH_2)_{0-1}$-5-6 membered heterocycloalkyl optionally substituted with 1-4 $Z^3$, —$(CH_2)_{0-1}$-5-6 membered heteroaryl optionally substituted with 1-3 $Z^5$, or 4-chloropyridazin-3-one-5-yl, provided that when $T^6$ is attached to a heteroatom of G, G cannot be attached to an oxygen or nitrogen atom of $T^6$;

$R^a$ is H or $C_1$-$C_4$alkyl;

$R^b$ is F, Cl, CN, $CF_3$, or hydroxyl, provided that not more than 1 $R^b$ can be $CF_3$;

$R^2$ is H, halogen, $C_1$-$C_4$alkyl, $C_2$-$C_4$alkenyl, $C_1$-$C_4$alkoxyl, $C_1$-$C_4$haloalkyl, $CF_3$, or CN;

$R^3$ is H, halogen, $C_1$-$C_4$alkyl, CN, or $C_1$-$C_4$haloalkyl;

each $R^4$ is independently halogen, CN, or $C_1$-$C_4$alkyl optionally substituted with 1-3 halogens;

$R^7$ is $C_1$-$C_4$alkyl optionally substituted with 1-3 $Z^4$, —$C_0$-$C_3$alkyl-$C_3$-$C_6$cycloalkyl optionally substituted with 1-3 $Z^3$, —$C_0$-$C_3$alkyl-phenyl optionally substituted with 1-3 $Z^3$, —$C_0$-$C_1$alkyl-5-6 membered heteroaryl optionally substituted with 1-3 $Z^5$, or —$C_0$-$C_1$alkyl-5-6 membered heterocycloalkyl optionally substituted with 1-3 $Z^5$;

$R^8$ is H, $C_1$-$C_4$alkyl optionally substituted with 1-3 $Z^4$, $C_2$-$C_4$alkenyl optionally substituted with 1-3 $Z^4$, —$C_0$-$C_1$alkyl-$C_3$-$C_6$cycloalkyl optionally substituted with 1-3 $Z^3$, —$C_0$-$C_1$alkyl-phenyl optionally substituted with 1-3 $Z^3$, —$C_0$-$C_1$alkyl-5-6 membered heteroaryl optionally substituted with 1-3 $Z^5$, —$C_0$-$C_1$alkyl-5-6 membered heterocycloalkyl optionally substituted with 1-3 $Z^5$, or a 5-9 membered bridged carbocyclic ring substituted with 0-3 Ti;

each $R^9$ is independently H or $C_1$-$C_4$alkyl optionally substituted with 1-3 $Z^4$;

$R^{10}$ is $C_1$-$C_4$alkyl substituted with 0-3 $Z^4$, —$C_0$-$C_1$alkyl-$C_3$-$C_6$cycloalkyl optionally substituted with 1-3 $Z^3$, —$C_0$-$C_1$alkyl-phenyl optionally substituted with 1-3 $Z^3$, —$C_0$-$C_1$alkyl-5-6 membered heteroaryl optionally substituted with 1-3 $Z^5$, or —$C_0$-$C_1$alkyl-5-6 membered heterocycloalkyl optionally substituted with 1-3 $Z^5$;

$Z^1$ is $C_1$-$C_4$cyanoalkyl, —$(CH_2)_{0-1}$—$C(O)OR^9$, —$(CH_2)_{0-1}$—$C(O)$—$N(R^8)R^9$, provided that when $Z^1$ is attached to a heteroatom, then $Z^1$ is not —$C(O)OR^9$;

each $Z^2$ is independently hydroxyl, halogen, or CN;

each $Z^3$ is independently $C_1$-$C_4$alkyl, halogen, $C_1$-$C_4$haloalkyl, hydroxyl, $C_1$-$C_4$hydroxyalkyl, $C_1$-$C_4$alkoxyl, or CN;

each $Z^4$ is independently hydroxyl, halogen, $C_1$-$C_4$alkoxyl, or CN; and each $Z^5$ is independently $C_1$-$C_4$alkyl, $C_1$-$C_6$haloalkyl, hydroxyl, $C_1$-$C_4$hydroxyalkyl, halogen, $C_1$-$C_4$alkoxyl, CN, or $C_1$-$C_4$cyanoalkyl, provided that when $Z^5$ is attached to a heteroatom, then $Z^5$ is not halogen, hydroxyl, $C_1$-$C_4$alkoxyl, or CN.

6. The compound according to claim 1, wherein $R^1$ is —$CH_2CH_2OH$, —$CH_2CH_2CH_2OH$, —$CH_2CH(OH)CH_2OH$, or —$CH_2CH(CH_3)OH$;

$R^2$ is $C_1$, Br, $CF_3$, or CN; and

E is pyridyl, phenyl, pyrimidinyl, or pyridazinyl.

7. The compound according to claim 6, wherein $R^2$ is Cl.

8. A compound according claim 1 having any one of the following formulae:

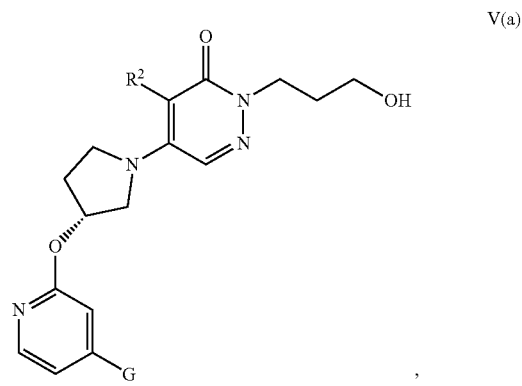

V(a)

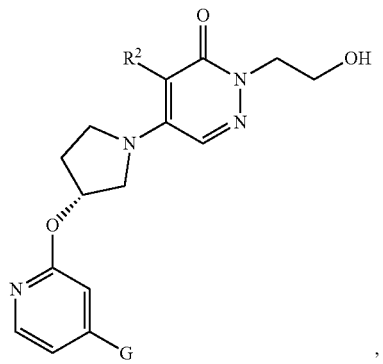 V(b),
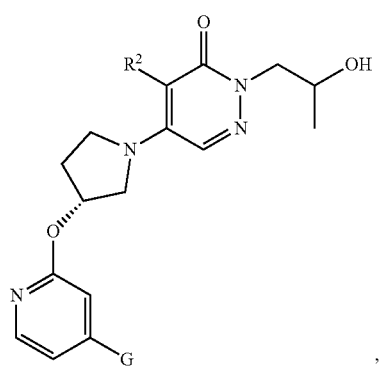 V(c),
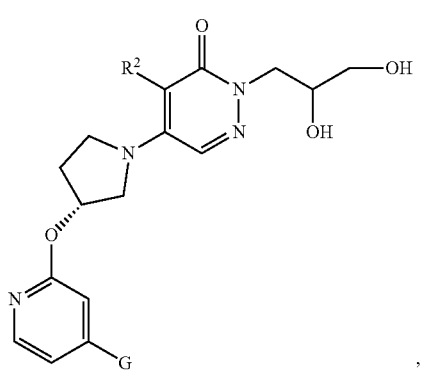 V(d),
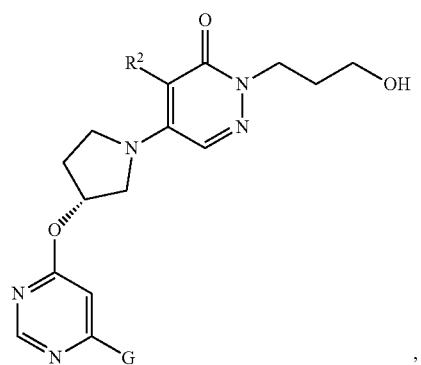 V(e),
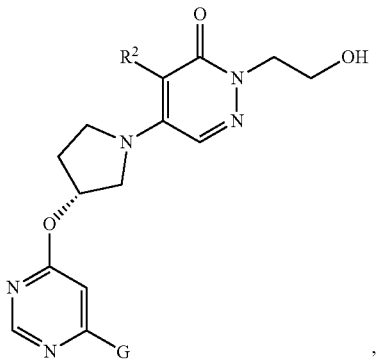 V(f),

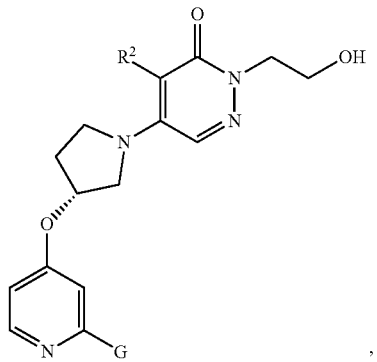 V(j)
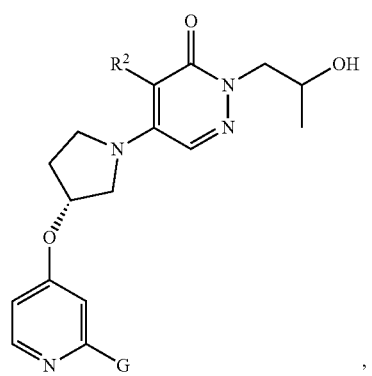 V(k)
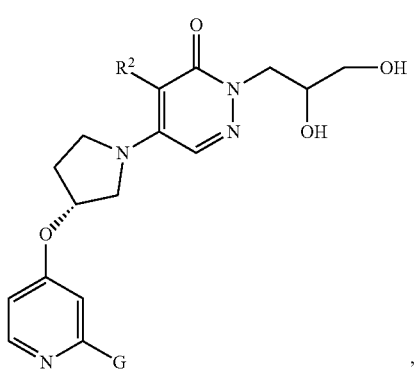 V(l)
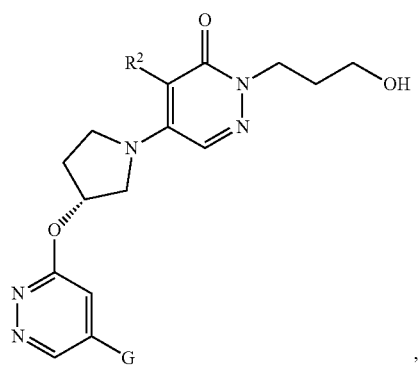 V(m)
 V(n)
 V(o)
 V(p)
 V(q)

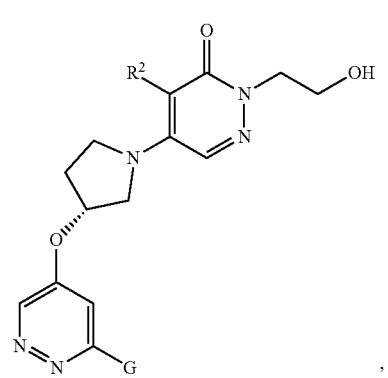
V(r)
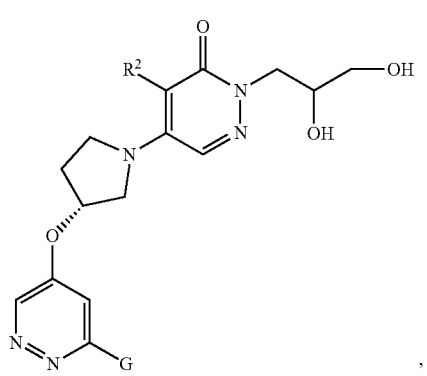
V(s)
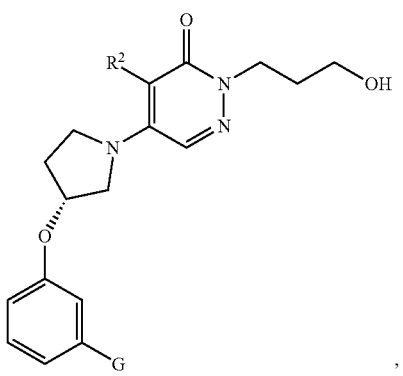
V(t)
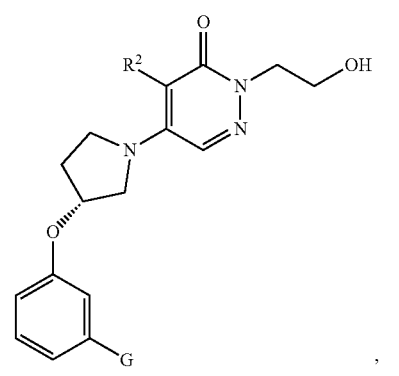
V(u)
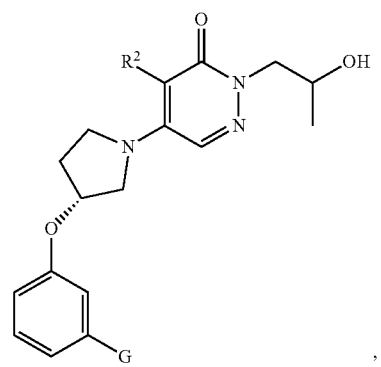
V(v)
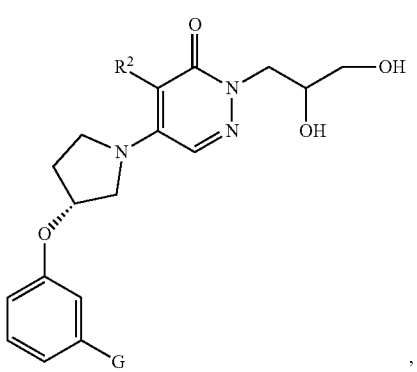
V(w)
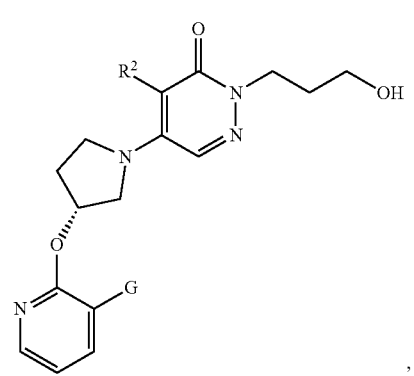
V(x)
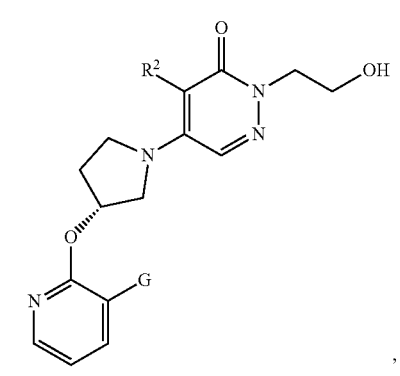
V(y)

-continued
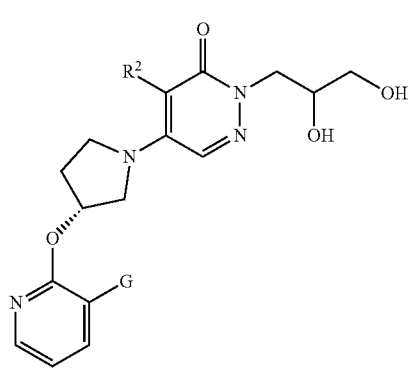
V(z)
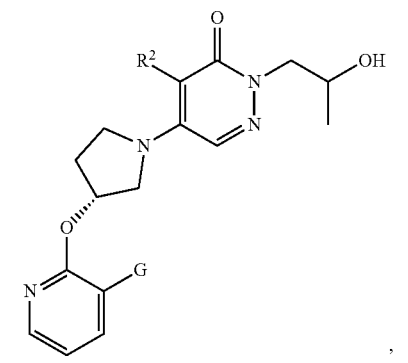
V(aa)
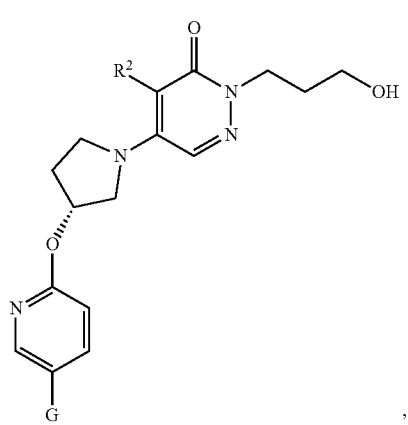
V(ab)
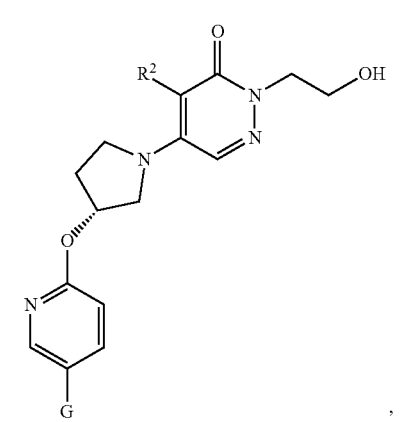
V(ac)
-continued
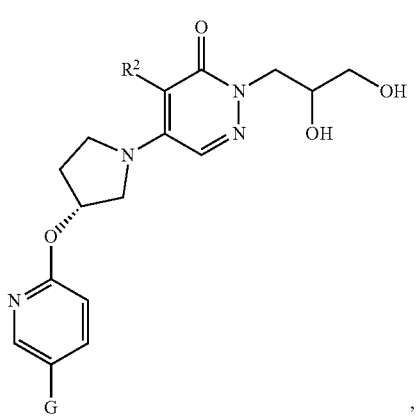
V(ad)
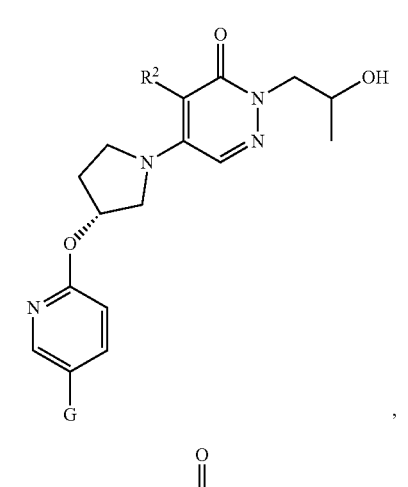
V(ae)
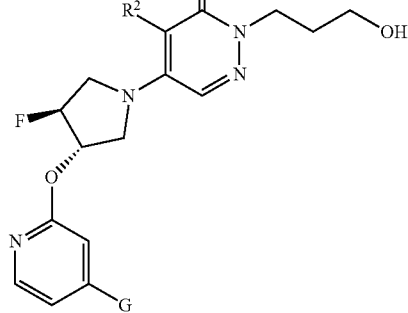
V(af)
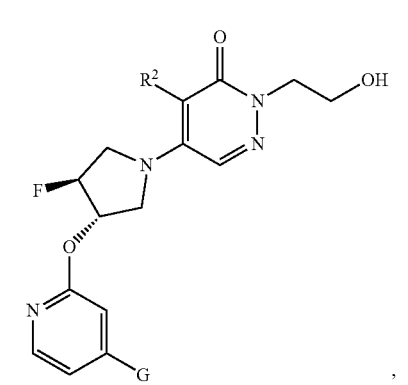
V(ag)

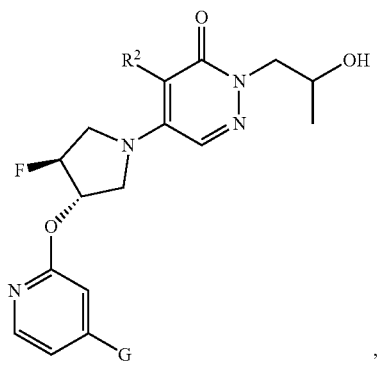
V(ah)
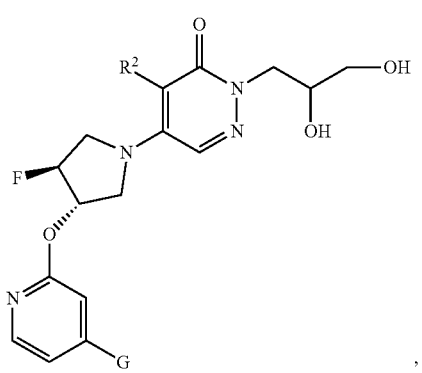
V(ai)
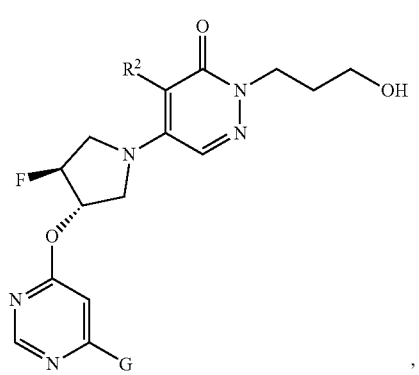
V(aj)
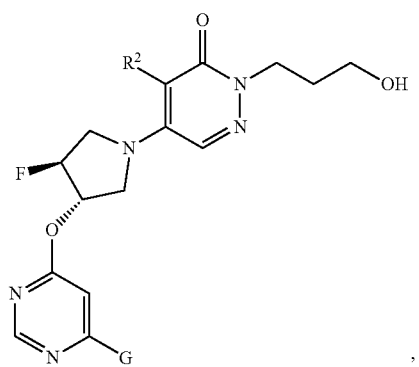
V(aj)
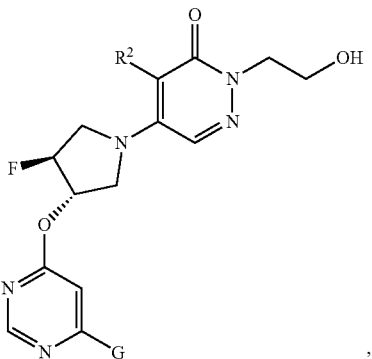
V(ak)
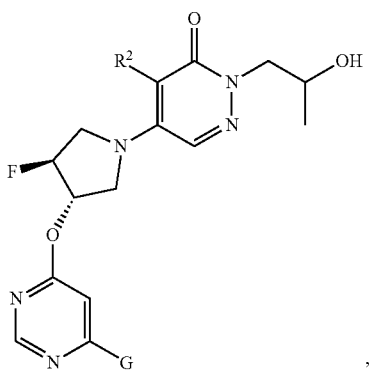
V(al)
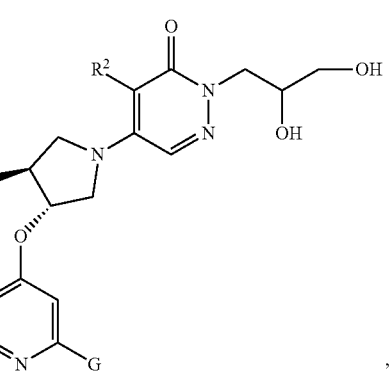
V(am)
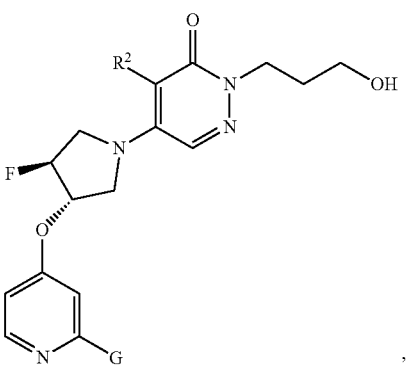
V(an)

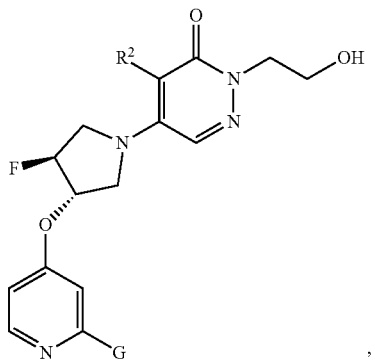
V(ao)
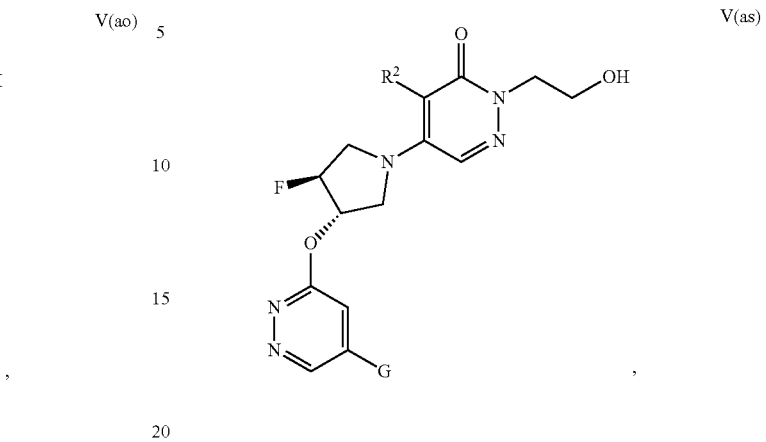
V(as)
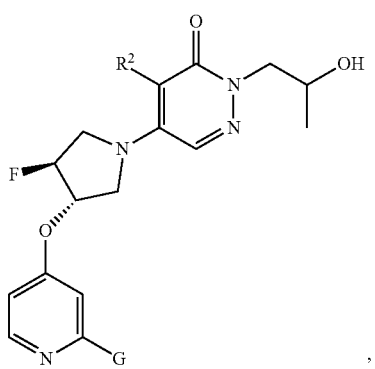
V(ap)
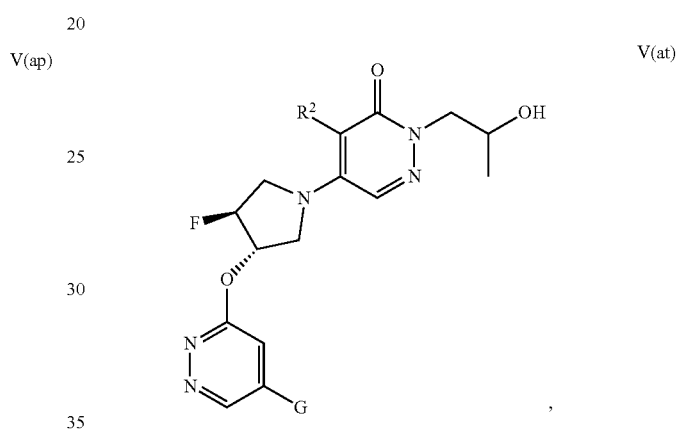
V(at)
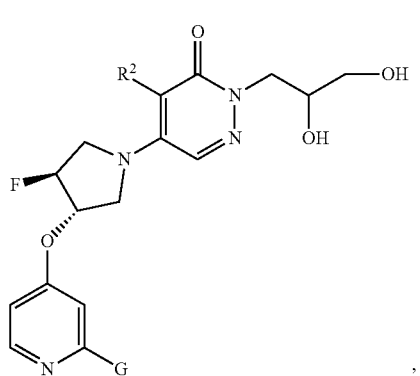
V(aq)
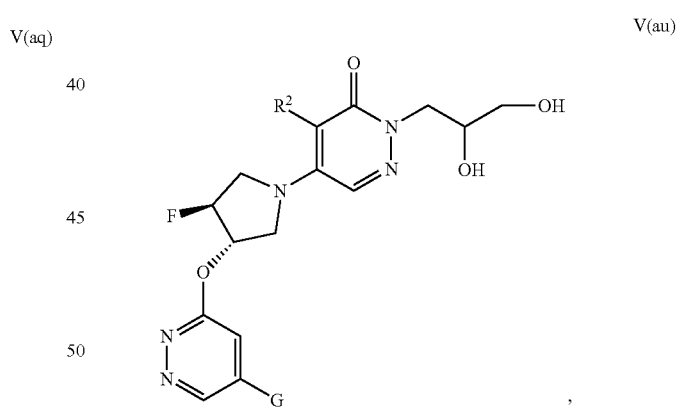
V(au)
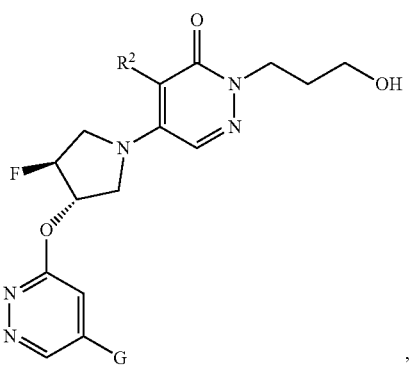
V(ar)
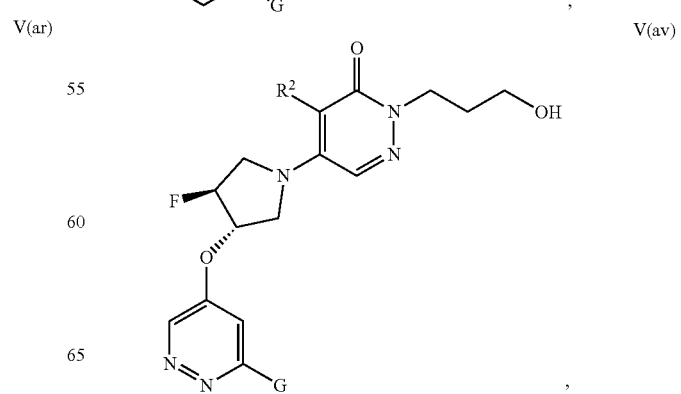
V(av)

V(aw) 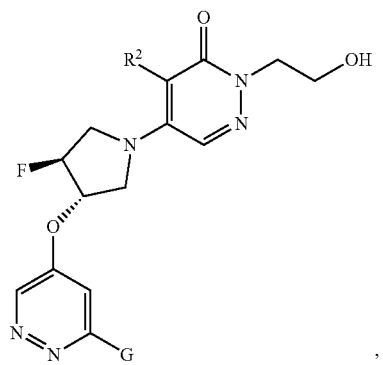
V(ax) 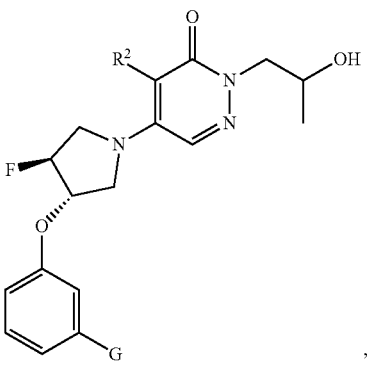
V(ay) 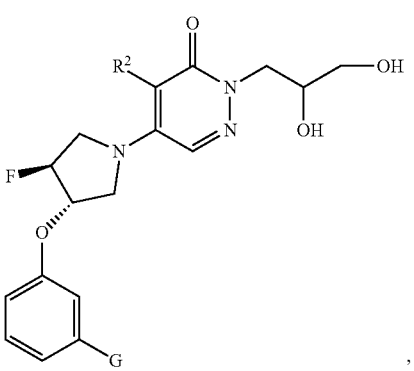
V(az) 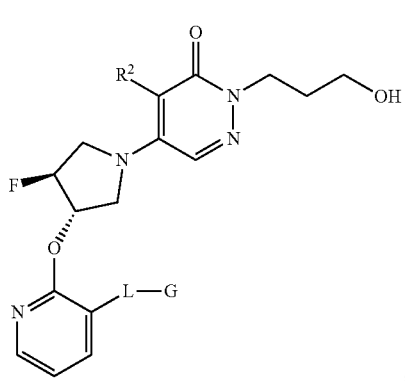
V(ba) 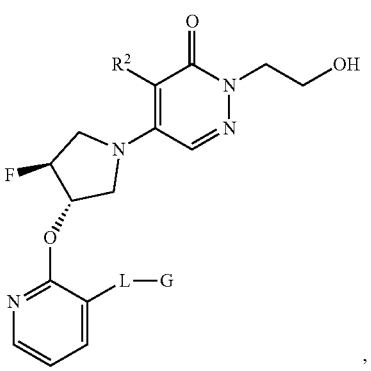
V(bb)
V(bc)
V(bd)

V(be) 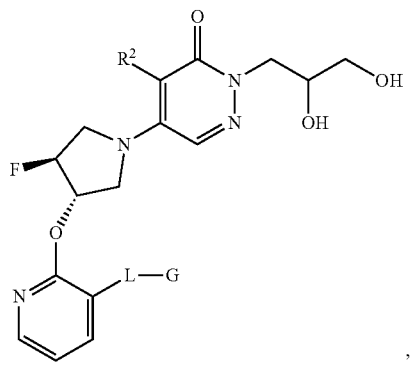

V(bf) 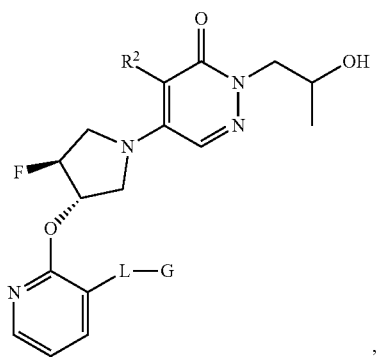

V(bg) 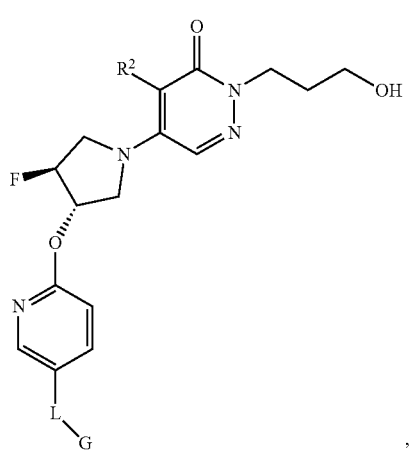

V(bh) 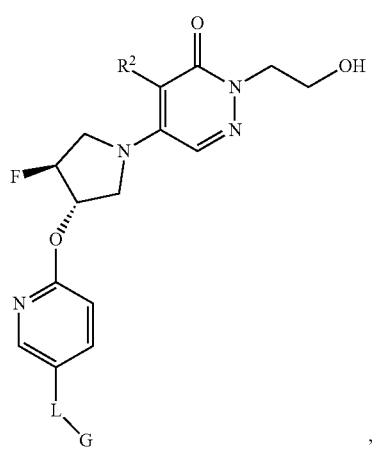

V(bi) 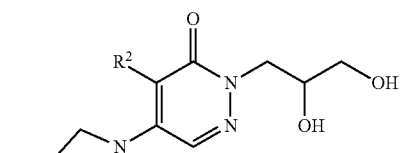

V(bj) 

or a pharmaceutically acceptable salt thereof, wherein $R^2$ is Cl, Br, $CF_3$, or CN.

9. The compound according to claim 1, wherein $T^3$ is —$CH_2C(O)N(H)$cyclopropyl, —$CH_2C(O)N(H)CH_3$, —$CH_2$—COOH, oxetanyl, —$(CH_2)_{0-2}$cyclopropyl, —$(CH_2)_{0-2}$cyclobutyl, —$(CH_2)_{0-2}$-tetrahydropyran, —$(CH_2)_{0-2}$-tetrahydrofuran, —$(CH_2)_{0-2}$azetidinyl, —$(CH_2)_{0-2}$pyrrolidinyl, or —$(CH_2)_{0-2}$morpholinyl.

10. The compound according to claim 1, wherein G is one of the following formulae:

(a) 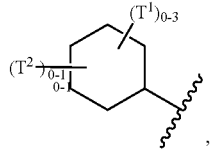

(b) 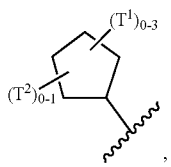

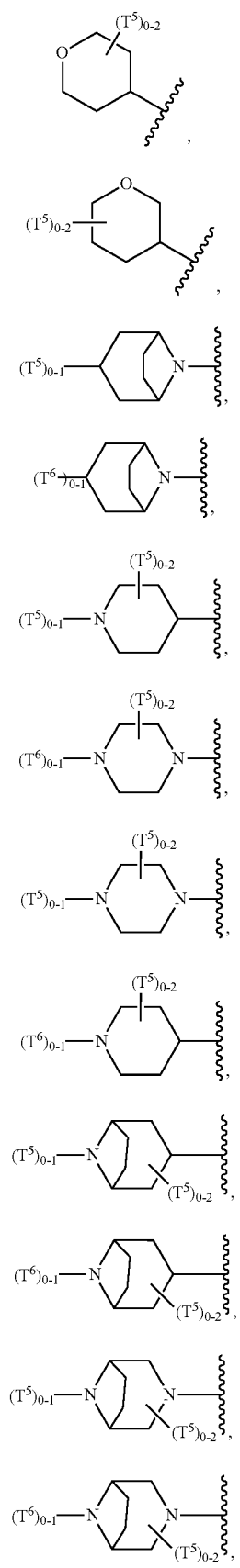
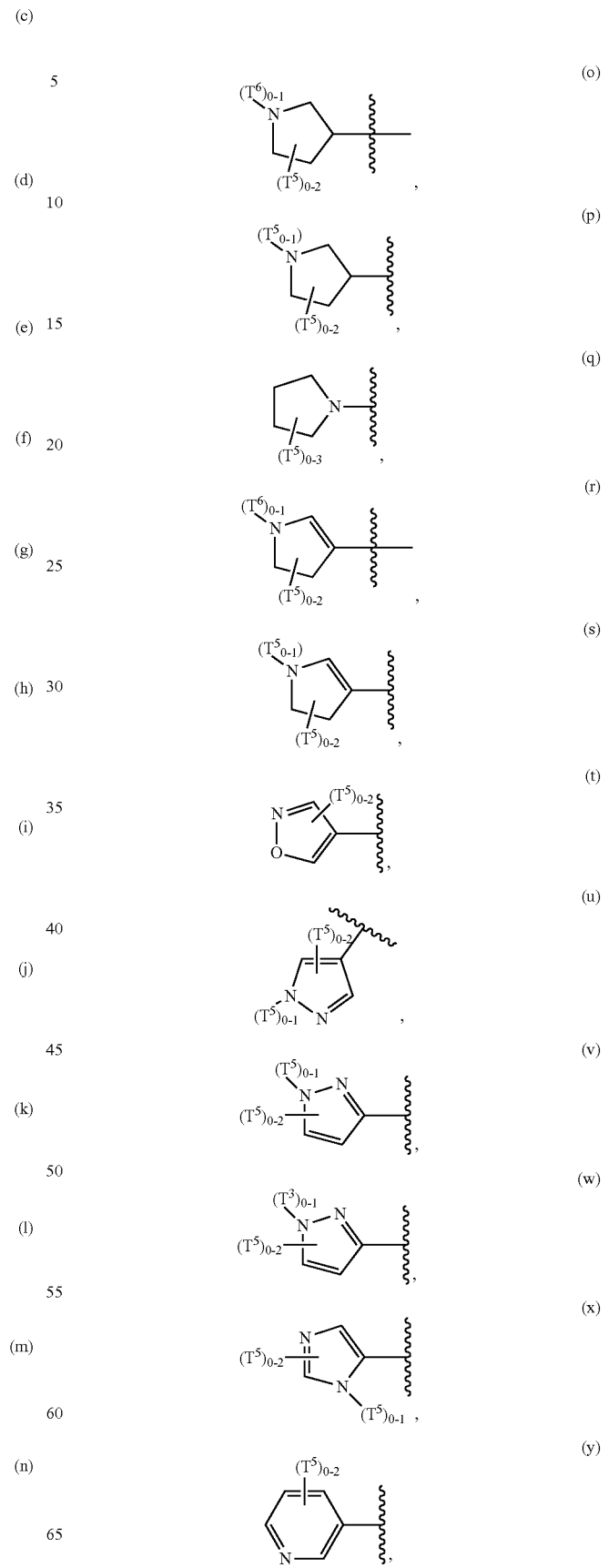

-continued
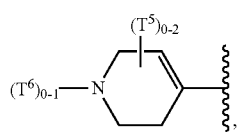 (z)
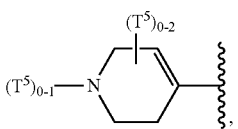 (aa)
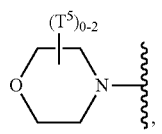 (ab)
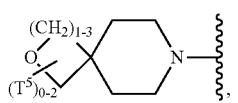 (ac)
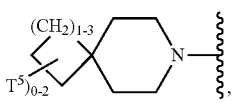 (ad)
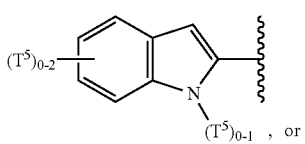 (ae)
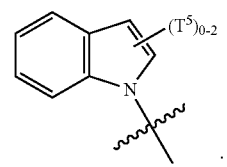 , or (af)
11. The compound according to claim 1, wherein G is one of the following formulae:
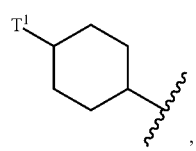 (a)
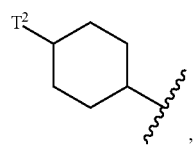 (b)
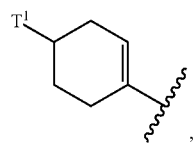 (c)
-continued
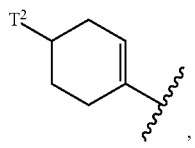 (d)
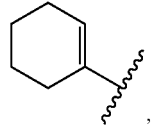 (e)
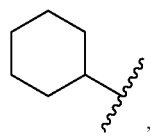 (f)
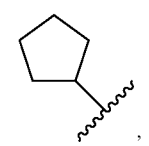 (g)
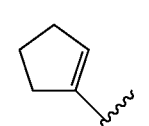 (h)
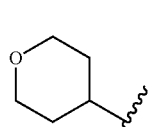 (i)
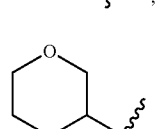 (j)
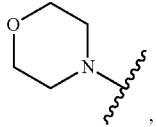 (k)
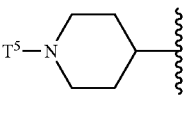 (l)
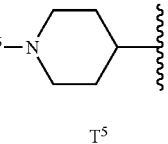 (m)
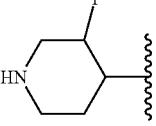 (n)

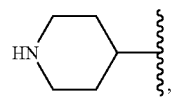 (o)
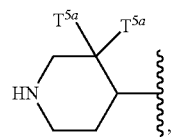 (p)
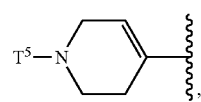 (q)
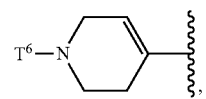 (r)
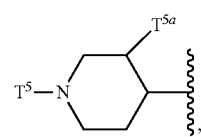 (s)
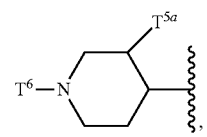 (t)
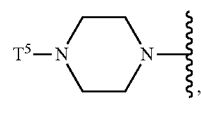 (u)
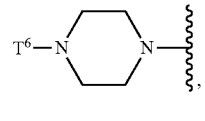 (v)
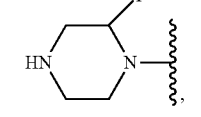 (w)
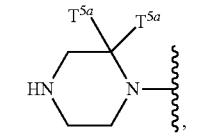 (x)
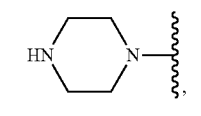 (y)
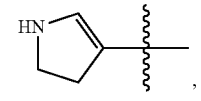 (z)
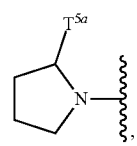 (aa)
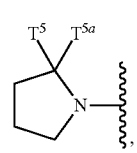 (ab)
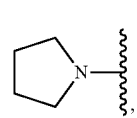 (ac)
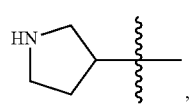 (ad)
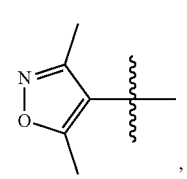 (ae)
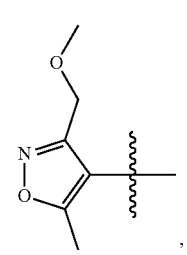 (af)
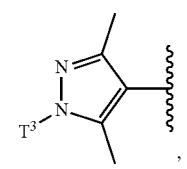 (ag)
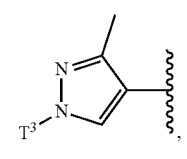 (ah)
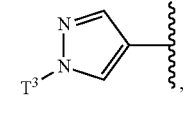 (ai)
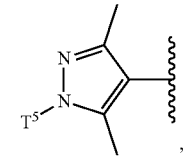 (aj)

-continued
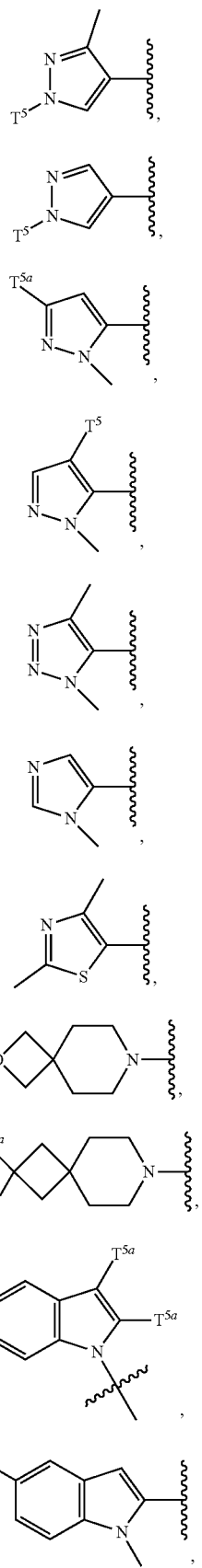
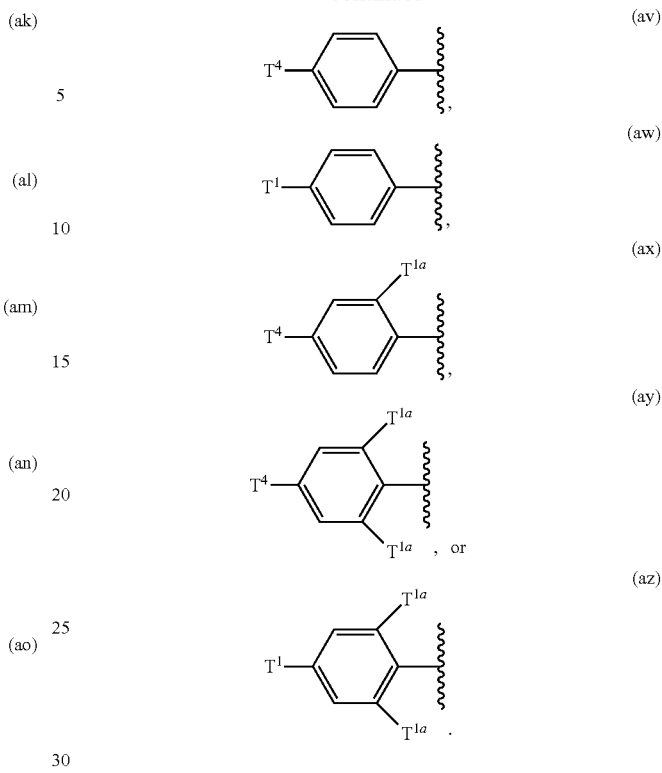
each T$^{1a}$ is independently F, Cl, or CH$_3$; and
each T$^{5a}$ is independently F, Cl, or CH$_3$.
12. The compound according to claim 11, wherein G is one of formulae (ae), (af), (ag), (ah), (ai), (aj), (ak), (al), (am), (an), (ao), (ap), or (aq).
13. A compound selected from the group consisting of:
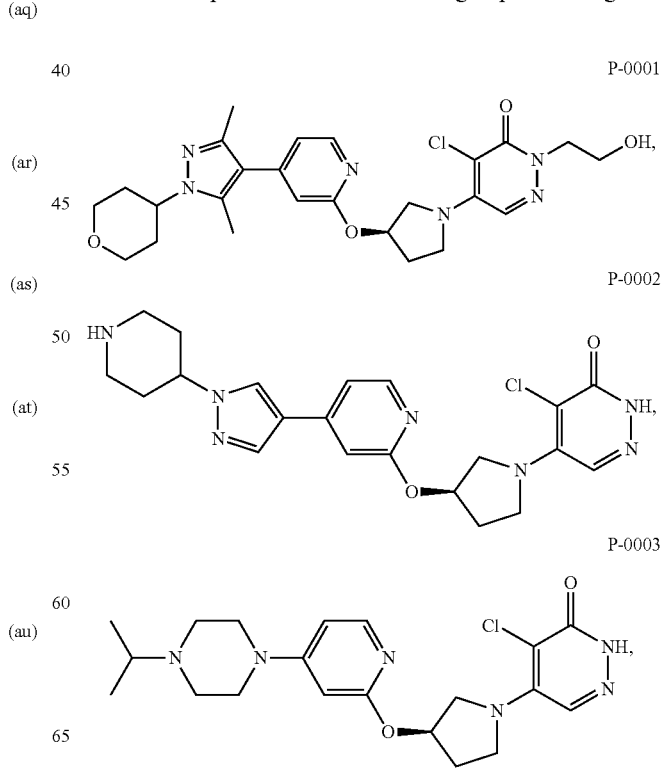

P-0004
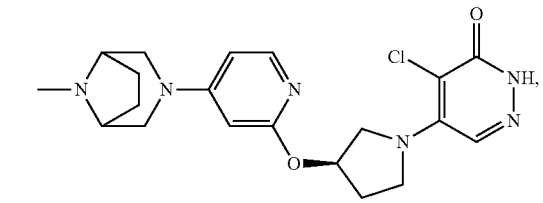
P-0005
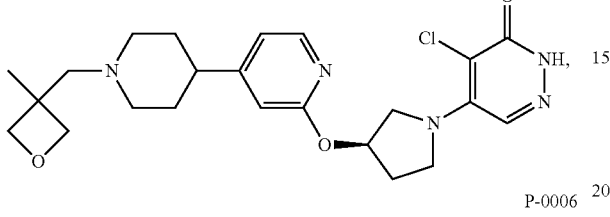
P-0006
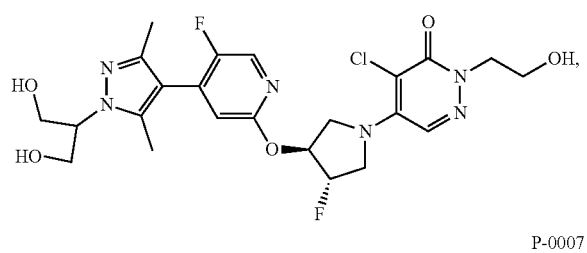
P-0007
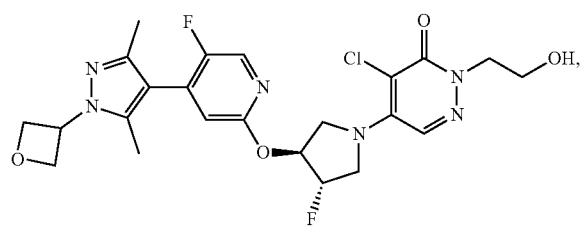
P-0008
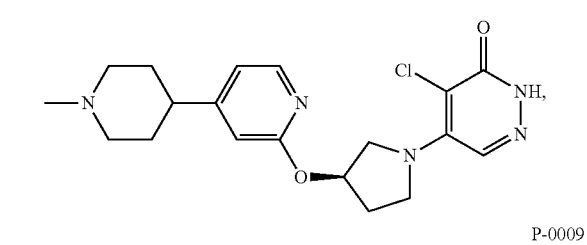
P-0009
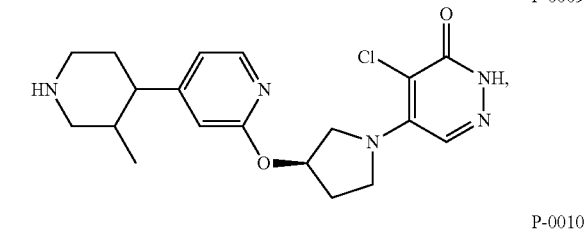
P-0010
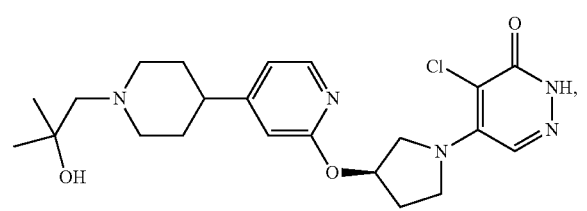
P-0011
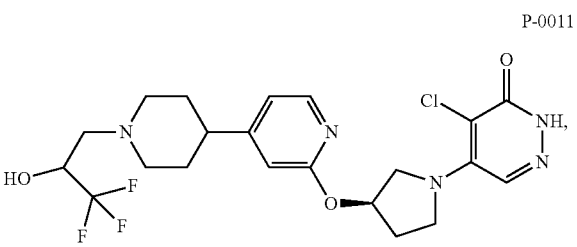
P-0012
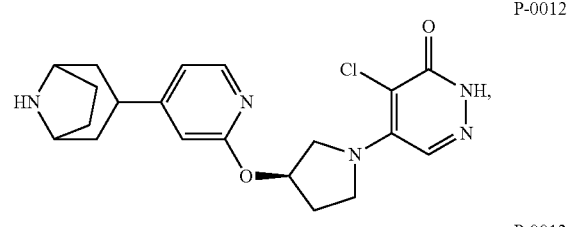
P-0013
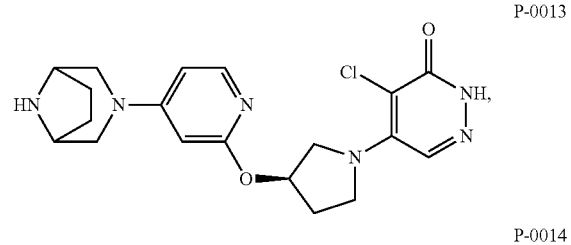
P-0014
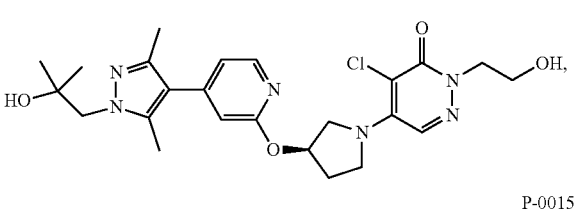
P-0015
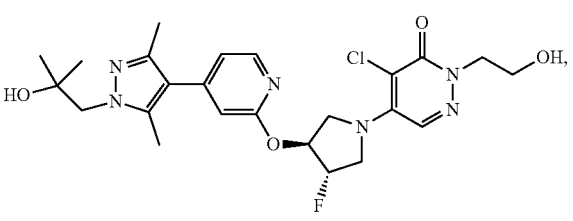
P-0016
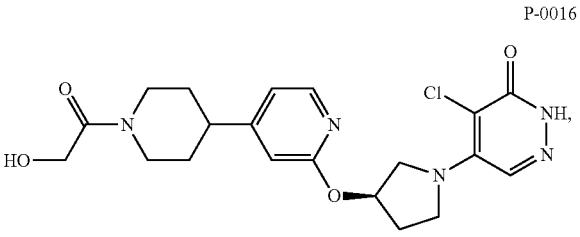
P-0017
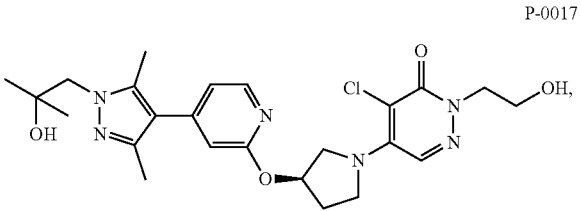

-continued
P-0018
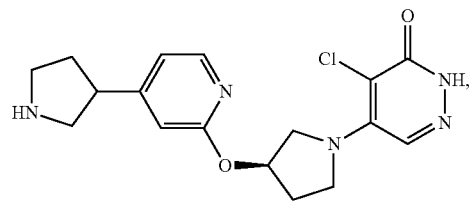
P-0019
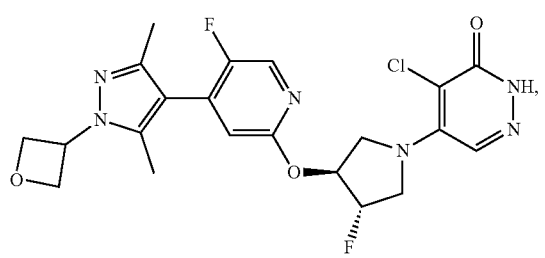
P-0020
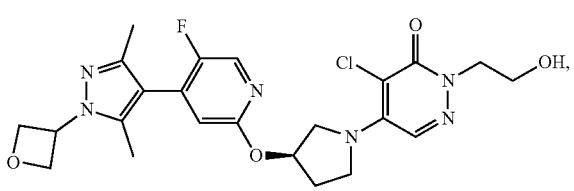
P-0021
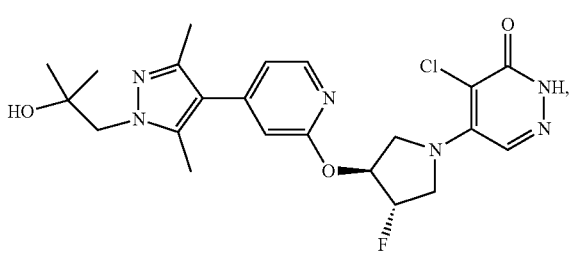
P-0022
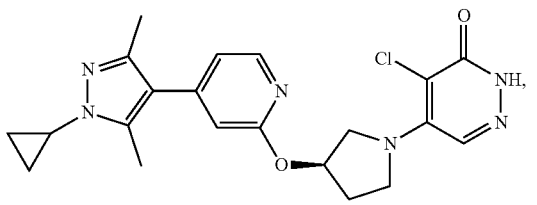
P-0023
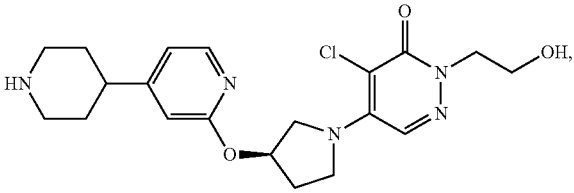
P-0024
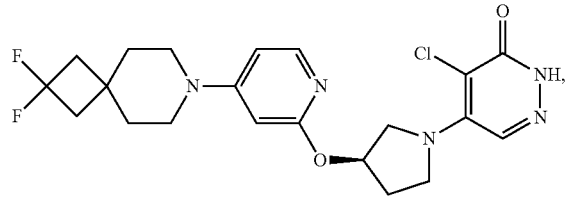
-continued
P-0025
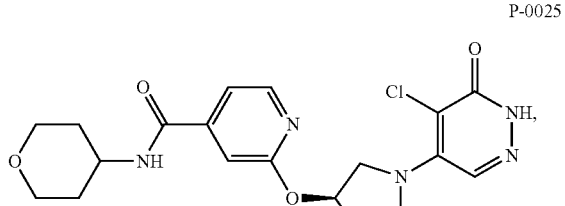
P-0026
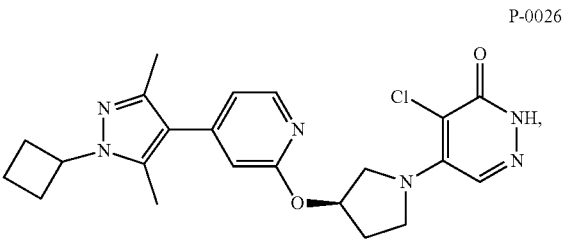
P-0027
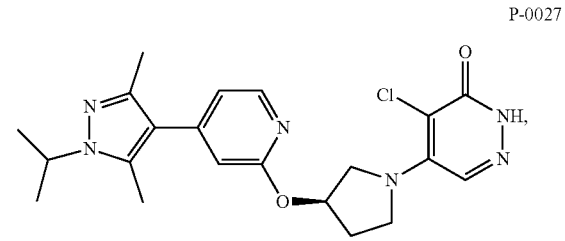
P-0028
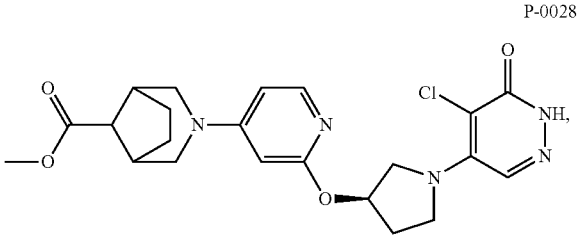
P-0029
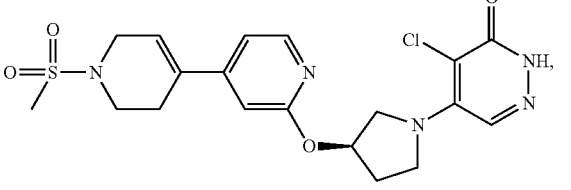
P-0030
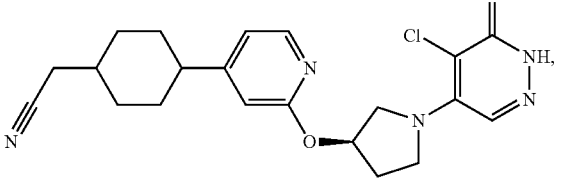
P-0031
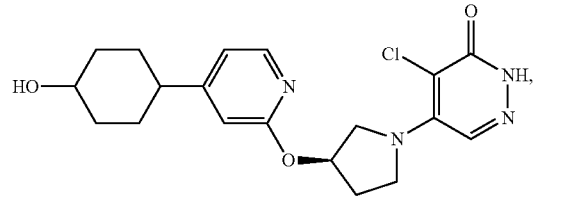

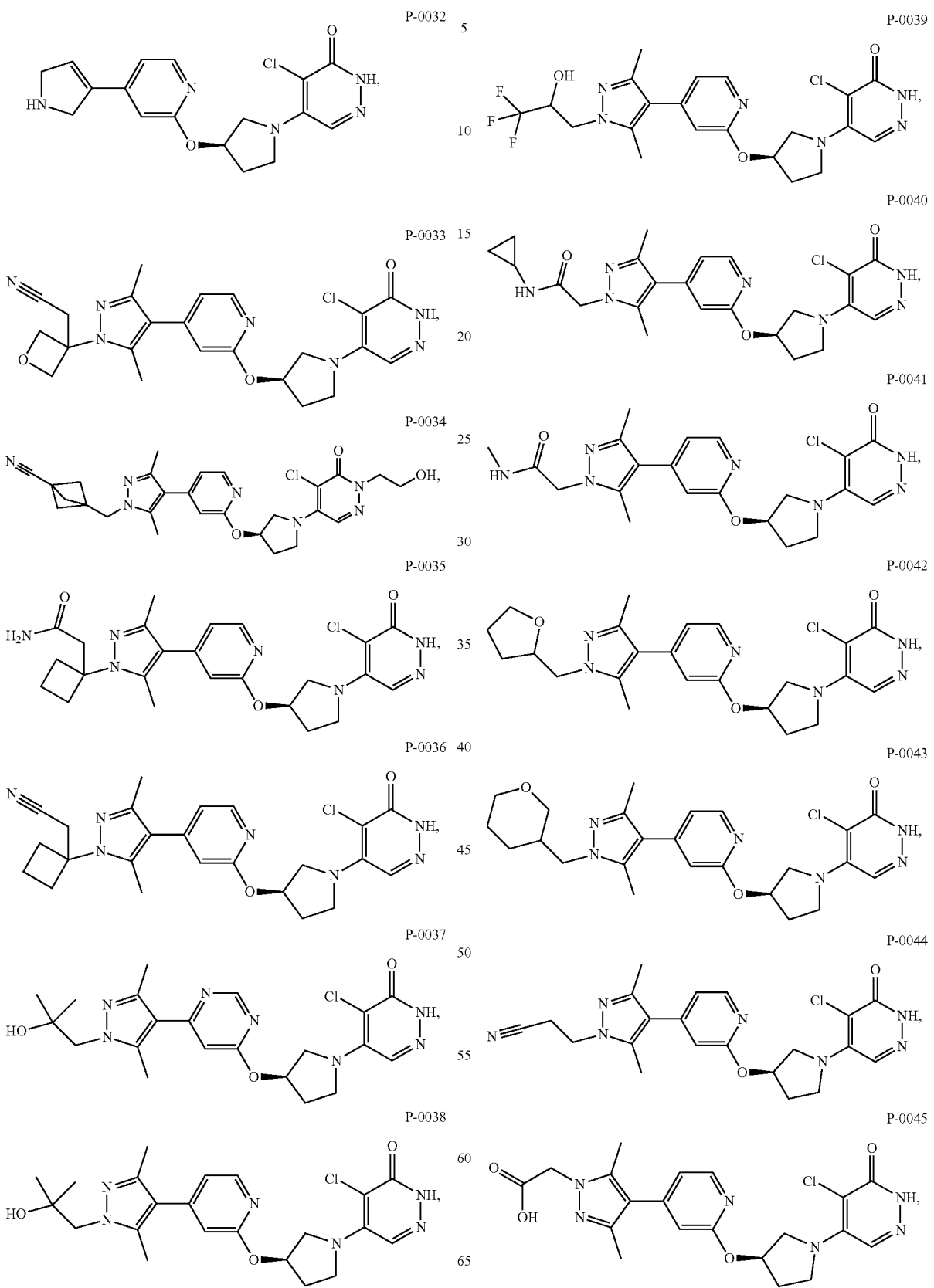

P-0046
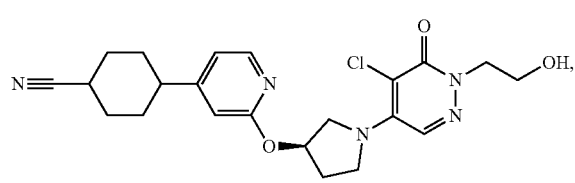
P-0047
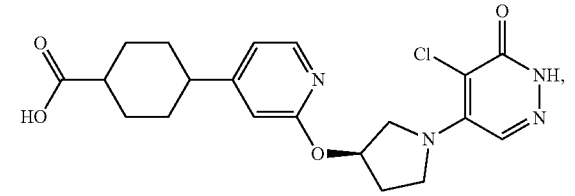
P-0048
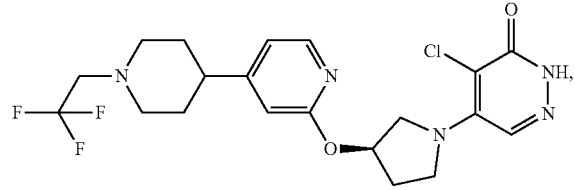
P-0049
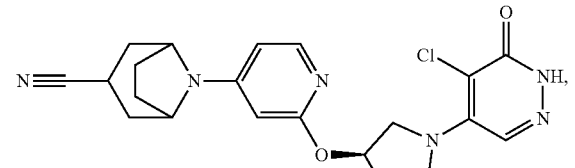
P-0050
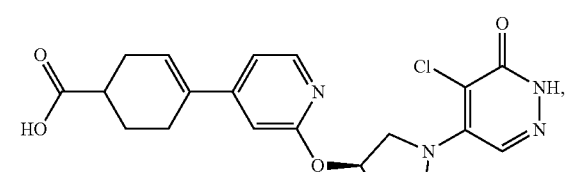
P-0051
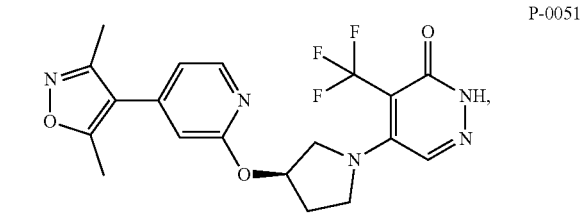
P-0052
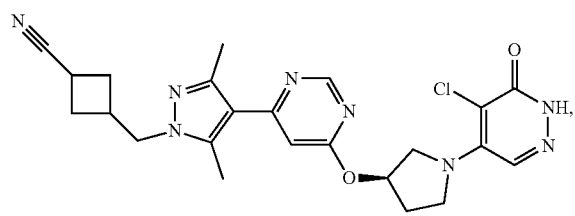
P-0053
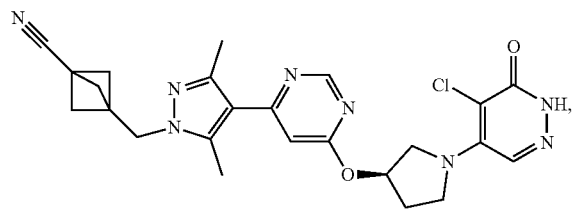
P-0054
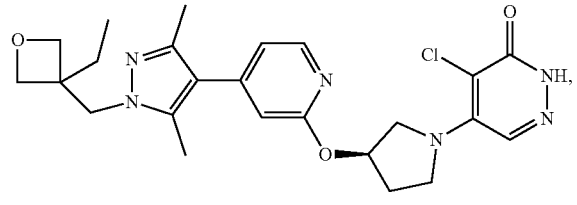
P-0055
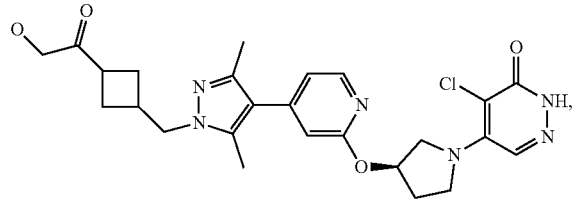
P-0056
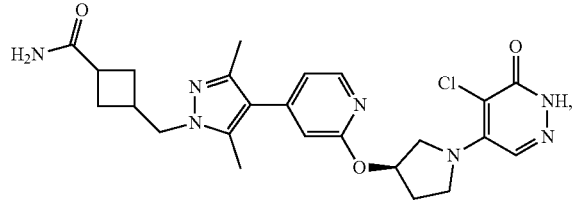
P-0057
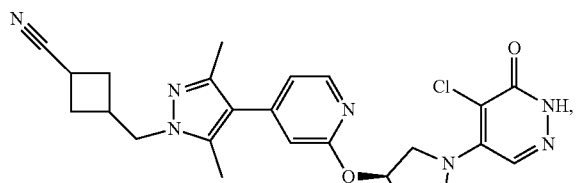
P-0058
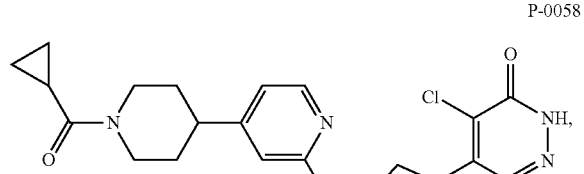
P-0059
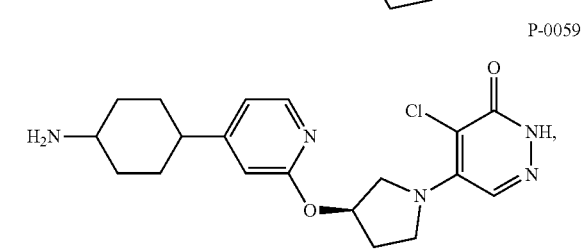

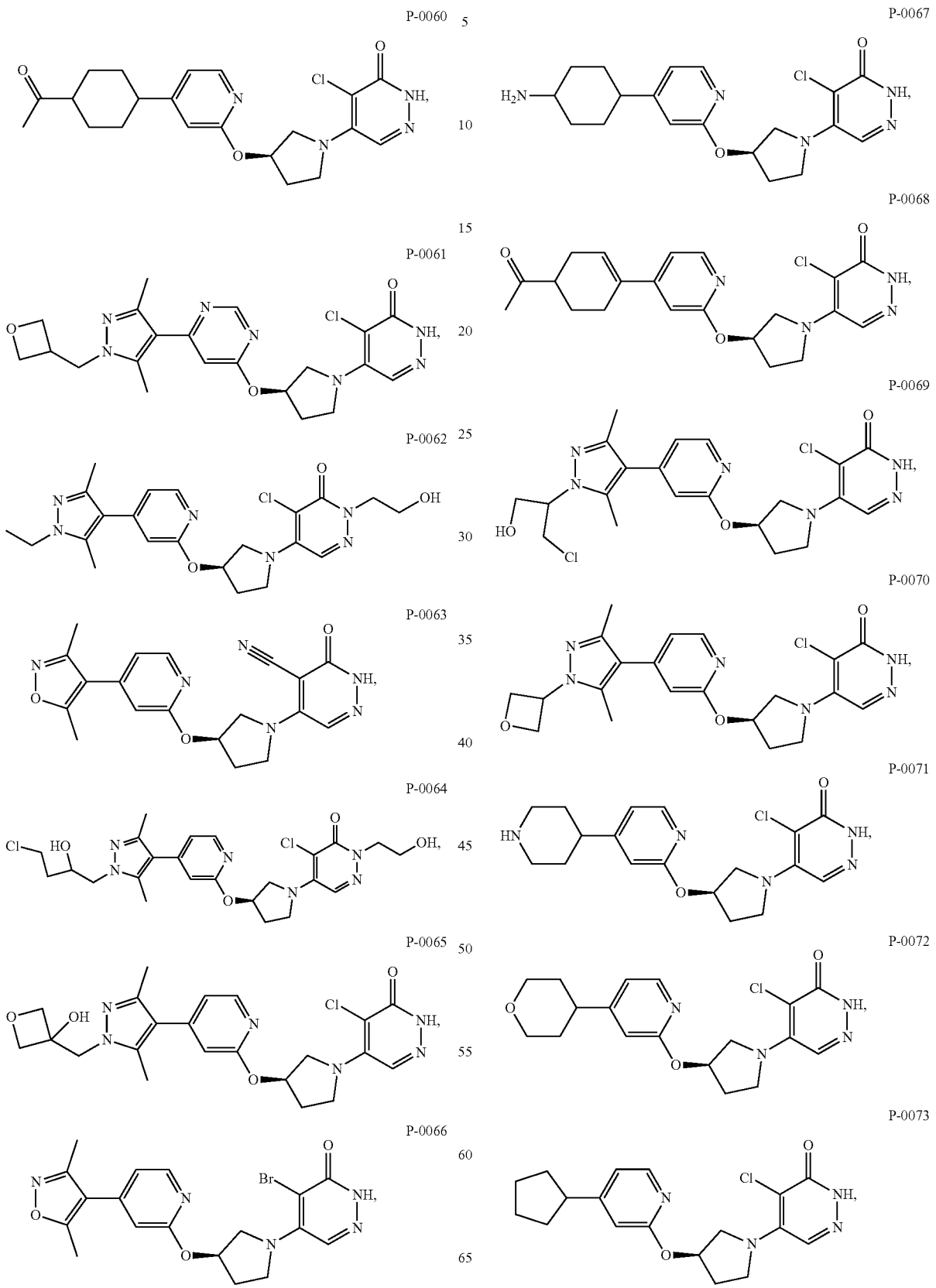

247
-continued
P-0074
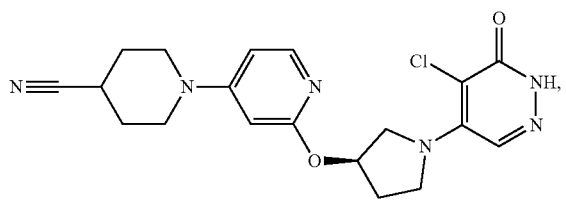
P-0075
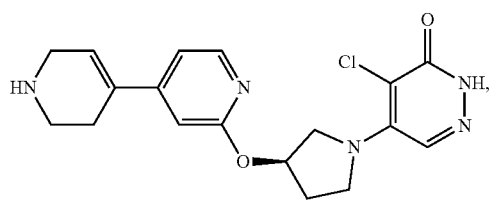
P-0076
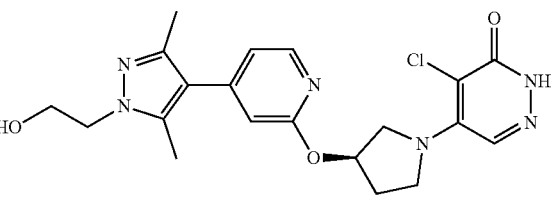
P-0077
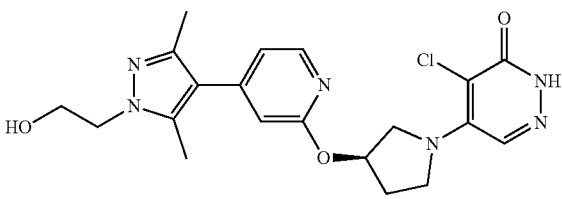
P-0078
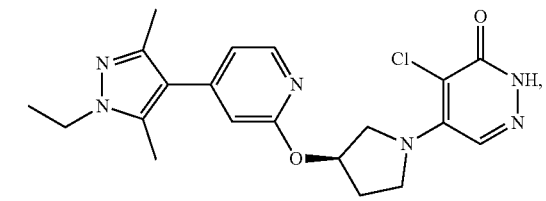
P-0079
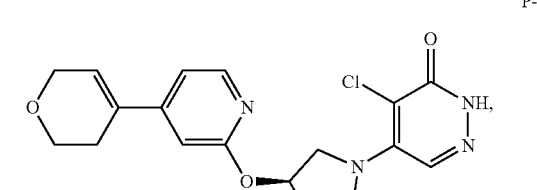
P-0080
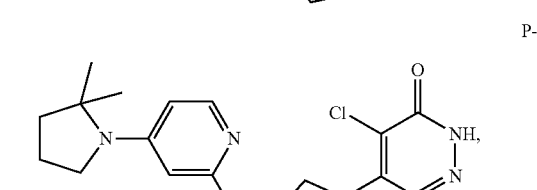
248
-continued
P-0081
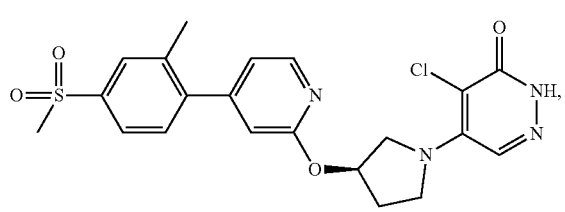
P-0082
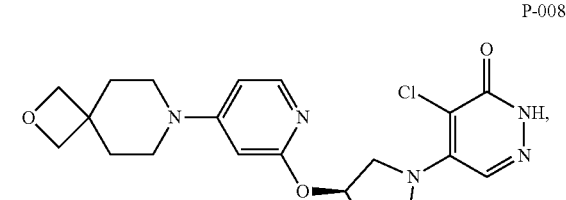
P-0083
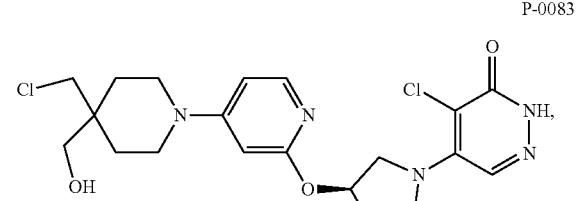
P-0084
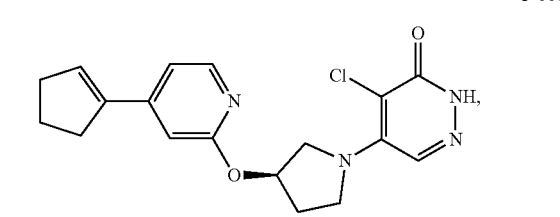
P-0085
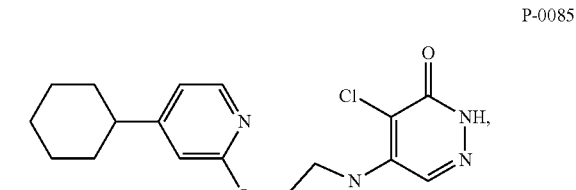
P-0086
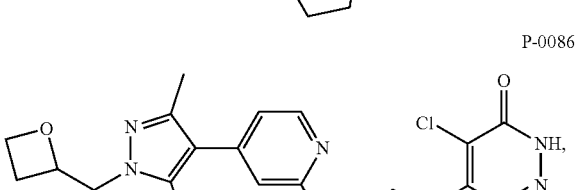
P-0087
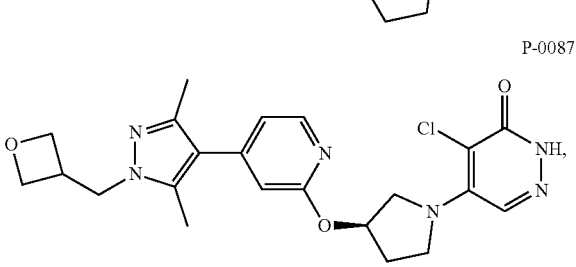

P-0088 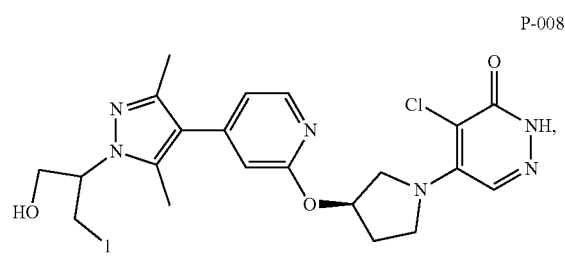
P-0089 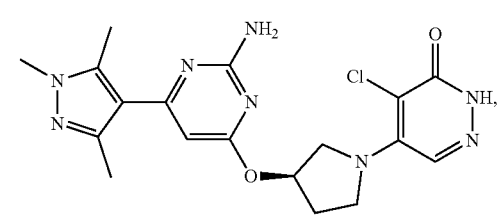
P-0090 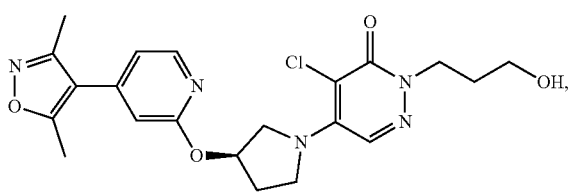 [SMILES: Cc1noc(C)c1-c1ccnc(O[C@@H]2CCN(c3cnn(CCCO)c(=O)c3Cl)C2)c1]
P-0091 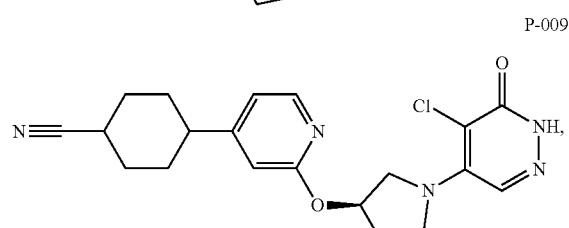
P-0092 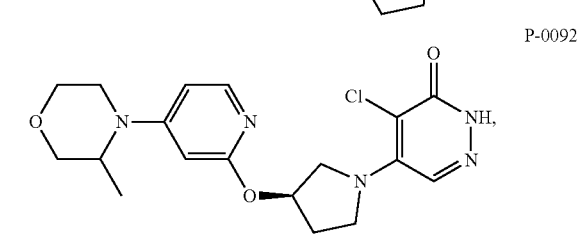
P-0093 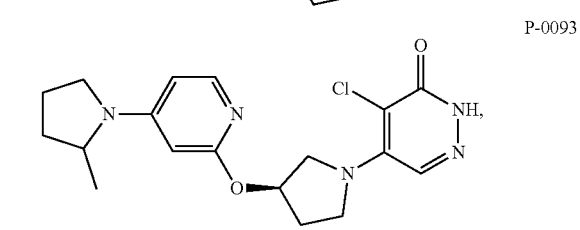
P-0094 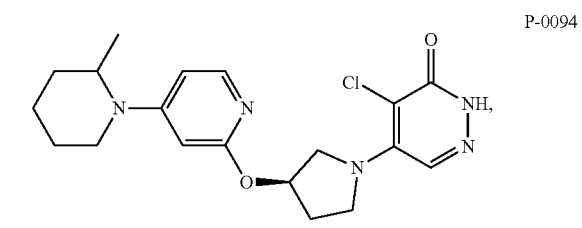
P-0095 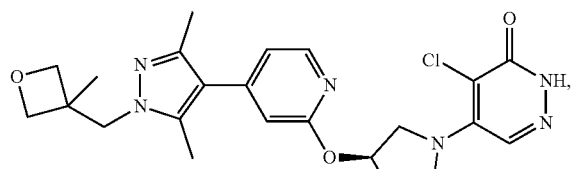
P-0096 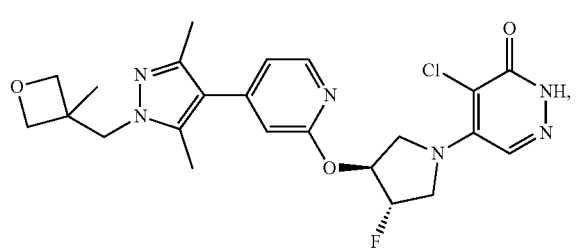
P-0097 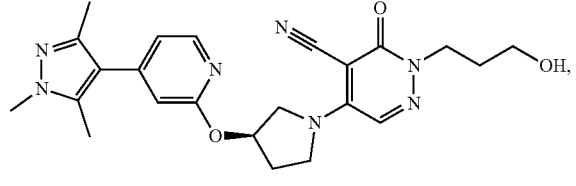 [SMILES: Cc1nn(C)c(C)c1-c1ccnc(O[C@@H]2CCN(c3cnn(CCCO)c(=O)c3C#N)C2)c1]
P-0098 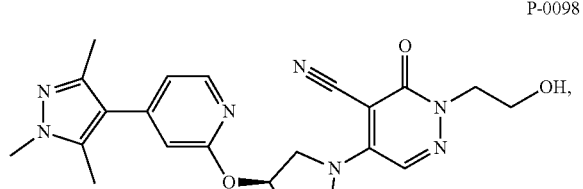
P-0099 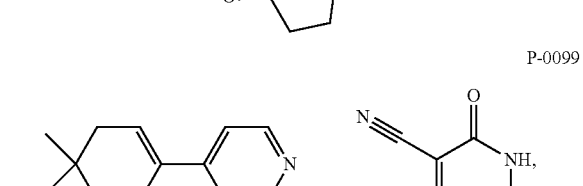
P-0100 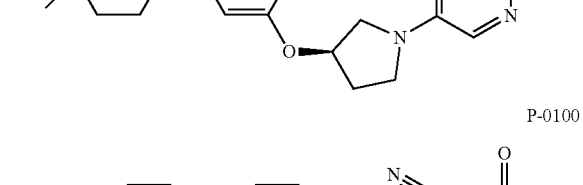
P-0101 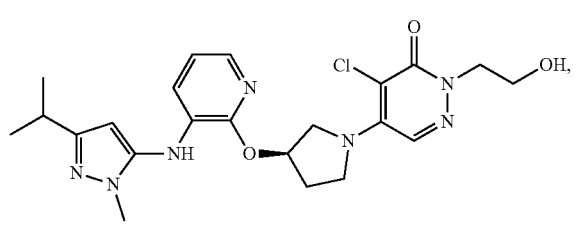

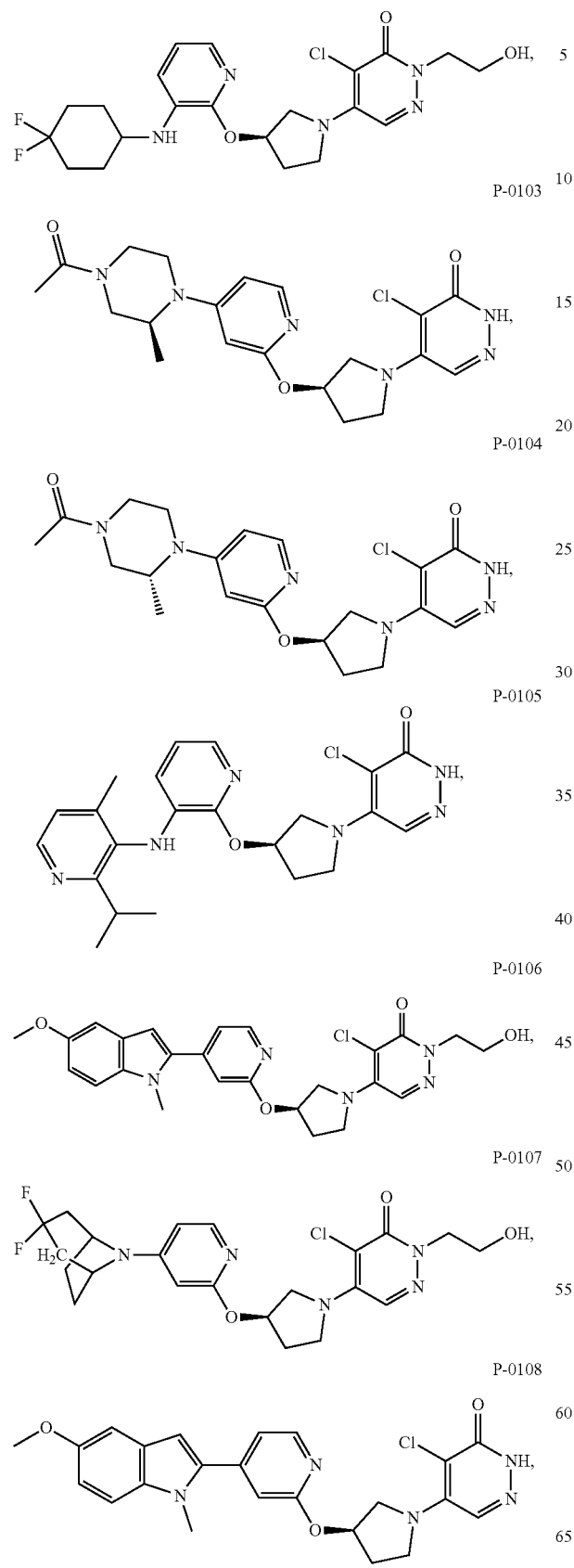
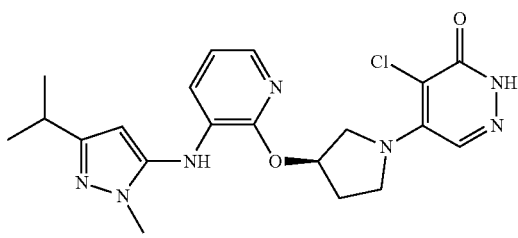
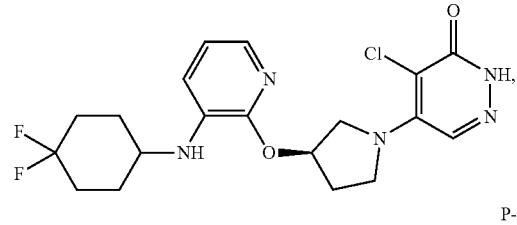
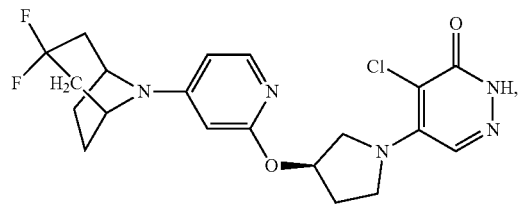
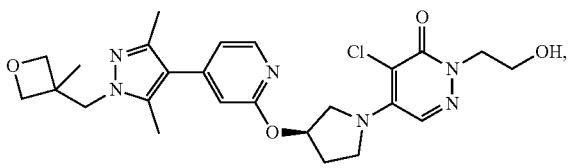
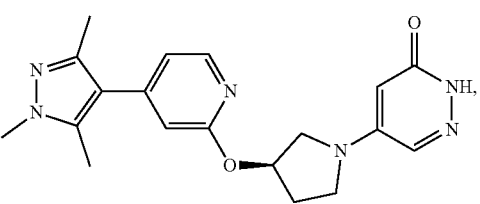
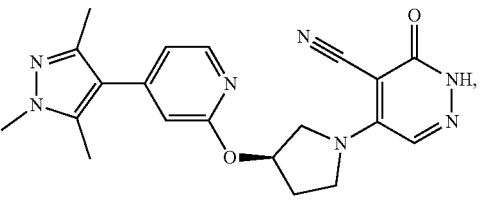
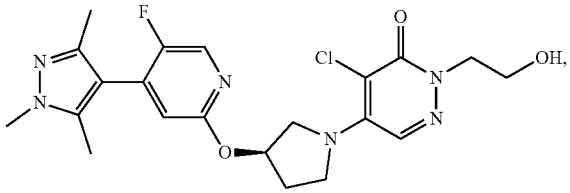

P-0116
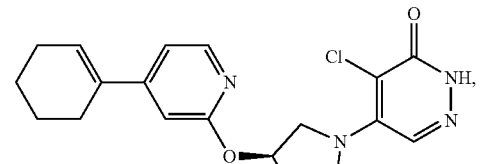
P-0117
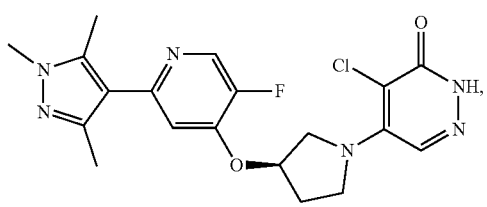
P-0118
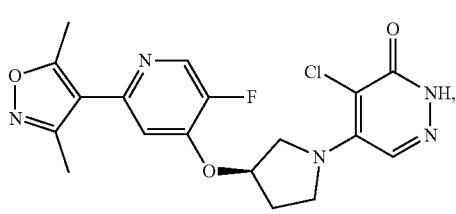
P-0119
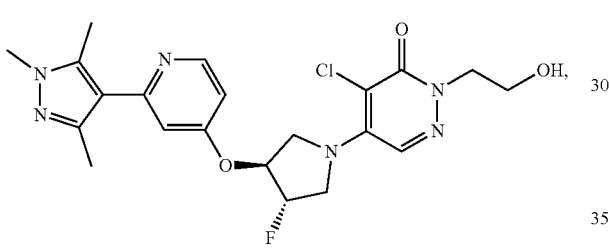
P-0120
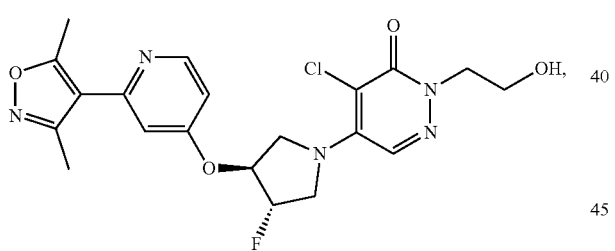
P-0121
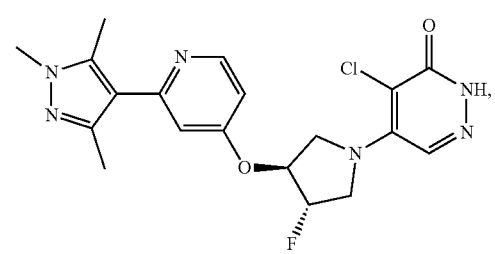
P-0122
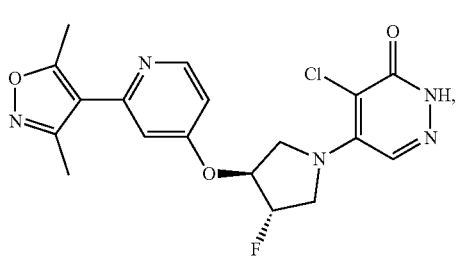
P-0123
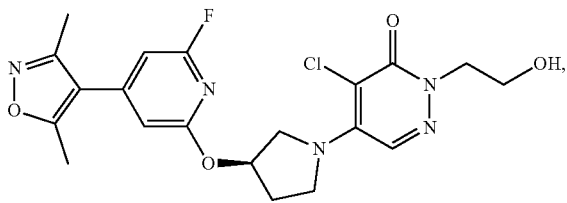
P-0124
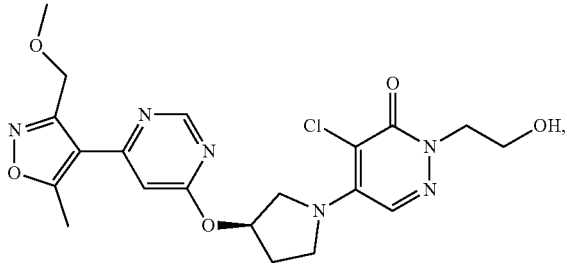
P-0125
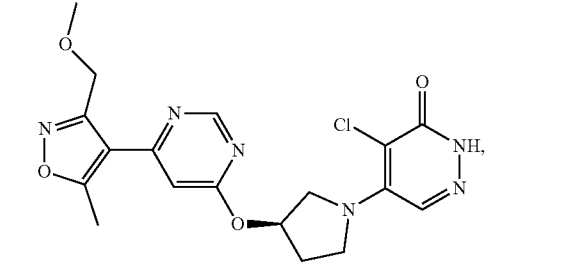
P-0126
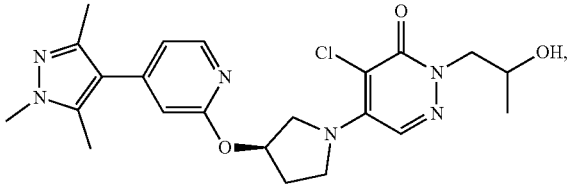 [SMILES: Cc1nn(C)c(C)c1-c1ccnc(O[C@@H]2CCN(c3cnn(CC(O)CO)c(=O)c3Cl)C2)c1]
P-0127
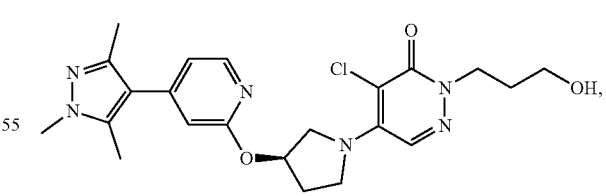
P-0128
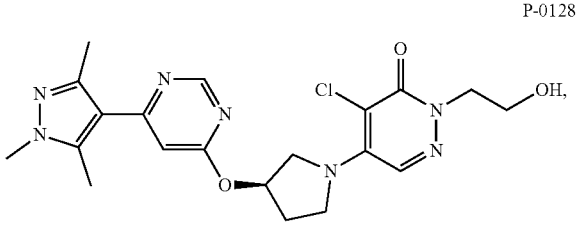

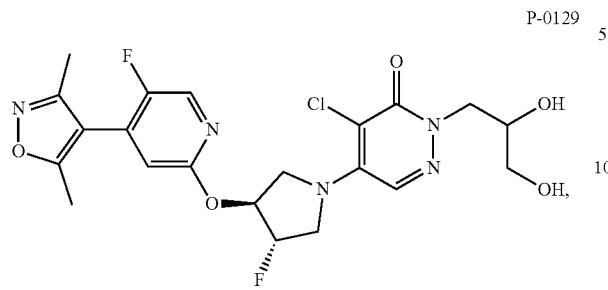
P-0129
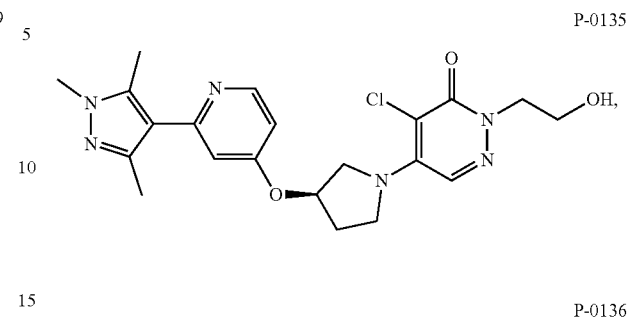
P-0135
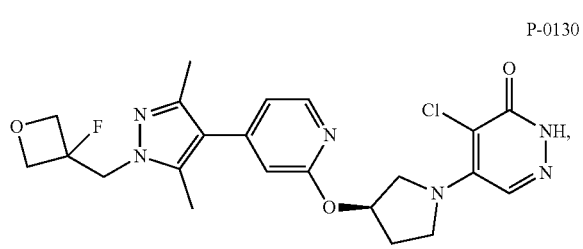
P-0130
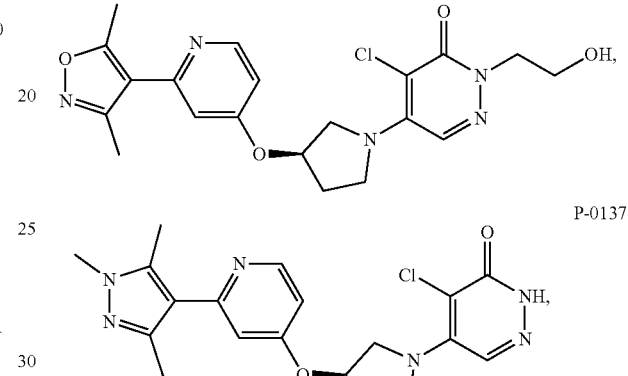
P-0136
P-0131
P-0137
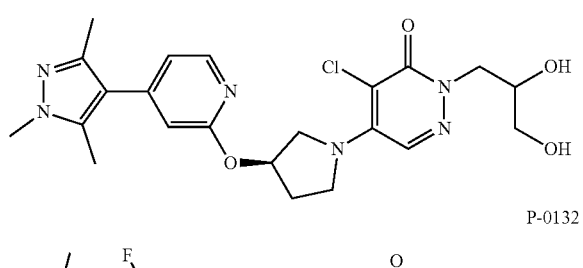
P-0132
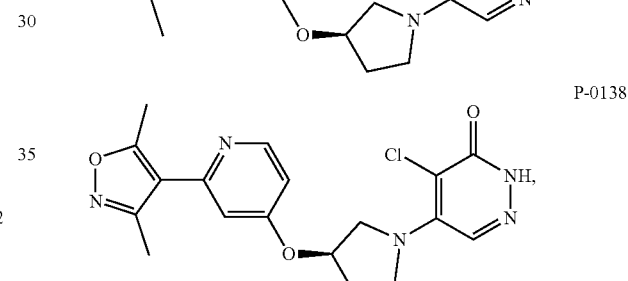
P-0138
P-0133
P-0139
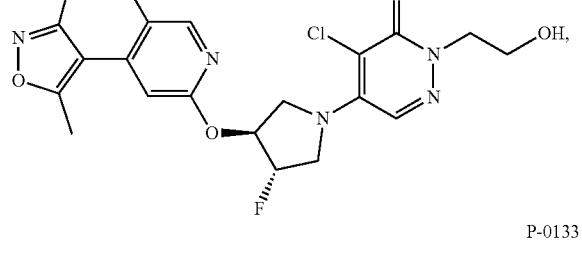
P-0134
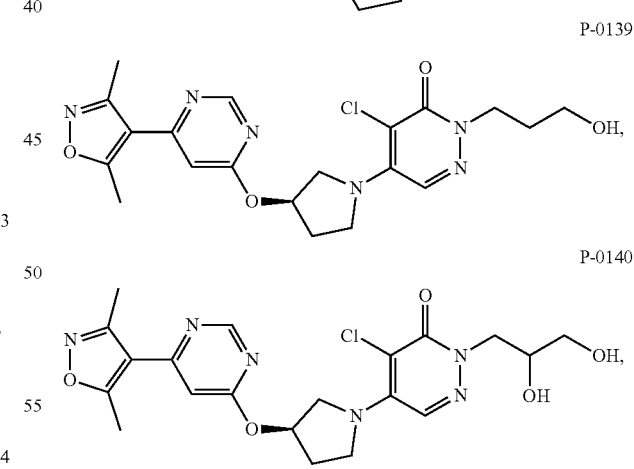
P-0140
P-0141

-continued

P-0142

P-0143

P-0144

P-0145

P-0146

P-0147

-continued

P-0148

P-0149

P-0150

P-0151

P-0152

P-0153

P-0154

-continued
P-0155
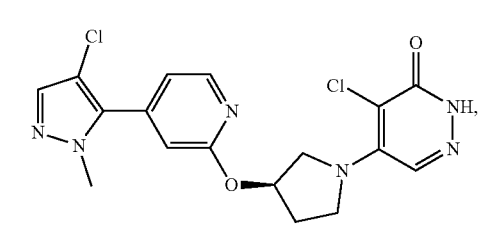
P-0156
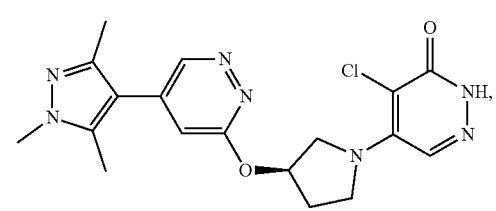
P-0157
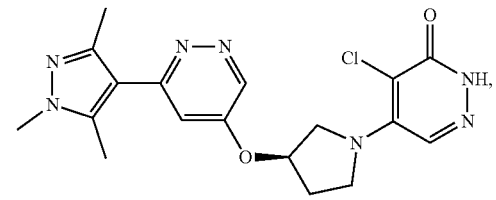
P-0158
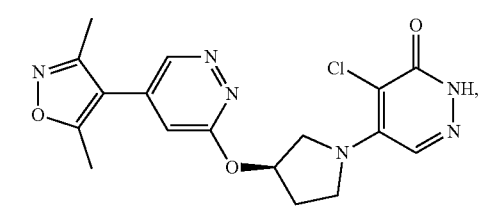
P-0159
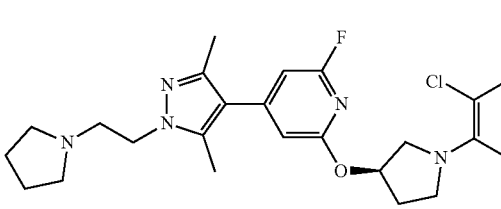
P-0160
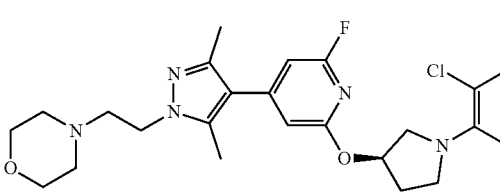
P-0161
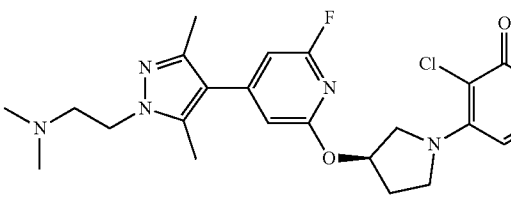
-continued
P-0162
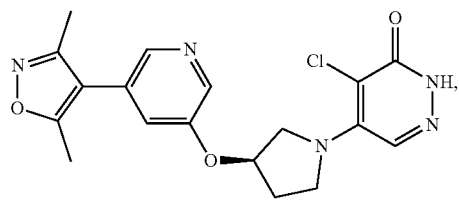
P-0163
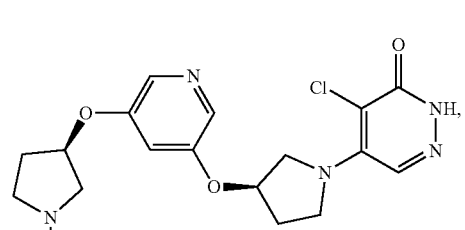
P-0164
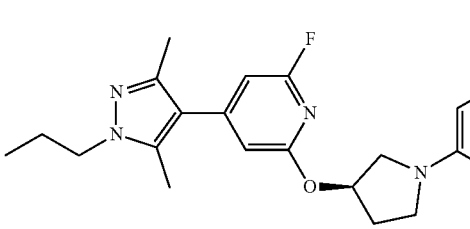
P-0165
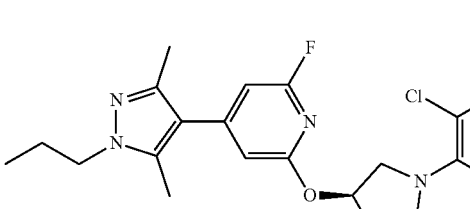
P-0166
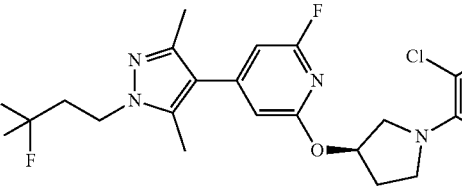
P-0167
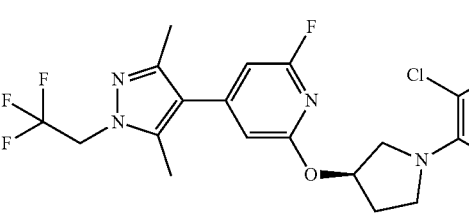

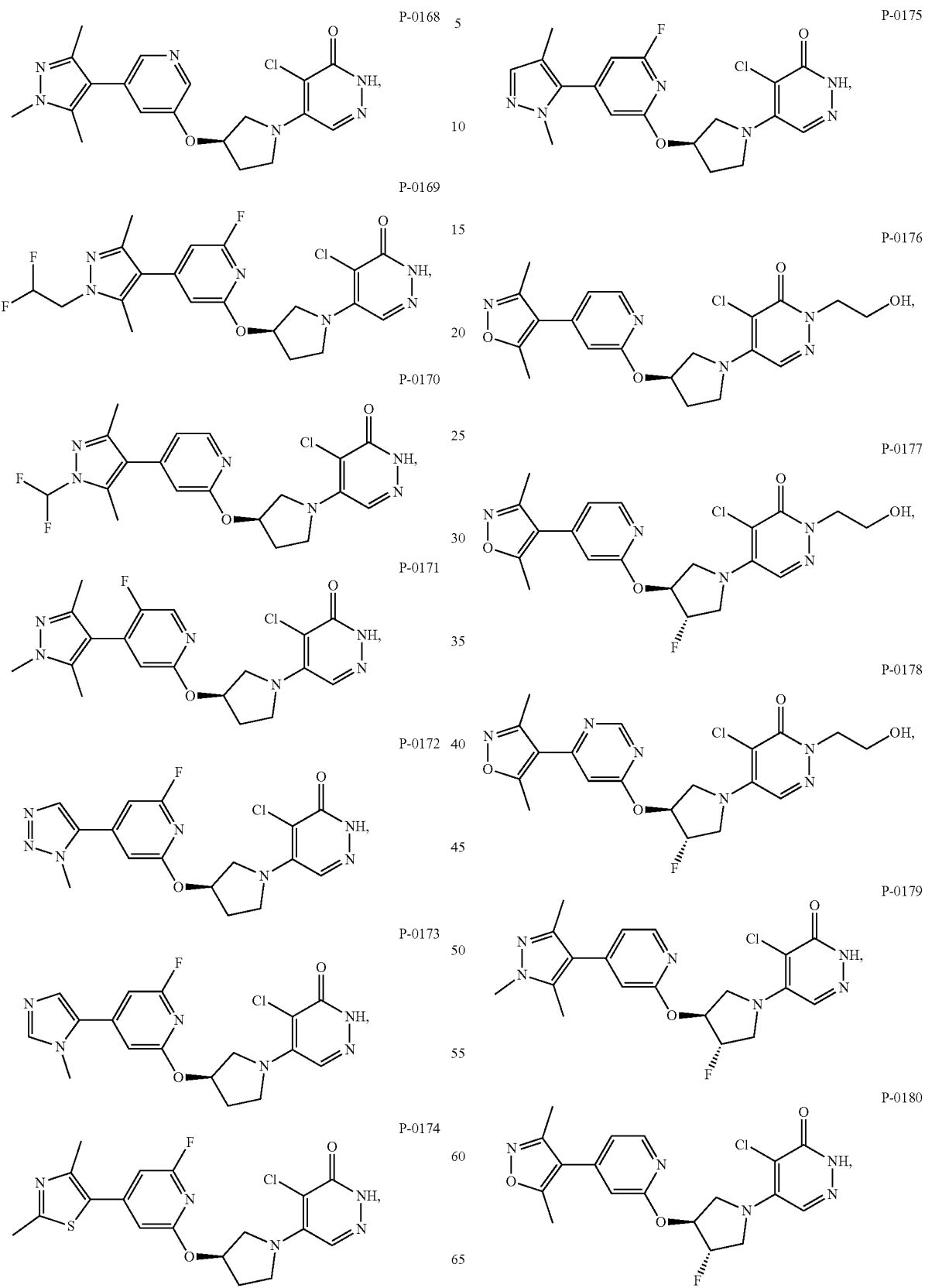

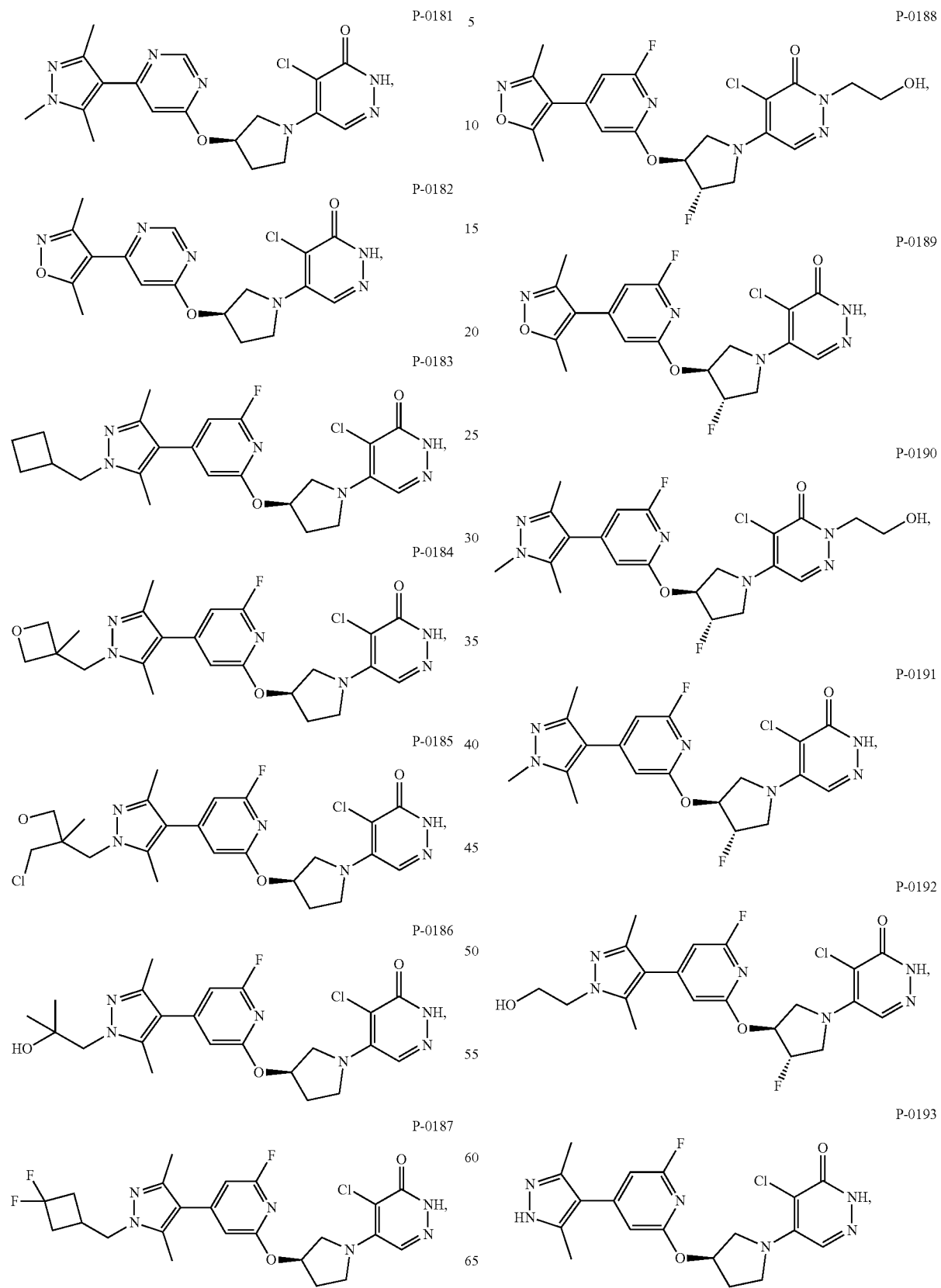

-continued

P-0194

P-0195

P-0196

P-0197

P-0198

P-0199

P-0200

-continued

P-0201

P-0202

P-0203

P-0204

P-0205

P-0206

P-0207

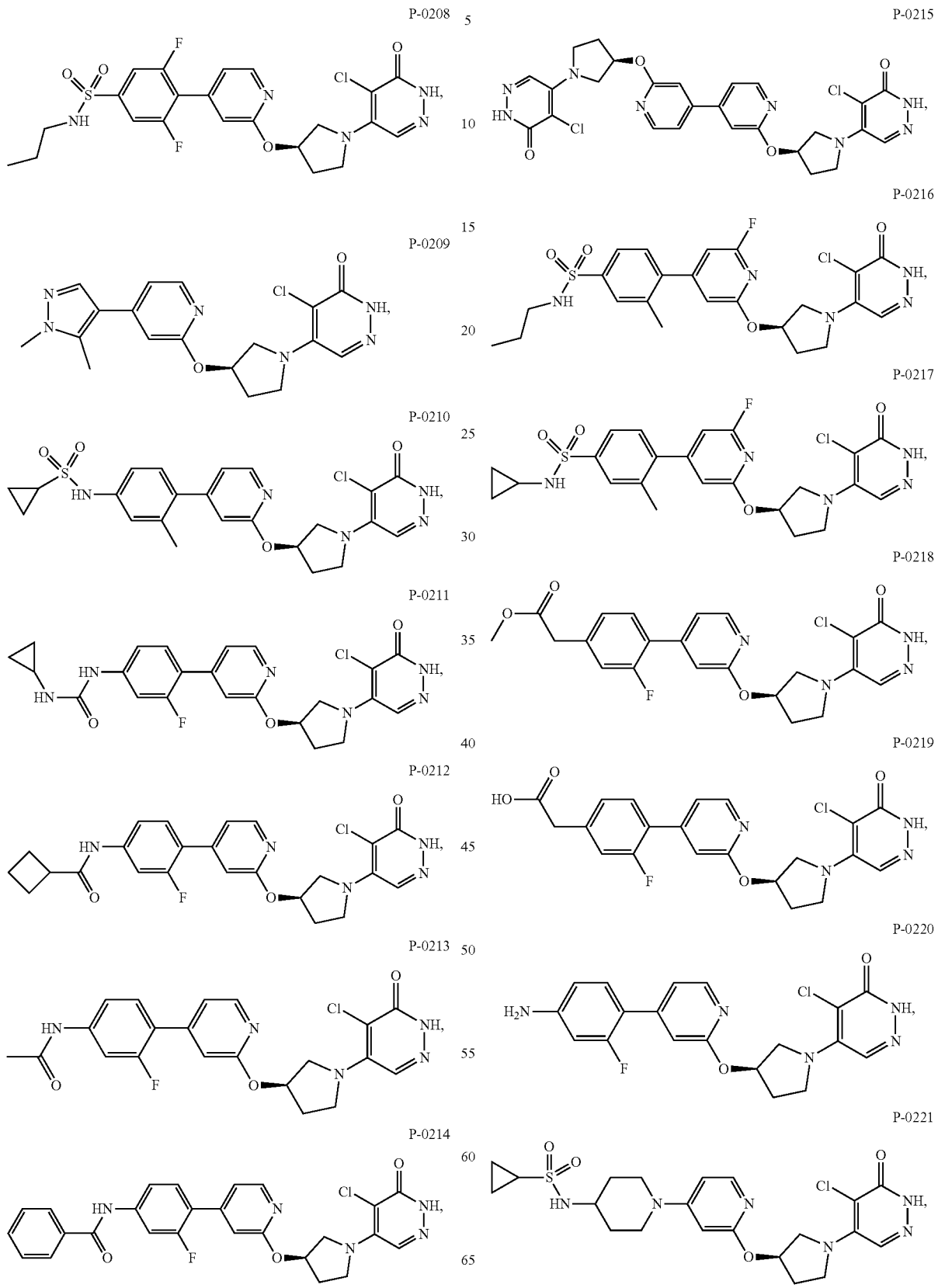

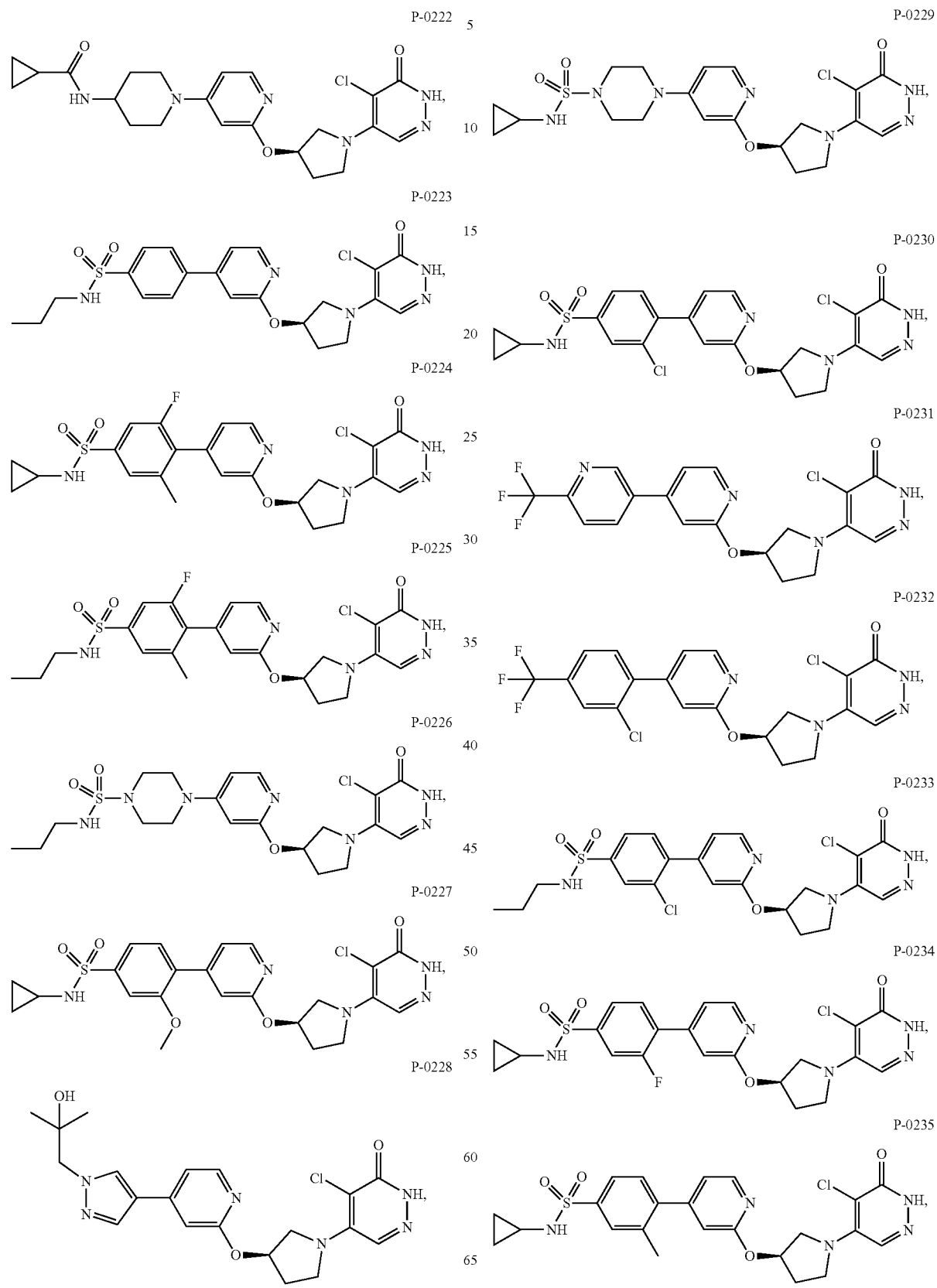

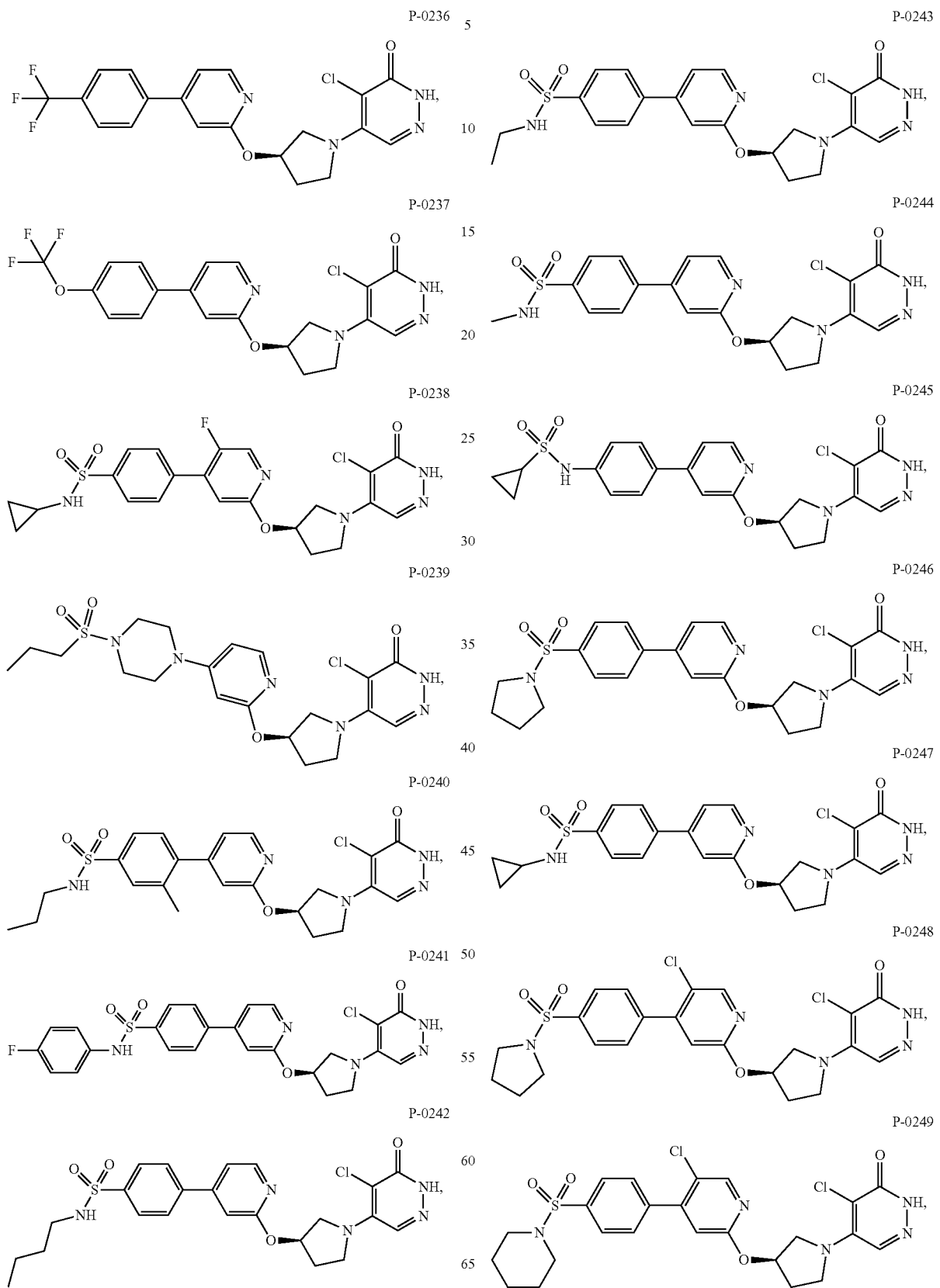

-continued

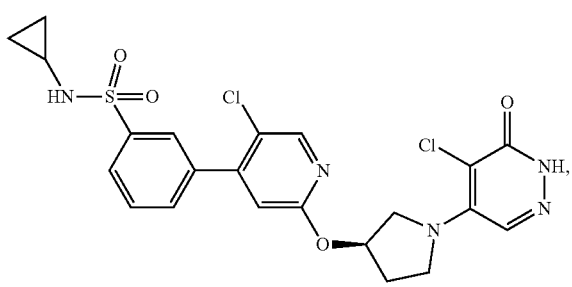
P-0250

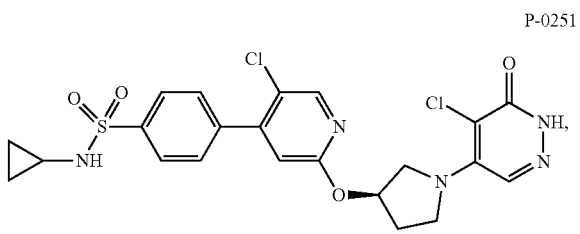
P-0251

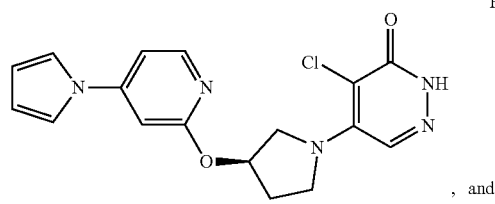
P-0252

, and

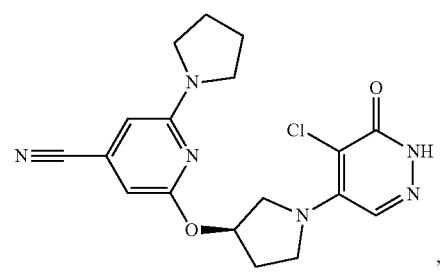
P-0253 or a pharmaceutically acceptable salt thereof.

14. The compound according to claim 13, wherein the compound is

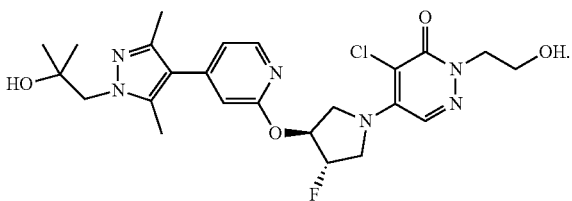

15. The compound according to claim 13, wherein the compound is

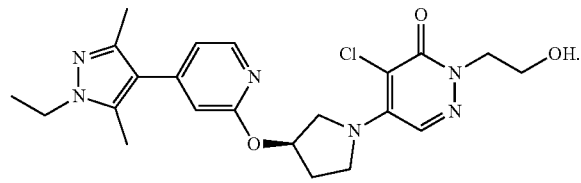

16. The compound according to claim 13, wherein the compound is

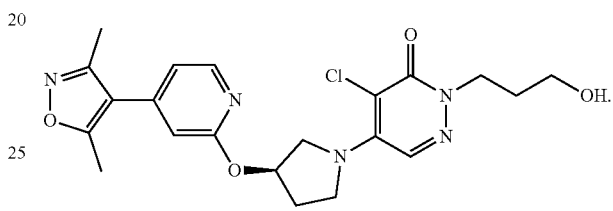

17. The compound according to claim 13, wherein the compound is

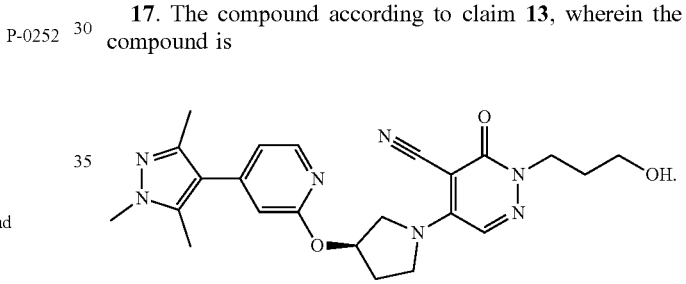

18. The compound according to claim 13, wherein the compound is

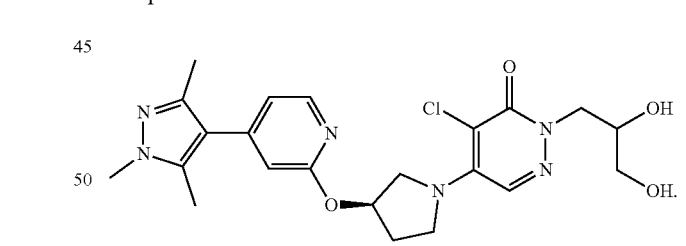

19. The compound according to claim 13, wherein the compound is

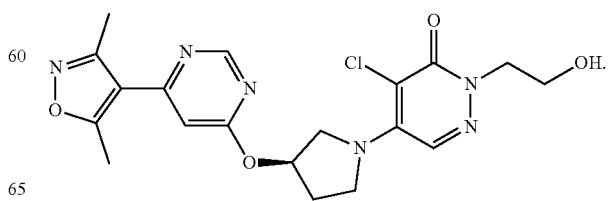

20. The compound according to claim 13, wherein the compound is

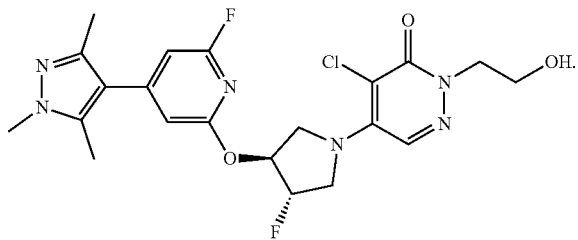 [SMILES: Cc1nn(C)c(C)c1-c1cc(F)nc(O[C@H]2CN(c3cnn(CCO)c(=O)c3Cl)C[C@@H]2F)c1]

21. The compound according to claim 13, wherein the compound is

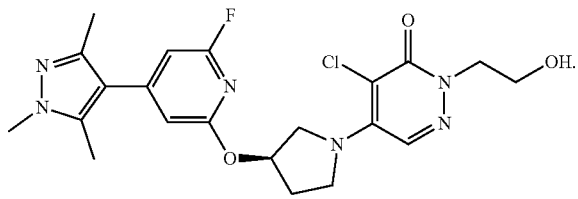 [SMILES: Cc1nn(C)c(C)c1-c1cc(F)nc(O[C@@H]2CCN(c3cnn(CCO)c(=O)c3Cl)C2)c1]

22. The compound according to claim 13, wherein the compound is

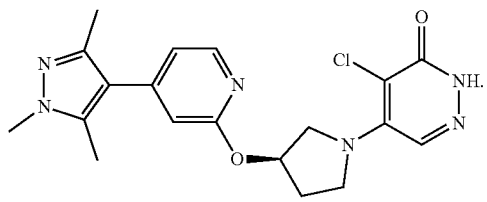 [SMILES: Cc1nn(C)c(C)c1-c1ccnc(O[C@@H]2CCN(c3cn[nH]c(=O)c3Cl)C2)c1]

23. A pharmaceutical composition comprising a compound of claim 1, and a pharmaceutically acceptable carrier.

24. A method for treating a subject with a disease or condition mediated by CD73, said method comprising administering to the subject an effective amount of a compound of claim 1, or a pharmaceutically acceptable salt, a solvate, a tautomer, a stereoisomer, or a deuterated analog thereof; wherein the disease or condition is a neoplastic disorder, a cancer, an age-related disease, an inflammatory disorder, a cognitive disorder, a neurodegenerative disease, bladder cancer, colorectal cancer, gastric cancer, gall bladder cancer, glioblastoma multiforme, glioma, leukemia, lymphoma, lung cancer, breast cancer, melanoma, multiple myeloma, ovarian cancer, prostate cancer, pancreatic cancer, thyroid cancer, lung fibrosis, liver fibrosis, Alzheimer's disease, multiple sclerosis, or Parkinson's disease.

25. The method of claim 24, wherein the disease or condition is renal cancer, small-cell lung cancer, non-small cell lung cancer, acute myeloid leukemia, multiple myeloma, diffuse large B-cell lymphoma, breast cancer or prostate cancer.

26. The method according to claim 24, further comprising administering one or more additional therapeutic agents, wherein the one or more additional therapeutic agents is one or more of i) an alkylating agent; ii) an antibiotic; iii) an antimetabolite; iv) an immunotherapy agent; v) a hormone or hormone antagonist; vi) a taxane; vii) a retinoid; viii) an alkaloid; ix) an antiangiogenic agent; x) a topoisomerase inhibitor; xi) a kinase inhibitor; xii) a targeted signal transduction inhibitor; xiii) a biological response modifier; xiv) an IDO inhibitor; xv) a chemotherapeutic agent; xvi) a Mek inhibitor; xvii) a tyrosine kinase inhibitor; xviii) a c-Kit mutant inhibitor; xix) an EGFR inhibitor; and xx) an epigenetic modulator.

27. The method according to claim 26, wherein the one or more additional therapeutic agents is one or more of an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan.

28. The method according to claim 26, wherein the one or more additional therapeutic agents is one or more of an antibiotic selected from bleomycin, dactinomycin, daunorubicin, doxorubicin, epirubicin, idarubicin, menogaril, mitomycin, mitoxantrone, neocarzinostatin, pentostatin, and plicamycin.

29. The method according to claim 26, wherein the one or more additional therapeutic agents is one or more of an antimetabolite selected from the group consisting of azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate.

30. The method according to claim 26, wherein the one or more additional therapeutic agents is one or more of an immunotherapy agent selected from a PD-1 or PD-L1 inhibitor.

31. The method according to claim 26, wherein the one or more additional therapeutic agents is one or more of a hormone or hormone antagonist selected from the group consisting of enzalutamide, abiraterone, anastrozole, androgens, buserelin, diethylstilbestrol, exemestane, flutamide, fulvestrant, goserelin, idoxifene, letrozole, leuprolide, magestrol, raloxifene, tamoxifen, and toremifene.

32. The method according to claim 26, wherein the one or more additional therapeutic agents is one or more of a taxane selected from DJ-927, docetaxel, TPI 287, paclitaxel and DHA-paclitaxel.

33. The method according to claim 26, wherein the one or more additional therapeutic agents is one or more of a retinoid selected from alitretinoin, bexarotene, fenretinide, isotretinoin, and tretinoin.

34. The method according to claim 26, wherein the one or more additional therapeutic agents is one or more of an alkaloid selected from etoposide, homoharringtonine, teniposide, vinblastine, vincristine, vindesine, and vinorelbine.

35. The method according to claim 26, wherein the one or more additional therapeutic agents is one or more of an antiangiogenic agent selected from AE-941, ABT-510, 2-methoxyestradiol, lenalidomide, and thalidomide.

36. The method according to claim 26, wherein the one or more additional therapeutic agents is one or more of a topoisomerase inhibitor selected from amsacrine, edotecarin, exatecan, irinotecan, SN-38, rubitecan, topotecan, and 9-aminocamptothecin.

37. The method according to claim 26, wherein the one or more additional therapeutic agents is one or more of a kinase inhibitor selected from erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01, vemurafenib, dabrafenib, trametinib, cobimetinib selumetinib and vatalanib.

38. The method according to claim 26, wherein the one or more additional therapeutic agents is one or more of a targeted signal transduction inhibitor selected from bortezomib, geldanamycin, and rapamycin.

39. The method according to claim 26, wherein the one or more additional therapeutic agents is one or more of a biological response modifier selected from imiquimod, interferon-α and interleukin-2.

40. The method according to claim 26, wherein the one or more additional therapeutic agents is one or more of a chemotherapeutic agent selected from 3-amino-2-carboxyaldehyde thiosemicarbazone, altrasentan, aminoglutethimide, anagrelide, asparaginase, bryostatin-1, cilengitide, elesclomol, eribulin mesylate, ixabepilone, lonidamine, masoprocol, mitoguanazone, oblimersen, sulindac, testolactone, tiazofurin, a mTOR inhibitor, a PI3K inhibitor, a Cdk4 inhibitor, an Akt inhibitor, a Hsp90 inhibitor, a farnesyltransferase inhibitor or an aromatase inhibitor.

\* \* \* \* \*